US010590158B2

(12) United States Patent
Nicolaou et al.

(10) Patent No.: US 10,590,158 B2
(45) Date of Patent: Mar. 17, 2020

(54) TOTAL SYNTHESIS OF SHISHIJIMICIN A AND ANALOGS THEREOF

(71) Applicant: WILLIAM MARSH RICE UNIVERSITY, Houston, TX (US)

(72) Inventors: Kyriacos C. Nicolaou, Houston, TX (US); Ruofan Li, Houston, TX (US); Zhaoyong Lu, Houston, TX (US); Te-ik Sohn, Andong (KR); James Woods, Houston, TX (US); Emmanouil N. Pitsinos, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 15/740,656

(22) PCT Filed: Jun. 29, 2016

(86) PCT No.: PCT/US2016/040047
§ 371 (c)(1),
(2) Date: Dec. 28, 2017

(87) PCT Pub. No.: WO2017/004172
PCT Pub. Date: Jan. 5, 2017

(65) Prior Publication Data
US 2018/0327439 A1 Nov. 15, 2018

Related U.S. Application Data

(60) Provisional application No. 62/186,191, filed on Jun. 29, 2015.

(51) Int. Cl.
*C07H 15/24* (2006.01)
*A61K 45/06* (2006.01)
*C07D 471/04* (2006.01)
*C07D 405/06* (2006.01)
*C07D 519/00* (2006.01)
*C07H 15/203* (2006.01)
*A61K 47/68* (2017.01)
*C07H 15/20* (2006.01)
*C07D 487/04* (2006.01)
*A61P 35/00* (2006.01)
*A61K 31/706* (2006.01)
*C07D 498/10* (2006.01)

(52) U.S. Cl.
CPC ........... *C07H 15/24* (2013.01); *A61K 31/706* (2013.01); *A61K 45/06* (2013.01); *A61K 47/6803* (2017.08); *A61K 47/6807* (2017.08); *A61P 35/00* (2018.01); *C07D 405/06* (2013.01); *C07D 471/04* (2013.01); *C07D 487/04* (2013.01); *C07D 498/10* (2013.01); *C07D 519/00* (2013.01); *C07H 15/20* (2013.01); *C07H 15/203* (2013.01)

(58) Field of Classification Search
None
See application file for complete search history.

(56) References Cited

U.S. PATENT DOCUMENTS 5,264,586 A 11/1993 Nicolaou et al.
5,550,246 A 8/1996 Nicolaou et al.

OTHER PUBLICATIONS

Hamann, Bioconjugate Chem. 2002, 13, 40-46.*
Myers et al., "A Study of the Reaction of Calicheamicin $\gamma_1$ with Glutathione in the Presence of Double-Stranded DNA", *J. Am. Chem. Soc.*, 116(4):1255-1271, 1994.
Nicolaou et al., "Calicheamicin $\theta^I_1$: A Rationally Designed Molecule with Extremely Potent and Selective DNA Cleaving Properties and Apoptosis Inducing Activity", *Ang. Chem. Int. Ed.*, 33(2):183-186, 1994.
Partial Search Report issued in corresponding European Application No. 16818662.5, dated Feb. 28, 2019.
Wittman et al., "The synthesis and biological activity of enediyne minor groove binding hybrids", *Bioorg. Med. Chem. Lett.*, 5(10):1049-1052, 1995.
Gomez Paloma et al., "Interaction of calicheamicin with duplex DNA: role of the oligosaccharide domain and identification of multiple binding modes." *J. Am. Chem. Soc.*, 116:3697-3708, 1994.
Groneberg et al., "Total synthesis of calicheamicin $\gamma$1I. 1. Synthesis of the oligosaccharide fragment." *J. Am. Chem. Soc.* 115:7593-7611, 1993.
Jones & Bergman, "p-Benzyne. Generation as an intermediate in a thermal isomerization reaction and trapping evidence for the 1,4-benzenediyl structure." *J. Am. Chem. Soc.*, 94:660-661, 1972.
Lee, et al., "Calicheamicins, a novel family of antitumor antibiotics. 1. Chemistry and partial structure of calicheamicin $\gamma_1^I$." J. Am. Chem. Soc., 109:3464-3466, 1987a.
Lee et al., "Calicheamicins, a novel family of antitumor antibiotics. 2. Chemistry and structure of calicheamicin $\gamma_1^I$." *J. Am. Chem. Soc.*, 109:3466-3468, 1987a and 1987b.
Nicolaou et al., "Total synthesis of calicheamicin $\gamma_1^I$." *J. Am. Chem. Soc.*, 114:10082-10084, 1992.
Nicolaou et al., "Total synthesis of calicheamicin $\gamma 1^I.3$. The final stages." J. Am. Chem. Soc., 115:7625-7635, 1993.
Nicolaou et al., "Synthesis of the carboline disaccharide domain of shishijimicin A." *Org. Lett.*, 13:3924-3927, 2011.
Oku et al., "Shishijimicins A—C, Novel enediyne antitumor antibiotics from the ascidian Didemnum proliferum." *J. Am. Chem. Soc.*, 125:2044-2045, 2003.

(Continued)

*Primary Examiner* — Layla D Berry
(74) *Attorney, Agent, or Firm* — Parker Highlander PLLC

(57) ABSTRACT

In one aspect, the present disclosure provides shishijimicin analogs of the formula: wherein the variables are as defined herein. In another aspect, the present disclosure also provides methods of preparing the compounds disclosed herein. In another aspect, the present disclosure also provides pharmaceutical compositions and methods of use of the compounds disclosed herein. Additionally, antibody drug conjugates of the compounds are also provided.

19 Claims, 4 Drawing Sheets

(56) References Cited

OTHER PUBLICATIONS

International Search Report and Written Opinion issued in International Application No. PCT/US2016/040047 dated Nov. 30, 2016.
Smith et al., Total synthesis of calicheamicin γ1I. 2. Development of an enantioselective route to (−)-calicheamicinone. *J. Am. Chem. Soc.*, 115:7612-7624, 1993.
Xiao et al., "Synthesis and biological evaluation of DNA targeting flexible side-chain substituted β-carboline derivatives." *Bioorg. Med. Chem. Lett.*, 11:437-441, 2001.

* cited by examiner

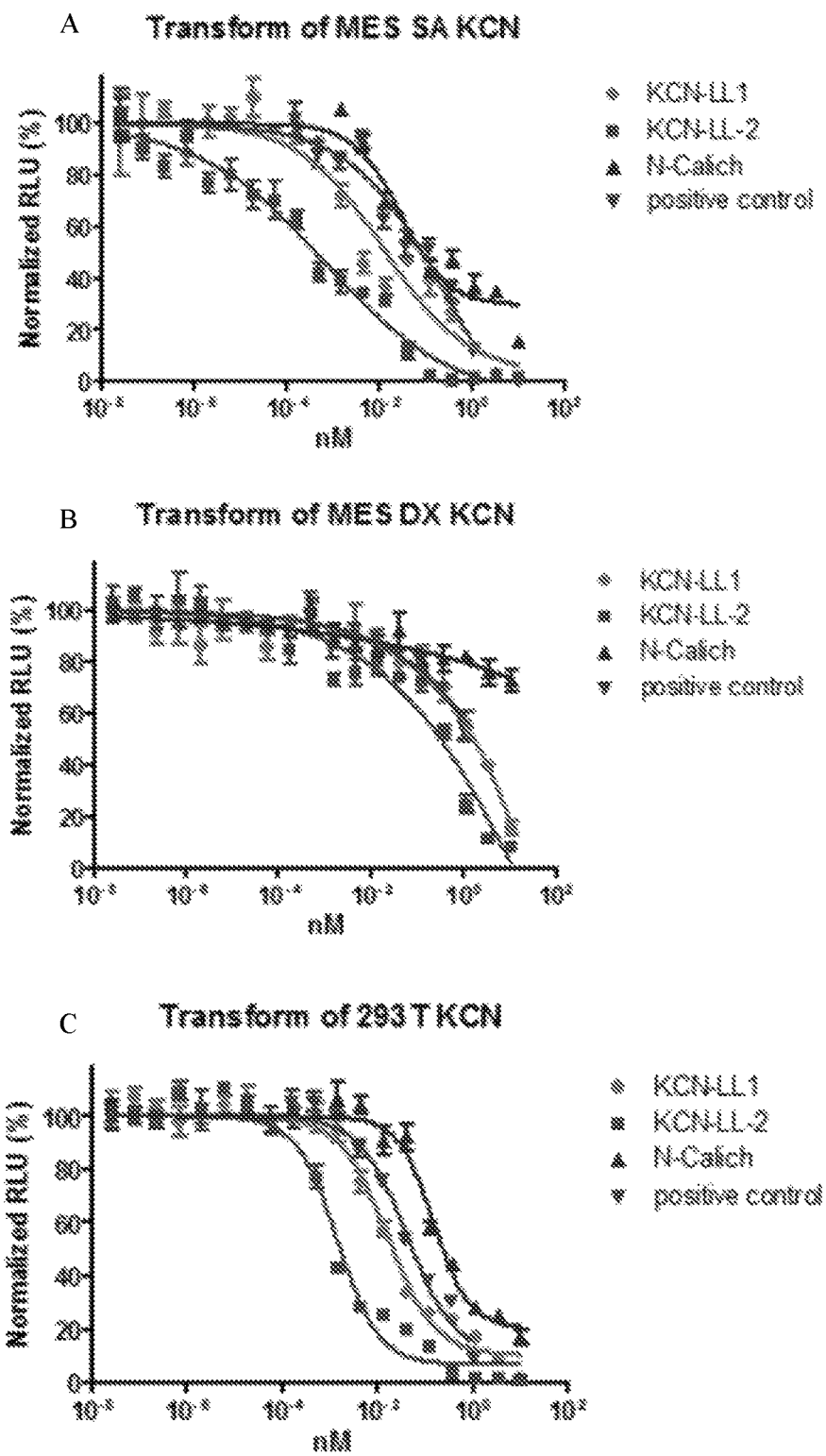
FIGS. 2A-C

TOTAL SYNTHESIS OF SHISHIJIMICIN A AND ANALOGS THEREOF

This application is a national phase application under 35 U.S.C. § 371 of International Application No. PCT/US2016/040047 filed on Jun. 29, 2016 and claims the benefit of priority to U.S. Provisional Application Ser. No. 62/186,191 filed on Jun. 29, 2015, the entire contents of which are hereby incorporated by reference.

BACKGROUND

1. Field

This disclosure relates to the fields of medicine, pharmacology, chemistry, and oncology. In particular, new compounds, compositions, methods of treatment, and methods of synthesis relating to analogs of shishijimicin are disclosed.

2. Related Art

Naturally occurring substances provided the first medications to treat disease and continue to be a rich source and inspiration for drug discovery and development (Nicolaou & Montagnon, 2008 and Nicolaou, Angew, 2014). Several of the compounds have proven to be cytotoxic and thus are useful for treating cancer. While these compounds exhibit significant cytotoxicity, many of the compounds have failed to make it to the clinic due to the severe side effects. Since the development of antibody drug conjugates (ADCs), such as Mylotarg®, a new paradigm has developed for using these highly toxic compounds which had otherwise failed to make it to the clinic (Lee et al., 1987a and Lee et al., 1987b). These compounds could be conjugated to an antibody as a payload which delivers these compounds to the site of the cancer (Wu & Senter, 2005 and Chari et al., 2014). Shishijimicin A (1, FIG. 1) is a rare marine natural product endowed with extremely potent antitumor properties ($IC_{50}$=0.48 pM against P388 leukemia cells) (Oku et al., 2003). Due to potent antitumor properties, shishijimicin A and analogs thereof are valuable potential payloads for antibody drug conjugates but this potential has been hindered by the lack of shishijimicin. Thus, new methods of preparing shishijimicin and analogs thereof which may be used as anticancer agents or as payload for antibody drug conjugates are needed.

SUMMARY

The present disclosure provides analogs of shishijimicin which may be useful in the treatment of cancer. Thus, there is provided compounds of the formula:

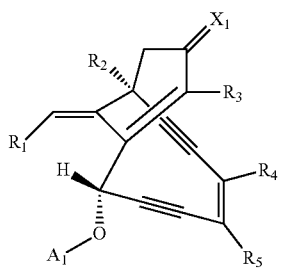

(I)

wherein:
$R_1$ is -alkanediyl$_{(C \leq 8)}$-(S)$_x$-$A_3$ or -substituted alkanediyl$_{(C \leq 8)}$-(S)$_x$-$A_3$; wherein:
  $A_3$ is hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, heteroaryl$_{(C \leq 12)}$, aralkyl$_{(C \leq 12)}$, acyl$_{(C \leq 12)}$, or a substituted version of any of these groups; and
  x is 1, 2, or 3;
$R_2$ is hydroxy, or alkoxy$_{(C \leq 8)}$, acyloxy$_{(C \leq 8)}$, or substituted version of either of these groups;
$R_3$ is NHC(Y$_2$)R$_{16}$, wherein:
  $Y_2$ is O, NH, or NOH; and
  $R_{16}$ is alkoxy$_{(C \leq 8)}$, alkenyloxy$_{(C \leq 8)}$, alkylamino$_{(C \leq 8)}$, dialkylamino$_{(C \leq 8)}$, or substituted version of any of these groups;
$R_4$ and $R_5$ are each independently selected from hydrogen and halo;
$X_1$ is O, S, or NH;
$A_1$ is -alkanediyl$_{(C \leq 12)}$-C(O)-$A_2$ or -substituted alkanediyl$_{(C \leq 12)}$-C(O)-$A_2$, or

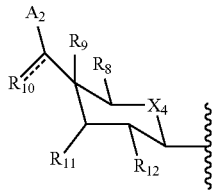

wherein:
$X_4$ is —CH$_2$— or —O—;
$R_8$ is hydrogen, alkyl$_{(C \leq 8)}$, cycloalkyl$_{(C \leq 8)}$, substituted alkyl$_{(C \leq 8)}$, or substituted cycloalkyl$_{(C \leq 8)}$;
$R_9$ is hydrogen, halo, hydroxy, mercapto, alkyl$_{(C \leq 8)}$, substituted alkyl$_{(C \leq 8)}$, alkoxy$_{(C \leq 8)}$, substituted alkoxy$_{(C \leq 8)}$, alkylthio$_{(C \leq 8)}$, substituted alkylthio$_{(C \leq 8)}$;
$R_{10}$ is hydroxy, oxo, or $R_{10}$ is taken together with $R_{11}$ and is —OCHA$_4$O—; provided that when $R_{10}$ is oxo then $R_{10}$ and the carbon atom to which it is bound are joined by a double bond, and when $R_{10}$ is taken together with $R_{11}$ then $R_{10}$ and the carbon atom to which it is bound are joined by a single bond;
wherein $A_4$ is aryl$_{(C \leq 12)}$ or substituted aryl$_{(C \leq 12)}$, or

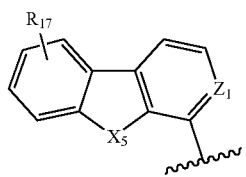

wherein:
$X_5$ is O, S, or NR$_{18}$; wherein:
  $R_{18}$ is hydrogen, alkyl$_{(C \leq 8)}$, substituted alkyl$_{(C \leq 8)}$, acyl$_{(C \leq 8)}$, or substituted acyl$_{(C \leq 8)}$;
$Z_1$ is CH or N; and
$R_{17}$ is hydrogen, hydroxy, amino, hydrazino, carboxy, halo, or nitro; or alkyl$_{(C \leq 12)}$, alkoxy$_{(C \leq 12)}$, or a substituted version of either of these groups;
$R_{11}$ is hydrogen, hydroxy, alkoxy$_{(C \leq 8)}$, or substituted alkoxy$_{(C \leq 8)}$;

$R_{12}$ is hydrogen, hydroxy, alkoxy$_{(C\leq 8)}$, substituted alkoxy$_{(C\leq 8)}$, or —O-alkanediyl$_{(C\leq 8)}$-alkylamino$_{(C\leq 12)}$, —OC(O)-alkanediyl$_{(C\leq 8)}$-alkylamino$_{(C\leq 12)}$, or —OC(O)NH-alkanediyl$_{(C\leq 8)}$-alkylamino$_{(C\leq 12)}$, or a substituted version of any of these groups; or

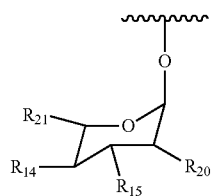

wherein:

$R_{14}$ is amino or hydroxy; or alkoxy$_{(C\leq 12)}$, alkylamino$_{(C\leq 12)}$, dialkyl-amino$_{(C\leq 12)}$, or a substituted version of any of these groups, or —NR$_a$R$_b$, wherein:

$R_a$ and $R_b$ are each hydrogen, alkyl$_{(C\leq 12)}$, substituted alkyl$_{(C\leq 12)}$, alkenyl$_{(C\leq 12)}$, substituted alkenyl$_{(C\leq 12)}$, —C(O)O-alkanediyl$_{(C\leq 6)}$-R$_c$, —C(O)-alkanediyl$_{(C\leq 6)}$-R$_c$, -alkanediyl$_{(C\leq 6)}$-R$_c$, or a substituted version of either of these group; wherein:

$R_c$ is hydrogen, amino, carboxy, hydroxyl, acyl$_{(C\leq 8)}$, alkoxy$_{(C\leq 8)}$, alkylamino$_{(C\leq 8)}$, dialkylamino$_{(C\leq 8)}$, alkylsulfonyl$_{(C\leq 8)}$, arylsulfonyl$_{(C\leq 8)}$, or a substituted version of either of these groups;

$R_{15}$ is hydrogen, hydroxy, alkoxy$_{(C\leq 8)}$, or substituted alkoxy$_{(C\leq 8)}$;

$R_{20}$ and $R_{21}$ are hydrogen, alkyl$_{(C\leq 8)}$, substituted alkyl$_{(C\leq 8)}$, alkoxy$_{(C\leq 8)}$, or substituted alkoxy$_{(C\leq 8)}$;

$A_2$ is hydrogen or

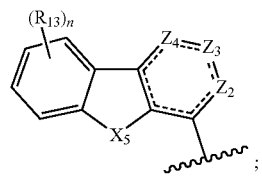

wherein:

$X_5$ is O, S, or NR$_{18}$; wherein:

$R_{18}$ is hydrogen, alkyl$_{(C\leq 8)}$, substituted alkyl$_{(C\leq 8)}$, acyl$_{(C\leq 8)}$, or substituted acyl$_{(C\leq 8)}$;

n is 1, 2, 3, 4, or 5;

$Z_2$, $Z_3$, and $Z_4$ are each independently N or CR$_{13}$; and $R_{13}$ is hydrogen, amino, carboxy, hydroxy, hydrazino, halo, nitro, or mercapto;

alkyl$_{(C\leq 12)}$, acyl$_{(C\leq 12)}$, alkoxy$_{(C\leq 12)}$, acyloxy$_{(C\leq 12)}$, or a substituted version of either of these groups; or $A_1$ is

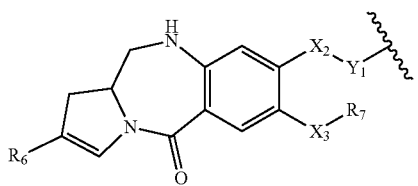

wherein:

$Y_1$ is alkanediyl$_{(C\leq 8)}$ or substituted alkanediyl$_{(C\leq 8)}$;

$X_2$ and $X_3$ are each independently selected from —O—, —S—, or —NR$_{19}$—, wherein:

$R_{19}$ is hydrogen, alkyl$_{(C\leq 6)}$, or substituted alkyl$_{(C\leq 6)}$;

$R_6$ is aryl$_{(C\leq 18)}$, heteroaryl$_{(C\leq 18)}$, or a substituted version of either of these groups;

$R_7$ is alkyl$_{(C\leq 12)}$ or substituted alkyl$_{(C\leq 12)}$;

provided that the compound is not:

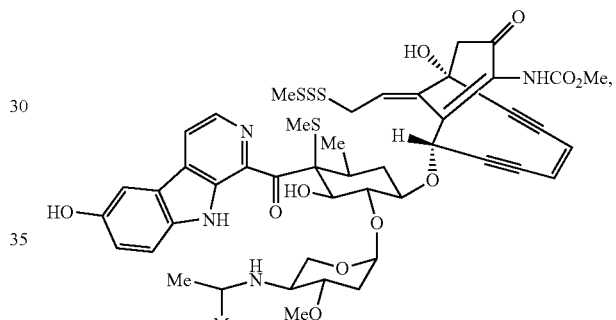

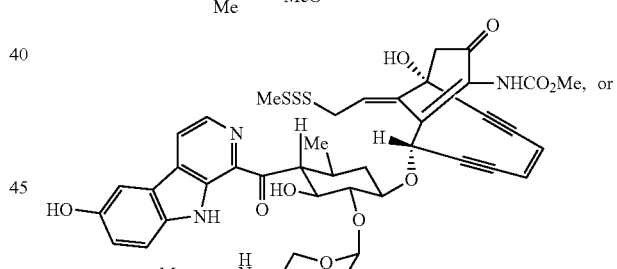

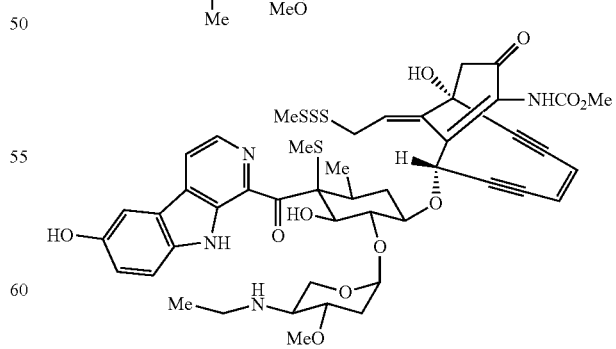

or a pharmaceutically acceptable salt thereof.

In some embodiments, the compound is further defined as:

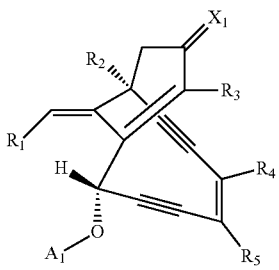

(I)

wherein:
R$_1$ is -alkanediyl$_{(C\leq 8)}$-(S)$_x$-A$_3$ or -substituted alkanediyl$_{(C\leq 8)}$-(S)$_x$-A$_3$; wherein:
  A$_3$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, heteroaryl$_{(C\leq 12)}$, aralkyl$_{(C\leq 12)}$, acyl$_{(C\leq 12)}$, or a substituted version of any of these groups; and
  x is 1, 2, or 3;
R$_2$ is hydroxy, or alkoxy$_{(C\leq 8)}$, acyloxy$_{(C\leq 8)}$, or substituted version of either of these groups;
R$_3$ is NHC(Y$_2$)R$_{16}$, wherein:
  Y$_2$ is O, NH, or NOH; and
  R$_{16}$ is alkoxy$_{(C\leq 8)}$, alkylamino$_{(C\leq 8)}$, dialkylamino$_{(C\leq 8)}$, or substituted version of any of these groups;
R$_4$ and R$_5$ are each independently selected from hydrogen and halo;
X$_1$ is O, S, or NH;
A$_1$ is -alkanediyl$_{(C\leq 12)}$-C(O)-A$_2$ or -substituted alkanediyl$_{(C\leq 12)}$-C(O)-A$_2$, or

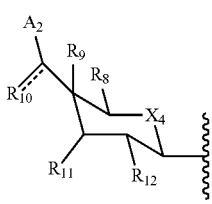

wherein:
X$_4$ is —CH$_2$— or —O—;
R$_8$ is hydrogen, alkyl$_{(C\leq 8)}$, cycloalkyl$_{(C\leq 8)}$, substituted alkyl$_{(C\leq 8)}$, or substituted cycloalkyl$_{(C\leq 8)}$;
R$_9$ is hydrogen, hydroxy, mercapto, alkoxy$_{(C\leq 8)}$, substituted alkoxy$_{(C\leq 8)}$, alkylthio$_{(C\leq 8)}$, substituted alkylthio$_{(C\leq 8)}$;
R$_{10}$ is oxo or R$_{10}$ is taken together with R$_{11}$ and is —OCHA$_4$O—; provided that when R$_{10}$ is oxo then R$_{10}$ and the carbon atom to which it is bound are joined by a double bond, and when R$_{10}$ is taken together with R$_{11}$ then R$_{10}$ and the carbon atom to which it is bound are joined by a single bond;
  wherein A$_4$ is aryl$_{(C\leq 12)}$ or substituted aryl$_{(C\leq 12)}$, or

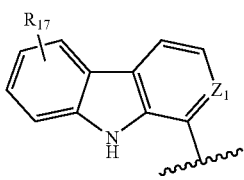

wherein:
Z$_1$ is CH or N; and
R$_{17}$ is hydrogen, hydroxy, amino, hydrazino, carboxy, halo, or nitro; or alkyl$_{(C\leq 12)}$, alkoxy$_{(C\leq 12)}$, or a substituted version of either of these groups;
R$_{11}$ is hydrogen, hydroxy, alkoxy$_{(C\leq 8)}$, or substituted alkoxy$_{(C\leq 8)}$;
R$_{12}$ is hydrogen, hydroxy, alkoxy$_{(C\leq 8)}$, substituted alkoxy$_{(C\leq 8)}$, or
—O-alkanediyl$_{(C\leq 8)}$-alkylamino$_{(C\leq 12)}$, —OC(O)-alkanediyl$_{(C\leq 8)}$-alkylamino$_{(C\leq 12)}$, or —OC(O)NH-alkanediyl$_{(C\leq 8)}$-alkylamino$_{(C\leq 12)}$, or a substituted version of any of these groups; or

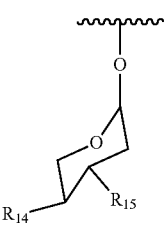

wherein:
R$_{14}$ is amino or hydroxy; or alkoxy$_{(C\leq 12)}$, alkylamino$_{(C\leq 12)}$, dialkyl-amino$_{(C\leq 12)}$, or a substituted version of any of these groups;
R$_{15}$ is hydrogen, hydroxy, alkoxy$_{(C\leq 8)}$, or substituted alkoxy$_{(C\leq 8)}$;
A$_2$ is hydrogen, heteroaryl$_{(C\leq 18)}$, substituted heteroaryl$_{(C\leq 18)}$, or

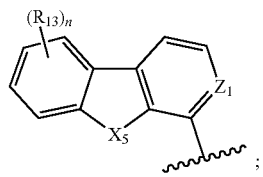

wherein:
X$_5$ is O, S, or NR$_{18}$; wherein:
  R$_{18}$ is hydrogen, alkyl$_{(C\leq 8)}$, substituted alkyl$_{(C\leq 8)}$, acyl$_{(C\leq 8)}$, or substituted acyl$_{(C\leq 8)}$;
n is 1, 2, 3, or 4;
Z$_2$ is N or CH; and
R$_{13}$ is hydrogen, amino, carboxy, hydroxy, hydrazino, halo, or nitro;
alkyl$_{(C\leq 12)}$, acyl$_{(C\leq 12)}$, alkoxy$_{(C\leq 12)}$, acyloxy$_{(C\leq 12)}$, or a substituted version of either of these groups; or
A$_1$ is

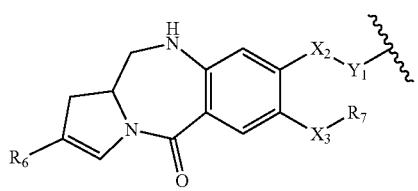

wherein:
Y$_1$ is alkanediyl$_{(C\leq 8)}$ or substituted alkanediyl$_{(C\leq 8)}$;
X$_2$ and X$_3$ are each independently selected from —O—, —S—, or —NR$_{19}$—, wherein:
R$_{19}$ is hydrogen, alkyl$_{(C\leq 6)}$, or substituted alkyl$_{(C\leq 6)}$;
R$_6$ is aryl$_{(C\leq 18)}$, heteroaryl$_{(C\leq 18)}$, or a substituted version of either of these groups;
R$_7$ is alkyl$_{(C\leq 12)}$ or substituted alkyl$_{(C\leq 12)}$;
provided that the compound is not:

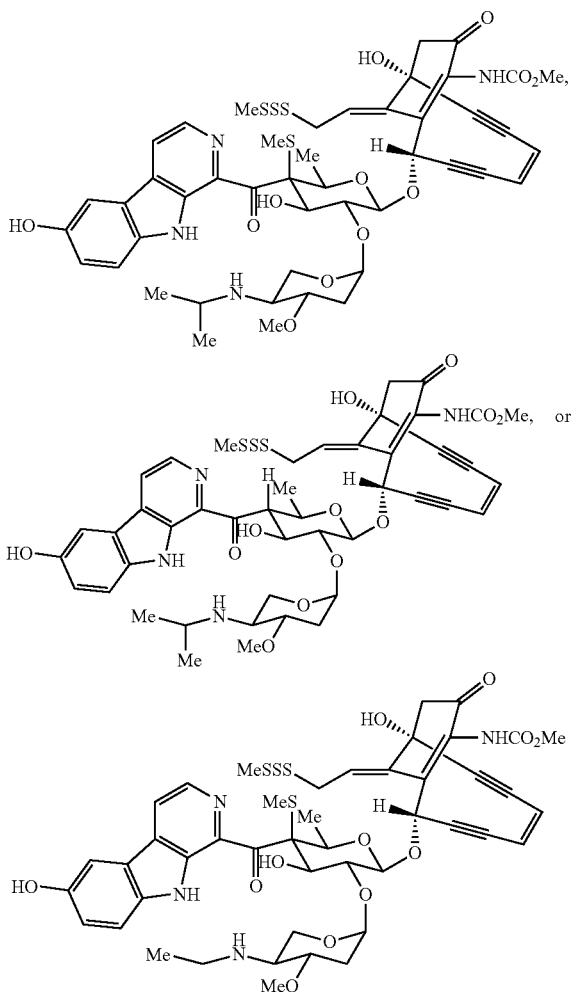

or a pharmaceutically acceptable salt thereof.

In some embodiments, the compound is further defined as:

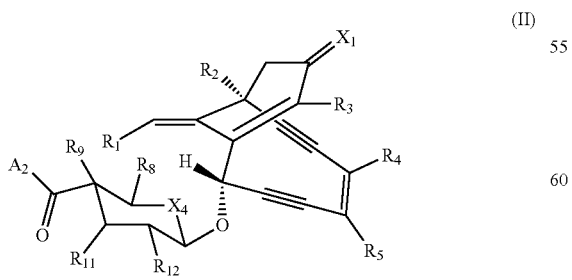

(II)

wherein: X$_1$, X$_4$, R$_1$, R$_2$, R$_3$, R$_4$, R$_5$, R$_8$, R$_9$, R$_{11}$, R$_{12}$, and A$_2$ are as defined above. In some embodiments, the compound is further defined as:

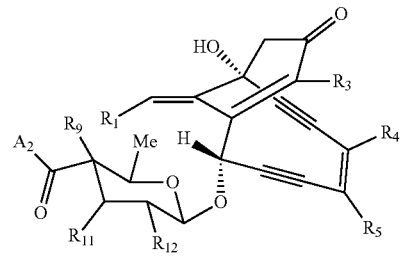

(III)

wherein: R$_1$, R$_3$, R$_4$, R$_5$, R$_9$, R$_{11}$, R$_{12}$, and A$_2$ are as defined above.

In some embodiments, the compound is further defined as:

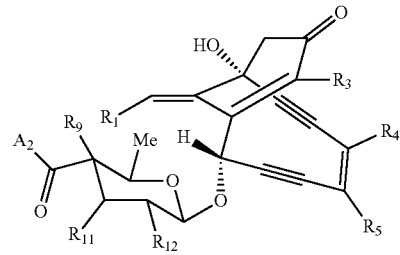

(III)

wherein:
R$_1$ is -alkanediyl$_{(C\leq 8)}$-(S)$_x$-A$_3$ or -substituted alkanediyl$_{(C\leq 8)}$-(S)$_x$-A$_3$; wherein:
A$_3$ is alkyl$_{(C\leq 12)}$, cycloalkyl$_{(C\leq 12)}$, acyl$_{(C\leq 12)}$, or a substituted version of any of these groups; and
x is 1, 2, or 3;
R$_3$ is NHC(O)R$_{16}$, wherein:
R$_{16}$ is alkoxy$_{(C\leq 8)}$, alkenyloxy$_{(C\leq 8)}$, alkylamino$_{(C\leq 8)}$, dialkylamino$_{(C\leq 8)}$, or substituted version of any of these groups;
R$_4$ and R$_5$ are each independently selected from hydrogen and halo;
R$_9$ is hydrogen, halo, hydroxy, mercapto, alkyl$_{(C\leq 8)}$, substituted alkyl$_{(C\leq 8)}$, alkoxy$_{(C\leq 8)}$, substituted alkoxy$_{(C\leq 8)}$, alkylthio$_{(C\leq 8)}$, substituted alkylthio$_{(C\leq 8)}$;
R$_{11}$ is hydrogen, hydroxy, alkoxy$_{(C\leq 8)}$, or substituted alkoxy$_{(C\leq 8)}$;
R$_{12}$ is hydrogen, hydroxy, alkoxy$_{(C\leq 8)}$, substituted alkoxy$_{(C\leq 8)}$, or

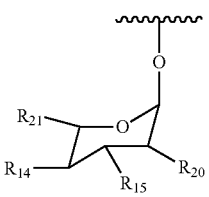

wherein:
R$_{14}$ is amino or hydroxy; or alkoxy$_{(C\leq 12)}$, alkylamino$_{(C\leq 12)}$, dialkyl-amino$_{(C\leq 12)}$, or a substituted version of any of these groups, or —NR$_a$R$_b$, wherein:

$R_a$ and $R_b$ are each hydrogen, alkyl$_{(C≤12)}$, substituted alkyl$_{(C≤12)}$, alkenyl$_{(C≤12)}$, substituted alkenyl$_{(C≤12)}$, —C(O)O-alkanediyl$_{(C≤6)}$-$R_c$, —C(O)-alkanediyl$_{(C≤6)}$-$R_c$, -alkanediyl$_{(C≤6)}$-$R_c$, or a substituted version of either of these group; wherein:

$R_c$ is hydrogen, amino, carboxy, hydroxyl, acyl$_{(C≤8)}$, alkoxy$_{(C≤8)}$, alkylamino$_{(C≤8)}$, dialkylamino$_{(C≤8)}$, alkylsulfonyl$_{(C≤8)}$, arylsulfonyl$_{(C≤8)}$, or a substituted version of either of these groups;

$R_{15}$ is hydrogen, hydroxy, alkoxy$_{(C≤8)}$, or substituted alkoxy$_{(C≤8)}$;

$R_{20}$ and $R_{21}$ are hydrogen, alkyl$_{(C≤8)}$, substituted alkyl$_{(C≤8)}$, alkoxy$_{(C≤8)}$, or substituted alkoxy$_{(C≤8)}$;

$A_2$ is

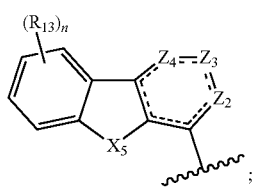

wherein:

$X_5$ is O, S, or $NR_{18}$; wherein:

$R_{18}$ is hydrogen, alkyl$_{(C≤8)}$, substituted alkyl$_{(C≤8)}$, acyl$_{(C≤8)}$, or substituted acyl$_{(C≤8)}$;

n is 1, 2, 3, 4, or 5;

$Z_2$, $Z_3$, and $Z_4$ are each independently N or $CR_{13}$; and $R_{13}$ is hydrogen, amino, carboxy, hydroxy, hydrazino, halo, nitro, or mercapto;

alkyl$_{(C≤12)}$, acyl$_{(C≤12)}$, alkoxy$_{(C≤12)}$, acyloxy$_{(C≤12)}$, or a substituted version of either of these groups; or or a pharmaceutically acceptable salt thereof.

In other embodiments, the compound is further defined as:

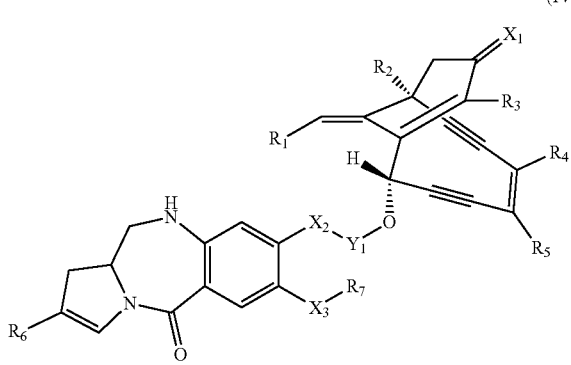

wherein: $X_1$, $X_2$, $X_3$, $R_1$, $R_2$, $R_3$, $R_4$, $R_5$, $R_6$, $R_7$, and $Y_1$ are as defined above. In some embodiments, the compound is further defined as:

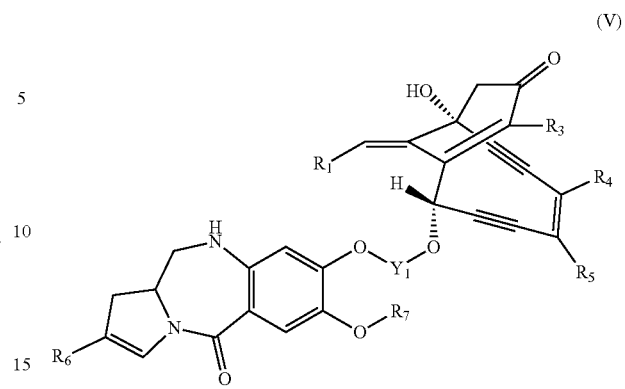

wherein: $R_1$, $R_2$, $R_3$, $R_4$, $R_5$, $R_6$, $R_7$, and $Y_1$ are as defined above.

In other embodiments, the compound is further defined as:

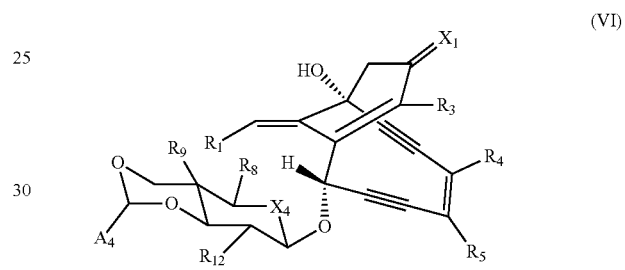

wherein: $X_1$, $X_4$, $R_1$, $R_2$, $R_3$, $R_4$, $R_5$, $R_8$, $R_9$, $R_{12}$, and $A_3$ are as defined above. In some embodiments, the compound is further defined as:

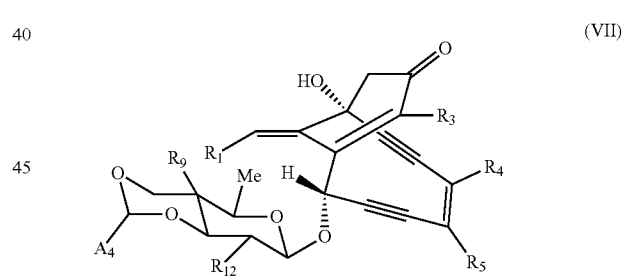

wherein: $R_1$, $R_3$, $R_4$, $R_5$, $R_9$, $R_{12}$, and $A_3$ are as defined above.

In some embodiments, $R_1$ is -alkanediyl$_{(C≤8)}$-$(S)_x$-$A_3$, wherein:

$A_3$ is hydrogen, alkyl$_{(C≤12)}$, alkenyl$_{(C≤12)}$, alkynyl$_{(C≤12)}$, aryl$_{(C≤12)}$, heteroaryl$_{(C≤12)}$, aralkyl$_{(C≤12)}$, acyl$_{(C≤12)}$, or a substituted version of any of these groups; and x is 2 or 3.

In some embodiments, the alkanediyl$_{(C≤8)}$ is —CH$_2$—. In some embodiments, $A_3$ is alkyl$_{(C≤12)}$ or substituted alkyl$_{(C≤12)}$. In some embodiments, $A_3$ is methyl. In other embodiments, $A_3$ is acyl$_{(C≤12)}$ or substituted acyl$_{(C≤12)}$. In some embodiments, $A_3$ is acetyl. In some embodiments, x is 2. In some embodiments, x is 3.

In some embodiments, $R_2$ is hydroxy. In some embodiments, $R_3$ is $NHC(O)R_{16}$, wherein: $R_{16}$ is alkoxy$_{(C≤8)}$, alkylamino$_{(C\leq 8)}$, dialkylamino$_{(C\leq 8)}$, or substituted version of any of these groups. In some embodiments, R$_{16}$ is alkoxy$_{(C\leq 8)}$ or substituted alkoxy$_{(C\leq 8)}$. In some embodiments, R$_{16}$ is alkoxy$_{(C\leq 8)}$. In some embodiments, R$_{16}$ is methoxy or ethoxy. In other embodiments, R$_3$ is NHC(NH)R$_{16}$, wherein: R$_{16}$ is alkoxy$_{(C\leq 8)}$, alkylamino$_{(C\leq 8)}$, dialkylamino$_{(C\leq 8)}$, or substituted version of any of these groups. In some embodiments, R$_{16}$ is alkylamino$_{(C\leq 8)}$ or substituted alkylamino$_{(C\leq 8)}$. In some embodiments, R$_{16}$ is alkylamino$_{(C\leq 8)}$. In some embodiments, R$_{16}$ is methylamino. In some embodiments, R$_4$ is hydrogen. In other embodiments, R$_4$ is halo. In some embodiments, R$_4$ is fluoro. In some embodiments, R$_5$ is hydrogen. In other embodiments, R$_5$ is halo. In some embodiments, R$_5$ is fluoro. In some embodiments, X$_1$ is O.

In some embodiments, A$_1$ is -alkanediyl$_{(C\leq 12)}$-C(O)-A$_2$ or -substituted alkanediyl$_{(C\leq 12)}$-C(O)-A$_2$. In some embodiments, the alkanediyl$_{(C\leq 12)}$ or substituted alkanediyl$_{(C\leq 12)}$ of A$_1$ is —CH$_2$CH$_2$CH$_2$CH$_2$—. In some embodiments, A$_2$ is:

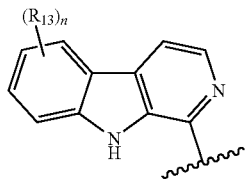

wherein:
  n is 1 or 2; and
  R$_{13}$ is hydrogen, amino, carboxy, hydroxy, hydrazino, halo, or nitro; or alkyl$_{(C\leq 12)}$, alkoxy$_{(C\leq 12)}$, or a substituted version of either of these groups.
In some embodiments, n is 1. In some embodiments, A$_2$ is further defined as:

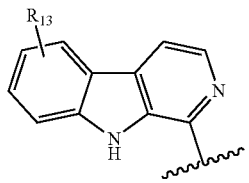

wherein:
  R$_{13}$ is hydrogen, amino, carboxy, hydroxy, hydrazino, halo, or nitro; or alkyl$_{(C\leq 12)}$, alkoxy$_{(C\leq 12)}$, or a substituted version of either of these groups.
In some embodiments, R$_{13}$ is hydroxy.
  In some embodiments, A$_1$ is:

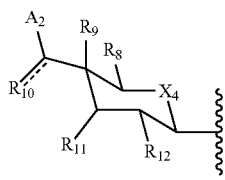

wherein:
  X$_4$ is —CH$_2$— or —O—;
  R$_8$ is hydrogen, alkyl$_{(C\leq 8)}$, cycloalkyl$_{(C\leq 8)}$, substituted alkyl$_{(C\leq 8)}$, or substituted cycloalkyl$_{(C\leq 8)}$;
  R$_9$ is hydrogen, halo, hydroxy, mercapto, alkyl$_{(C\leq 8)}$, substituted alkyl$_{(C\leq 8)}$, alkoxy$_{(C\leq 8)}$, substituted alkoxy$_{(C\leq 8)}$, alkylthio$_{(C\leq 8)}$, substituted alkylthio$_{(C\leq 8)}$;

R$_{10}$ is hydroxy, oxo, or R$_{10}$ is taken together with R$_{11}$ and is —OCHA$_4$O—; provided that when R$_{10}$ is oxo then R$_{10}$ and the carbon atom to which it is bound are joined by a double bond, and when R$_{10}$ is taken together with R$_{11}$ then R$_{10}$ and the carbon atom to which it is bound are joined by a single bond;
  wherein A$_4$ is aryl$_{(C\leq 12)}$ or substituted aryl$_{(C\leq 12)}$, or

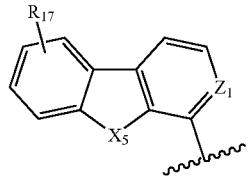

wherein:
  X$_5$ is O, S, or NR$_{18}$; wherein:
    R$_{18}$ is hydrogen, alkyl$_{(C\leq 8)}$, substituted alkyl$_{(C\leq 8)}$, acyl$_{(C\leq 8)}$, or substituted acyl$_{(C\leq 8)}$;
  Z$_1$ is CR$_{17}$ or N; and
  R$_{17}$ is hydrogen, hydroxy, amino, hydrazino, carboxy, halo, or nitro; or alkyl$_{(C\leq 12)}$, alkoxy$_{(C\leq 12)}$, or a substituted version of either of these groups;
R$_{11}$ is hydrogen, hydroxy, alkoxy$_{(C\leq 8)}$, or substituted alkoxy$_{(C\leq 8)}$;
R$_{12}$ is hydrogen, hydroxy, alkoxy$_{(C\leq 8)}$, substituted alkoxy$_{(C\leq 8)}$, or
—O-alkanediyl$_{(C\leq 8)}$-alkylamino$_{(C\leq 12)}$, —OC(O)-alkanediyl$_{(C\leq 8)}$-alkylamino$_{(C\leq 12)}$, or —OC(O)NH-alkanediyl$_{(C\leq 8)}$-alkylamino$_{(C\leq 12)}$, or a substituted version of any of these groups; or

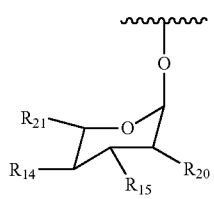

wherein:
  R$_{14}$ is amino or hydroxy; or alkoxy$_{(C\leq 12)}$, alkylamino$_{(C\leq 12)}$, dialkyl-amino$_{(C\leq 12)}$, or a substituted version of any of these groups, or —NR$_a$R$_b$, wherein:
    R$_a$ and R$_b$ are each hydrogen, alkyl$_{(C\leq 12)}$, substituted alkyl$_{(C\leq 12)}$, alkenyl$_{(C\leq 12)}$, substituted alkenyl$_{(C\leq 12)}$, —C(O)O-alkanediyl$_{(C\leq 6)}$-R$_c$, —C(O)-alkanediyl$_{(C\leq 6)}$-R$_c$, -alkanediyl$_{(C\leq 6)}$-R$_c$, or a substituted version of either of these group; wherein:
      R$_c$ is hydrogen, amino, carboxy, hydroxyl, acyl$_{(C\leq 8)}$, alkoxy$_{(C\leq 8)}$, alkylamino$_{(C\leq 8)}$, dialkylamino$_{(C\leq 8)}$, alkylsulfonyl$_{(C\leq 8)}$, arylsulfonyl$_{(C\leq 8)}$, or a substituted version of either of these groups;
  R$_{15}$ is hydrogen, hydroxy, alkoxy$_{(C\leq 8)}$, or substituted alkoxy$_{(C\leq 8)}$;
  R$_{20}$ and R$_{21}$ are hydrogen, alkyl$_{(C\leq 8)}$, substituted alkyl$_{(C\leq 8)}$, alkoxy$_{(C\leq 8)}$, or substituted alkoxy$_{(C\leq 8)}$.

In some embodiments, $A_1$ is:

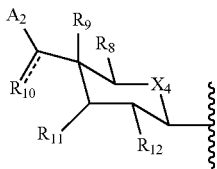

wherein:
- $X_4$ is —$CH_2$— or —O—;
- $R_8$ is hydrogen, $alkyl_{(C\leq 8)}$, or substituted $alkyl_{(C\leq 8)}$;
- $R_9$ is hydrogen, $alkoxy_{(C\leq 8)}$, substituted $alkoxy_{(C\leq 8)}$, $alkylthio_{(C\leq 8)}$, substituted $alkylthio_{(C\leq 8)}$;
- $R_{10}$ is oxo or $R_{10}$ is taken together with $R_{11}$ and is —$OCHA_4O$—; provided that when $R_{10}$ is oxo then $R_{10}$ and the carbon atom to which it is bound are joined by a double bond, and when $R_{10}$ is taken together with $R_{11}$ then $R_{10}$ and the carbon atom to which it is bound are joined by a single bond;
  wherein $A_4$ is $aryl_{(C\leq 12)}$ or substituted $aryl_{(C\leq 12)}$, or

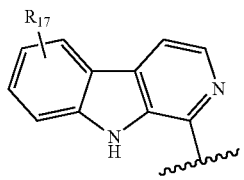

wherein:
- $R_{17}$ is hydrogen, hydroxy, amino, hydrazino, carboxy, halo, $alkyl_{(C\leq 12)}$, $alkoxy_{(C\leq 12)}$, or a substituted version of either of these groups;
- $R_{11}$ is hydrogen, hydroxy, $alkoxy_{(C\leq 8)}$, or substituted $alkoxy_{(C\leq 8)}$;
- $R_{12}$ is hydrogen, hydroxy, $alkoxy_{(C\leq 8)}$, substituted $alkoxy_{(C\leq 8)}$, or
  —O-$alkanediyl_{(C\leq 8)}$-$alkylamino_{(C\leq 12)}$, —OC(O)-$alkanediyl_{(C\leq 8)}$-$alkylamino_{(C\leq 12)}$, or —OC(O)NH-$alkanediyl_{(C\leq 8)}$-$alkylamino_{(C\leq 12)}$, or a substituted version of any of these groups; or

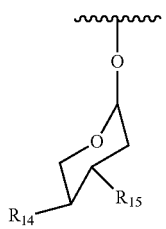

wherein:
- $R_{14}$ is $alkoxy_{(C\leq 12)}$, $alkylamino_{(C\leq 12)}$, or $dialkylamino_{(C\leq 12)}$;
- $R_{15}$ is hydrogen, hydroxy, $alkoxy_{(C\leq 8)}$, substituted $alkoxy_{(C\leq 8)}$;

$A_2$ is

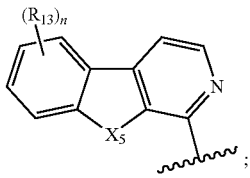

wherein:
- $X_5$ is O, S, or $NR_{18}$; wherein:
  - $R_{18}$ is hydrogen, $alkyl_{(C\leq 8)}$, substituted $alkyl_{(C\leq 8)}$, $acyl_{(C\leq 8)}$, or substituted $acyl_{(C\leq 8)}$;
- n is 1, 2, 3, or 4;
- $R_{13}$ is hydrogen, amino, carboxy, hydroxy, hydrazino, halo, or nitro;
  $alkyl_{(C\leq 12)}$, $alkoxy_{(C\leq 12)}$, or a substituted version of either of these groups.

In some embodiments, $X_4$ is —O—. In other embodiments, $X_4$ is —$CH_2$—. In some embodiments, $R_8$ is hydrogen. In other embodiments, $R_8$ is $alkyl_{(C\leq 8)}$ or substituted $alkyl_{(C\leq 8)}$. In some embodiments, $R_8$ is methyl. In other embodiments, $R_9$ is $alkoxy_{(C\leq 8)}$ or substituted $alkoxy_{(C\leq 8)}$. In some embodiments, $R_9$ is methoxy. In other embodiments, $R_9$ is $alkylthio_{(C\leq 8)}$ or substituted $alkylthio_{(C\leq 8)}$. In some embodiments, $R_9$ is —$SCH_3$. In some embodiments, $R_{10}$ is oxo.

In some embodiments, $R_{10}$ is taken together with $R_{11}$ and is —$OCHA_4O$—, wherein:
$A_4$ is $aryl_{(C\leq 12)}$ or substituted $aryl_{(C\leq 12)}$, or

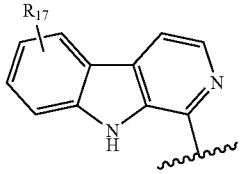

wherein:
- $R_{17}$ is hydrogen, hydroxy, amino, hydrazino, carboxy, halo, or nitro; or $alkyl_{(C\leq 12)}$, $alkoxy_{(C\leq 12)}$, or a substituted version of either of these groups.

In some embodiments, $A_4$ is $aryl_{(C\leq 12)}$ or substituted $aryl_{(C\leq 12)}$. In some embodiments, $A_4$ is $aryl_{(C\leq 12)}$. In some embodiments, $A_4$ is phenyl. In other embodiments, $A_4$ is substituted $aryl_{(C\leq 12)}$. In some embodiments, $A_4$ is 4-hydroxyphenyl. In other embodiments, $A_4$ is:

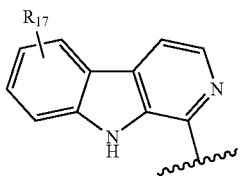

wherein:
- $R_{17}$ is hydrogen, hydroxy, amino, hydrazino, carboxy, halo, or nitro; or $alkyl_{(C\leq 12)}$, $alkoxy_{(C\leq 12)}$, or a substituted version of either of these groups.

In some embodiments, $R_{17}$ is hydroxy. In some embodiments, $R_{11}$ is hydrogen. In other embodiments, $R_{11}$ is hydroxy. In some embodiments, $R_{12}$ is hydrogen. In other embodiments, $R_{12}$ is alkoxy$_{(C \leq 8)}$ or substituted alkoxy$_{(C \leq 8)}$. In some embodiments, $R_{12}$ is methoxy.

In other embodiments, $R_{12}$ is —O-alkanediyl$_{(C \leq 8)}$-alkylamino$_{(C \leq 12)}$ or a substituted version thereof. In some embodiments, the alkanediyl$_{(C \leq 8)}$ or substituted alkanediyl$_{(C \leq 8)}$ of $R_{12}$ is —CH$_2$CH$_2$CH$_2$CH$_2$—. In some embodiments, the alkylamino$_{(C \leq 12)}$ or substituted alkylamino$_{(C \leq 12)}$ of $R_{12}$ is —NHCH(CH$_3$)$_2$. In some embodiments, $R_{12}$ is —OCH$_2$CH$_2$CH$_2$CH$_2$NHCH(CH$_3$)$_2$. In other embodiments, $R_{12}$ is —OC(O)-alkanediyl$_{(C \leq 8)}$-alkylamino$_{(C \leq 12)}$ or a substituted version thereof. In some embodiments, the alkanediyl$_{(C \leq 8)}$ or substituted alkanediyl$_{(C \leq 8)}$ of $R_{12}$ is —CH$_2$CH$_2$CH$_2$—. In some embodiments, the alkylamino$_{(C \leq 12)}$ or substituted alkylamino$_{(C \leq 12)}$ of $R_{12}$ is —NHCH(CH$_3$)$_2$. In some embodiments, $R_{12}$ is —OC(O)CH$_2$CH$_2$CH$_2$NHCH(CH$_3$)$_2$. In other embodiments, $R_{12}$ is —OC(O)NH-alkanediyl$_{(C \leq 8)}$-alkylamino$_{(C \leq 12)}$ or a substituted version thereof. In some embodiments, the alkanediyl$_{(C \leq 8)}$ or substituted alkanediyl$_{(C \leq 8)}$ of $R_{12}$ is —CH$_2$CH$_2$—. In some embodiments, the alkylamino$_{(C \leq 12)}$ or substituted alkylamino$_{(C \leq 12)}$ of $R_{12}$ is —NHCH(CH$_3$)$_2$. In some embodiments, $R_{12}$ is —OC(O)NHCH$_2$CH$_2$NHCH(CH$_3$)$_2$.

In other embodiments, $R_{12}$ is further defined as:

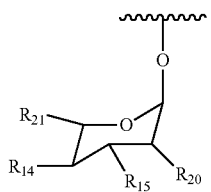

wherein:
- $R_{14}$ is amino or hydroxy; or alkoxy$_{(C \leq 12)}$, alkylamino$_{(C \leq 12)}$, dialkyl-amino$_{(C \leq 12)}$, or a substituted version of any of these groups, or $NR_aR_b$, wherein:
  - $R_a$ and $R_b$ are each hydrogen, alkyl$_{(C \leq 12)}$, substituted alkyl$_{(C \leq 12)}$, alkenyl$_{(C \leq 12)}$, substituted alkenyl$_{(C \leq 12)}$, —C(O)O-alkanediyl$_{(C \leq 6)}$-$R_c$, —C(O)-alkanediyl$_{(C \leq 6)}$-$R_c$, -alkanediyl$_{(C \leq 6)}$-$R_c$, or a substituted version of either of these group; wherein:
    - $R_c$ is hydrogen, amino, carboxy, hydroxyl, acyl$_{(C \leq 8)}$, alkoxy$_{(C \leq 8)}$, alkylamino$_{(C \leq 8)}$, dialkylamino$_{(C \leq 8)}$, alkylsulfonyl$_{(C \leq 8)}$, arylsulfonyl$_{(C \leq 8)}$, or a substituted version of either of these groups;
- $R_{15}$ is hydrogen, hydroxy, alkoxy$_{(C \leq 8)}$, or substituted alkoxy$_{(C \leq 8)}$; and
- $R_{20}$ and $R_{21}$ are hydrogen, alkyl$_{(C \leq 8)}$, substituted alkyl$_{(C \leq 8)}$, alkoxy$_{(C \leq 8)}$, or substituted alkoxy$_{(C \leq 8)}$. In some embodiments, $R_{12}$ is:

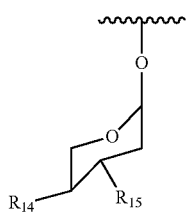

wherein:
- $R_{14}$ is amino or hydroxy; or alkoxy$_{(C \leq 12)}$, alkylamino$_{(C \leq 12)}$, dialkylamino$_{(C \leq 12)}$, or a substituted version of any of these groups; and
- $R_{15}$ is hydrogen, hydroxy, alkoxy$_{(C \leq 8)}$, or substituted alkoxy$_{(C \leq 8)}$.

In some embodiments, $R_{14}$ is alkylamino$_{(C \leq 12)}$ or substituted alkylamino$_{(C \leq 12)}$. In some embodiments, $R_{14}$ is isopropylamino. In other embodiments, $R_{14}$ is alkoxy$_{(C \leq 12)}$ or substituted alkoxy$_{(C \leq 12)}$. In some embodiments, $R_{14}$ is isopropoxy. In some embodiments, $R_{15}$ is hydrogen. In other embodiments, $R_{15}$ is alkoxy$_{(C \leq 8)}$ or substituted alkoxy$_{(C \leq 8)}$. In some embodiments, $R_{15}$ is methoxy.

In some embodiments, $A_2$ is hydrogen. In other embodiments, $A_2$ is:

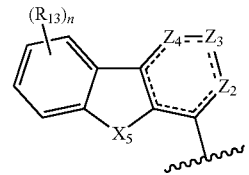

wherein:
- $X_5$ is O, S, or $NR_{18}$; wherein:
  - $R_{18}$ is hydrogen, alkyl$_{(C \leq 8)}$, substituted alkyl$_{(C \leq 8)}$, acyl$_{(C \leq 8)}$, or substituted acyl$_{(C \leq 8)}$;
- n is 1, 2, 3, 4, or 5;
- $Z_2$, $Z_3$, and $Z_4$ are each independently N or $CR_{13}$; and
- $R_{13}$ is hydrogen, amino, carboxy, hydroxy, hydrazino, halo, nitro, or mercapto; alkyl$_{(C \leq 12)}$, acyl$_{(C \leq 12)}$, alkoxy$_{(C \leq 12)}$, acyloxy$_{(C \leq 12)}$, or a substituted version of either of these groups.

In some embodiments, $A_2$ is further defined as:

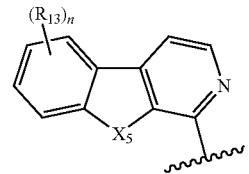

wherein:
- $X_5$ is O, S, or $NR_{18}$; wherein:
  - $R_{18}$ is hydrogen, alkyl$_{(C \leq 8)}$, substituted alkyl$_{(C \leq 8)}$, acyl$_{(C \leq 8)}$, or substituted acyl$_{(C \leq 8)}$;
- n is 1, 2, 3, or 4;
- $R_{13}$ is hydrogen, amino, carboxy, hydroxy, hydrazino, halo, or nitro; or alkyl$_{(C \leq 12)}$, acyl$_{(C \leq 12)}$, alkoxy$_{(C \leq 12)}$, acyloxy$_{(C \leq 12)}$, or a substituted version of either of these groups.

In some embodiments, n is 1 or 2. In some embodiments, n is 1. In some embodiments, $A_2$ is further defined as:

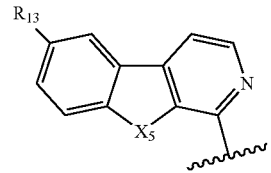

wherein:
- $X_5$ is O, S, or $NR_{18}$; wherein:
  - $R_{18}$ is hydrogen, alkyl$_{(C \leq 8)}$, substituted alkyl$_{(C \leq 8)}$, acyl$_{(C \leq 8)}$, or substituted acyl$_{(C \leq 8)}$; and R$_{13}$ is hydrogen, amino, carboxy, hydroxy, hydrazino, halo, or nitro; or alkyl$_{(C≤12)}$, acyl$_{(C≤12)}$, alkoxy$_{(C≤12)}$, acyloxy$_{(C≤12)}$, or a substituted version of any of these groups.

In some embodiments, X$_5$ is —O—. In other embodiments, X$_5$ is NR$_{18}$. In some embodiments, R$_{18}$ is hydrogen. In some embodiments, R$_{13}$ is hydrogen. In other embodiments, R$_{13}$ is amino. In other embodiments, R$_{13}$ is carboxy. In other embodiments, R$_{13}$ is hydrazino. In other embodiments, R$_{13}$ is hydroxy. In other embodiments, R$_{13}$ is halo. In some embodiments, R$_{13}$ is fluoro. In other embodiments, R$_{13}$ is iodo. In other embodiments, R$_{13}$ is alkyl$_{(C≤12)}$ or substituted alkyl$_{(C≤12)}$. In some embodiments, R$_{13}$ is haloalkyl$_{(C≤12)}$. In some embodiments, R$_{13}$ is trifluoromethyl. In other embodiments, R$_{13}$ is alkoxy$_{(C≤12)}$ or substituted alkoxy$_{(C≤12)}$. In other embodiments, R$_{13}$ is alkoxy$_{(C≤12)}$. In some embodiments, R$_{13}$ is methoxy. In other embodiments, R$_{13}$ is substituted alkoxy$_{(C≤12)}$. In some embodiments, R$_{13}$ is 2-aminoethoxy, 2-methylaminoethoxy, 2-azidoethoxy, carboxymethoxy, or carboxyethoxy. In other embodiments, R$_{13}$ is acyloxy$_{(C≤12)}$ or substituted acyloxy$_{(C≤12)}$. In some embodiments, R$_{13}$ is acyloxy$_{(C≤12)}$. In some embodiments, R$_{13}$ is acetoxy.

In other embodiments, A$_1$ is:

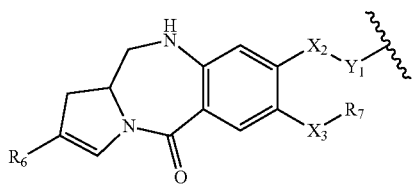

wherein:

Y$_1$ is alkanediyl$_{(C≤8)}$ or substituted alkanediyl$_{(C≤8)}$;

X$_2$ and X$_3$ are each independently selected from —O—, —S—, or —NR$_{19}$—, wherein:

R$_{19}$ is hydrogen, alkyl$_{(C≤6)}$, or substituted alkyl$_{(C≤6)}$;

R$_6$ is aryl$_{(C≤18)}$, heteroaryl$_{(C≤18)}$, or a substituted version of either of these groups;

R$_7$ is alkyl$_{(C≤12)}$ or substituted alkyl$_{(C≤12)}$.

In some embodiments, Y$_1$ is alkanediyl$_{(C≤8)}$. In some embodiments, Y$_1$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, or —CH$_2$CH$_2$CH$_2$CH$_2$CH$_2$CH$_2$CH$_2$—. In some embodiments, X$_2$ is —O—. In some embodiments, X$_3$ is —O—.

In some embodiments, R$_6$ is aryl$_{(C≤18)}$ or substituted aryl$_{(C≤18)}$. In some embodiments, R$_6$ is 4-methoxyphenyl or 5-iodo-2,3,4-trimethoxy-6-methylphenyl. In other embodiments, R$_6$ is heteroaryl$_{(C≤18)}$ or substituted heteroaryl$_{(C≤18)}$. In some embodiments, R$_6$ is:

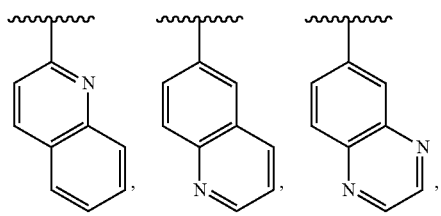

In some embodiments, R$_7$ is alkyl$_{(C≤12)}$. In some embodiments, R$_7$ is substituted alkyl$_{(C≤12)}$. In some embodiments, R$_7$ is 2-hydroxyethyl, 3-hydroxypropyl, 4-hydroxybutyl, 5-hydroxypentyl, or 6-hydroxyhexyl.

In some embodiments, the compound is further defined as:

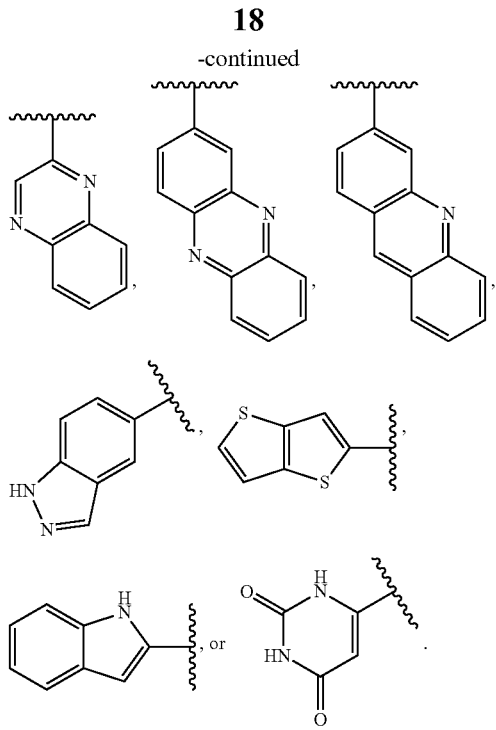

-continued
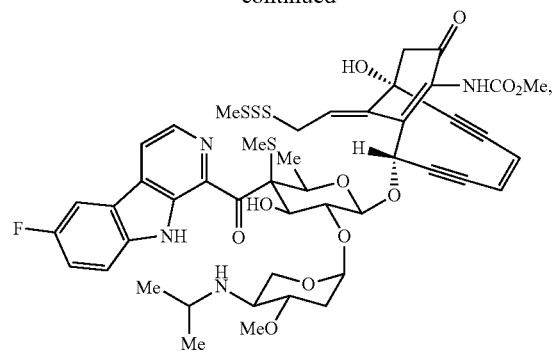
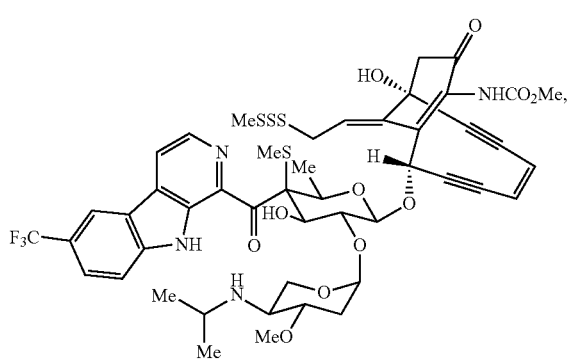
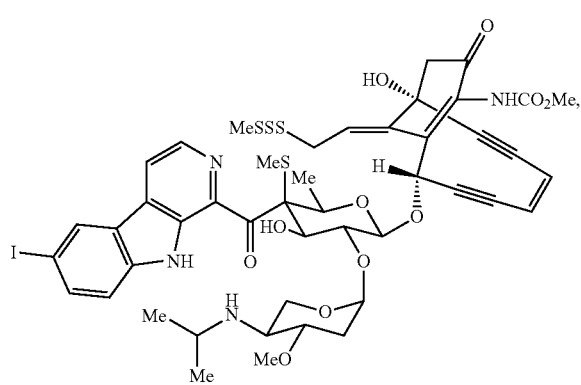
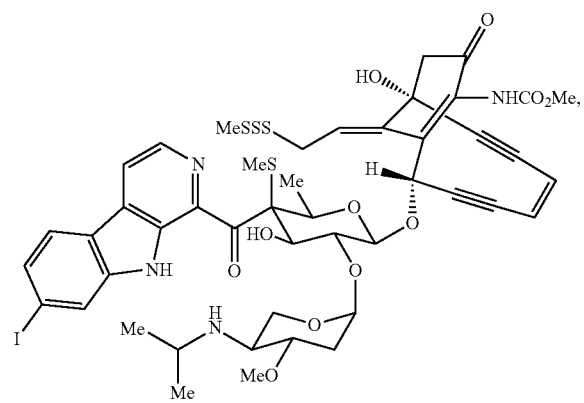
-continued
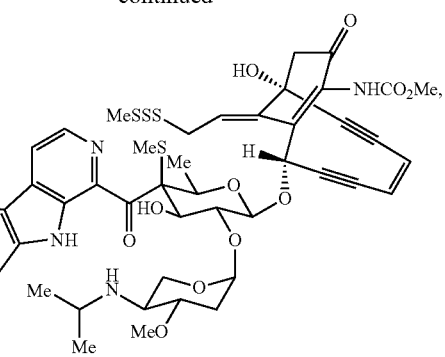
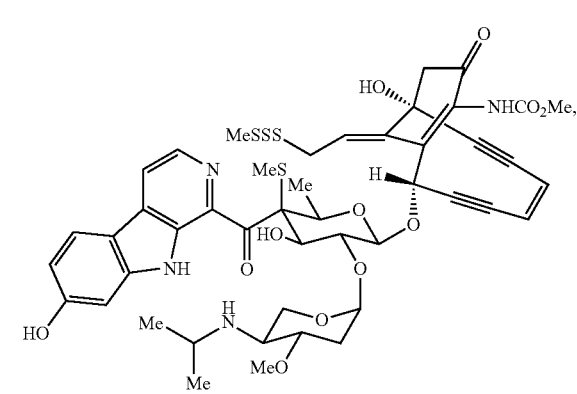
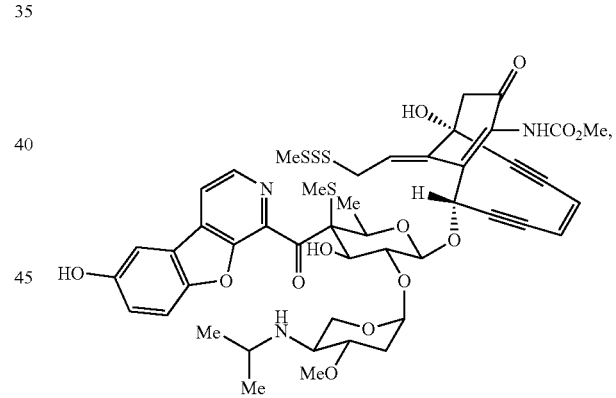
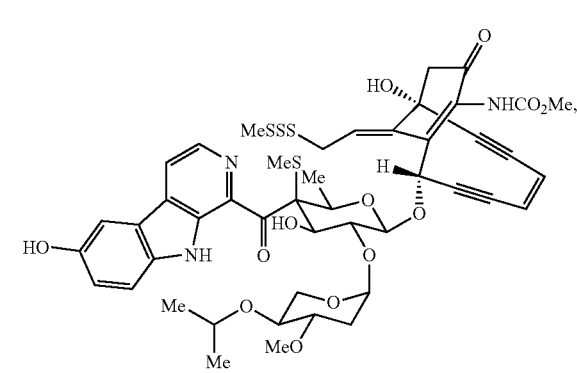

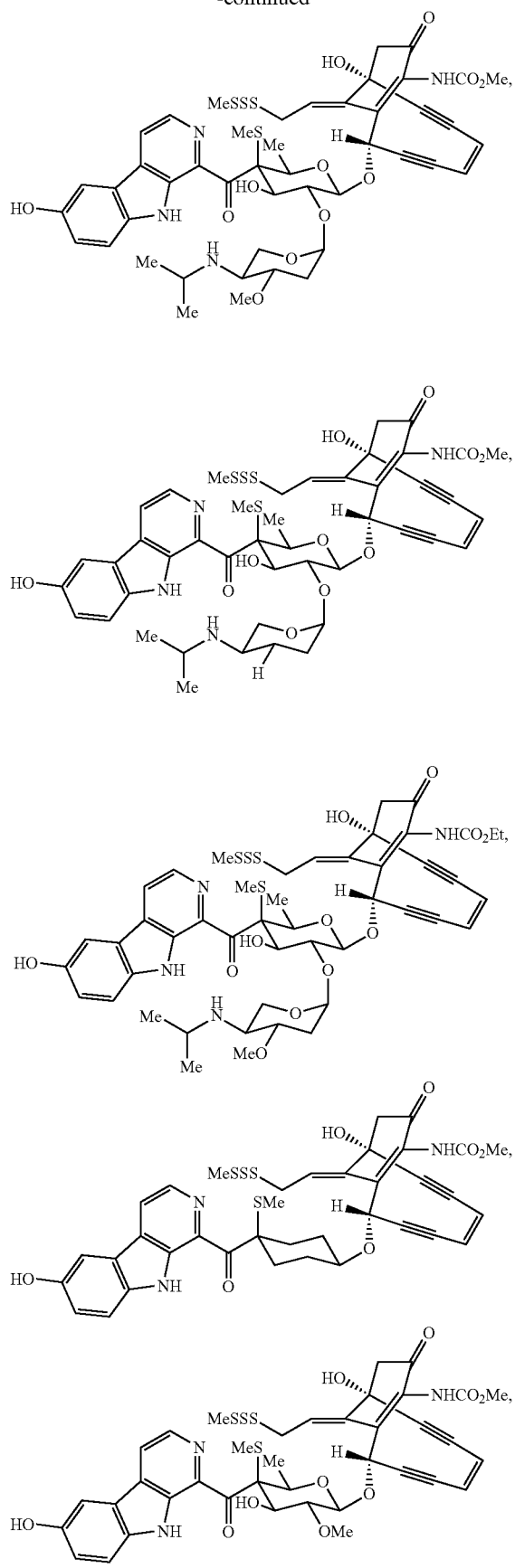
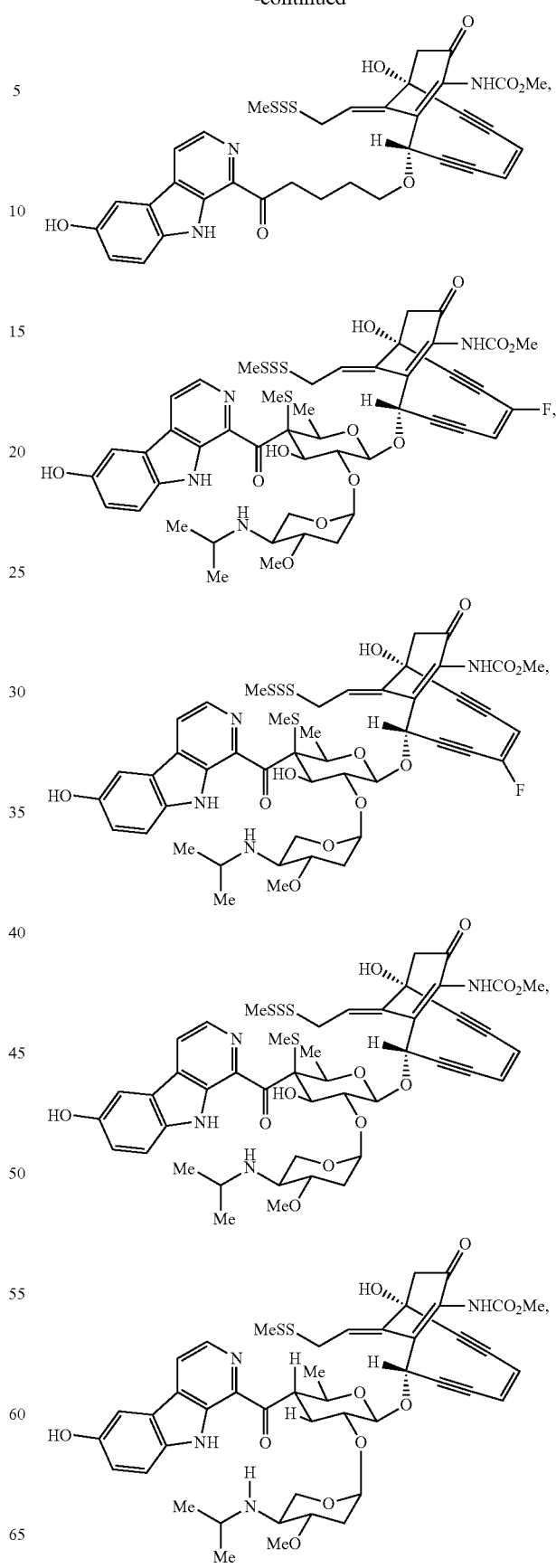

23
-continued
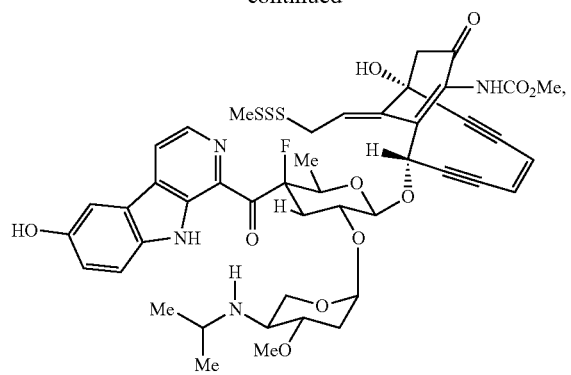
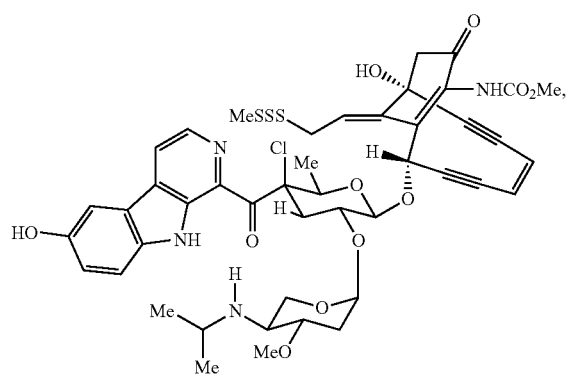
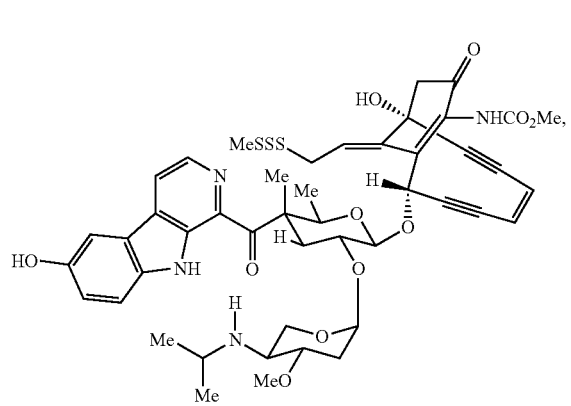
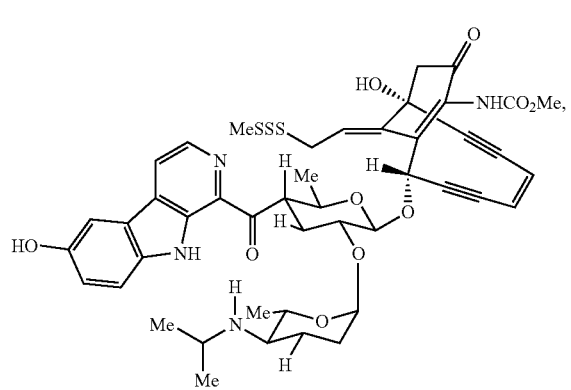
24
-continued
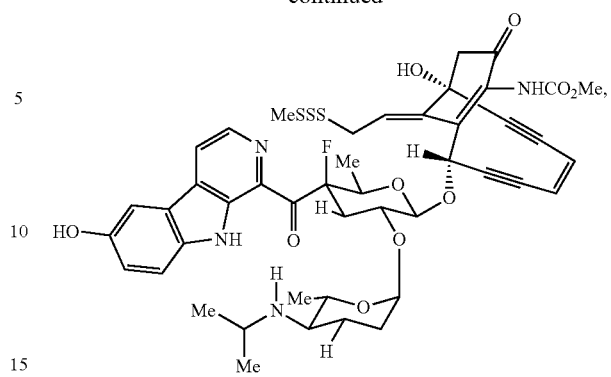
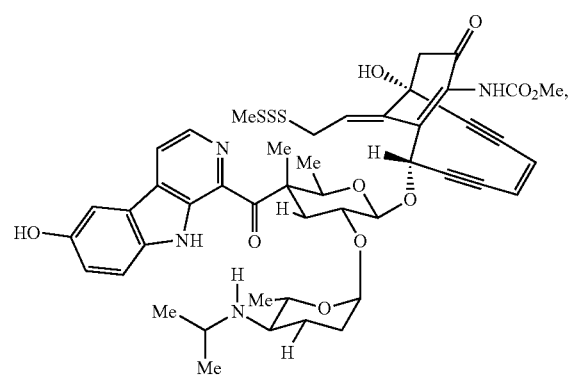
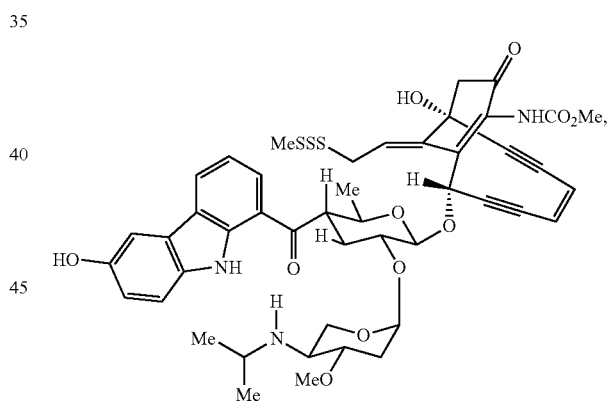
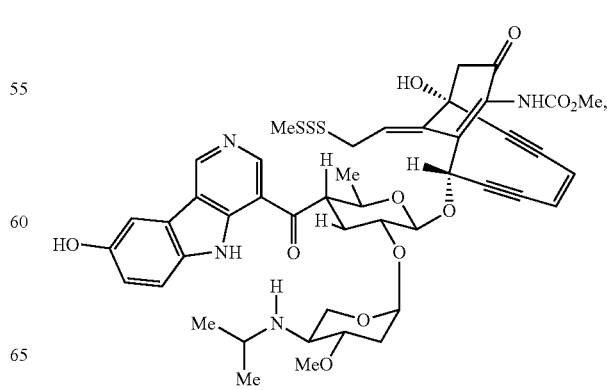

25
-continued
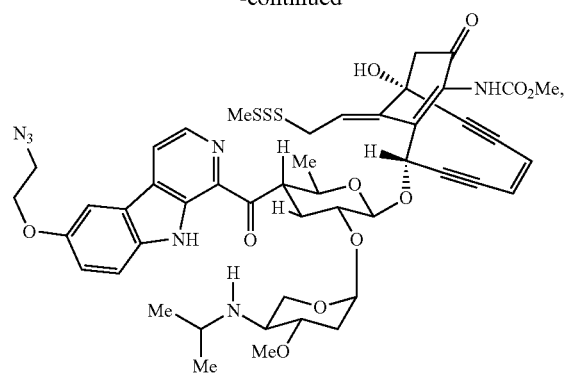
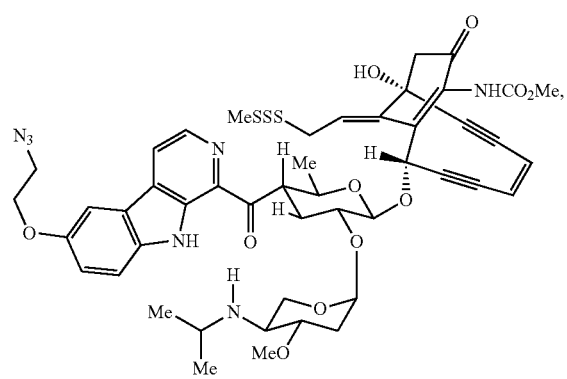
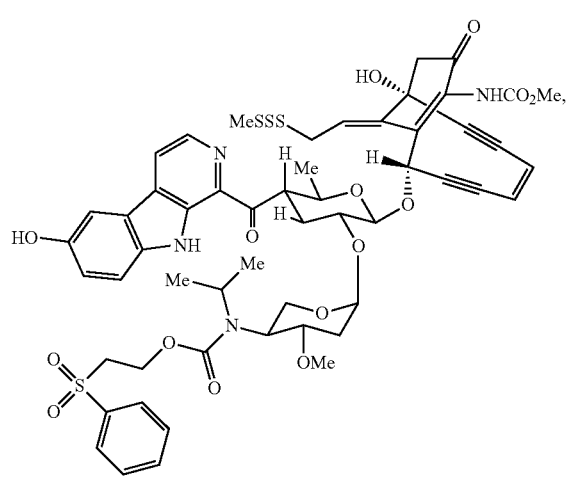
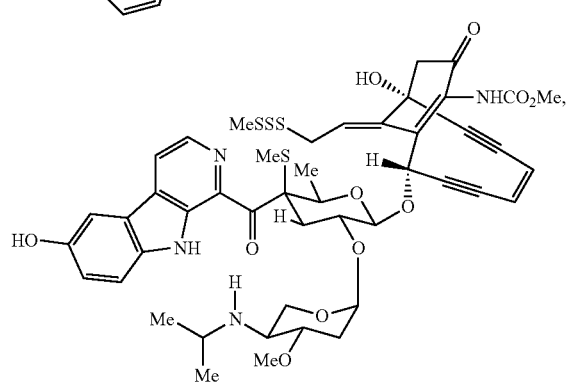
26
-continued
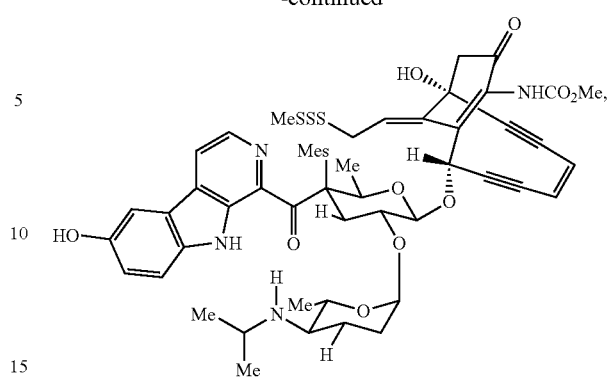
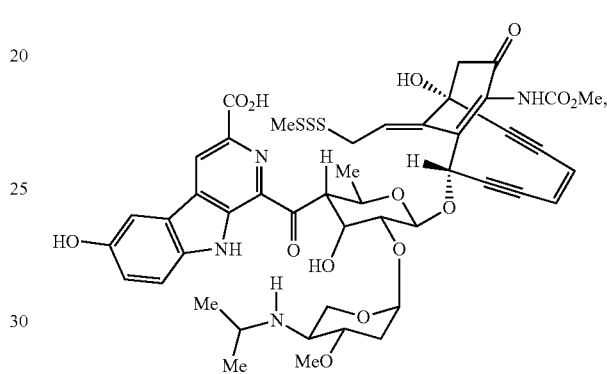
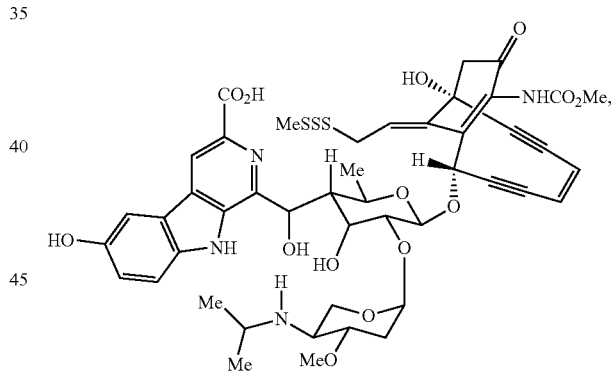
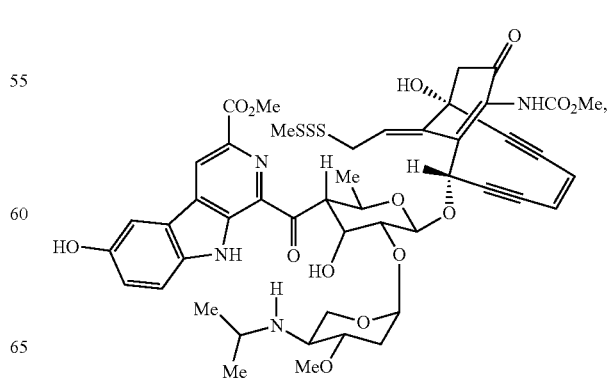

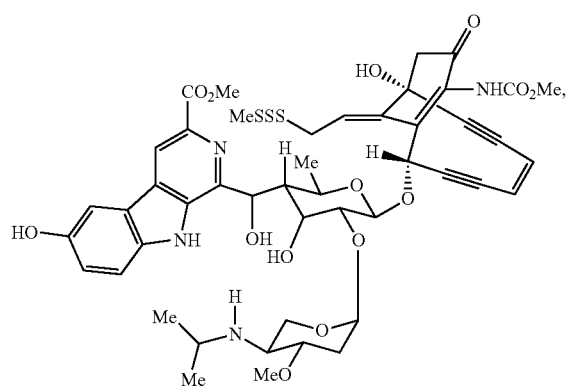
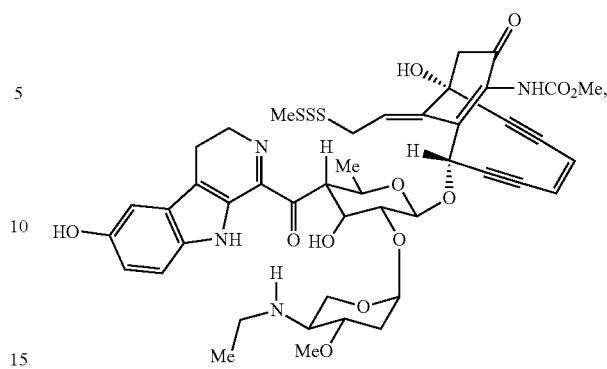
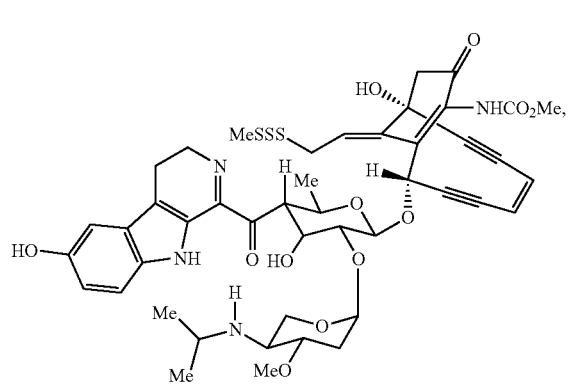
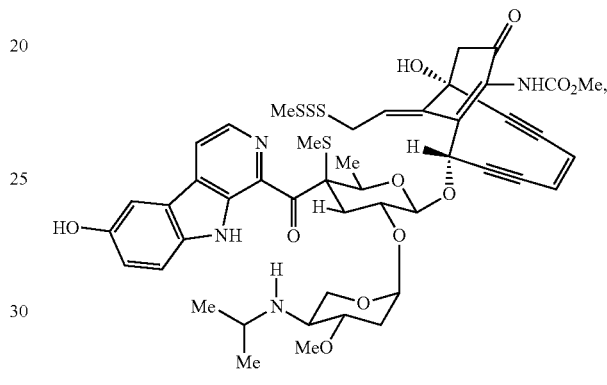
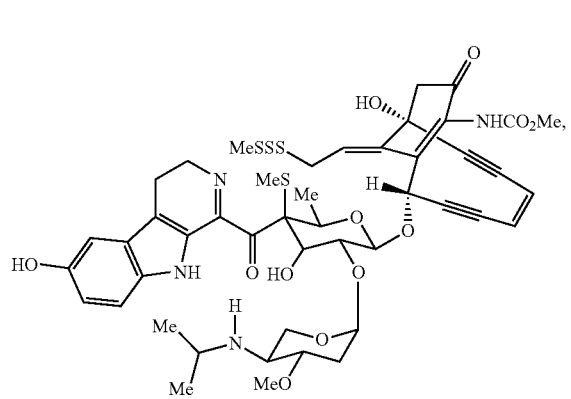
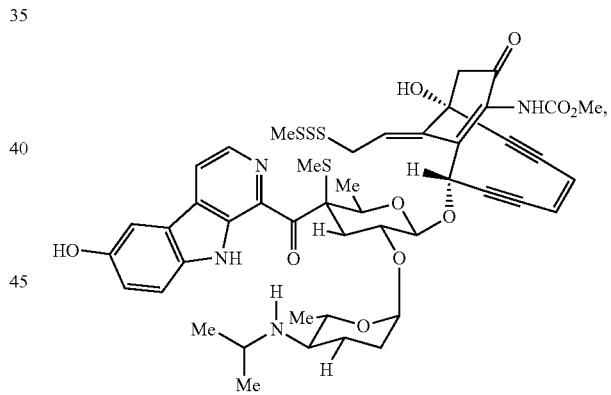
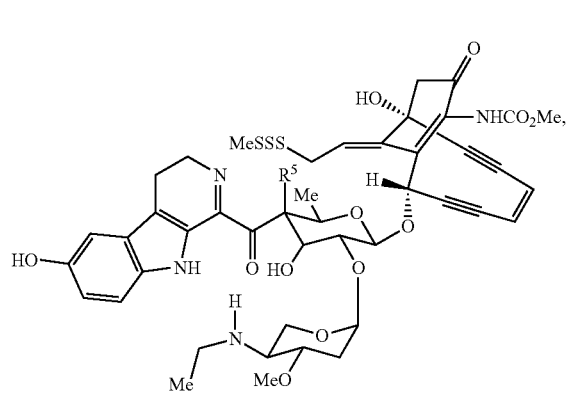
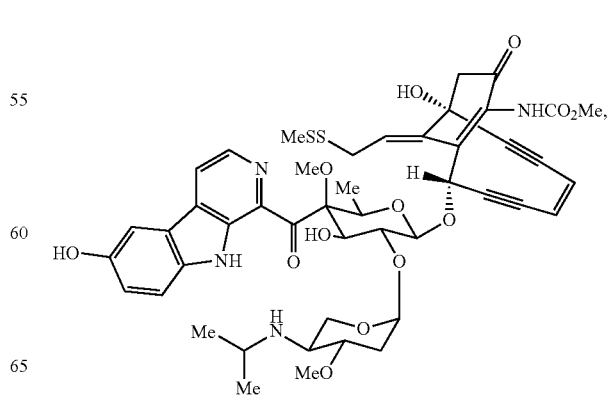

29
-continued
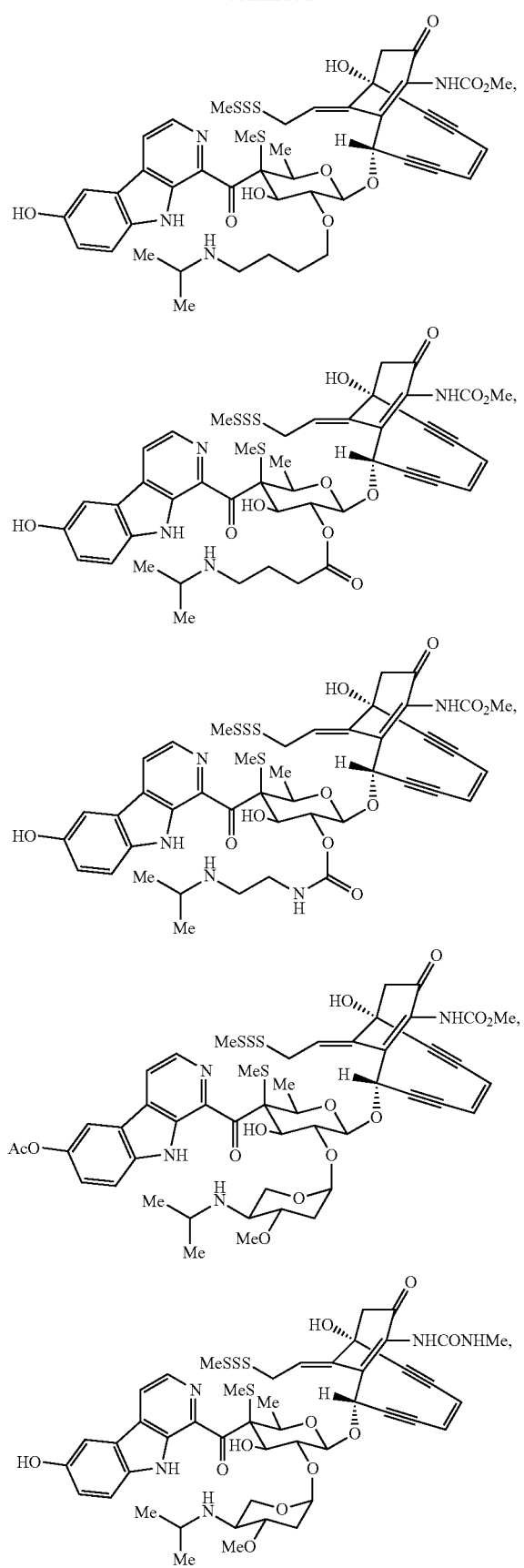
30
-continued
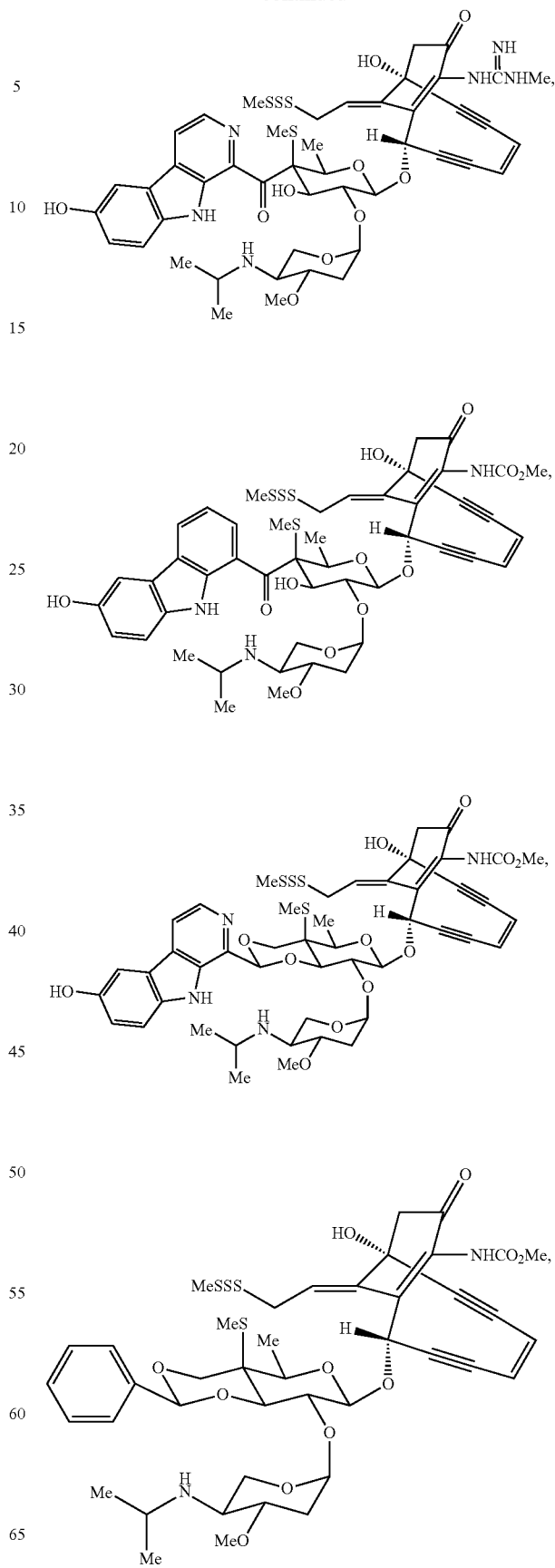

31
-continued
32
-continued
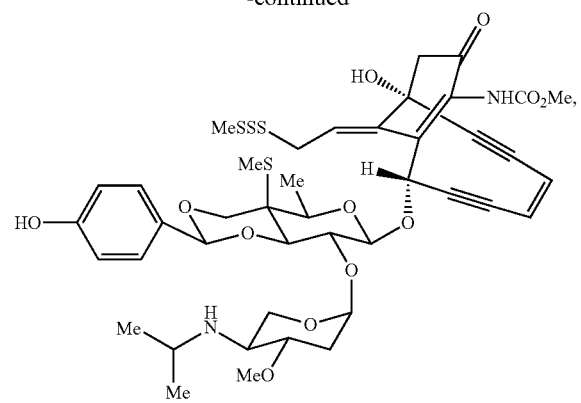
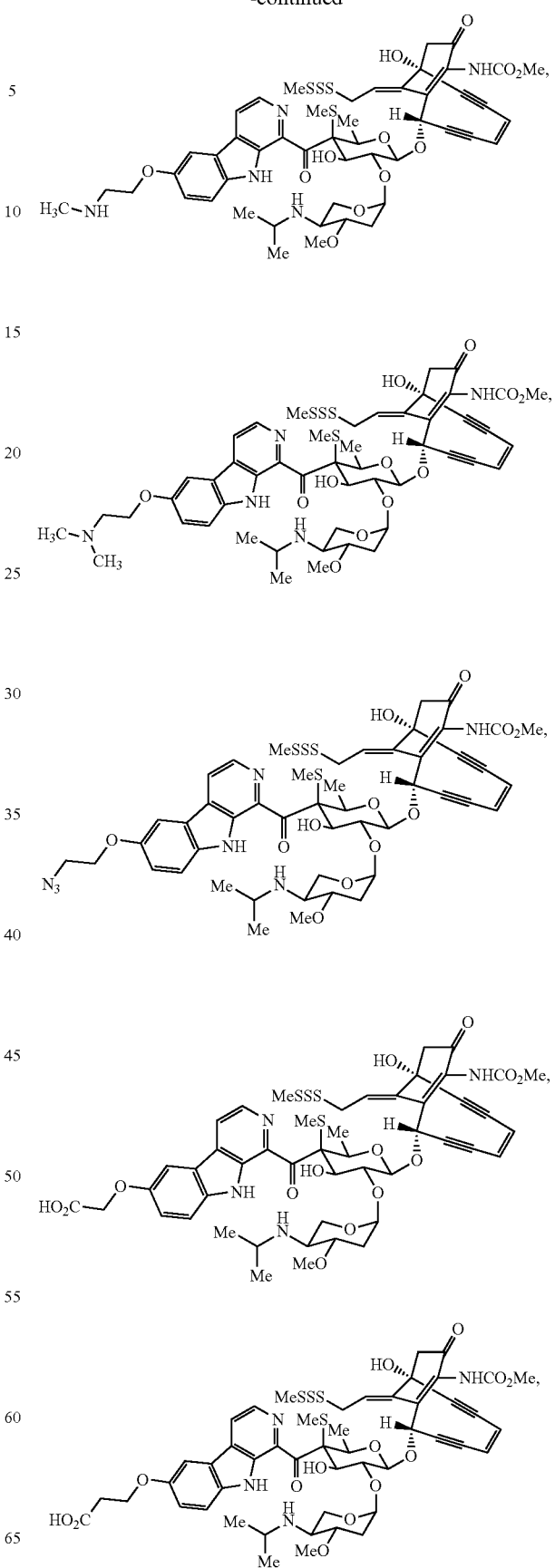

33
-continued
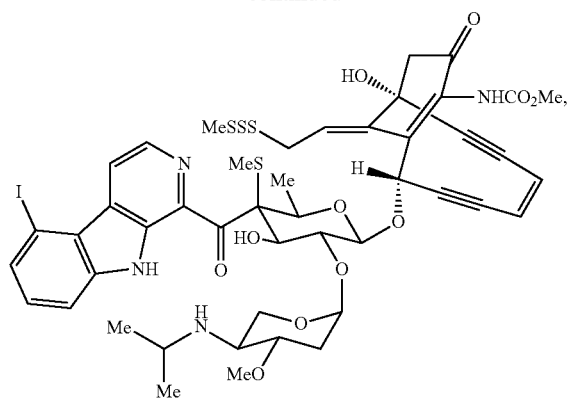
34
-continued
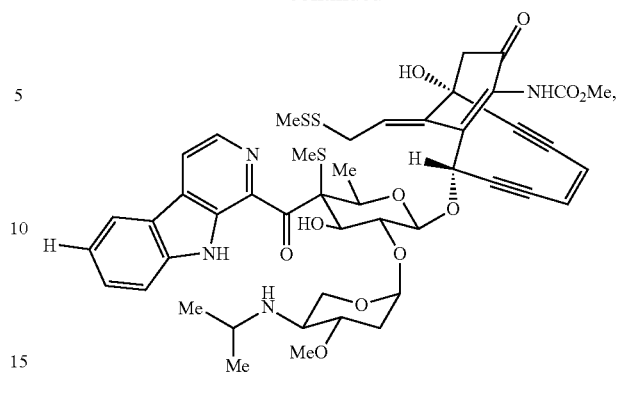
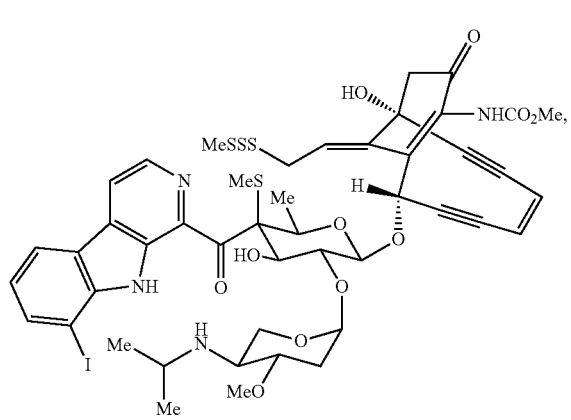
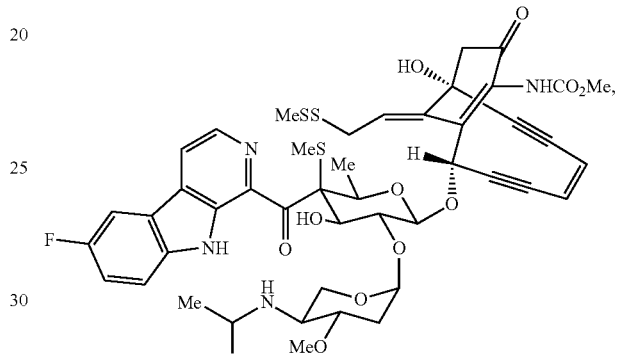
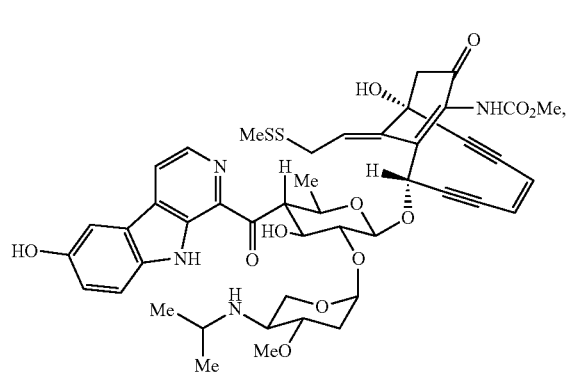
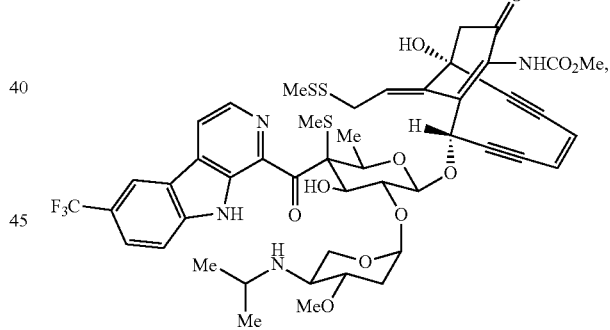
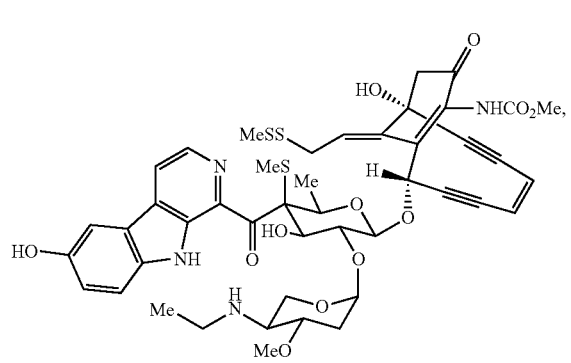
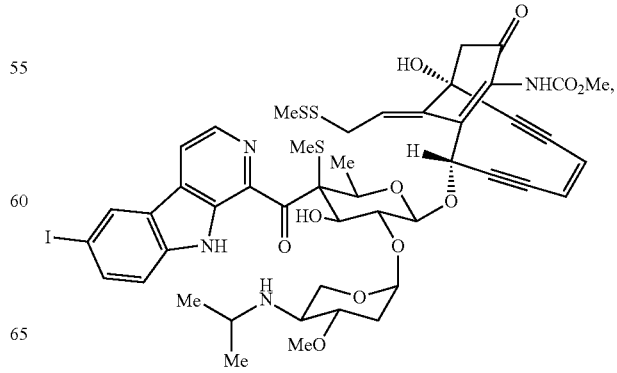

35
-continued
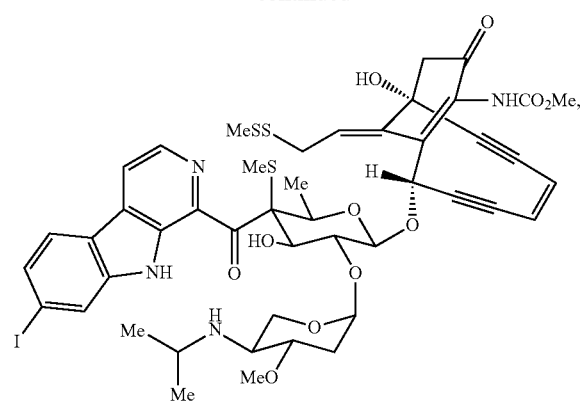
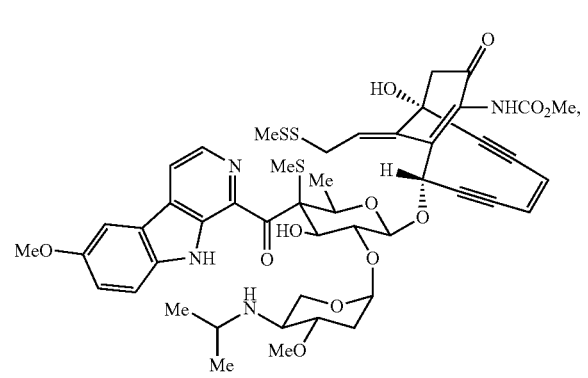
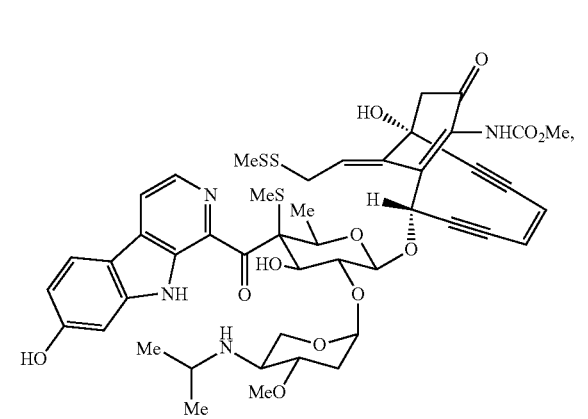
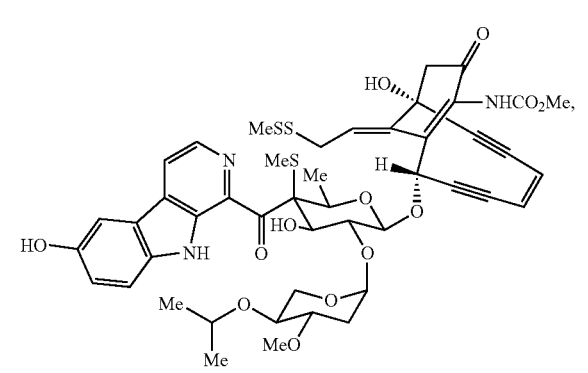
36
-continued
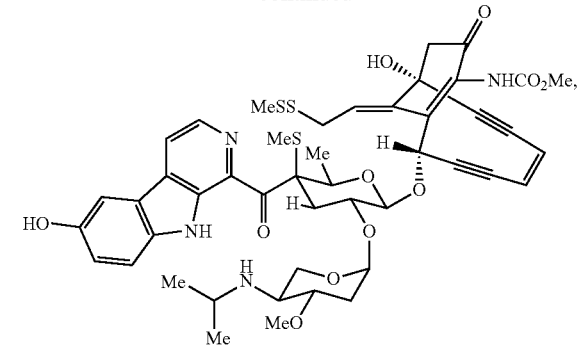
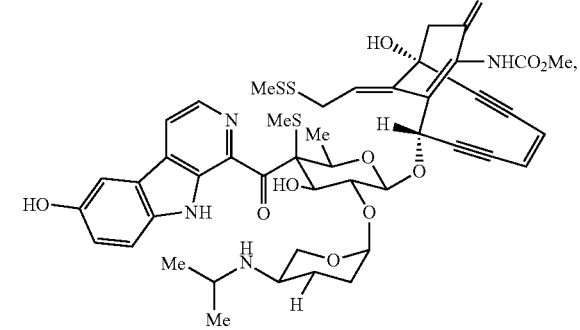
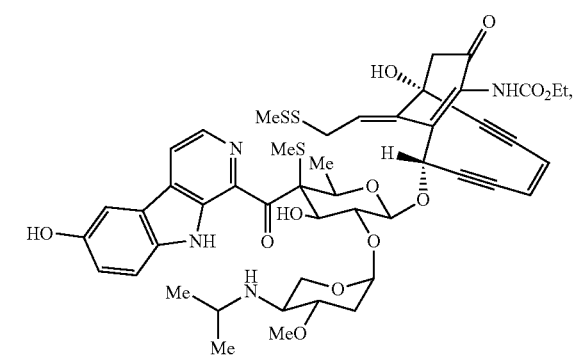
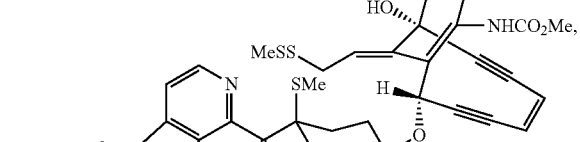
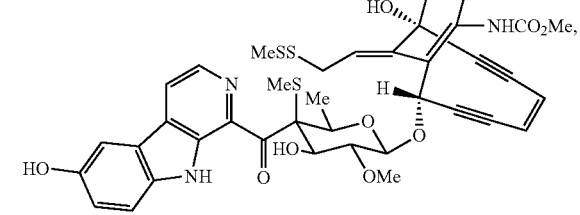

37
-continued
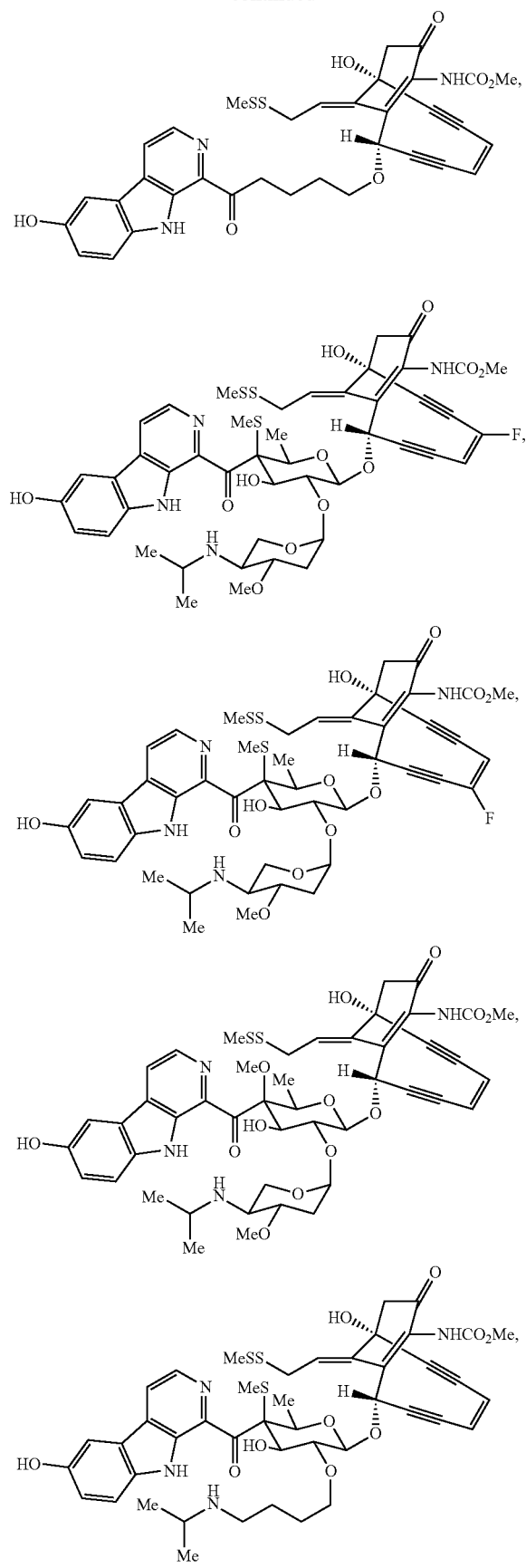
38
-continued
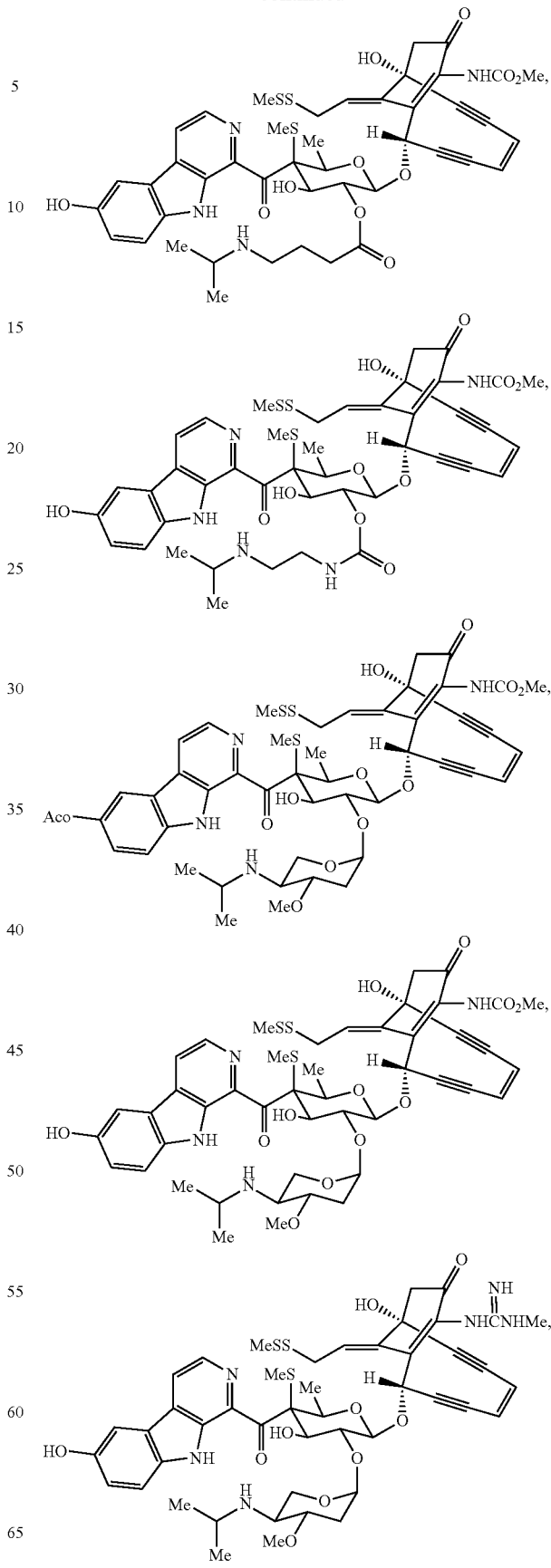

39
-continued
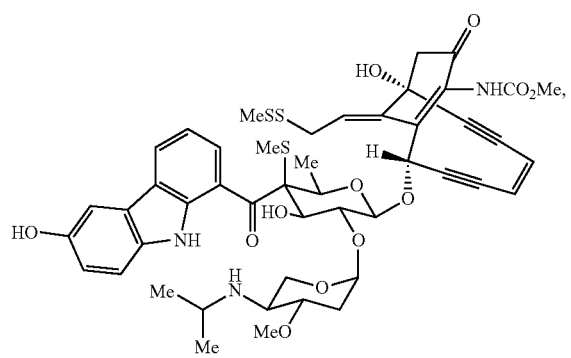
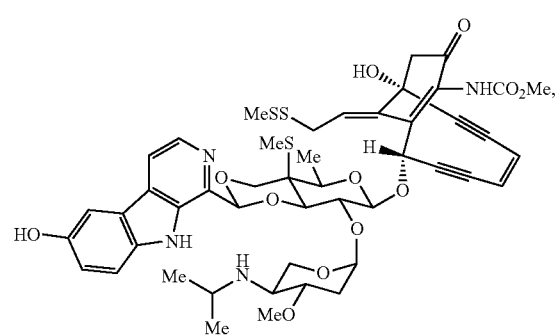
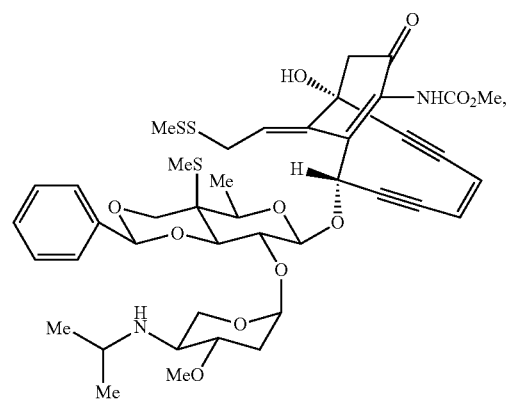
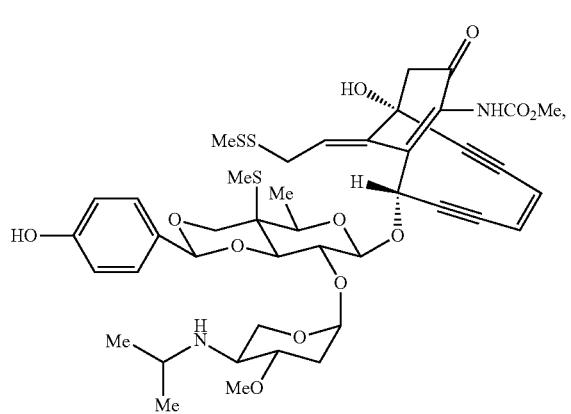
40
-continued
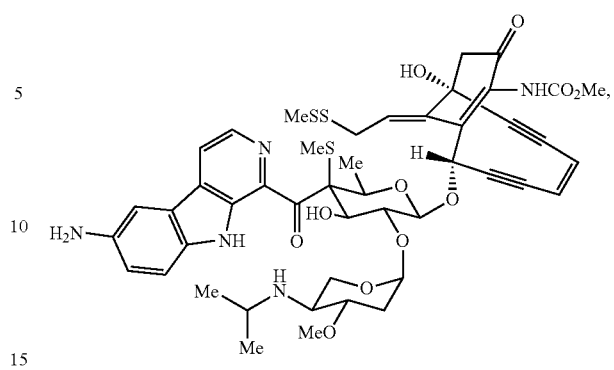
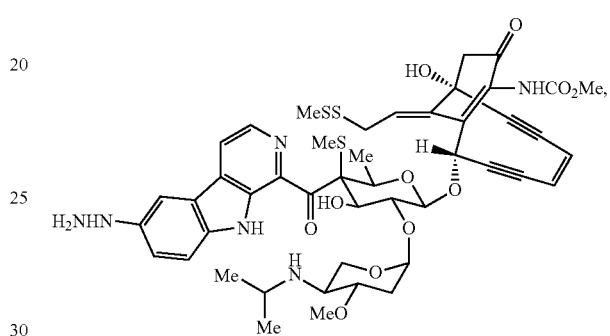
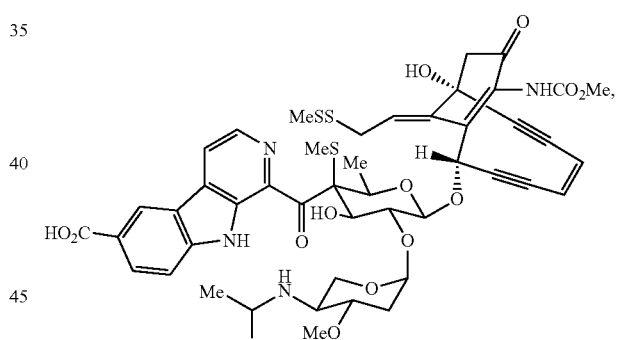
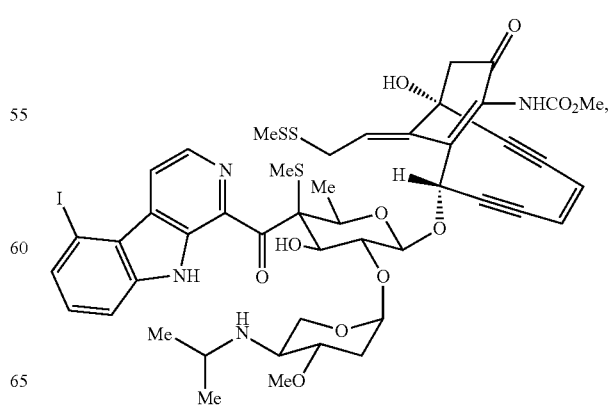

41
-continued
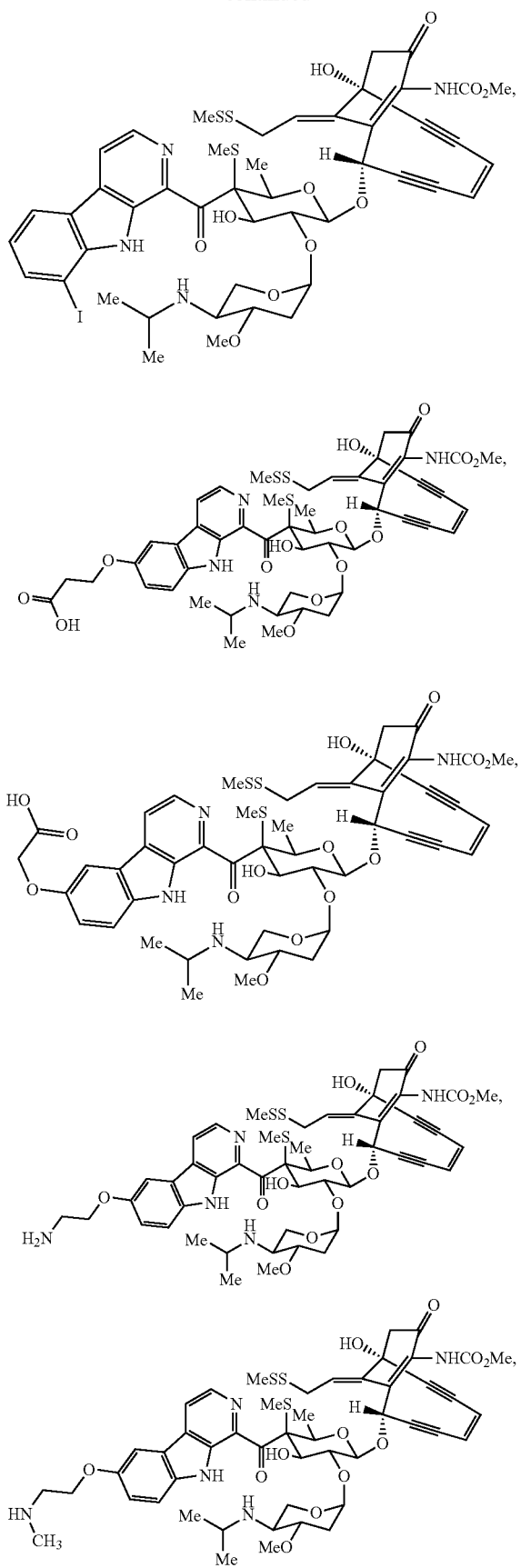
42
-continued
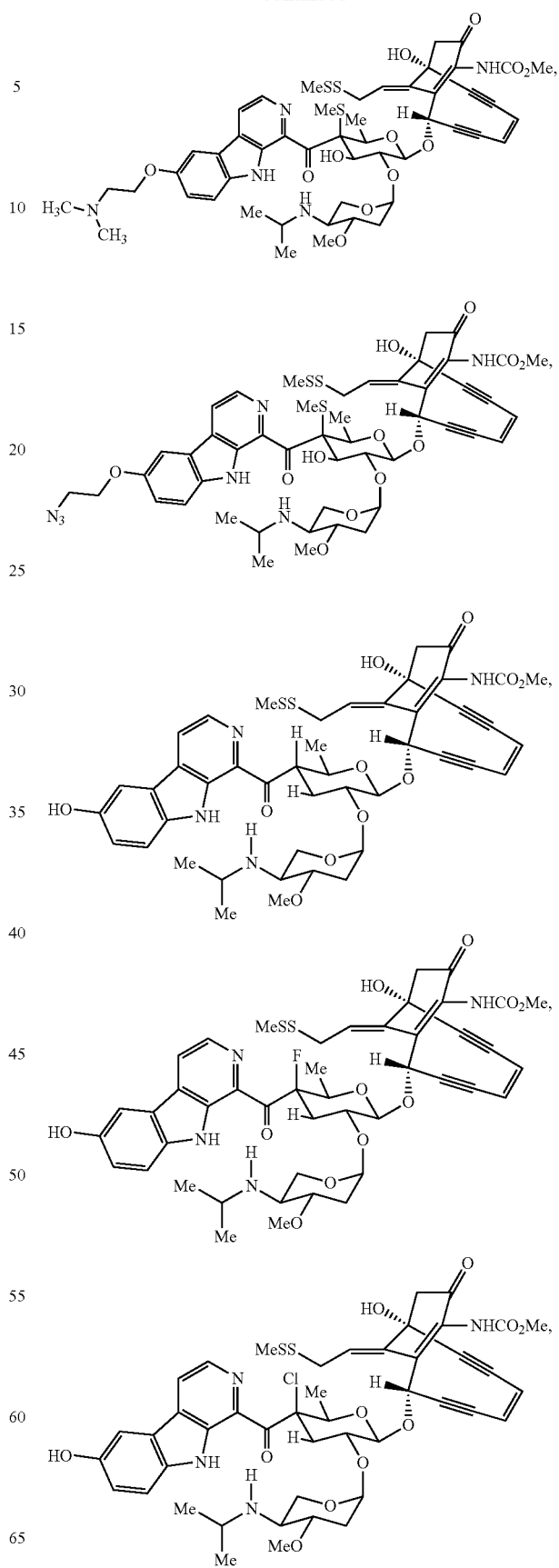

43
-continued
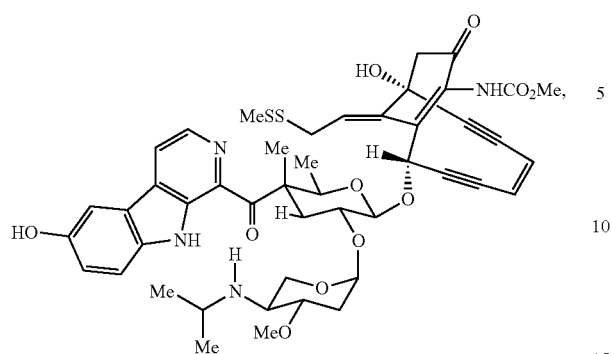
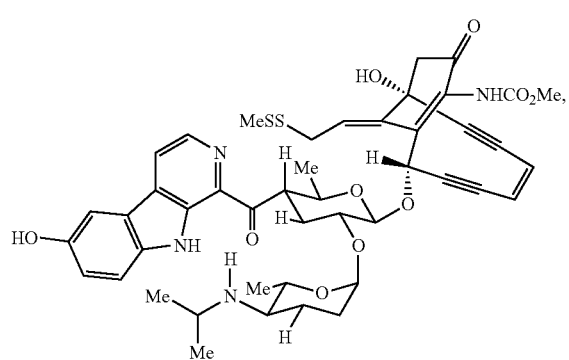
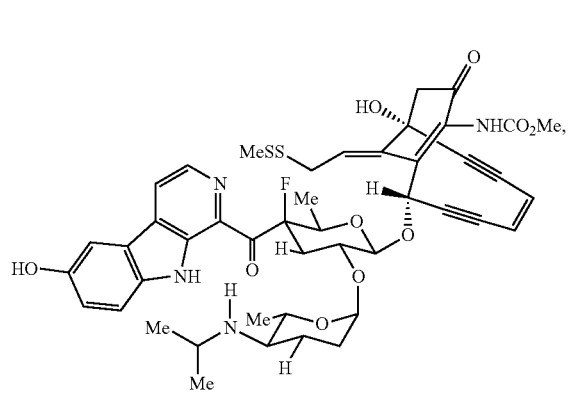
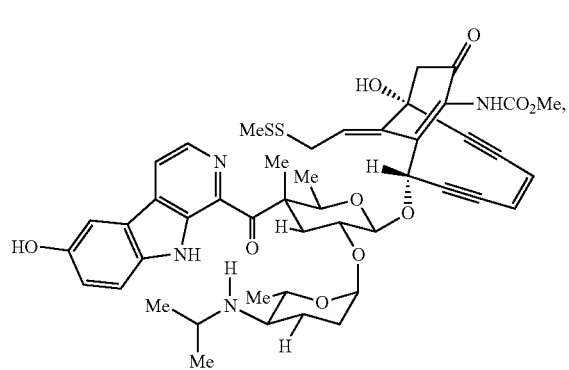
44
-continued
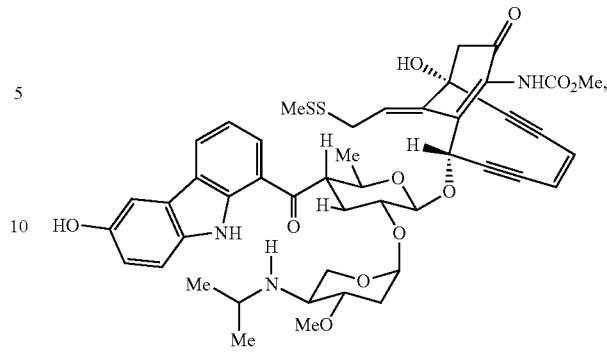
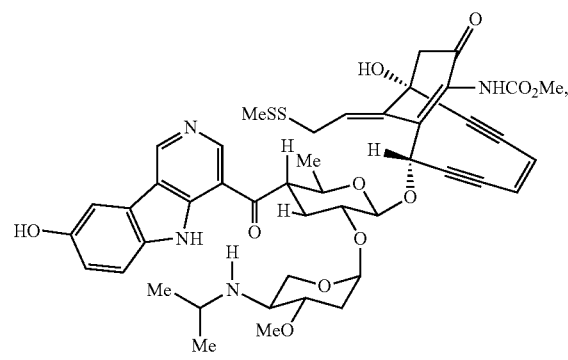
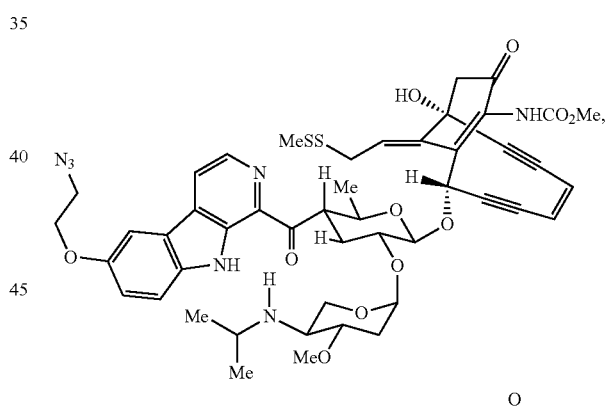
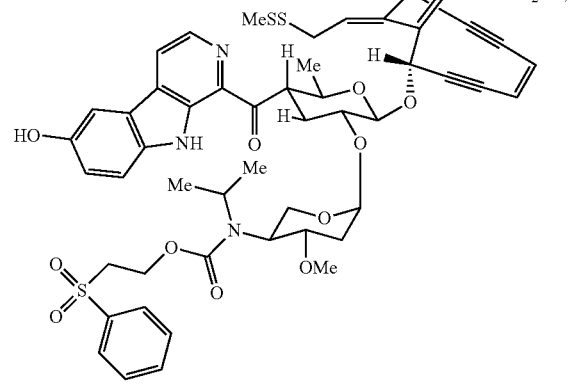

-continued
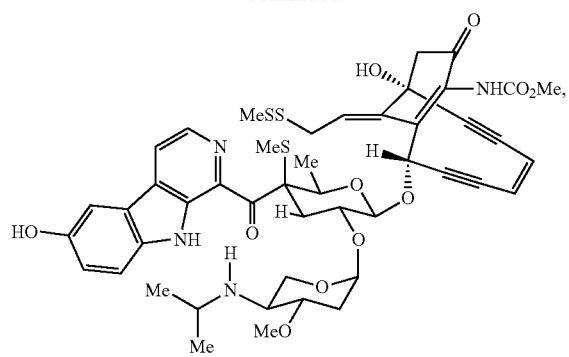
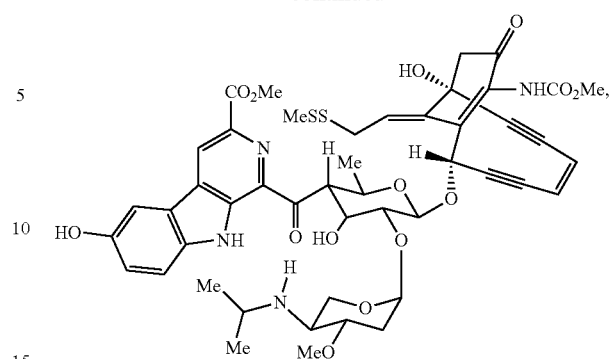
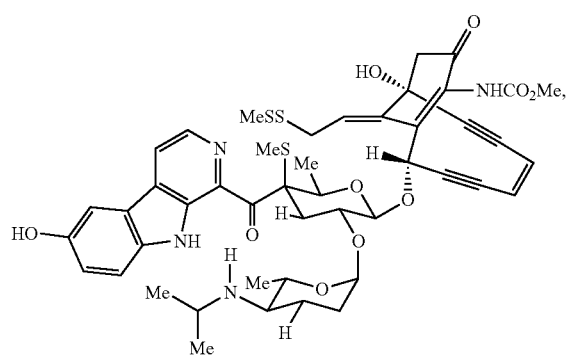
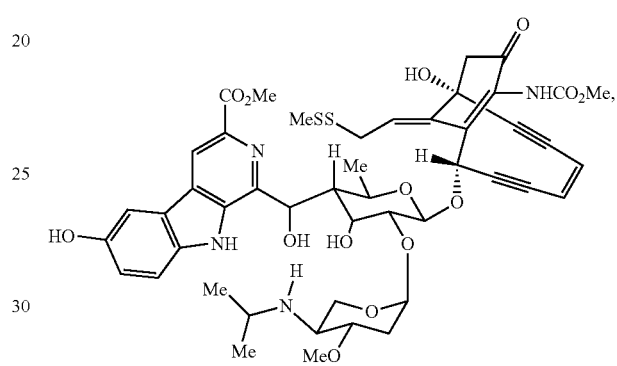
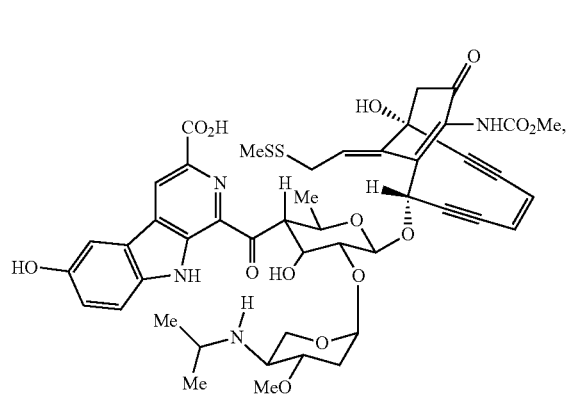
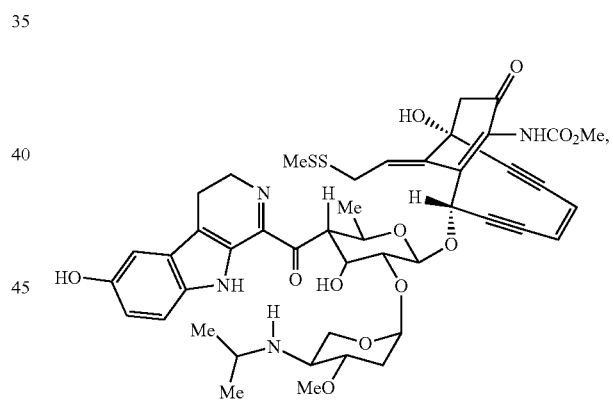
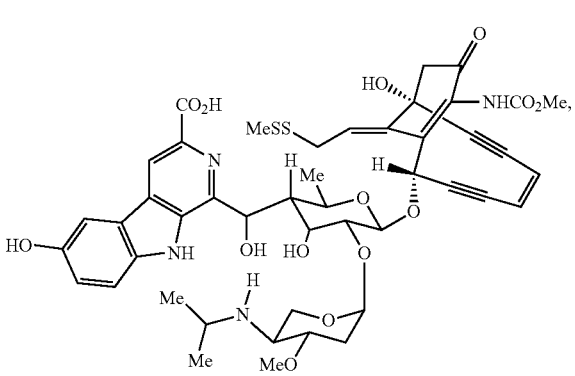
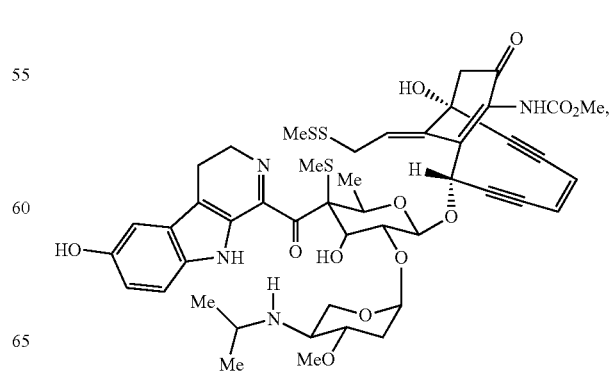

-continued
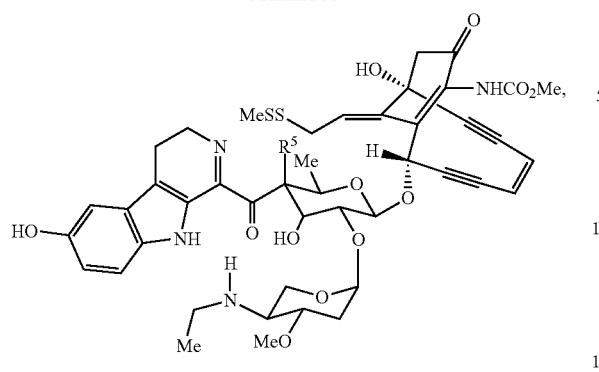
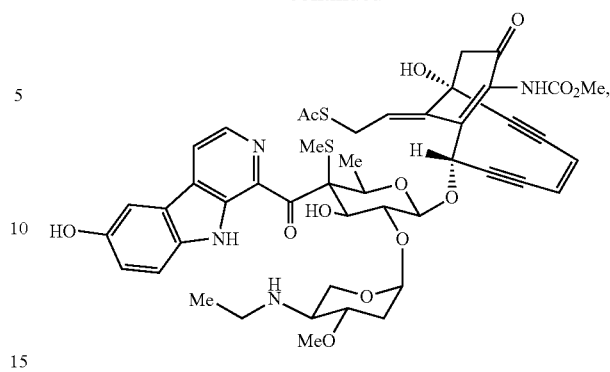
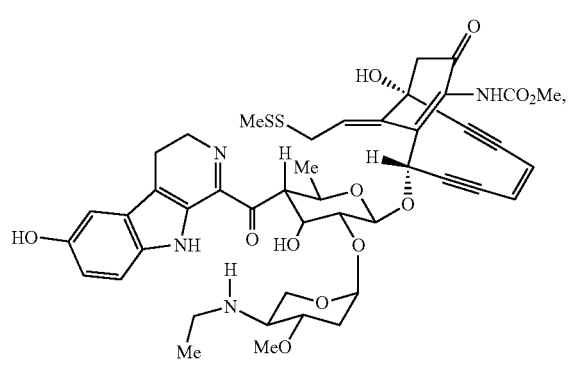
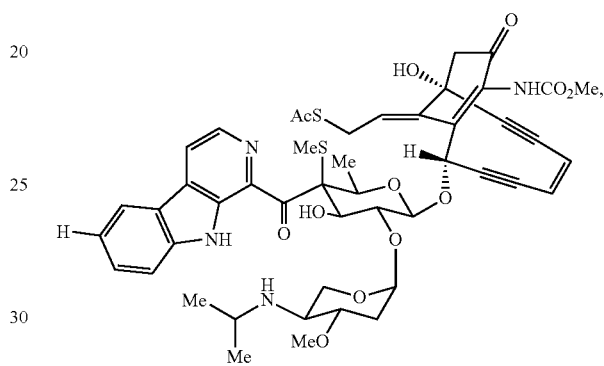
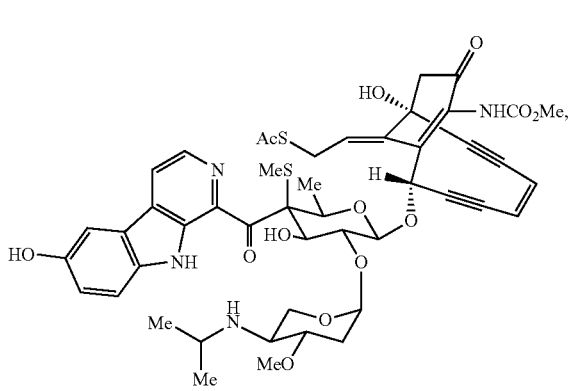
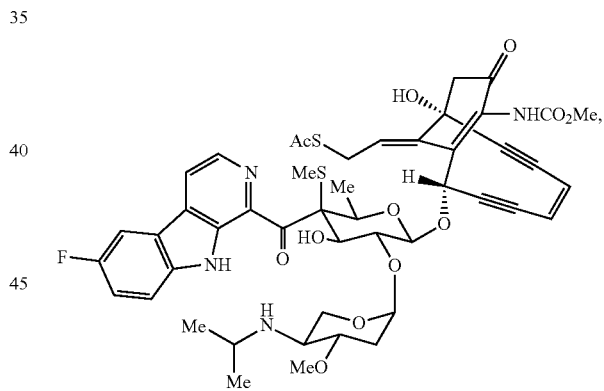
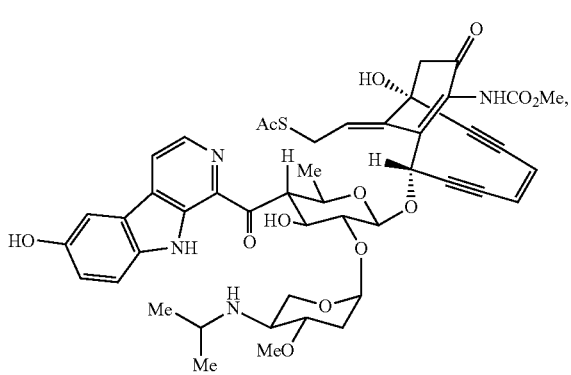
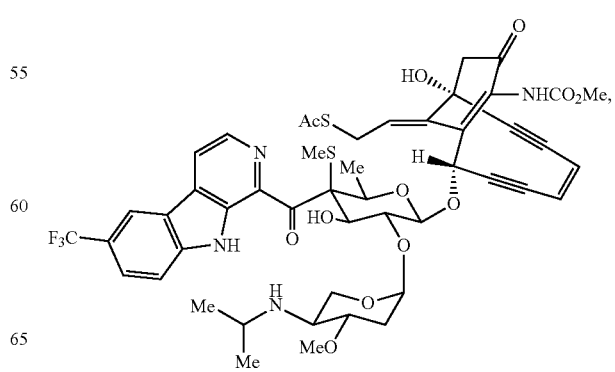

49
-continued
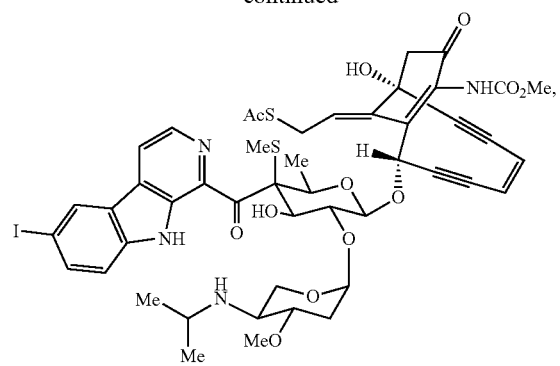
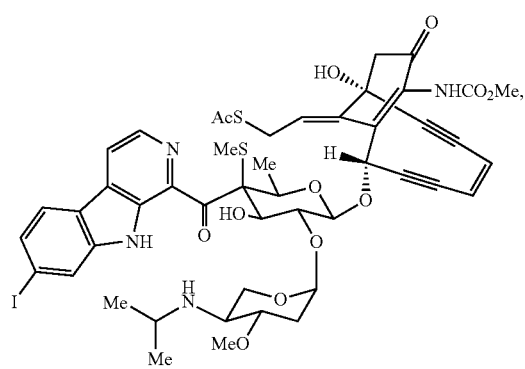
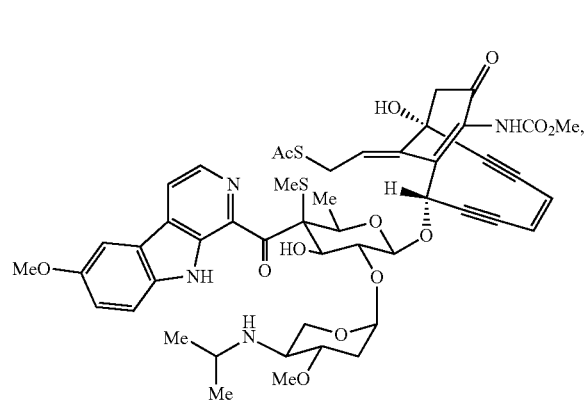
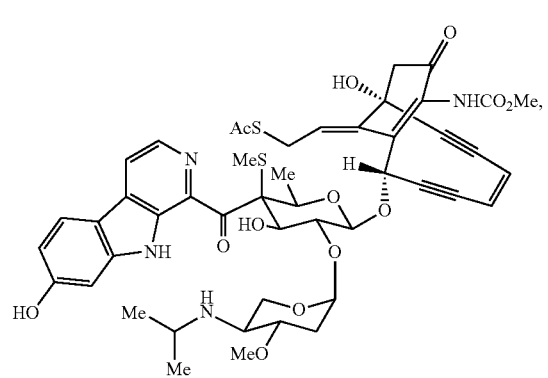
50
-continued
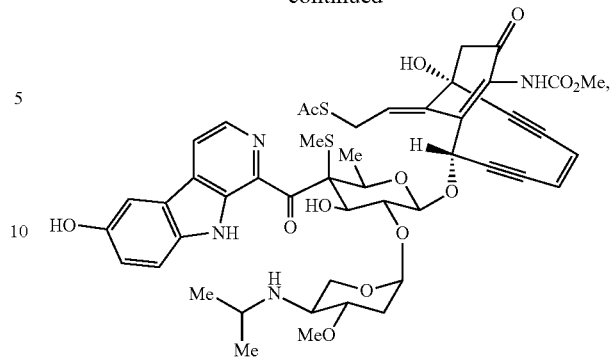
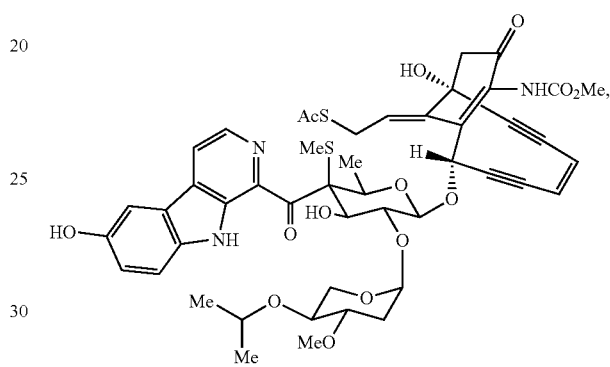
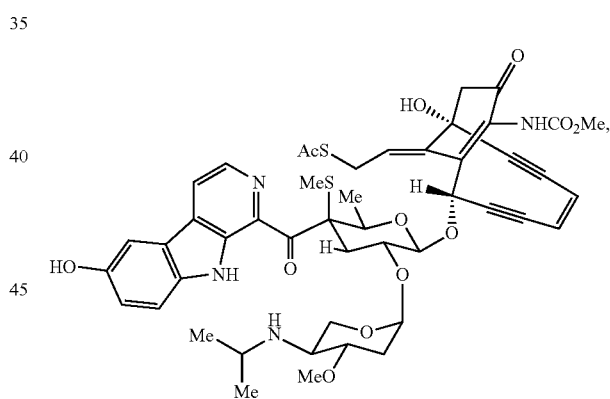
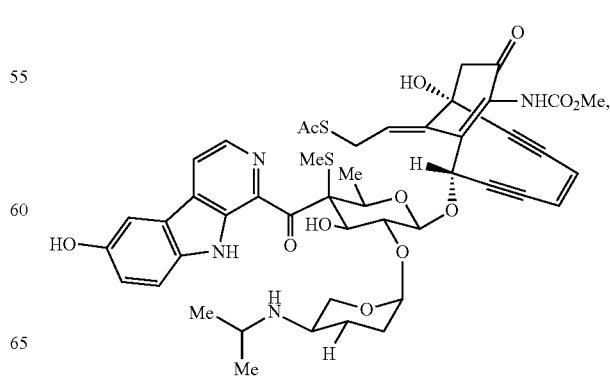

51
-continued
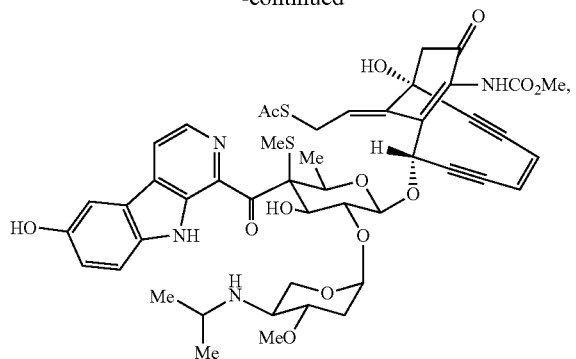
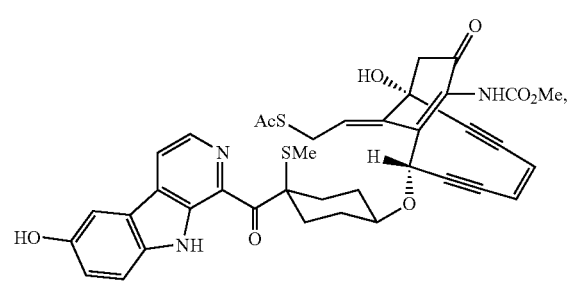
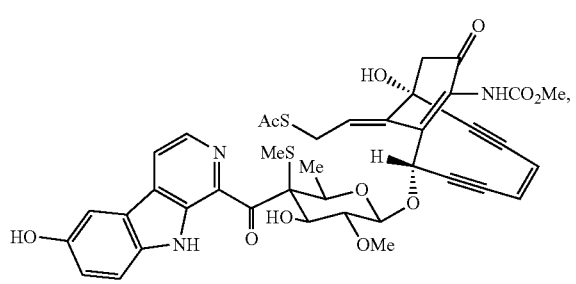
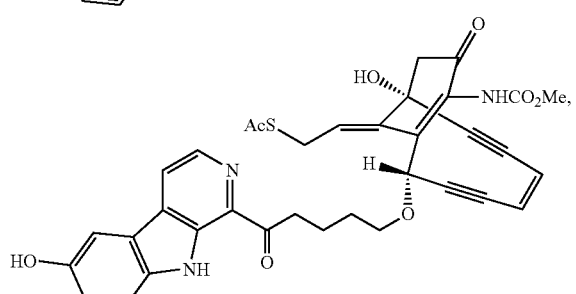
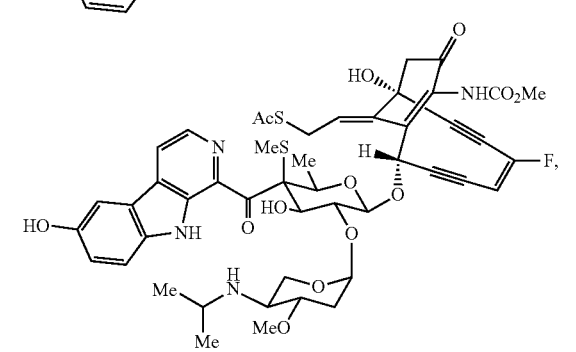
52
-continued
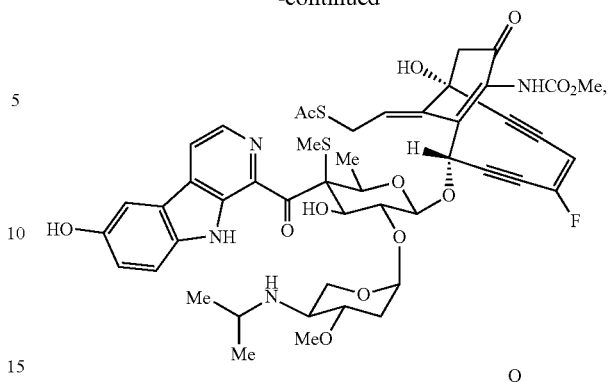
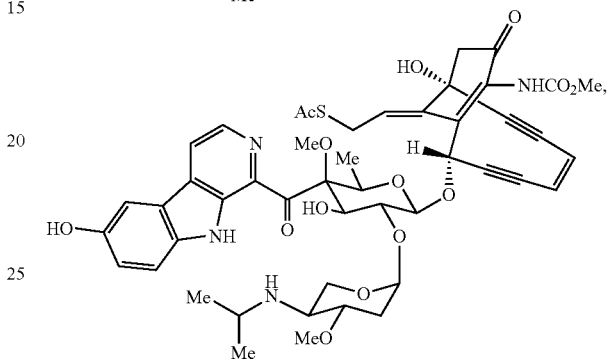
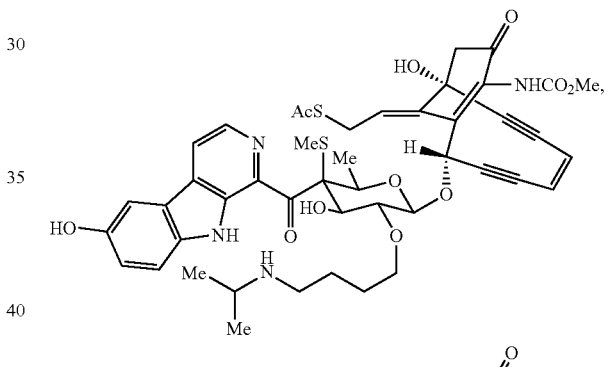
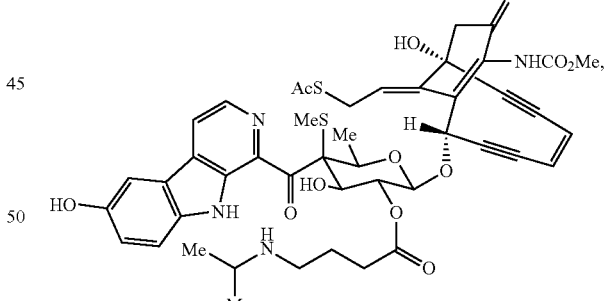
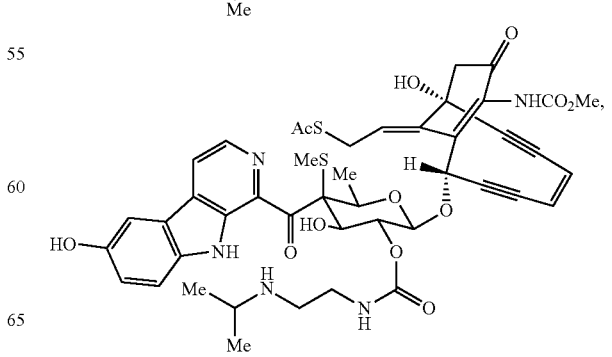

53
-continued
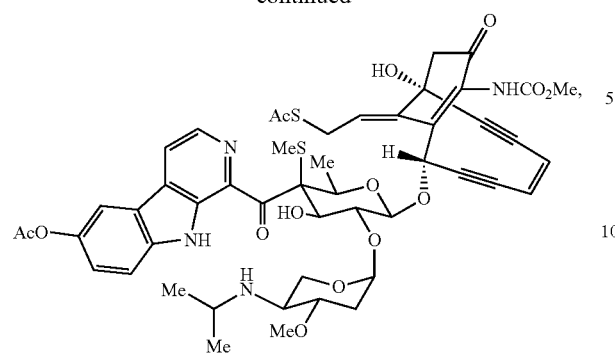
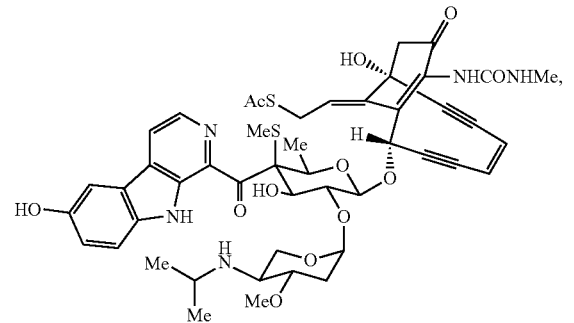
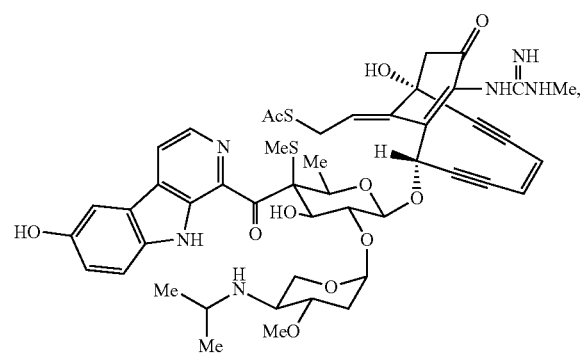
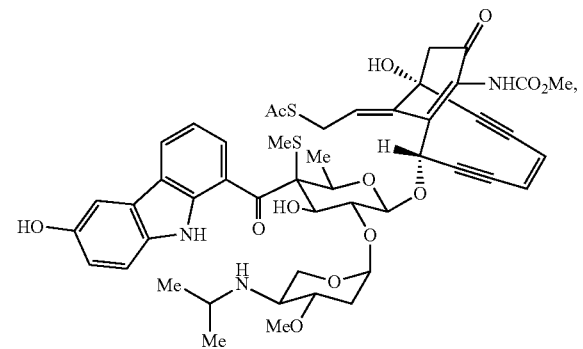
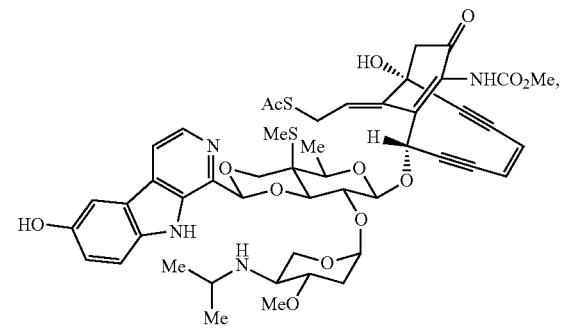
54
-continued
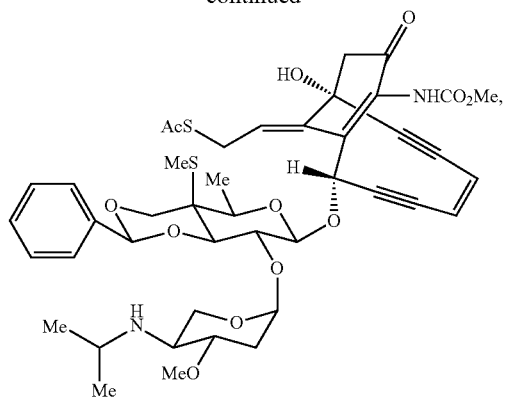
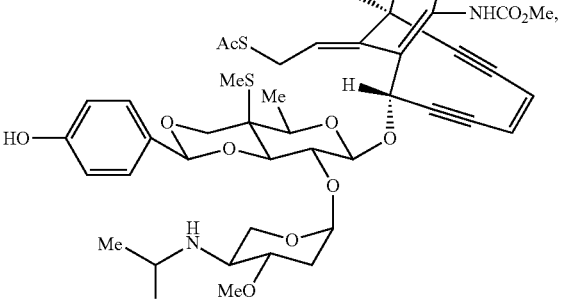
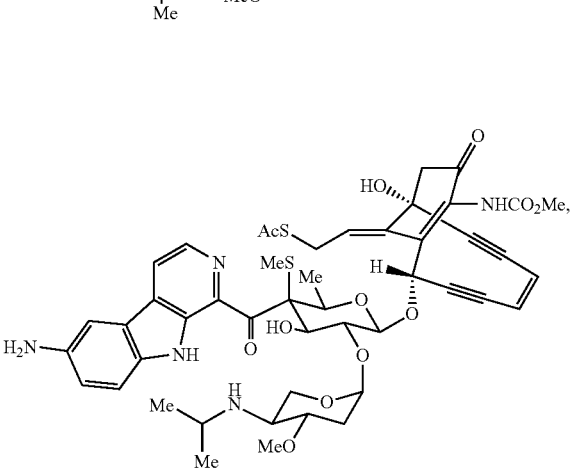
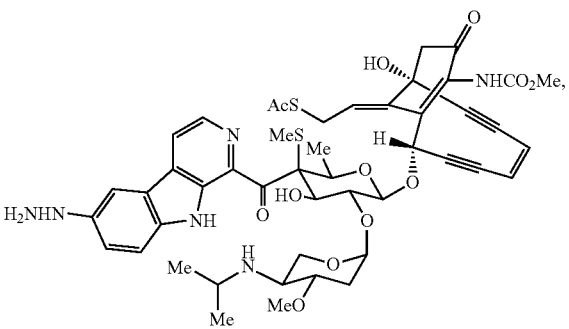

55
-continued
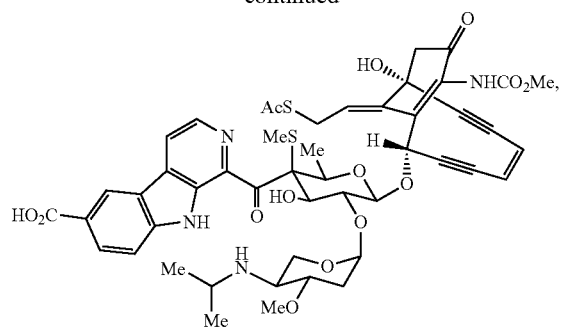
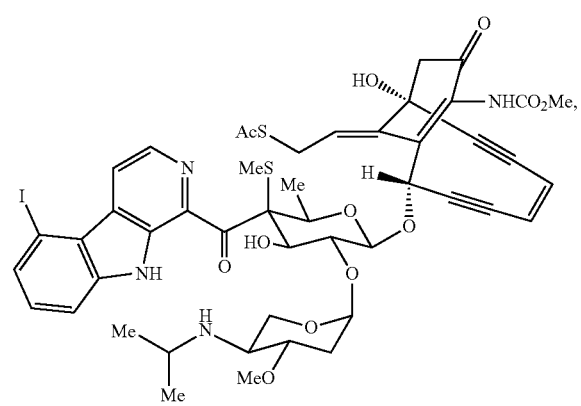
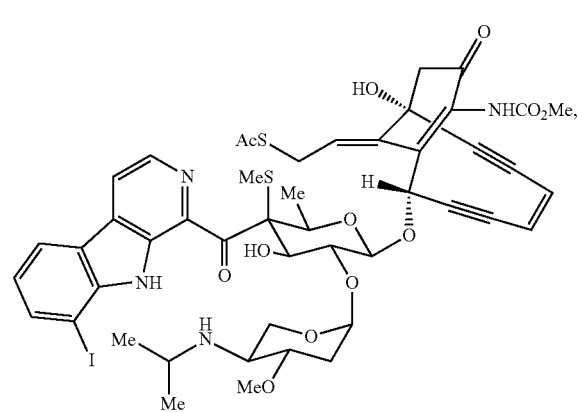
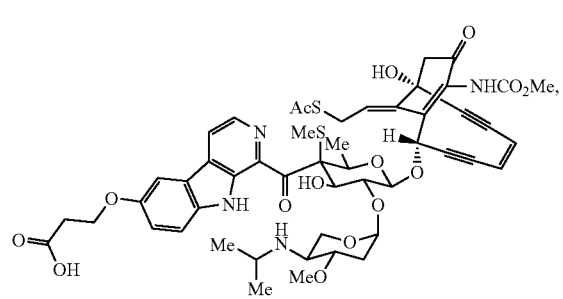
56
-continued
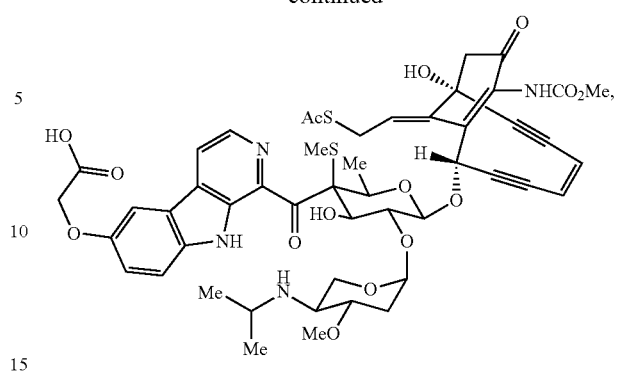
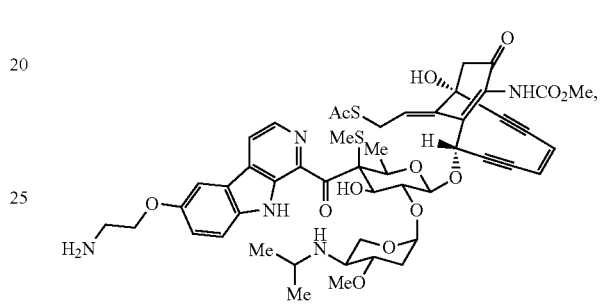
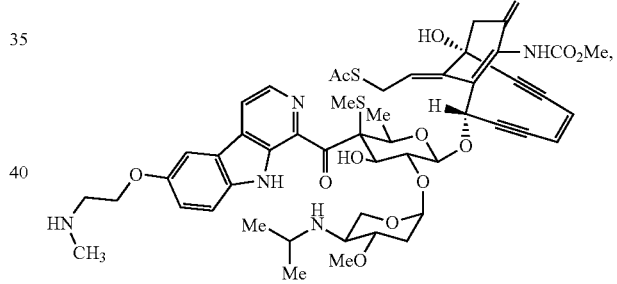
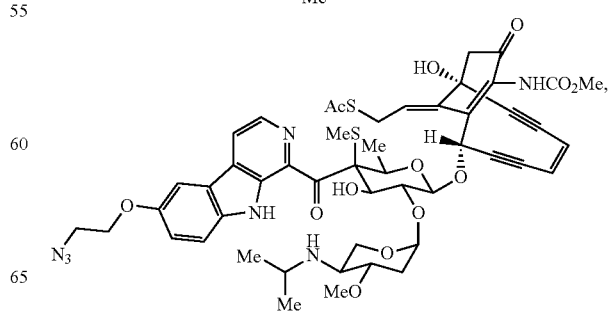

57
-continued
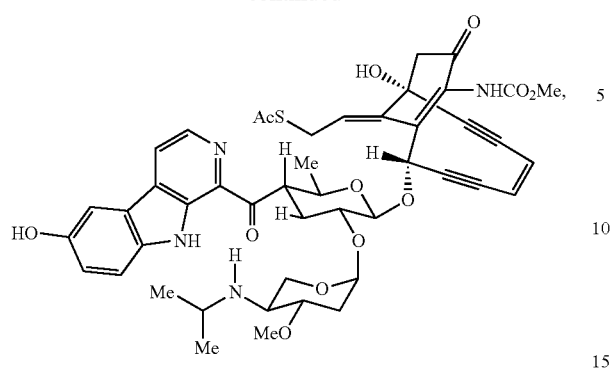
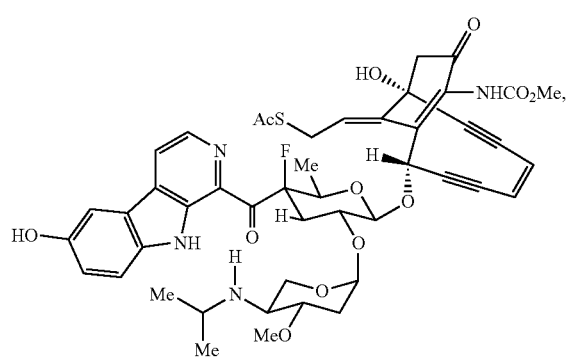
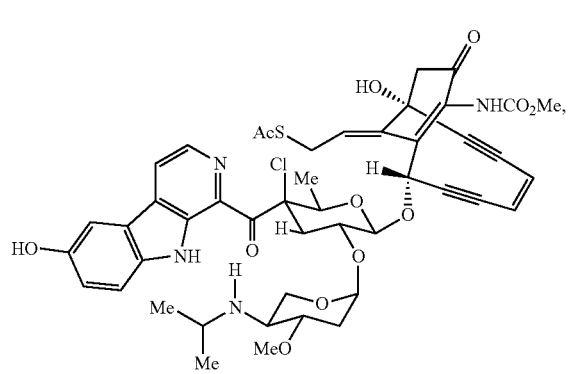
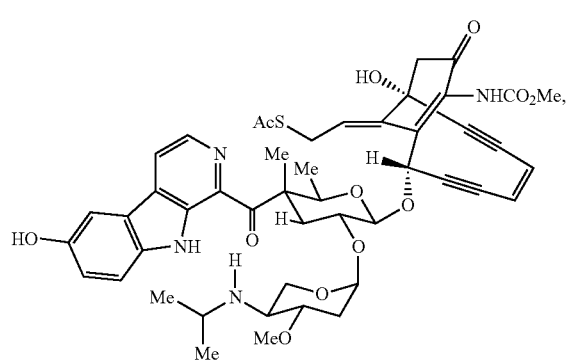
58
-continued
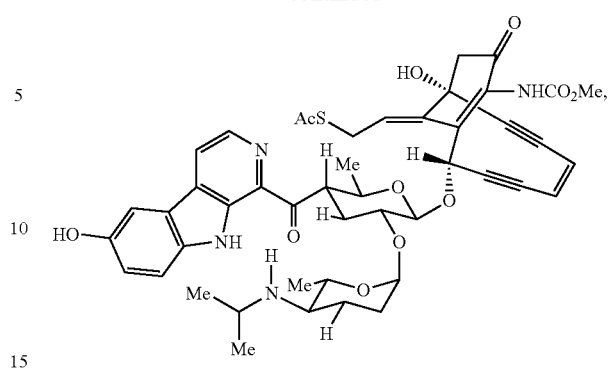
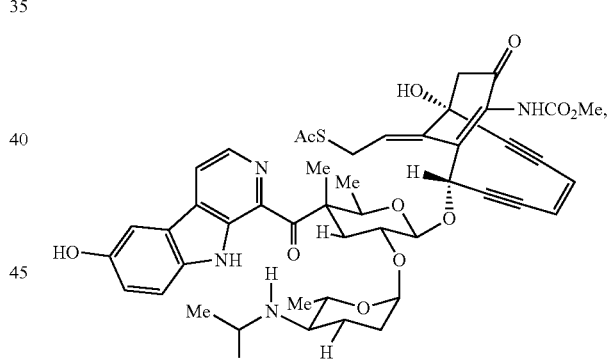
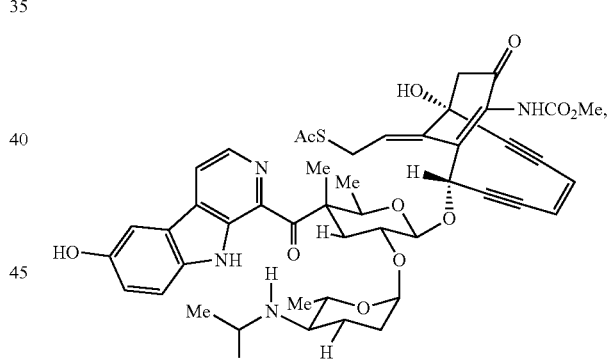

59
-continued
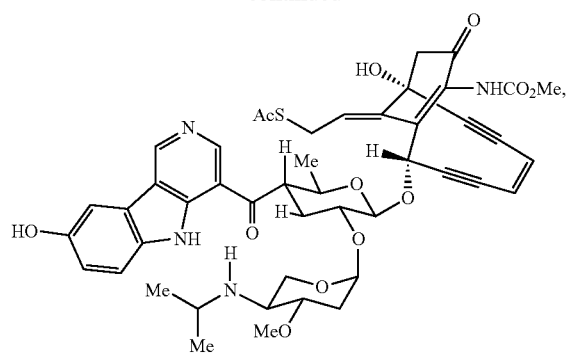
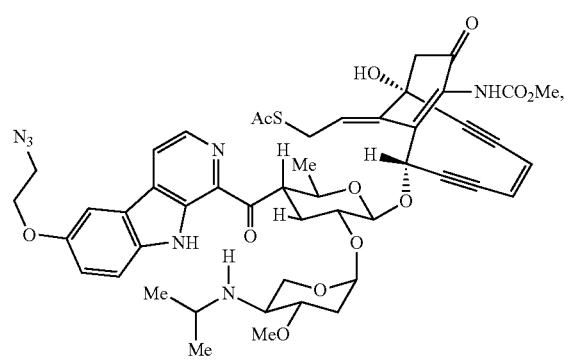
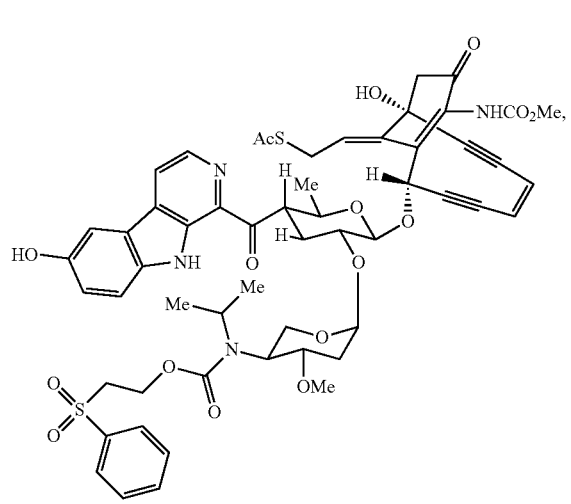
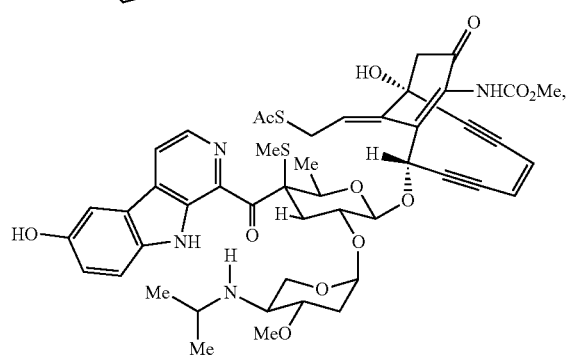
60
-continued
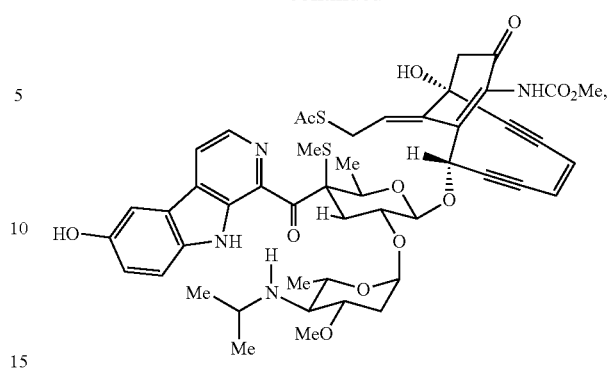
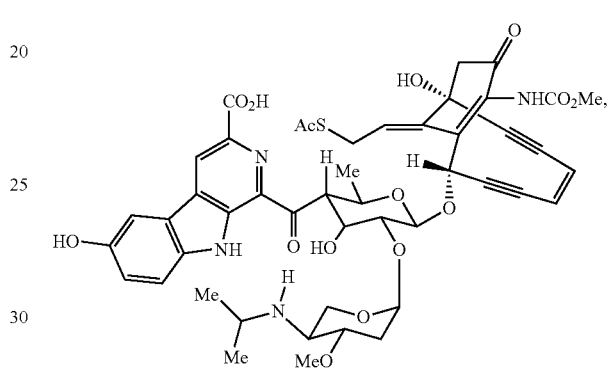
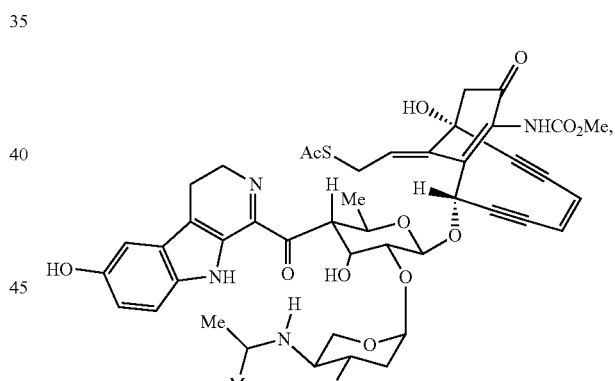
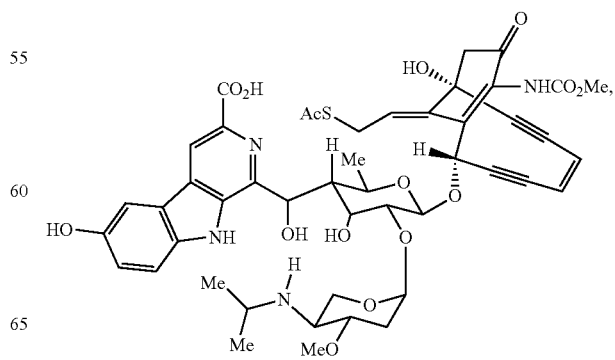

61
-continued
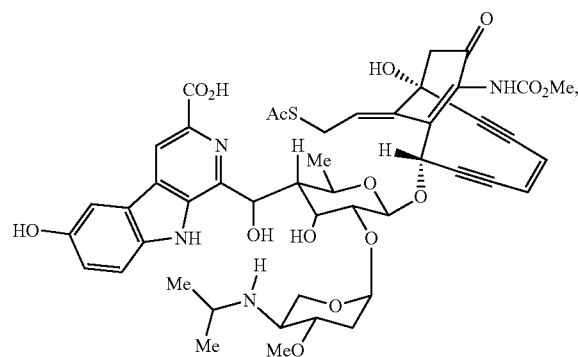
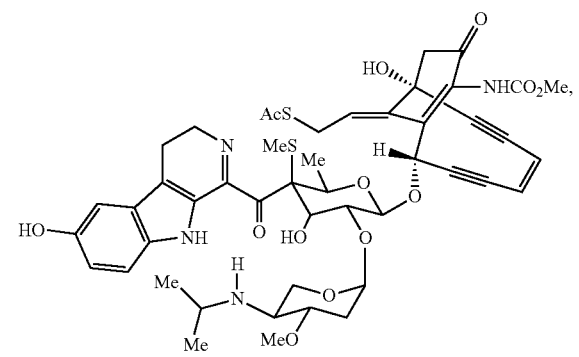
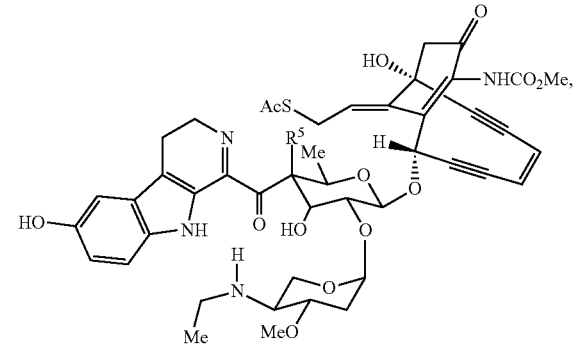
62
-continued
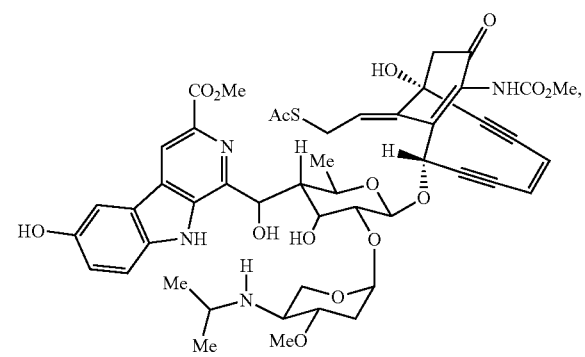
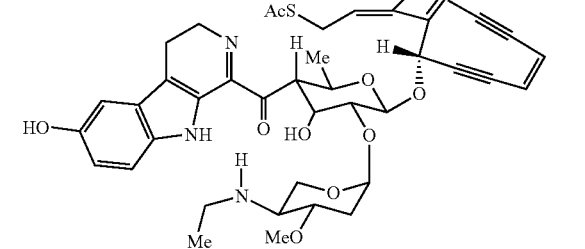
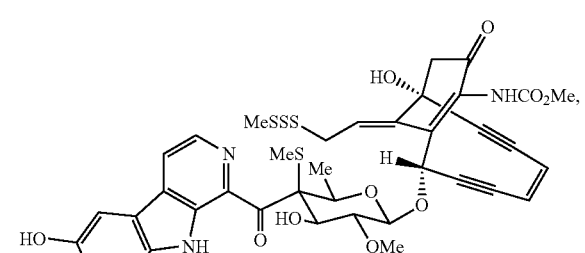
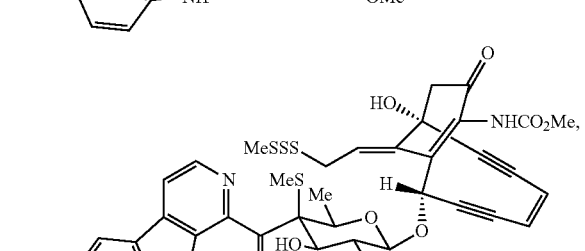
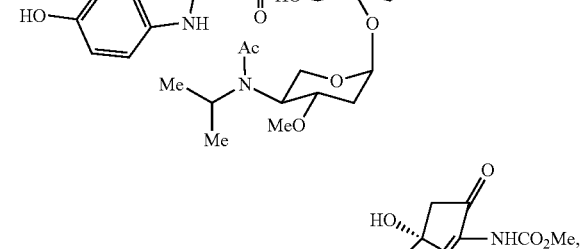
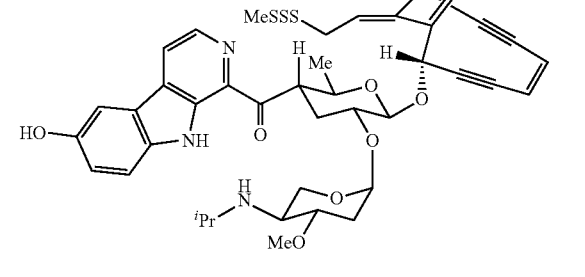

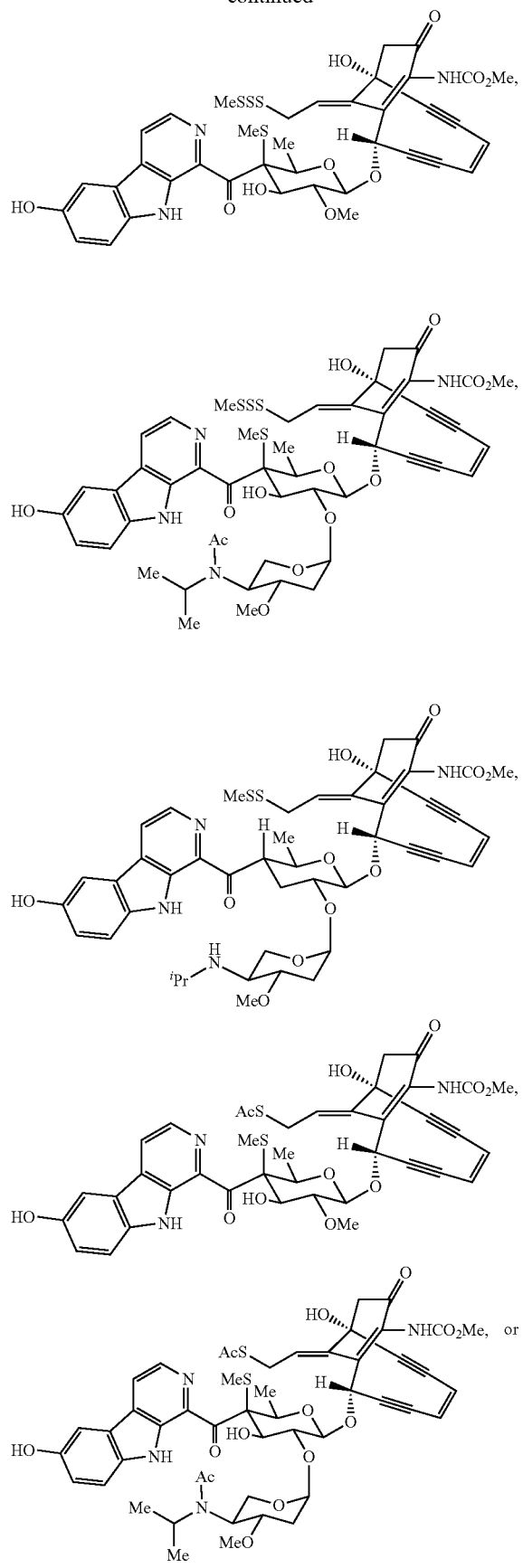
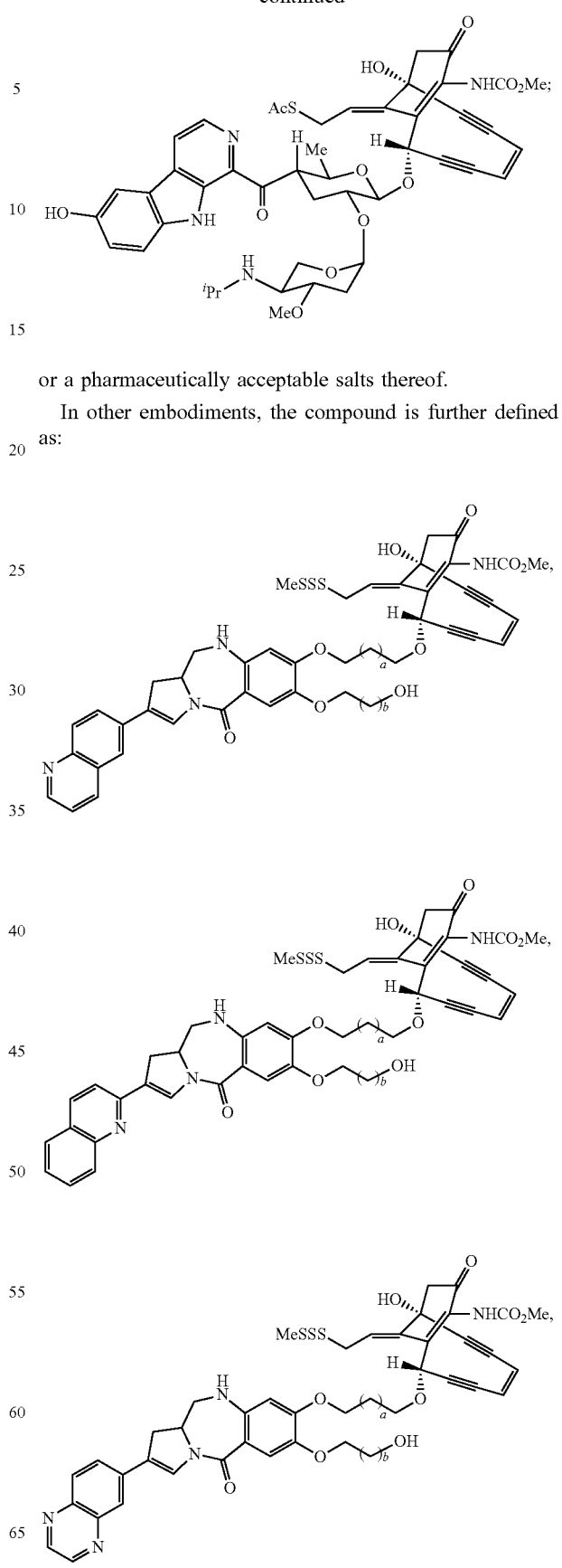
or a pharmaceutically acceptable salts thereof.
In other embodiments, the compound is further defined as:

-continued
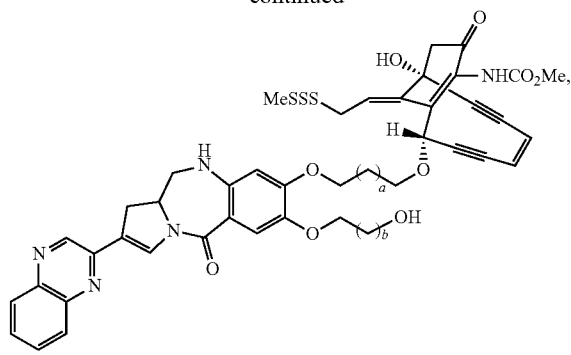
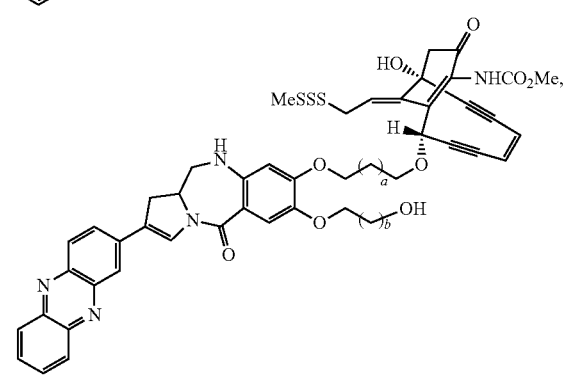
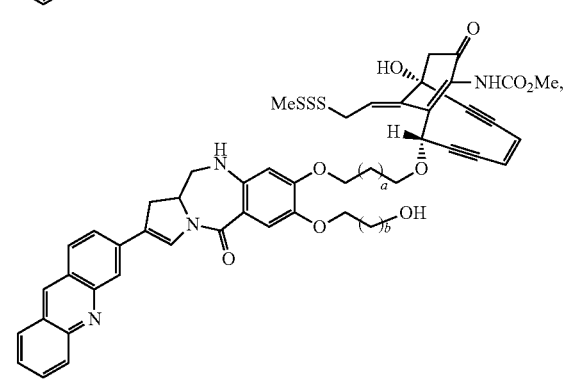
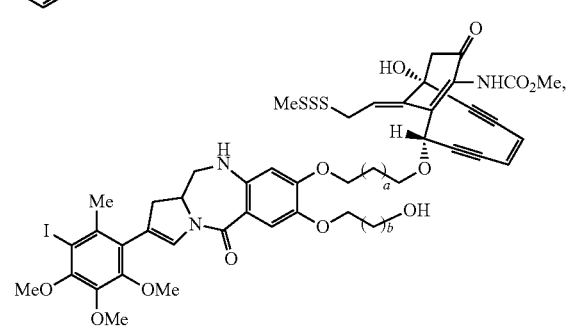
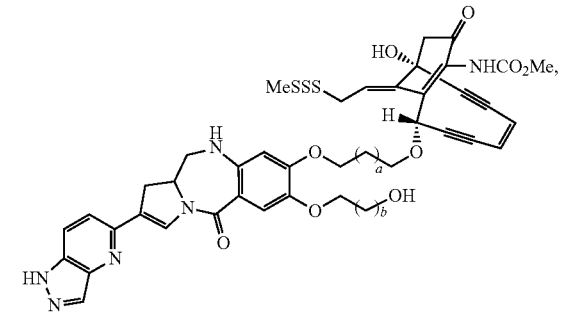
-continued
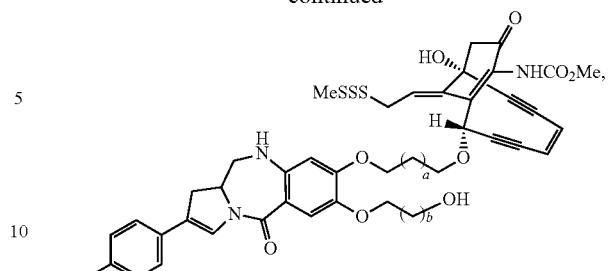
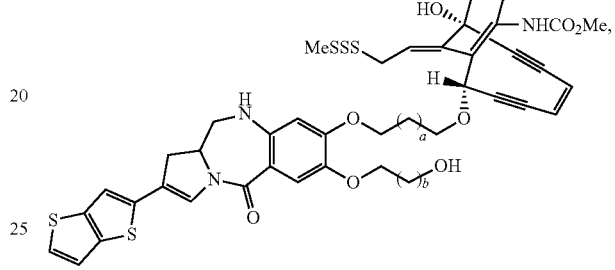
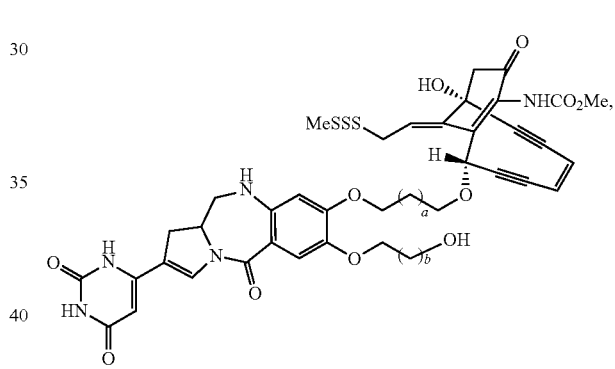
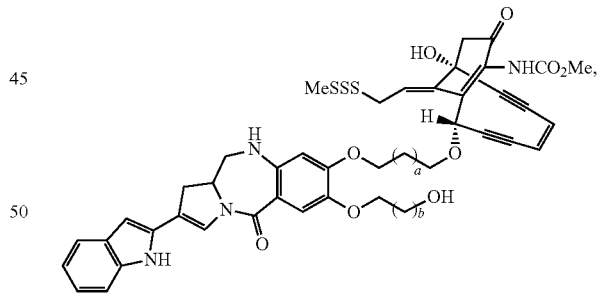
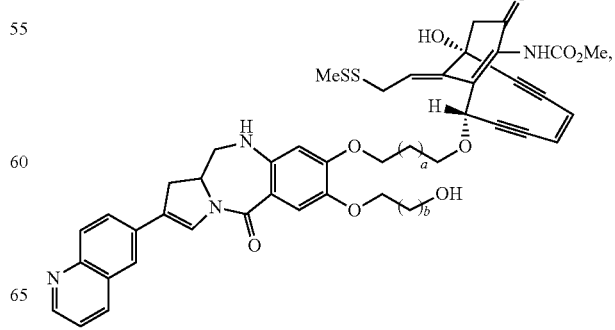

67
-continued
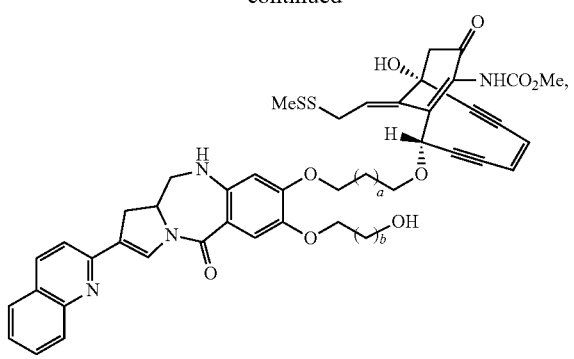
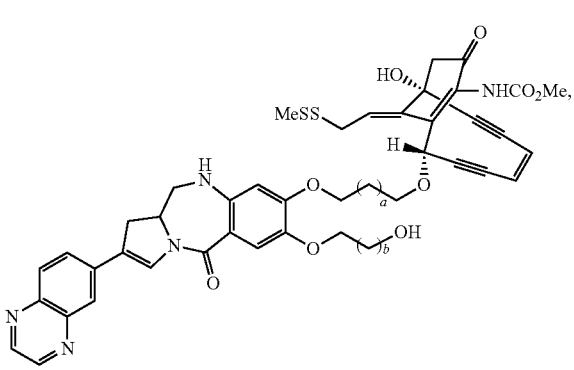
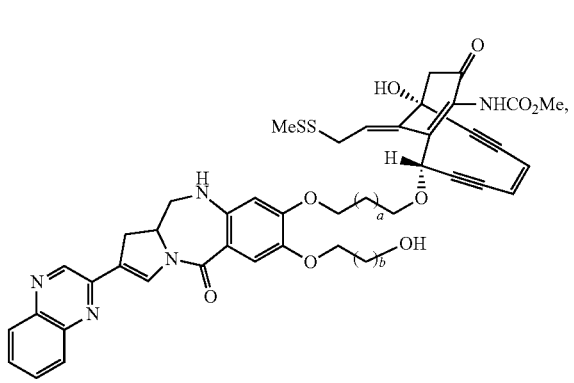
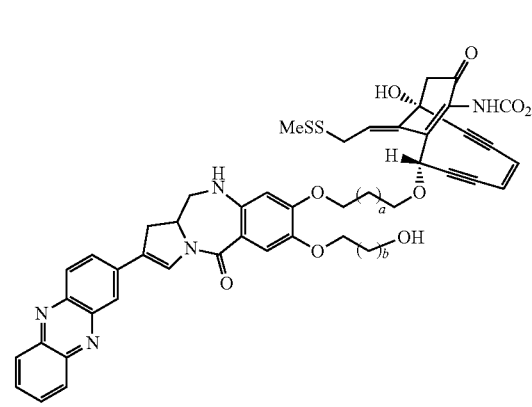
68
-continued
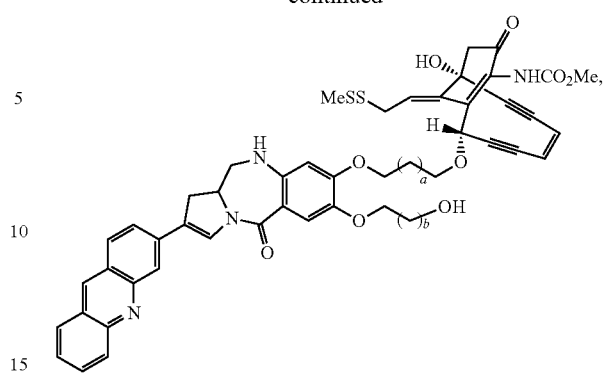
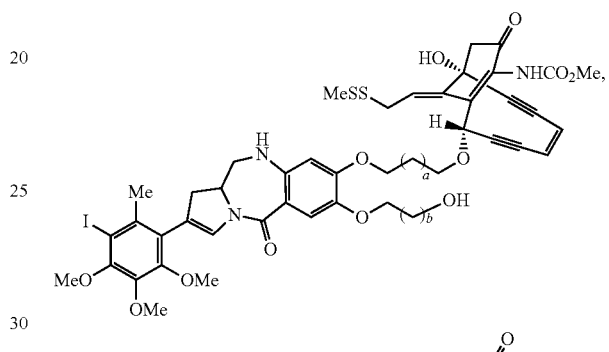
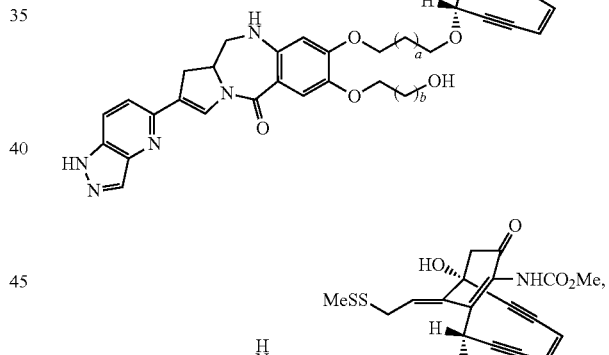
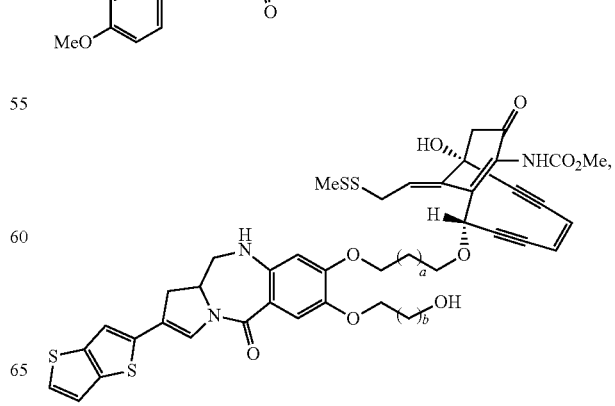

69
-continued
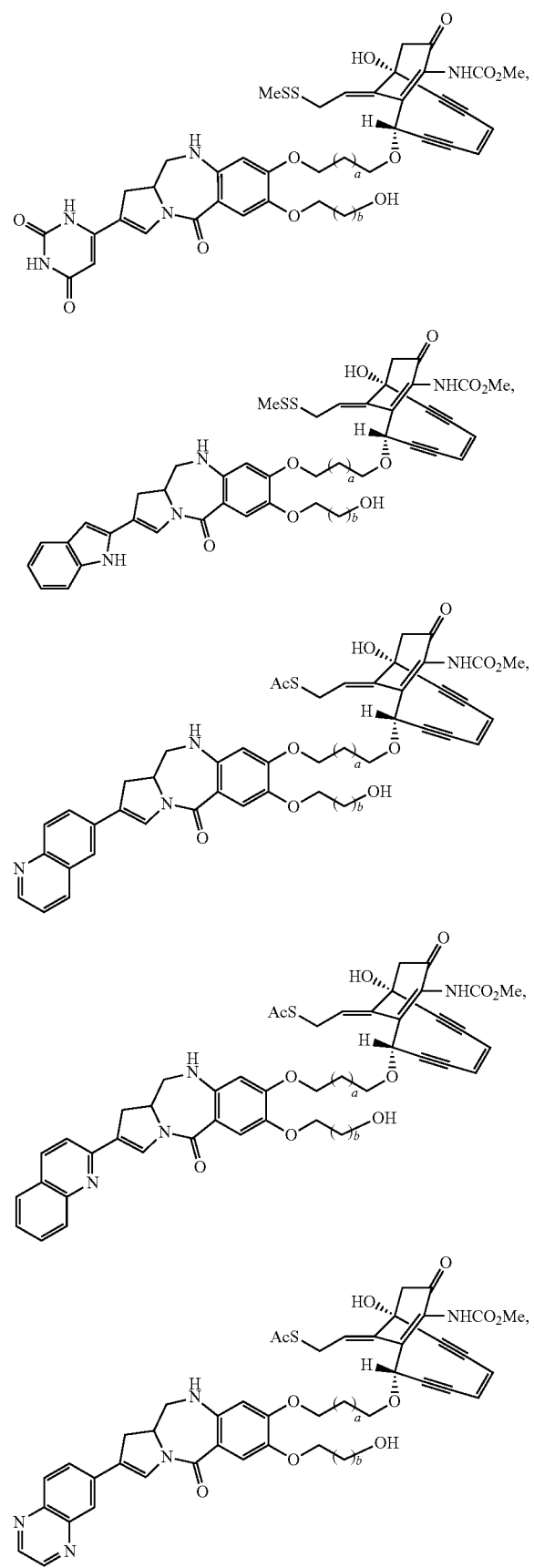
70
-continued
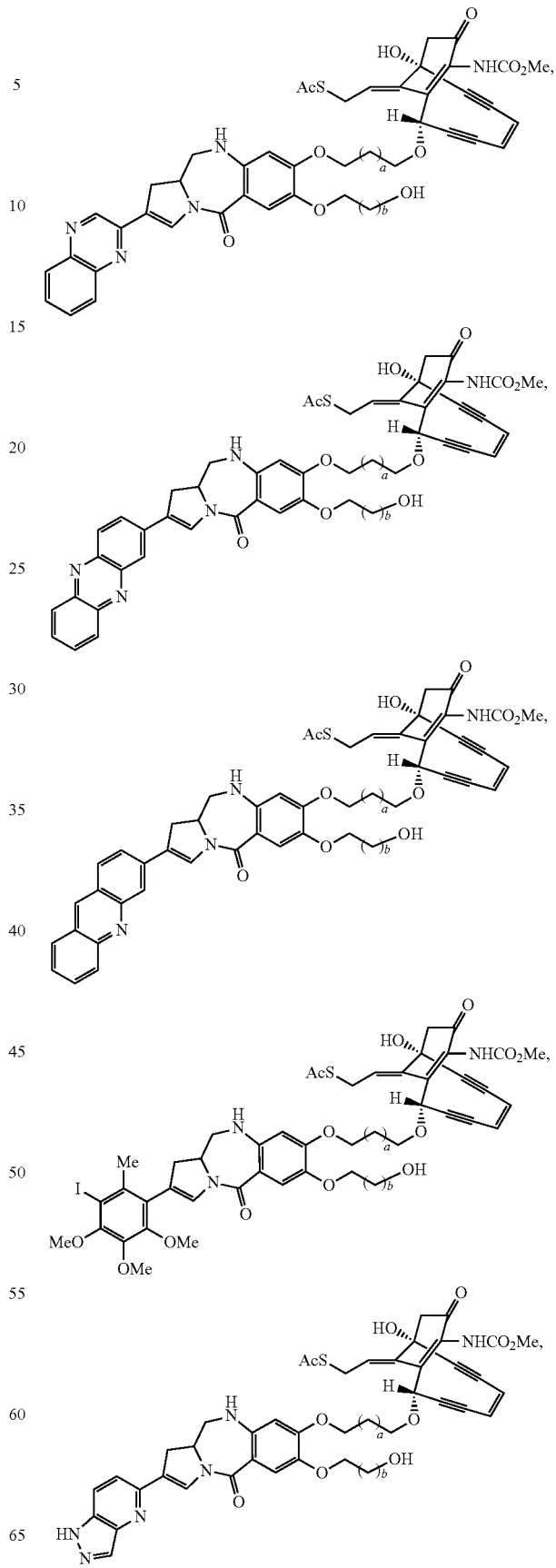

-continued

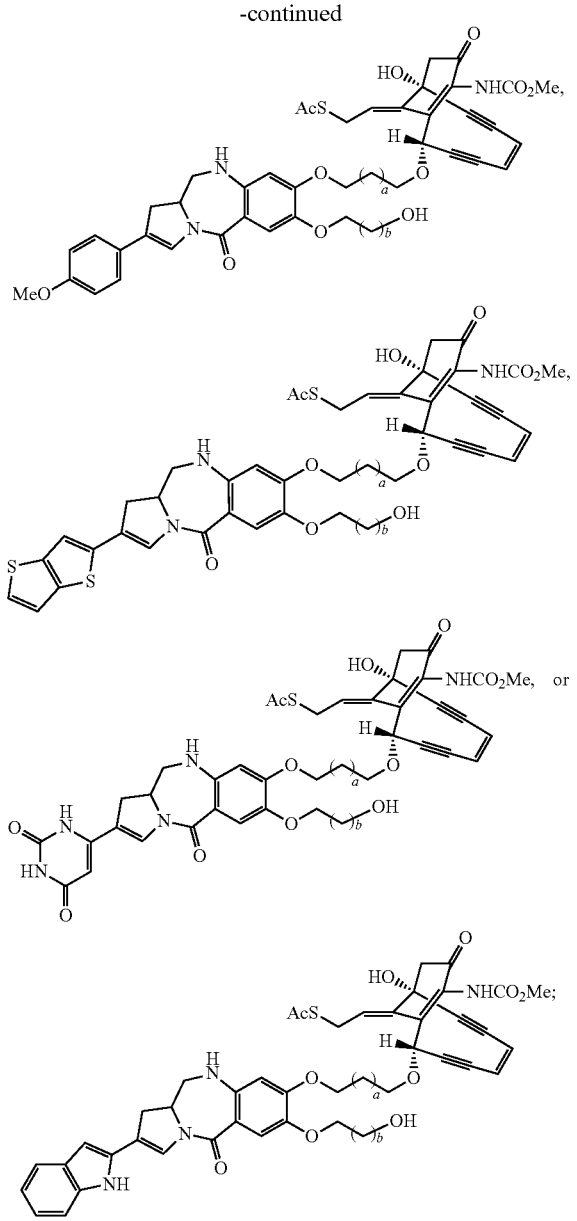

wherein:
  a is 0, 1, 2, 3, 4, or 5; and
  b is 1, 2, 3, 4, or 5;
or a pharmaceutically acceptable salt thereof.

In still yet another aspect, the present disclosure provides pharmaceutical compositions comprising:
  (A) a compound of the present disclosure; and
  (B) a pharmaceutically acceptable carrier.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical composition is formulated as a unit dose.

In still yet another aspect, present disclosure provides methods of treating a disease or disorder in a patient comprising administering to the patient in need thereof a therapeutically effective amount of a compound or composition of the present disclosure. In some embodiments, the disease or disorder is cancer. In some embodiments, the cancer is a carcinoma, sarcoma, lymphoma, leukemia, melanoma, mesothelioma, multiple myeloma, or seminoma. In other embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the method comprises administering the compound or composition with a second therapeutic agent. In some embodiments, the second therapeutic agent is surgery, a second chemotherapeutic, radiotherapy, or immunotherapy. In some embodiments, the patient is a mammal such as a human. In some embodiments, the compound is administered once. In other embodiments, the compound is administered two or more times.

In still yet another aspect, the present disclosure provides antibody-drug conjugates comprising:

$$A\text{-}L\text{-}(X)_y \qquad (VIII)$$

wherein:
  A is an antibody or a nanoparticle;
  L is a covalent bond or a difunctional linker;
  X is a compound or composition of the present disclosure; and
  y is an integer selected from 1, 2, 3, 4, 5, 6, 7, 8, 9, 10, 11, 12, 13, 14, 15, 16, 17, 18, 19, or 20.

In still yet another aspect, the present disclosure provides methods of preparing a compound of the formula:

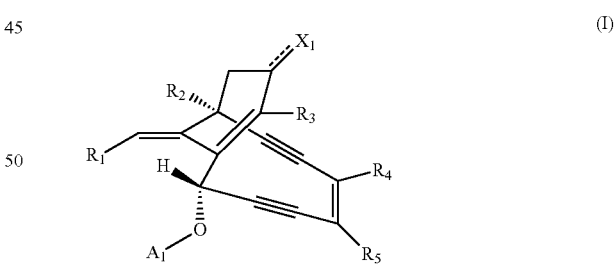

wherein:
  $R_1$ is -alkanediyl$_{(C \leq 8)}$-(S)$_x$-A$_3$ or -substituted alkanediyl$_{(C \leq 8)}$-(S)$_x$-A$_3$; wherein:
    $A_3$ is hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, heteroaryl$_{(C \leq 12)}$, aralkyl$_{(C \leq 12)}$, acyl$_{(C \leq 12)}$, or a substituted version of any of these groups; and
    x is 1, 2, or 3;
  $R_2$ is hydroxy, or alkoxy$_{(C \leq 8)}$, acyloxy$_{(C \leq 8)}$, or -substituted version of either of these groups, or a protected hydroxy group;

$R_3$ is $NHC(Y_2)R_{16}$, wherein:

$Y_2$ is O, NH, or NOH; and $R_{16}$ is $alkoxy_{(C \leq 8)}$, $alkenyloxy_{(C \leq 8)}$, $alkylamino_{(C \leq 8)}$, $dialkylamino_{(C \leq 8)}$, or -substituted version of any of these groups;

$R_4$ and $R_5$ are each independently selected from hydrogen and halo;

$X_1$ is O, S, or NH, or $X_1$ is a protected carbonyl wherein the protected carbonyl is a group of the formula —O(CH$_2$)$_c$O—, wherein c is 1, 2, 3, or 4;

$A_1$ is -alkanediyl$_{(C \leq 12)}$-C(O)-$A_2$ or -substituted alkanediyl$_{(C \leq 12)}$-C(O)-$A_2$; or $A_1$ is:

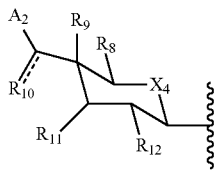

wherein:

$X_4$ is —CH$_2$— or —O—;

$R_8$ is hydrogen, alkyl$_{(C \leq 8)}$, cycloalkyl$_{(C \leq 8)}$, substituted alkyl$_{(C \leq 8)}$, or -substituted cycloalkyl$_{(C \leq 8)}$;

$R_9$ is hydrogen, halo, hydroxy, mercapto, alkyl$_{(C \leq 8)}$, substituted alkyl$_{(C \leq 8)}$, alkoxy$_{(C \leq 8)}$, substituted alkoxy$_{(C \leq 8)}$, alkylthio$_{(C \leq 8)}$, substituted alkylthio$_{(C \leq 8)}$, or a protected hydroxy group or a protected thiol group;

$R_{10}$ is hydroxy, oxo, or $R_{10}$ is taken together with $R_{11}$ and is —OCHA$_4$O—; provided that when $R_{10}$ is oxo then $R_{10}$ and the carbon atom to which it is bound are joined by a double bond, and when $R_{10}$ is taken together with $R_{11}$ then $R_{10}$ and the carbon atom to which it is bound are joined by a single bond;

wherein $A_4$ is aryl$_{(C \leq 12)}$ or substituted aryl$_{(C \leq 12)}$, or

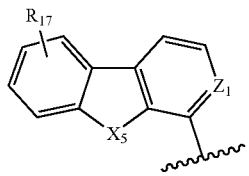

wherein:

$Z_1$ is CH or N; and $R_{17}$ is hydrogen, hydroxy, amino, hydrazino, carboxy, halo, or nitro; or alkyl$_{(C \leq 12)}$, alkoxy$_{(C \leq 12)}$, or a substituted version of either of these groups;

$R_{11}$ is hydrogen, hydroxy, alkoxy$_{(C \leq 8)}$, or substituted alkoxy$_{(C \leq 8)}$, or a protected hydroxy group;

$R_{12}$ is hydrogen, hydroxy, alkoxy$_{(C \leq 8)}$, substituted alkoxy$_{(C \leq 8)}$, or a protected hydroxy group, or —O-alkanediyl$_{(C \leq 8)}$-alkylamino$_{(C \leq 12)}$, —OC(O)-alkanediyl$_{(C \leq 8)}$-alkylamino$_{(C \leq 12)}$, or —OC(O)NH-alkanediyl$_{(C \leq 8)}$-alkylamino$_{(C \leq 12)}$, or a substituted version of any of these groups; or

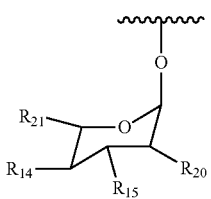

wherein:

$R_{14}$ is amino or hydroxy; or alkoxy$_{(C \leq 12)}$, alkylamino$_{(C \leq 12)}$, dialkyl-amino$_{(C \leq 12)}$, or a substituted version of any of these groups, or —NR$_a$R$_b$, wherein:

$R_a$ and $R_b$ are each hydrogen, alkyl$_{(C \leq 12)}$, substituted alkyl$_{(C \leq 12)}$, alkenyl$_{(C \leq 12)}$, substituted alkenyl$_{(C \leq 12)}$, —C(O)O-alkanediyl$_{(C \leq 6)}$-R$_c$, —C(O)-alkanediyl$_{(C \leq 6)}$-R$_c$, -alkanediyl$_{(C \leq 6)}$-R$_c$, or a substituted version of either of these group; wherein:

$R_c$ is hydrogen, amino, carboxy, hydroxyl, acyl$_{(C \leq 8)}$, alkoxy$_{(C \leq 8)}$, alkylamino$_{(C \leq 8)}$, dialkylamino$_{(C \leq 8)}$, alkylsulfonyl$_{(C \leq 8)}$, arylsulfonyl$_{(C \leq 8)}$, or a substituted version of either of these groups, or a protected amino or hydroxy group;

$R_{15}$ is hydrogen, hydroxy, alkoxy$_{(C \leq 8)}$, or substituted alkoxy$_{(C \leq 8)}$, or a protected hydroxy group;

$R_{20}$ and $R_{21}$ are hydrogen, alkyl$_{(C \leq 8)}$, substituted alkyl$_{(C \leq 8)}$, alkoxy$_{(C \leq 8)}$, or substituted alkoxy$_{(C \leq 8)}$;

$A_2$ is hydrogen or

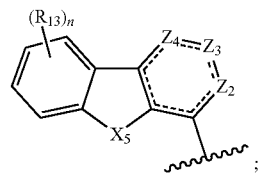

wherein:

$X_5$ is O, S, or NR$_{18}$; wherein:

$R_{18}$ is hydrogen, alkyl$_{(C \leq 8)}$, substituted alkyl$_{(C \leq 8)}$, acyl$_{(C \leq 8)}$, or substituted acyl$_{(C \leq 8)}$, or;

n is 1, 2, 3, 4, or 5;

$Z_2$, $Z_3$, and $Z_4$ are each independently N or CR$_{13}$; and $R_{13}$ is hydrogen, amino, carboxy, hydroxy, hydrazino, halo, or nitro;

alkyl$_{(C \leq 12)}$, acyl$_{(C \leq 12)}$, alkoxy$_{(C \leq 12)}$, acyloxy$_{(C \leq 12)}$, or a substituted version of either of these groups, or a protected thiol, amino, or hydroxy group; or $A_1$ is

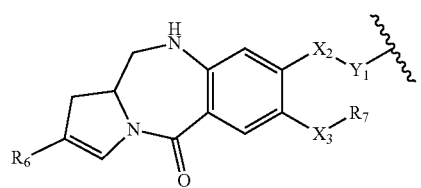

wherein:

$Y_1$ is -alkanediyl$_{(C \leq 8)}$ or substituted alkanediyl$_{(C \leq 8)}$;

$X_2$ and $X_3$ are each independently selected from —O—, —S—, or —NR$_{19}$—, wherein:

$R_{19}$ is hydrogen, alkyl$_{(C \leq 6)}$, or -substituted alkyl$_{(C \leq 6)}$;

$R_6$ is aryl$_{(C \leq 18)}$, heteroaryl$_{(C \leq 18)}$, or a substituted version of either of these groups;

$R_7$ is alkyl$_{(C \leq 12)}$ or substituted alkyl$_{(C \leq 12)}$;

comprising reacting a compound of the formula:

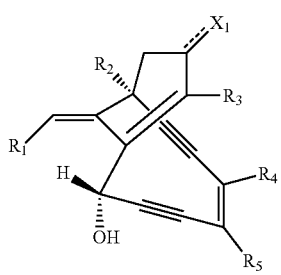

(IX)

wherein:

$X_1$, $R_1$, $R_2$, $R_3$, $R_4$, and $R_5$ are as defined above;

with a compound of the formula:

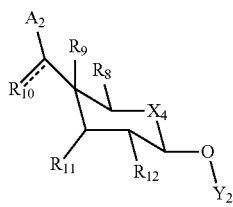

(X)

wherein:

$X_4$, $A_2$, $R_8$, $R_9$, $R_{10}$, $R_{11}$, and $R_{12}$ are as defined above; and $Y_2$ is hydrogen or an activating group; or with a compound of the formula:

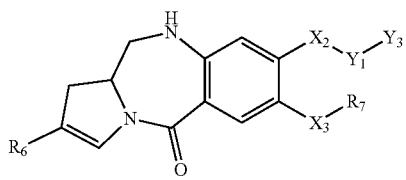

(XI)

wherein:

$Y_1$, $X_2$, $X_3$, $R_6$, and $R_7$ are as defined above; and $Y_3$ is a leaving group;

with a compound of the formula: $Y_4$-alkanediyl$_{(C \leq 12)}$-C(O)-A$_2$ or $Y_4$-substituted alkanediyl$_{(C \leq 12)}$-C(O)-A$_2$;

wherein:

$Y_4$ is a leaving group;

in the presence of a Lewis acid.

In some embodiments, the compound is further defined as:

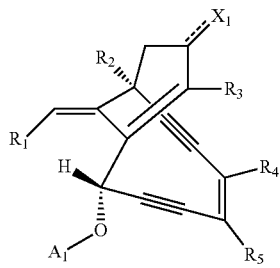

(I)

wherein:

$R_1$ is -alkanediyl$_{(C \leq 8)}$-(S)$_x$-A$_3$ or -substituted alkanediyl$_{(C \leq 8)}$-(S)$_x$-A$_3$; wherein:

$A_3$ is hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, heteroaryl$_{(C \leq 12)}$, aralkyl$_{(C \leq 12)}$, acyl$_{(C \leq 12)}$, or a substituted version of any of these groups; and x is 1, 2, or 3;

$R_2$ is hydroxy, or alkoxy$_{(C \leq 8)}$, acyloxy$_{(C \leq 8)}$, or -substituted version of either of these groups, or a protected hydroxy group;

$R_3$ is NHC(Y$_2$)R$_{16}$, wherein:

$Y_2$ is O, NH, or NOH; and $R_{16}$ is alkoxy$_{(C \leq 8)}$, alkylamino$_{(C \leq 8)}$, dialkylamino$_{(C \leq 8)}$, or -substituted version of any of these groups;

$R_4$ and $R_5$ are each independently selected from hydrogen and halo;

$X_1$ is O, S, or NH, or $X_1$ is a protected carbonyl wherein the protected carbonyl is a group of the formula —O(CH$_2$)$_c$O—, wherein c is 1, 2, 3, or 4;

$A_1$ is -alkanediyl$_{(C \leq 12)}$-C(O)-A$_2$ or -substituted alkanediyl$_{(C \leq 12)}$-C(O)-A$_2$; or $A_1$ is:

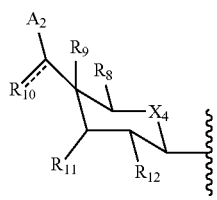

wherein:

$X_4$ is —CH$_2$— or —O—;

$R_8$ is hydrogen, alkyl$_{(C \leq 8)}$, cycloalkyl$_{(C \leq 8)}$, substituted alkyl$_{(C \leq 8)}$, or -substituted cycloalkyl$_{(C \leq 8)}$;

$R_9$ is hydrogen, hydroxy, mercapto, alkoxy$_{(C \leq 8)}$, substituted alkoxy$_{(C \leq 8)}$, alkylthio$_{(C \leq 8)}$, substituted alkylthio$_{(C \leq 8)}$, or a protected hydroxy group or a protected thiol group;

$R_{10}$ is oxo or $R_{10}$ is taken together with $R_{11}$ and is —OCHA$_4$O—; provided that when $R_{10}$ is oxo then $R_{10}$ and the carbon atom to which it is bound are joined by a double bond, and when $R_{10}$ is taken together with $R_{11}$ then $R_{10}$ and the carbon atom to which it is bound are joined by a single bond;
wherein $A_4$ is aryl$_{(C\leq12)}$ or substituted aryl$_{(C\leq12)}$, or

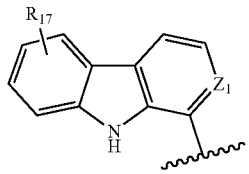

wherein:
$Z_1$ is CH or N; and
$R_{17}$ is hydrogen, hydroxy, amino, hydrazino, carboxy, halo, or nitro; or alkyl$_{(C\leq12)}$, alkoxy$_{(C\leq12)}$, or a substituted version of either of these groups;
$R_{11}$ is hydrogen, hydroxy, alkoxy$_{(C\leq8)}$, or substituted alkoxy$_{(C\leq8)}$, or a protected hydroxy group;
$R_{12}$ is hydrogen, hydroxy, alkoxy$_{(C\leq8)}$, substituted alkoxy$_{(C\leq8)}$, or a protected hydroxy group, or
—O-alkanediyl$_{(C\leq8)}$-alkylamino$_{(C\leq12)}$, —OC(O)-alkanediyl$_{(C\leq8)}$-alkylamino$_{(C\leq12)}$, or —OC(O)NH-alkanediyl$_{(C\leq8)}$-alkylamino$_{(C\leq12)}$, or a substituted version of any of these groups; or

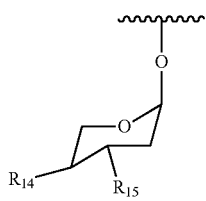

wherein:
$R_{14}$ is amino or hydroxy; or alkoxy$_{(C\leq12)}$, alkylamino$_{(C\leq12)}$, dialkyl-amino$_{(C\leq12)}$, or a substituted version of any of these groups, or a protected amino or hydroxy group;
$R_{15}$ is hydrogen, hydroxy, alkoxy$_{(C\leq8)}$, or substituted alkoxy$_{(C\leq8)}$, or a protected hydroxy group;
$A_2$ is hydrogen or

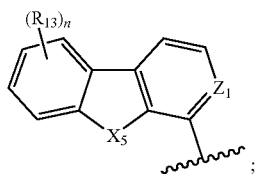

wherein:
$X_5$ is O, S, or NR$_{18}$; wherein:
$R_{18}$ is hydrogen, alkyl$_{(C\leq8)}$, substituted alkyl$_{(C\leq8)}$, acyl$_{(C\leq8)}$, or -substituted acyl$_{(C\leq8)}$, or;
n is 1, 2, 3, or 4;
$Z_2$ is N or CH; and
$R_{13}$ is hydrogen, amino, carboxy, hydroxy, hydrazino, halo, or nitro;
alkyl$_{(C\leq12)}$, acyl$_{(C\leq12)}$, alkoxy$_{(C\leq12)}$, acyloxy$_{(C\leq12)}$, or a substituted version of either of these groups, or a protected thiol, amino, or hydroxy group; or $A_1$ is

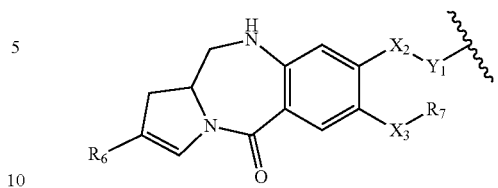

wherein:
$Y_1$ is alkanediyl$_{(C\leq8)}$ or substituted alkanediyl$_{(C\leq8)}$;
$X_2$ and $X_3$ are each independently selected from —O—, —S—, or —NR$_{19}$—, wherein:
$R_{19}$ is hydrogen, alkyl$_{(C\leq6)}$, or -substituted alkyl$_{(C\leq6)}$;
$R_6$ is aryl$_{(C\leq18)}$, heteroaryl$_{(C\leq18)}$, or a substituted version of either of these groups;
$R_7$ is alkyl$_{(C\leq12)}$ or substituted alkyl$_{(C\leq12)}$;
comprising reacting a compound of the formula:

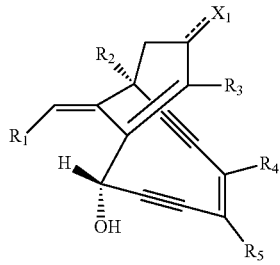

(IX)

wherein:
$X_1$, $R_1$, $R_2$, $R_3$, $R_4$, and $R_5$ are as defined above;
with a compound of the formula:

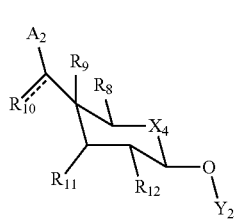

(X)

wherein:
$X_4$, $A_2$, $R_8$, $R_9$, $R_{10}$, $R_{11}$, and $R_{12}$ are as defined above; and
$Y_2$ is hydrogen or an activating group; or
with a compound of the formula:

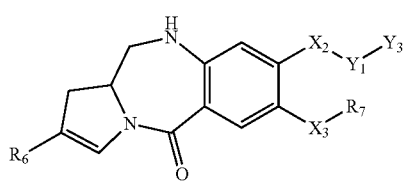

(XI)

wherein:
$Y_1$, $X_2$, $X_3$, $R_6$, and $R_7$ are as defined above; and
$Y_3$ is a leaving group;
with a compound of the formula: $Y_4$-alkanediyl$_{(C\leq12)}$-C(O)-$A_2$ or $Y_4$-substituted alkanediyl$_{(C\leq12)}$-C(O)-$A_2$;

wherein:
$Y_4$ is a leaving group;
in the presence of a Lewis acid. In some embodiments, the Lewis acid is a boron compound. In some embodiments, the Lewis acid is boron trifluoride etherate. In some embodiments, the method further comprises one or more deprotection steps. In some embodiments, the method further comprises:
(A) deprotecting the $R_1$ group in the presence of a base to form the group: -alkanediyl$_{(C \leq 8)}$-SH or -substituted alkanediyl$_{(C \leq 8)}$-SH; and
(B) reacting the free mercapto group with a group of the formula:

$$R_{20}-(S)_y-R_{21} \quad \text{(XII)}$$

wherein:
$R_{20}$ is an activating group;
y is 1 or 2; and
$R_{21}$ is hydrogen, alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, heteroaryl$_{(C \leq 12)}$, aralkyl$_{(C \leq 12)}$, acyl$_{(C \leq 12)}$, or a substituted version of any of these groups;
to form a compound of formula I, wherein $R_1$ is:
-alkanediyl$_{(C \leq 8)}$-$(S)_x$-$A_3$ or -substituted alkanediyl$_{(C \leq 8)}$-$(S)_x$-$A_3$; wherein:
$A_3$ is hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, heteroaryl$_{(C \leq 12)}$, aralkyl$_{(C \leq 12)}$, acyl$_{(C \leq 12)}$, or a substituted version of any of these groups; and
x is 2 or 3.
In some embodiments, the activating group is a phthalimide group. In some embodiments, the method comprises one or more deprotection steps.

In yet another aspect, the present disclosure provides methods of preparing a compound of the formula:

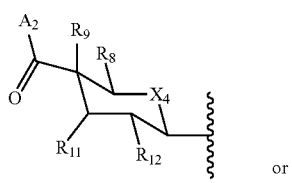
(XIIA)

or

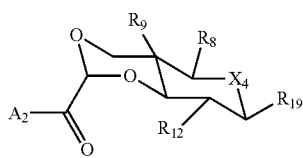
(XIIB)

wherein:
$X_4$ is —CH$_2$— or —O—;
$R_8$ is hydrogen, alkyl$_{(C \leq 8)}$, substituted alkyl$_{(C \leq 8)}$, cycloalkyl$_{(C \leq 8)}$, or -substituted cycloalkyl$_{(C \leq 8)}$;
$R_9$ is hydrogen, halo, hydroxy, mercapto, alkyl$_{(C \leq 8)}$, substituted alkyl$_{(C \leq 8)}$, alkoxy$_{(C \leq 8)}$, substituted alkoxy$_{(C \leq 8)}$, alkylthio$_{(C \leq 8)}$, substituted alkylthio$_{(C \leq 8)}$, or a protected hydroxy group or a protected thiol group;
$R_{11}$ is hydrogen, hydroxy, alkoxy$_{(C \leq 8)}$, or -substituted alkoxy$_{(C \leq 8)}$, or a protected hydroxy group;
$R_{12}$ is hydrogen, hydroxy, alkoxy$_{(C \leq 8)}$, substituted alkoxy$_{(C \leq 8)}$, or a protected hydroxy group, or —O-alkanediyl$_{(C \leq 8)}$-alkylamino$_{(C \leq 12)}$, —OC(O)-alkanediyl$_{(C \leq 8)}$-alkylamino$_{(C \leq 12)}$, or —OC(O)NH-alkanediyl$_{(C \leq 8)}$-alkylamino$_{(C \leq 12)}$, or a substituted version of any of these groups; or

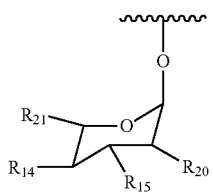

wherein:
$R_{14}$ is amino or hydroxy; or alkoxy$_{(C \leq 12)}$, alkylamino$_{(C \leq 12)}$, dialkyl-amino$_{(C \leq 12)}$, or a substituted version of any of these groups, or —NR$_a$R$_b$, wherein:
$R_a$ and $R_b$ are each hydrogen, alkyl$_{(C \leq 12)}$, substituted alkyl$_{(C \leq 12)}$, alkenyl$_{(C \leq 12)}$, substituted alkenyl$_{(C \leq 12)}$, —C(O)O-alkanediyl$_{(C \leq 6)}$-$R_c$, —C(O)-alkanediyl$_{(C \leq 6)}$-$R_c$, -alkanediyl$_{(C \leq 6)}$-$R_c$, or a substituted version of either of these group; wherein:
$R_c$ is hydrogen, amino, carboxy, hydroxyl, acyl$_{(C \leq 8)}$, alkoxy$_{(C \leq 8)}$, alkylamino$_{(C \leq 8)}$, dialkylamino$_{(C \leq 8)}$, alkylsulfonyl$_{(C \leq 8)}$, arylsulfonyl$_{(C \leq 8)}$, or a substituted version of either of these groups; or
a protected amino or hydroxy group;
$R_{15}$ is hydrogen, hydroxy, alkoxy$_{(C \leq 8)}$, or substituted alkoxy$_{(C \leq 8)}$, or a protected hydroxy group;
$R_{20}$ and $R_{21}$ are hydrogen, alkyl$_{(C \leq 8)}$, substituted alkyl$_{(C \leq 8)}$, alkoxy$_{(C \leq 8)}$, or substituted alkoxy$_{(C \leq 8)}$;
$A_2$ is:

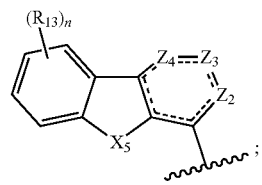

wherein:
$X_5$ is O, S, or NR$_{18}$; wherein:
$R_{18}$ is hydrogen, alkyl$_{(C \leq 8)}$, substituted alkyl$_{(C \leq 8)}$, acyl$_{(C \leq 8)}$, or -substituted acyl$_{(C \leq 8)}$;
n is 1, 2, 3, 4, or 5;
$Z_2$, $Z_3$, and $Z_4$ are each independently N or CR$_{13}$; and
$R_{13}$ is hydrogen, amino, carboxy, hydroxy, hydrazino, halo, or nitro;
alkyl$_{(C \leq 12)}$, acyl$_{(C \leq 12)}$, alkoxy$_{(C \leq 12)}$, acyloxy$_{(C \leq 12)}$, or a substituted version of either of these groups, or a protected thiol, amino, or hydroxy group;
comprising:
(A) reacting a compound of the formula:

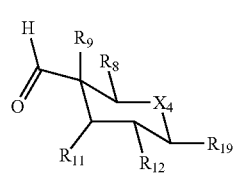
(XIIIA)

wherein:
$X_4$, $R_8$, $R_9$, $R_{10}$, $R_{11}$, and $R_{12}$ are as defined above; and
$R_{19}$ is hydroxy or a protected hydroxy group; or a compound of the formula:

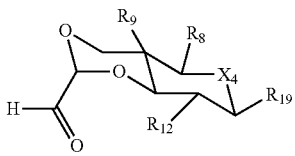
(XIIIB)

wherein:
$X_4$, $R_8$, $R_9$, $R_{10}$, $R_{11}$, and $R_{12}$ are as defined above; and
$R_{19}$ is hydroxy or a protected hydroxy group;
with a compound of the formula:

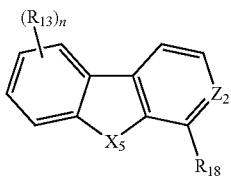
(XIV)

wherein:
$X_5$, n, $Z_2$, and $R_{13}$ are as defined above; and
$R_{18}$ is a halo group;
in the presence of an organolithium reagent to form a compound of the formula;

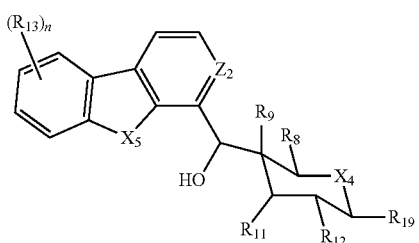
(XVA)

or

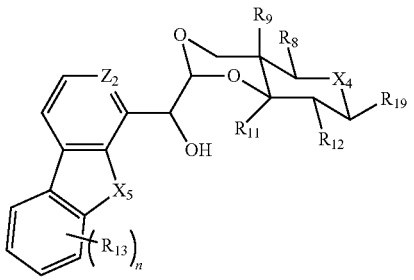
(XVB)

wherein:
n, $X_4$, $X_5$, $Z_2$, $R_8$, $R_9$, $R_{11}$, $R_{12}$, $R_{13}$, and $R_{19}$;
(B) reacting the compound of formulas (XVA or XVB) in the presence of an oxidizing agent to the compound of formulas XIIA or XIIB.

In some embodiments, the compounds are further defined as:

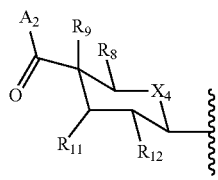
(XIIA)

or

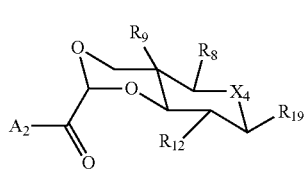
(XIIB)

wherein:
$X_4$ is —CH$_2$— or —O—;
$R_8$ is hydrogen, alkyl$_{(C\leq 8)}$, or substituted alkyl$_{(C\leq 8)}$;
$R_9$ is hydrogen, hydroxy, mercapto, alkoxy$_{(C\leq 8)}$, substituted alkoxy$_{(C\leq 8)}$, alkylthio$_{(C\leq 8)}$, substituted alkylthio$_{(C\leq 8)}$, or a protected hydroxy group or a protected thiol group;
$R_{11}$ is hydrogen, hydroxy, alkoxy$_{(C\leq 8)}$, or substituted alkoxy$_{(C\leq 8)}$, or a protected hydroxy group;
$R_{12}$ is hydrogen, hydroxy, alkoxy$_{(C\leq 8)}$, substituted alkoxy$_{(C\leq 8)}$, or a protected hydroxy group, or —O-alkanediyl$_{(C\leq 8)}$-alkylamino$_{(C\leq 12)}$, —OC(O)-alkanediyl$_{(C\leq 12)}$-alkylamino$_{(C\leq 12)}$, or —OC(O)NH-alkanediyl$_{(C\leq 8)}$-alkylamino$_{(C\leq 12)}$, or a substituted version of any of these groups; or

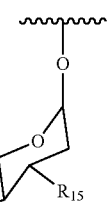

wherein:
$R_{14}$ is amino or hydroxy; or alkoxy$_{(C\leq 12)}$, alkylamino$_{(C\leq 12)}$, dialkyl-amino$_{(C\leq 12)}$, or a substituted version of any of these groups, or a protected amino or hydroxy group;
$R_{15}$ is hydrogen, hydroxy, alkoxy$_{(C\leq 8)}$, or substituted alkoxy$_{(C\leq 8)}$, or a protected hydroxy group;
$A_2$ is:

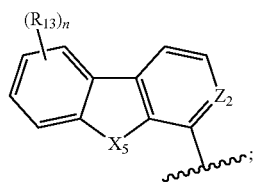

wherein:
$X_5$ is O, S, or NR$_{18}$; wherein:
$R_{18}$ is hydrogen, alkyl$_{(C\leq 8)}$, substituted alkyl$_{(C\leq 8)}$, acyl$_{(C\leq 8)}$, or substituted acyl$_{(C\leq 8)}$;
n is 1, 2, 3, or 4;
$Z_2$ is N or CH; and $R_{13}$ is hydrogen, amino, carboxy, hydroxy, hydrazino, halo, or nitro;

alkyl$_{(C\le12)}$, acyl$_{(C\le12)}$, alkoxy$_{(C\le12)}$, acyloxy$_{(C\le12)}$, or a substituted version of either of these groups, or a protected thiol, amino, or hydroxy group;

comprising:

(A) reacting a compound of the formula:

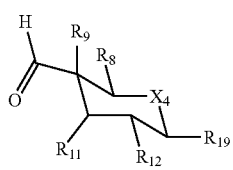
(XIIIA)

wherein:
$X_4$, $R_8$, $R_9$, $R_{10}$, $R_{11}$, and $R_{12}$ are as defined above; and
$R_{19}$ is hydroxy or a protected hydroxy group; or a compound of the formula:

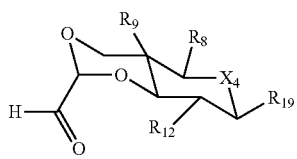
(XIIIB)

wherein:
$X_4$, $R_8$, $R_9$, $R_{10}$, $R_{11}$, and $R_{12}$ are as defined above; and
$R_{19}$ is hydroxy or a protected hydroxy group;

with a compound of the formula:

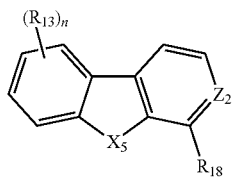
(XIV)

wherein:
$X_5$, n, $Z_2$, and $R_{13}$ are as defined above; and
$R_{18}$ is a halo group;

in the presence of an organolithium reagent to form a compound of the formula;

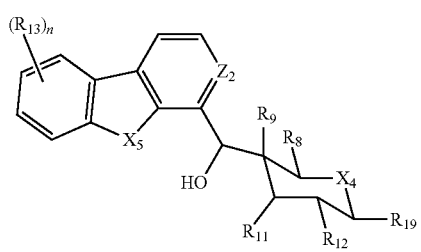
(XVA)

or

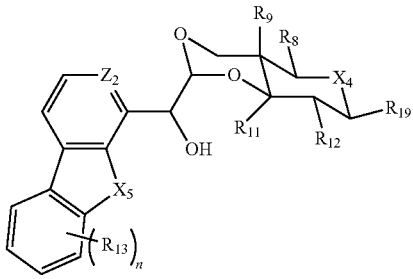
(XVB)

wherein:
n, $X_4$, $X_5$, $Z_2$, $R_8$, $R_9$, $R_{11}$, $R_{12}$, $R_{13}$, and $R_{19}$;

(B) reacting the compound of formulas (XVA or XVB) in the presence of an oxidizing agent to the compound of formulas XIIA or XIIB.

In some embodiments, the organolithium reagent is a butyllithium. In some embodiments, the organolithium reagent is t-butyllithium. In some embodiments, the compound of formula XIV is added before the compound of formula XIII. In some embodiments, the oxidizing agent is a hypervalent iodide reagent. In some embodiments, the oxidizing agent is Dess-Martin periodinane. In some embodiments, the method comprises one or more deprotection steps.

In still yet another aspect, the present disclosure provides methods of preparing a compound of the formula:

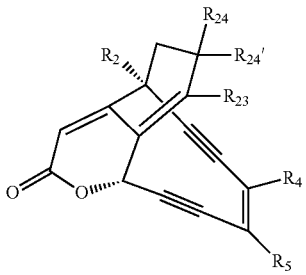
(XVI)

wherein:
$R_2$ is hydroxy, or alkoxy$_{(C\le8)}$, acyloxy$_{(C\le8)}$, or -substituted version of either of these groups, or a protected hydroxyl group;

$R_{23}$ is a divalently protected amino group; and $R_{24}$ and $R_{24}'$ are a group of the formula —O(CH$_2$)$_e$O—, wherein e is 1, 2, 3, or 4, or $R_{24}$ and $R_{24}'$ are taken together and are an oxo group; provided that when $R_{24}$ and $R_{24}'$ are taken together then the atom to which they are bound is part of a double bond and when the atom to which $R_{24}$ and $R_{24}'$ are bound then $R_{24}$ and $R_{24}'$ are oxo;

$R_4$ and $R_5$ are each independently selected from hydrogen and halo;

comprising:

(A) reacting a compound of the formula:

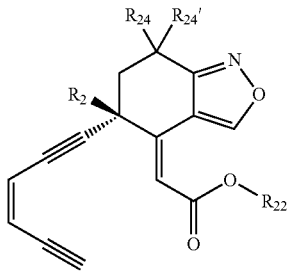
(XVII)

wherein:
R$_2$, R$_{24}$, and R$_{24}$' are as defined above; and
R$_{22}$ is alkyl$_{(C≤8)}$ or substituted alkyl$_{(C≤8)}$;

in the presence of an iron source and a protonated amine and followed by a divalent amine protecting agent to form a compound of the formula:

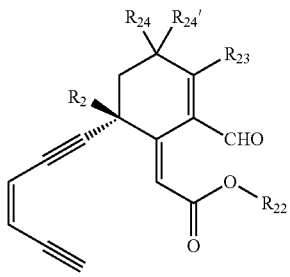
(XVIII)

wherein:
R$_2$, R$_{22}$, R$_{24}$, and R$_{24}$' are as defined above; and
R$_{23}$ is a divalently protected amino group;

(B) reacting the compound of the formula XVIII with a strong base in the presence of a Lewis acid to obtain a compound of the formula XVI.

In some embodiments, the iron source is metallic iron. In some embodiments, the protonated amine is a primary protonated amine. In some embodiments, the protonated amine is ammonium chloride. In some embodiments, the divalent amine protecting agent is phthaloyl chloride. In some embodiments, the strong base is a disilylamide. In some embodiments, the strong base is lithium bis(trimethylsilyl)amide. In some embodiments, the Lewis acid is a mixture of two or more metal salts. In some embodiments, the Lewis acid comprises a mixture of a first metal salt and a second metal salt. In some embodiments, the first metal salt is a lanthanum salt. In some embodiments, the first metal salt is LaCl$_3$. In some embodiments, the second metal salt is a lithium salt. In some embodiments, the second metal salt is lithium chloride. In some embodiments, the first metal salt and the second metal salt are present in a ratio from about 1:4 to about 4:1. In some embodiments, the ratio of the first metal salt to the second metal salt is 1:2. In some embodiments, the method further comprises one or more deprotection steps.

In yet another aspect, the present disclosure provides methods of preparing a compound of the formula:

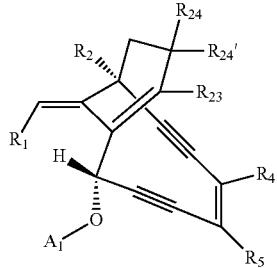
(XIX)

wherein:
R$_1$ is -alkanediyl$_{(C≤8)}$-(S)$_x$-A$_3$ or -substituted alkanediyl$_{(C≤8)}$-(S)$_x$-A$_3$; wherein:
A$_3$ is hydrogen or alkyl$_{(C≤12)}$, alkenyl$_{(C≤12)}$, alkynyl$_{(C≤12)}$, aryl$_{(C≤12)}$, heteroaryl$_{(C≤12)}$, aralkyl$_{(C≤12)}$, acyl$_{(C≤12)}$, or a substituted version of any of these groups; and
x is 1, 2, or 3;

R$_2$ is hydroxy, or alkoxy$_{(C≤8)}$, acyloxy$_{(C≤8)}$, or -substituted version of either of these groups, or a protected hydroxy group;

R$_3$ is NHC(Y$_2$)R$_{16}$, wherein:
Y$_2$ is O, NH, or NOH; and
R$_{16}$ is alkoxy$_{(C≤8)}$, alkylamino$_{(C≤8)}$, dialkylamino$_{(C≤8)}$, or substituted version of any of these groups;

R$_4$ and R$_5$ are each independently selected from hydrogen and halo; and

R$_{24}$ and R$_{24}$' are a group of the formula —O(CH$_2$)$_e$O—, wherein e is 1, 2, 3, or 4, or R$_{24}$ and R$_{24}$' are taken together and are an oxo group; provided that when R$_{24}$ and R$_{24}$' are taken together then the atom to which they are bound is part of a double bond and when the atom to which R$_{24}$ and R$_{24}$' are bound then R$_{24}$ and R$_{24}$' are oxo;

A$_1$ is hydrogen or a hydroxy protecting group;

comprising the following steps:

(A) reacting a compound of the formula:

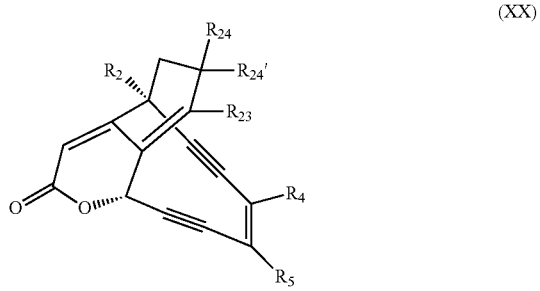
(XX)

wherein: X$_1$, R$_2$, R$_3$, R$_4$, R$_5$, R$_{24}$, and R$_{24}$' are as defined herein;

with a reducing agent in the presence of a transition metal additive to form a compound of the formula:

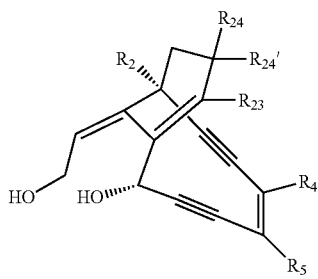

(XXI)

wherein: $X_1$, $R_2$, $R_3$, $R_4$, $R_5$, $R_{24}$, and $R_{24}'$ are as defined herein;

(B) reacting the compound of formula XXI with an activating agent to form a compound of the formula:

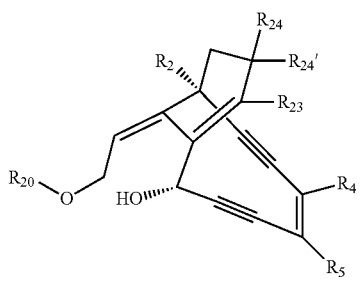

(XXIII)

wherein: $X_1$, $R_2$, $R_3$, $R_4$, $R_5$, $R_{24}$, and $R_{24}'$ are as defined herein; and $R_{20}$ is a leaving group; and (C) reacting the compound of the formula XXIII with a compound of the formula: $HSR_{21}$, wherein $R_{21}$ is alkyl$_{(C≤12)}$, alkenyl$_{(C≤12)}$, alkynyl$_{(C≤12)}$, aryl$_{(C≤12)}$, heteroaryl$_{(C≤12)}$, aralkyl$_{(C≤12)}$, acyl$_{(C≤12)}$, or a substituted version of any of these groups in the presence of a phosphine$_{(C≤24)}$ and an azo compound to form a compound of the formula XIX.

In some embodiments, the reducing agent is a boron compound. In some embodiments, the reducing agent is sodium borohydride. In some embodiments, the transition metal additive is lanthanide. In some embodiments, the transition metal additive is a cerium compound. In some embodiments, the transition metal additive is $CeCl_3$ or a hydrate thereof. In some embodiments, the transition metal additive is $CeCl_3 \cdot 7H_2O$. In some embodiments, the activating agent is trimethylsilyl cyanide. In some embodiments, $R_{21}$ is acyl$_{(C≤12)}$ or substituted acyl$_{(C≤12)}$. In some embodiments, $R_{21}$ is acetyl. In some embodiments, $H_3CC(O)SH$. In some embodiments, the phosphine$_{(C≤24)}$ is triphenyl phosphine. In some embodiments, the azo compound is diethyl azodicarboxylate or diisopropyl azodicarboxylate. In some embodiments, the azo compound is diethyl azodicarboxylate.

In still yet another aspect, the present disclosure provides methods of preparing a compound of the formula:

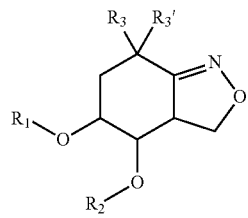

(XXIV)

wherein:
$R_1$ and $R_2$ are hydrogen or a hydroxy protecting group;
$R_3$ and $R_3'$ are a group of the formula $-O(CH_2)_eO-$, wherein e is 1, 2, 3, or 4, or $R_3$ and $R_3'$ are taken together and are an oxo group; provided that when $R_3$ and $R_3'$ are taken together then the atom to which they are bound is part of a double bond and when the atom to which $R_3$ and $R_3'$ are bound then $R_3$ and $R_3'$ are oxo;
comprising reacting a compound of the formula:

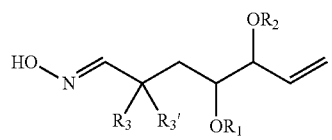

(XXV)

wherein: $R_1$, $R_2$, $R_3$, and $R_3'$ are as defined above;
in the presence of a compound of the formula $R_4OCl$ in a hydrocarbon$_{(C≤12)}$ solvent;
wherein:
$R_4$ is alkyl$_{(C≤8)}$ or a substituted alkyl$_{(C≤8)}$;
to form a compound of the formula XXV.

In some embodiments, $R_4$ is alkyl$_{(C≤8)}$. In some embodiments, $R_4$ is t-butyl. In some embodiments, the hydrocarbon$_{(C≤12)}$ solvent is an aromatic solvent$_{(C≤12)}$. In some embodiments, the hydrocarbon$_{(C≤12)}$ solvent is benzene.

In still yet another aspect, the present disclosure provides a method of preparing a compound of the formula:

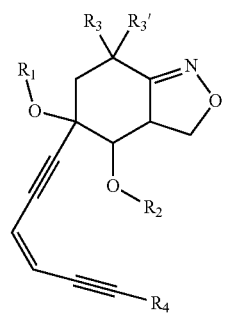

(XXVI)

wherein:
$R_1$ and $R_2$ are hydrogen or a hydroxy protecting group;
$R_3$ and $R_3'$ are a group of the formula $-O(CH_2)_eO-$, wherein e is 1, 2, 3, or 4, or $R_3$ and $R_3'$ are taken together and are an oxo group; provided that when $R_3$ and $R_3'$ are taken together then the atom to which they are bound is part of a double bond and when the atom to which $R_3$ and $R_3'$ are bound then $R_3$ and $R_3'$ are oxo;
$R_4$ is hydrogen, alkylsilyl$_{(C≤12)}$, or substituted alkylsilyl$_{(C≤12)}$;

comprising reacting a compound of the formula:

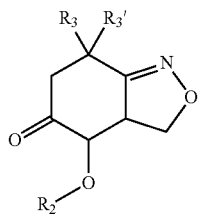

(XXVII)

wherein: $R_2$, $R_3$, and $R_3'$ are as defined above;
with a compound of the formula:

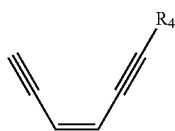

(XXVIII)

wherein: $R_4$ is as defined above;
in the presence of an organolithium compound and a metal salt followed by the addition of a electrophilic compound.

In some embodiments, the organolithium compound is a strong lithium base. In some embodiments, the organolithium compound is lithium bis(trimethylsilyl)amide. In some embodiments, the metal salt is a mixture of metal salt. In some embodiments, the mixture of metal salt is a first metal salt or a second metal salt. In some embodiments, the first metal salt is a lanthanide metal salt. In some embodiments, the first metal salt is $LaCl_3$. In some embodiments, the second metal salt is a lithium salt. In some embodiments, the second metal salt is lithium chloride. In some embodiments, the electrophilic compound is water. In other embodiments, the electrophilic compound is a diacyl$_{(C \leq 18)}$ anhydride. In some embodiments, the electrophilic compound is acetic anhydride.

In some embodiments, the method further comprises one or more deprotection steps. In still other embodiments, the method further comprises one or more purification steps.

It is contemplated that any method or composition described herein can be implemented with respect to any other method or composition described herein. For example, a compound synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description.

FIGS. 2A-2C—Plot of the cytotoxicity of shishijimicin A and analogs on MES SA cells (FIG. 2A), MES DX cells (FIG. 2B), and 293T cells (FIG. 2C).

DESCRIPTION OF ILLUSTRATIVE EMBODIMENTS

Figure 1:
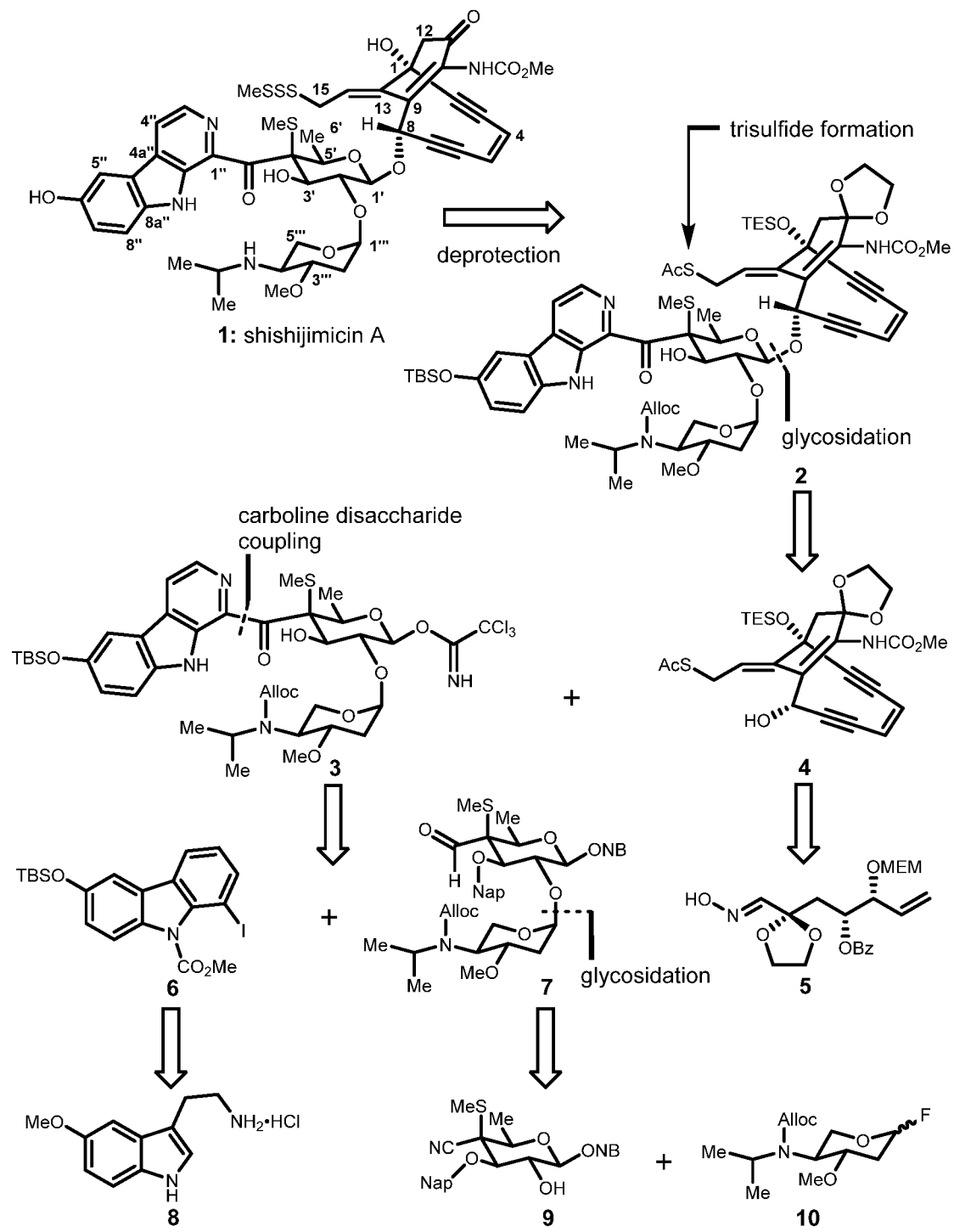
FIG. 1—Retrosynthesis of Shishijimicin A. TBS=t-butyldimethylsilyl; TES=triethylsilyl; Ac=acetyl; Alloc=allyloxycarbonyl; Bz=benzoyl; MEM=(2-methoxyethoxy)methyl; Nap=2-naphthylmethyl; NB=o-nitrobenzyl.
Figures 3A, 3B, 3C:
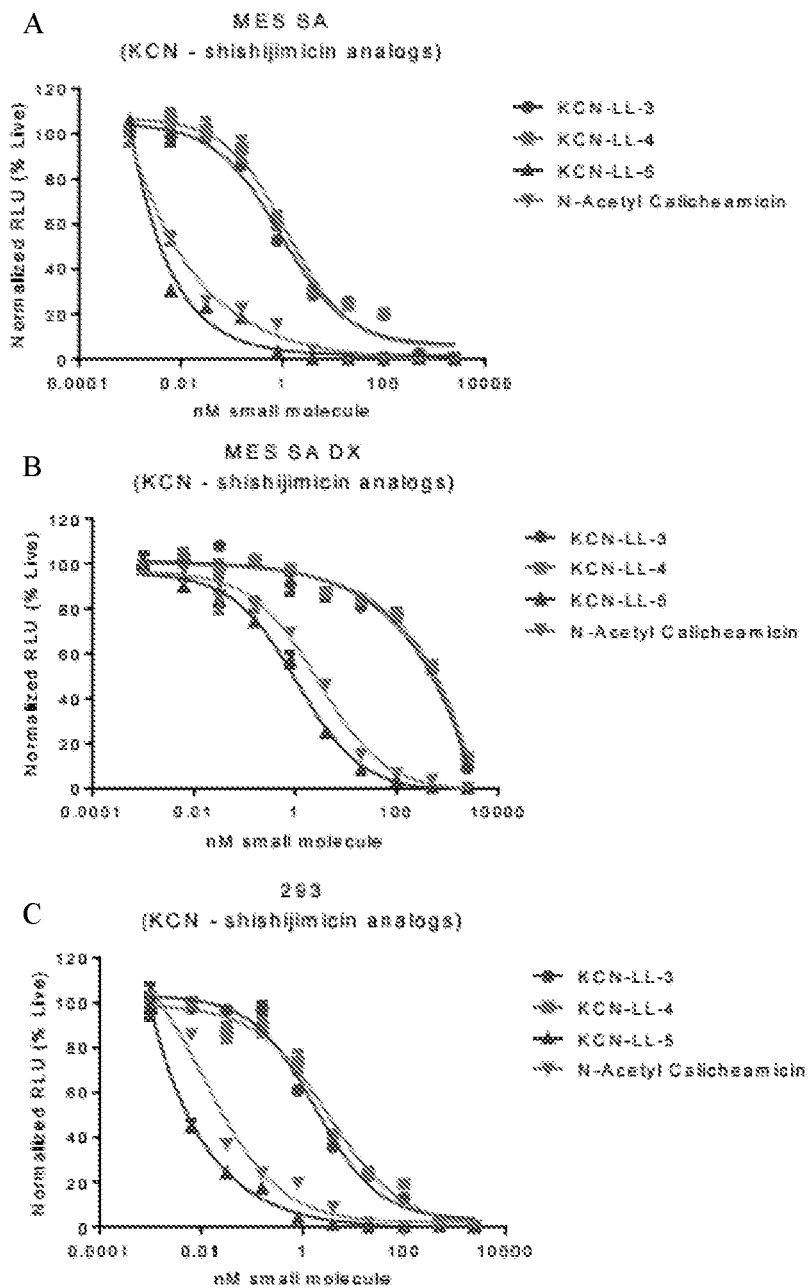
FIGS. 3A-3C—Plot of the cytotoxicity of shishijimicin A analogs (KCN-LL-3, KCN-LL-4, and KCN-LL-5 with positive control, N-acetyl calicheamicin) on MES SA cells (FIG. 3A), MES DX cells (FIG. 3B), and 293T cells (FIG. 3C).
Figures 4A, 4B, 4C:
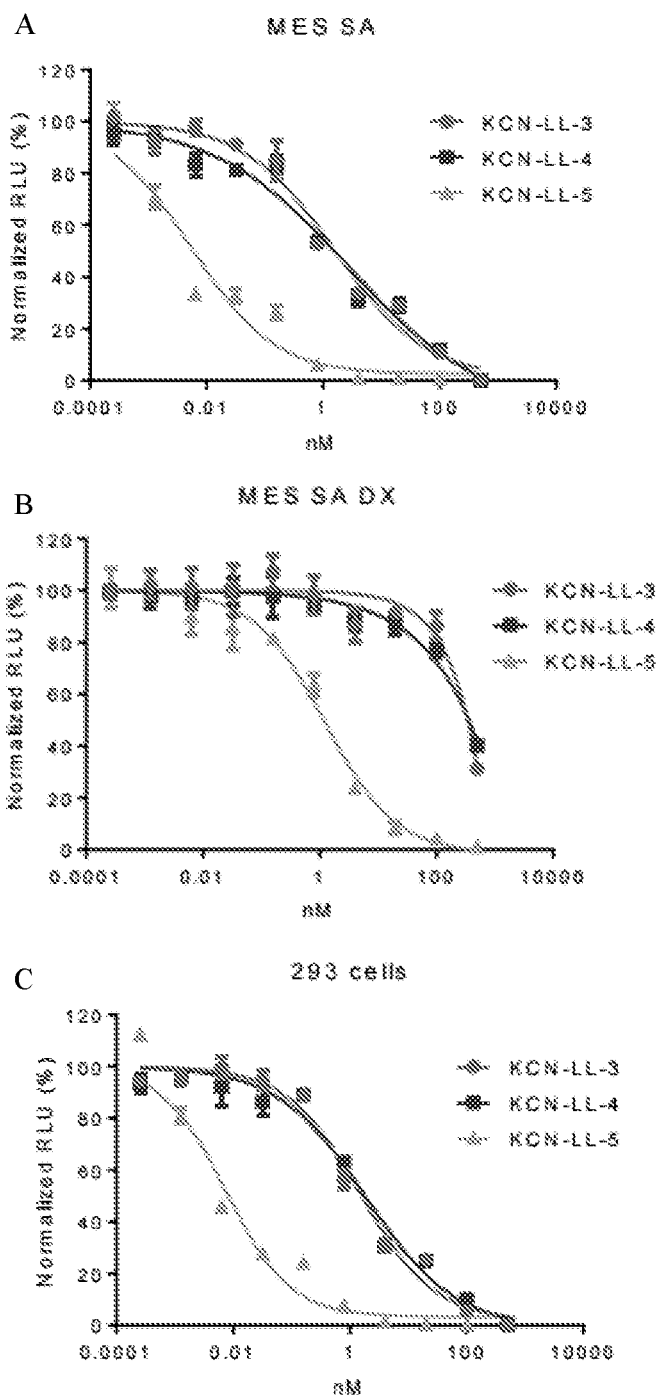
FIGS. 4A-4C—Plot of the cytotoxicity of shishijimicin analogs (KCN-LL-3, KCN-LL-4, and KCN-LL-5) on MES SA cells (FIG. 4A), MES DX cells (FIG. 4B), and 293T cells (FIG. 4C).

The present disclosure relates to new analogs of shishijimicin useful for the treatment of cancer or another hyperproliferative disease. In some embodiments, the trisulfur moiety has been replaced with a disulfide. In some embodiments, these compounds are used in antibody drug conjugates which may be useful for the treatment of cancer.

I. COMPOUNDS AND FORMULATIONS THEREOF

A. Compounds

The compounds provided by the present disclosure are shown, for example, above in the summary of the invention section and in the examples and claims below. They may be made using the methods outlined in the Examples section. The shishijimicin analogs described herein can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The shishijimicin analogs described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent the shishijimicin analogs described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The shishijimicin analogs described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the shishijimicin analogs described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The shishijimicin analogs described herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the invention contemplates prodrugs of compounds of the present invention as well as methods of delivering prodrugs. Prodrugs of the shishijimicin analogs described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the shishijimicin analogs described herein are within the scope of the invention. It will also be appreciated by those skilled in organic chemistry that many organic compounds can exist in more than one crystalline form. For example, crystalline form may vary from solvate to solvate. Thus, all crystalline forms of the shishijimicin analogs described herein are within the scope of the present invention.

B. Formulations

In some embodiments of the present disclosure, the compounds are included a pharmaceutical formulation. Materials for use in the preparation of microspheres and/or microcapsules are, e.g., biodegradable/bioerodible polymers such as polygalactia, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the shishijimicin analogs described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. CANCER AND OTHER HYPERPROLIFERATIVE DISEASES

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the shishijimicin analogs described herein may be used to lead to decreased cell counts and as such can potentially be used to treat a variety of types of cancer lines. In some aspects, it is anticipated that the shishijimicin analogs described herein may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; in situ pulmonary adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; me sonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. CELL TARGETING MOIETIES

In some aspects, the present disclosure provides compounds conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. For instance, a cell targeting moiety according the embodiments may bind to a liver cancer cell such as a Hep3B cell. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example is the cell targeting agents described in U.S. Patent Publication No. 2004/005647 and in Winthrop et al. (2003) that bind to MUC-1, an antigen that is expressed on a variety cancer types. Thus, it will be understood that in certain embodiments, cell targeting constructs according to the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used may include a cofactor, a sugar, a drug molecule, an imaging agent, or a fluorescent dye. Many cancerous cells are known to overexpress folate receptors and thus folic acid or other folate derivatives may be used as conjugates to trigger cell-specific interaction between the conjugates of the present disclosure and a cell (Campbell, et al., 1991; Weitman, et al., 1992).

Since a large number of cell surface receptors have been identified in hematopoietic cells of various lineages, ligands or antibodies specific for these receptors may be used as cell-specific targeting moieties. IL-2 may also be used as a cell-specific targeting moiety in a chimeric protein to target IL-2R+ cells. Alternatively, other molecules such as B7-1, B7-2 and CD40 may be used to specifically target activated T cells (The Leucocyte Antigen Facts Book, 1993, Barclay et al. (eds.), Academic Press). Furthermore, B cells express CD19, CD40 and IL-4 receptor and may be targeted by moieties that bind these receptors, such as CD40 ligand, IL-4, IL-5, IL-6 and CD28. The elimination of immune cells such as T cells and B cells is particularly useful in the treatment of lymphoid tumors.

Other cytokines that may be used to target specific cell subsets include the interleukins (IL-1 through IL-15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that binds to the Fn14 receptor, such as TWEAK (see, e.g., Winkles, 2008; Zhou et al., 2011 and Burkly et al., 2007, incorporated herein by reference).

A skilled artisan recognizes that there are a variety of known cytokines, including hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6, IL-4 (IFN-$\beta$2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-$\gamma$, IFN-$\alpha$, and IFN-$\beta$); immunoglobin superfamily (such as B7.1 (CD80), and B7.2 (B70, CD86)); TNF family (such as TNF-$\alpha$ (cachectin), TNF-$\beta$ (lymphotoxin, LT, LT-$\alpha$), LT-$\beta$, CD40 ligand (CD40L), Fas ligand (FasL), CD27 ligand (CD27L), CD30 ligand (CD30L), and 4-1BBL)); and those unassigned to a particular family (such as TGF-$\beta$, IL 1$\alpha$, IL-1$\beta$, IL-1 RA, IL-10 (cytokine synthesis inhibitor F), IL-12 (NK cell stimulatory factor), MIF, IL-16, IL-17 (mCTLA-8), and/or IL-18 (IGIF, interferon-$\gamma$ inducing factor)). Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used with the embodiments described herein are provided, for instance, in U.S. Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated against virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

Additionally, it is contemplated that the compounds described herein may be conjugated to a nanoparticle or other nanomaterial. Some non-limiting examples of nanoparticles include metal nanoparticles such as gold or silver nanoparticles or polymeric nanoparticles such as poly-L-lactic acid or poly (ethylene) glycol polymers. Nanoparticles and nanomaterials which may be conjugated to the instant compounds include those described in U.S. Patent Publications Nos. 2006/0034925, 2006/0115537, 2007/0148095, 2012/0141550, 2013/0138032, and 2014/0024610 and PCT Publication No. 2008/121949, 2011/053435, and 2014/087413, each incorporated herein by reference.

IV. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, intracranial, intrathecal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

For oral administration the shishijimicin analogs described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics Standards.

B. Methods of Treatment

In particular, the compositions that may be used in treating microbial infections and cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells or killing bacterial cells). Toxicity and therapeutic efficacy of the compositions utilized in methods of the invention can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that inhibits the growth or proliferation of a bacterial cell, inhibits the growth of a biofilm, or induces death of cancerous cells (e.g., induces apoptosis of a cancer cell), as assayed by identifying a reduction in hematological parameters (complete blood count—CBC), or cancer cell growth or proliferation. In some embodiments, amounts of the shishijimicin analogs used to inhibit bacterial growth or induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the derivatives of shishijimicin may be more efficacious and thus a smaller dose is required to achieve a similar effect. Such a dose is typically administered once a day for a few weeks or until sufficient reducing in cancer cells has been achieved.

The therapeutic methods of the invention (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the invention provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the shishijimicin analogs described herein may be used in combination therapies with one or more cancer therapies or a compound which mitigates one or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the shishijimicin analogs described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are also contemplated. The following is a general discussion of cancer therapies that may be used in combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin γ1 and calicheamicin ω1; dynemicin, including dynemicin A, uncialamycin and derivatives thereof; bisphosphonates, such as clodronate; an esperamicin; as well as neocarzinostatin chromophore and related chromoprotein enediyne antibiotic chromophores, aclacinomycins, actinomycin, anthramycin, azaserine, bleomycins, cactinomycin, carubicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozotocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosourea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabine, navelbine, farnesyl-protein tansferase inhibitors, transplatinum, 5-fluorouracil, vincristine, vinblastine and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurrence of the tumor. Additionally, the compounds of the present disclosure can also be used in a neoadjuvant setting.

5. Other Agents

It is contemplated that other agents may be used with the present invention. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

V. SYNTHETIC METHODS

In some aspects, the compounds of this invention can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of the shishijimicin analogs described herein.

B. Chemical Definitions

When used in the context of a chemical group: "hydrogen" means H; "hydroxy" means OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means N$_3$; "hydrazine" means —NHNH$_2$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "hydroxysulfonyl" means —SO$_3$H, "sulfonyl" means —S(O)$_2$—; and "sulfinyl" means —S(O)—.

In the context of chemical formulas, the symbol "—" means a single bond, "=" means a double bond, and "≡" means triple bond. The symbol "- - -" represents an optional bond, which if present is either single or double. The symbol "====" represents a single bond or a double bond. Thus, for example, the formula

includes

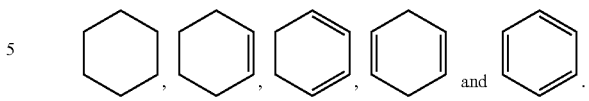

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⁓", when drawn perpendicularly across a bond (e.g.,

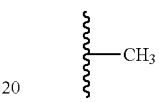

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⫿⫿⫿" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

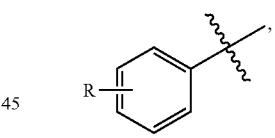

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

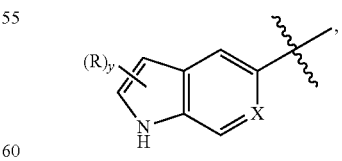

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C \leq 8)}$" or the class "alkene $_{(C \leq 8)}$" is two. For example, "alkoxy$_{(C \leq 10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, and —CH$_2$CH$_2$CH$_2$—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forms part of one or more non-aromatic ring structures, a cyclo or cyclic structure, no carbon-carbon double or triple bonds, and no atoms other than carbon and hydrogen. Non-limiting examples of cycloalkyl groups include: —CH(CH$_2$)$_2$ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, said carbon atom(s) forms part of one or more non-aromatic ring structures, a cyclo or cyclic structure, no carbon-carbon double or triple bonds, and no atoms other than carbon and hydrogen.

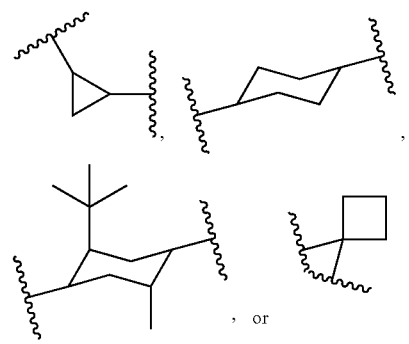

are non-limiting examples of cycloalkanediyl groups. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted cycloalkyl groups: —C(OH)(CH$_2$)$_2$,

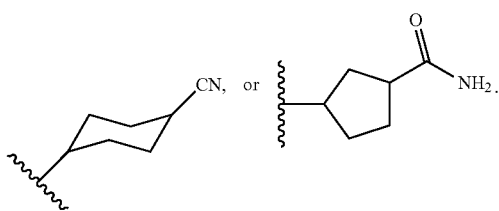 [SMILES: *C1CCC(C#N)CC1 ; *C1CCC(C(N)=O)C1]

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, and —CH=CHCH$_2$—, are non-limiting examples of alkenediyl groups. It is noted that while the alkenediyl group is aliphatic, once connected at both ends, this group is not precluded from forming part of an aromatic structure. The terms "alkene" and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, CH=CHF, CH=CHCl and CH=CHBr, are non-limiting examples of substituted alkenyl groups.

The term "alkynyl" when used without the "substituted" modifier refers to a monovalent unsaturated aliphatic group with a carbon atom as the point of attachment, a linear or branched, acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

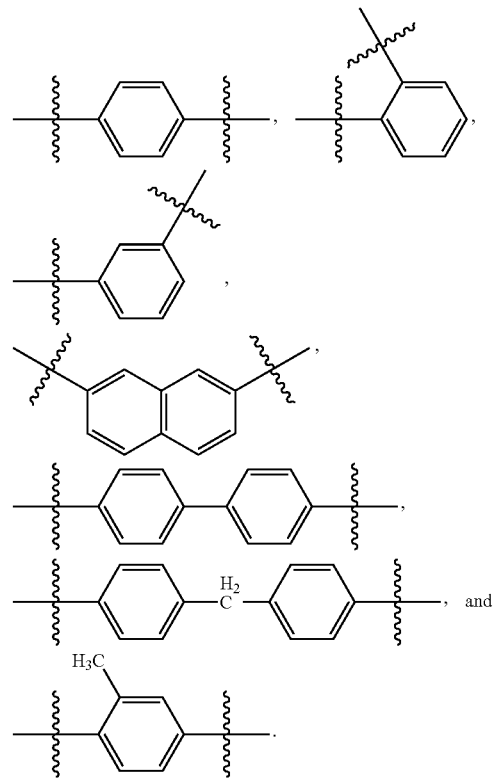

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl, isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. As the term is used herein, the term heteroaryl includes pyrimidine base and base analogs. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

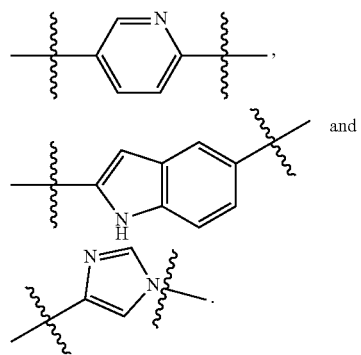

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R$_c$, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. An "anhydride" is a group of the formula ROR', wherein R and R' are acyl groups as defined above. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can each independently be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR$_c$, in which R is an alkyl, as that term is defined above. The term "alkylaminodiyl" refers to the divalent group —NH-alkanediyl-, —NH-alkanediyl-NH—, or -alkanediyl-NH-alkanediyl. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O, or -alkanediyl-O-alkanediyl-. The term "alkylthio" and "acylthio" when used without the "substituted" modifier refers to the group —SR, in which R is an alkyl and acyl, respectively. The term "alkylthiodiyl" refers to the divalent group —S-alkanediyl-, —S-alkanediyl-S, or -alkanediyl-S-alkanediyl-. The term "alcohol" corresponds to an alkane, as defined above, wherein at least one of the hydrogen atoms has been replaced with a hydroxy group. The term "ether" corresponds to an alkane or cycloalkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylsilyl" when used without the "substituted" modifier refers to the groups —SiR$_3$, respectively, in which each R is an alkyl, as that term is defined above. The terms "alkenylsilyl", "alkynylsilyl", "arylsilyl", "aralkylsilyl", "heteroarylsilyl", and "heterocycloalkylsilyl" are defined in an analogous manner. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The terms "phosphine" and "phosphane" are used synonymously herein. When used without the "substituted" modifier these terms refer to a compound of the formula PR$_3$, wherein each R is independently hydrogen, alkyl, cycloalkyl, alkenyl, aryl, or aralkyl, as those terms are defined above. Non-limiting examples include PMe$_3$, PPh$_3$, and PCy$_3$ (tricyclohexylphosphine). The terms "trialkylphosphine" and "trialkylphosphane" are also synonymous. Such groups are a subset of phosphine, wherein each R is an alkyl group. The term "diphosphine" when used without the "substituted" modifier refers to a compound of the formula R$_2$—P-L-P—R$_2$, wherein each R is independently hydrogen, alkyl, cycloalkyl, alkenyl, aryl, or aralkyl, and wherein L is -alkanediyl, cycloalkanediyl, alkenediyl, or arenediyl. When any of these terms is used with the "substituted" modifier one or more hydrogen atom attached to a carbon atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting. As used herein the term antibody also encompasses an antibody fragment such as a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. An oxygen linked antibody is an antibody which has a chemical function group such that the linkage between the antibody and the linker or compound is joined via an oxygen atom. Similarly, a nitrogen linked antibody is an antibody which has a chemical function group such that the linkage between the antibody and the linker or compound is joined via an nitrogen atom.

An "activating agent" in the context of this application is a reagent which enhances the reactivity of the compound. In some embodiments, an activating agent is a compound or complex which introduces a leaving group thus converting a group which has little to no reactivity into a reactive group which can be displaced through a displacement reaction. Some non-limiting examples of activating agents include dicarboxylates, cyanide containing compounds carbonyl diimidazole, dicyclohexylcarbodiimide, 2-methyl-6-nitrobenzoic anhydride, or a benzotriazole phosphonium reagent such as BOP and PyBOP. The term "leaving group" is the resultant product of the reaction of the functional group with an activating agent.

A "base" in the context of this application is a compound which has a lone pair of electron that can accept a proton. Non-limiting examples of a base can include triethylamine, a metal hydroxide, a metal alkoxide, a metal hydride, or a metal alkane. An alkyllithium or organolithium is a compound of the formula alkyl$_{(C\leq12)}$-Li. A nitrogenous base is an alkylamine, dialkylamino, trialkylamine, nitrogen containing heterocycloalkane or heteroarene wherein the base can accept a proton to form a positively charged species. For example, but not limited to, a nitrogenous base could be 4,4-dimethylpyridine, pyridine, 1,8-diazabicyclo[5.4.0]undec-7-ene, diisopropylethylamine, or triethylamine A metal alkoxide is an alkoxy group wherein the oxygen atom, which was the point of connectivity, has an extra electron and thus a negative charge which is charged balanced by the metal ion. For example, a metal alkoxide could be a sodium tert-butoxide or potassium methoxide. As used herein, the term "strong base" indicates a base which has a p$K_a$ of greater than 20.

An "electrophilic compound" in the context of this application is a compound which has a polarized bond which can undergo a nucleophilic attack. Some non-limiting examples of electrophilic compounds include water, anhydrides, or Lewis acids.

An "oxidizing agent" in the context of this application is a compound which causes the oxidation of a compound by accepting an electron. Some non-limiting examples of oxidizing agent are oxygen gas, peroxides, chlorite, hypochlorite, hypervalent iodide complexes, or a chromium compound such as pyridinium chlorochromate or hydrochromic acid.

A "reducing agent" in the context of this application is a compound which causes the reduction of a compound through the donation of an electron. A soft reducing agent is a reducing agent which contains electron delocalizing ligands which weaken the nucleophilic strength of the hydride. Some non-limiting examples of reducing agents are sodium borohydride, sodium triacetoxyborohydride, sodium cyanoborohydride, lithium aluminum hydride, diisobutylaluminum hydride, hydrogen gas, or metal hydride.

A "metal" in the context of this application is a transition metal or a metal of groups I or II. It may also be an element of Group 13 such as, but not limited to, boron and aluminum.

A "Lewis acid" is an atom or functional group which can accept a pair of electrons. In some embodiments, the Lewis acid is a metal atom. Without being bound by any theory, the Lewis acid increases the reactivity of one or more group to which it attached by increasing the polarization of a bond. Some non-limiting examples of Lewis acids include metal salts or boron compounds.

A "linker" in the context of this application is divalent chemical group which may be used to join one or more molecules to the compound of the instant disclosure. Linkers may also be an amino acid chain wherein the carboxy and amino terminus serve as the points of attachment for the linker. In some embodiments, the linker contains a reactive functional group, such as a carboxyl, an amide, a amine, a hydroxy, a mercapto, an aldehyde, or a ketone on each end that be used to join one or more molecules to the compounds of the instant disclosure. In some non-limiting examples, —CH$_2$CH$_2$CH$_2$CH$_2$—, —C(O)CH$_2$CH$_2$CH$_2$—, —OCH$_2$CH$_2$NH—, —NHCH$_2$CH$_2$NH—, and —(OCH$_2$CH$_2$)$_n$—, wherein n is between 1-1000, are linkers.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxy carbonyl, p-nitrobenzyloxy carbonyl, 2-nitrobenzyloxycarbonyl, p-bromobenzyloxycarbonyl, 3,4-dimethoxybenzyloxycarbonyl, 3,5-dimethoxybenzyloxy carbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxy carbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula PG$_{MA}$NH— or PG$_{DA}$N— wherein PG$_{MA}$ is a monovalent amine protecting group, which may also be described as a "monvalently protected amino group" and PG$_{DA}$ is a divalent amine protecting group as described above, which may also be described as a "divalently protected amino group".

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxy carbonyl, 3,5-dimethoxybenzyloxy carbonyl, 2,4-dimethoxybenzyloxy carbonyl, 4-methoxybenzyloxy carbonyl, 2-nitro-4,5-dimethoxybenzyloxy carbonyl, 3,4,5-trimethoxybenzyloxycarbonyl, 1-(p-biphenylyl)-1-methylethoxycarbonyl, α,α-dimethyl-3,5-dimethoxybenzyloxy carbonyl, benzhydryloxycarbonyl, t-butyloxy carbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxy carbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected hydroxy group is a group of the formula $PG_HO$— wherein $PG_H$ is a hydroxyl protecting group as described above.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxy carbonyl, p-methoxybenzyloxy carbonyl, p-nitrobenzyloxycarbonyl, 2-nitrobenzyloxycarbonyl, p-bromobenzyloxycarbonyl, 3,4-dimethoxybenzyloxy carbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxy carbonyl, benzhydryloxycarbonyl, t-butyloxycarbonyl (Boc), diisopropylmethoxycarbonyl, isopropyloxycarbonyl, ethoxy carbonyl, methoxy carbonyl, allyloxycarbonyl (Alloc), 2,2,2-trichloroethoxycarbonyl, 2-trimethylsilylethyloxycarbonyl (Teoc), phenoxy carbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected thiol group is a group of the formula $PG_TS$— wherein $PG_T$ is a thiol protecting group as described above.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Synthesis of Shishijimicin and Analogs

The similarities of shishijimicin A (1) (Oku et al., 2003) with calicheamicin $\gamma_1^I$ (Lee et al., 1987a and Lee et al., 1987b) extend from their common enediyne moiety to their Bergman cycloaromatization-based mechanism of action involving double strand DNA cleavage (Jones & Bergman, 1972). Their structures, however, differ substantially with regards to the constitution of their pentacyclic DNA binding domain that includes a carboline system for shishijimicin A and a fully substituted iodophenyl ring for calicheamicin $\gamma_1^I$, both known DNA binding structural motifs (Xiao et al., 2001 and Gomez Paloma et al., 1994). The synthetic roadmap toward shishijimicin A (1) was developed on the basis of the retrosynthetic analysis shown in FIG. 1. Thus, protection of the phenolic (TBS), amino (Alloc) and tertiary hydroxyl (TES) groups and transformation of the methyl trisulfide of the target molecule to a thioacetate moiety in the retrosynthetic sense led to its protected enediyne thioacetate 2 as a potential precursor. Disconnection of the glycoside bond linking the enediyne domain of thioacetate precursor 2 with its pentacyclic appendage revealed enediyne thioacetate fragment 4 and trichloroacetimidate 3 as potential advanced intermediates for coupling in the synthetic direction. The enediyne thioacetate fragment 4 was traced back to the readily available key building block 5, previously employed in the total synthesis (Nicolaou et al., 1992; Groneberg et al., 1993; Smith et al., 1993 and Nicolaou et al., 1993) of calicheamicin $\gamma_1^I$. The pentacyclic advanced intermediate 3 was further disconnected at the indicated carbon-carbon bond bridging the carboline structural motif to the disaccharide domain, furnishing iodocarboline 6 and disaccharide aldehyde 7 [upon modification of the trichloroacetimidate group to the photolabile o-nitrobenzyl (NB) ether protecting group] as potential precursors. Finally, iodocarboline 6 was traced back to tryptamine derivative 8, while disaccharide 7 was disconnected to its obvious monosaccharide units 9 (acceptor) and 10 (donor) as building blocks (Nicolaou et al., 2011).

The synthesis of the required enediyne thioacetate precursor 4 from building block 5 (Smith et al., 1993) proceeded as shown in Scheme 1. This route represents a streamlined and improved version of the original synthesis of the benzoate counterpart of thioacetate enediyne 4 employed in the total synthesis of calicheamicin $\gamma_1^I$ (19 steps, 21% overall yield from 5, vs. 21 steps, 1.7% overall yield from 5) (Nicolaou et al., 1992; Groneberg et al., 1993; Smith et al., 1993 and Nicolaou et al., 1993). It should also be noted that thioacetate 4 is a more advanced precursor for the methyl trisulfide unit required for both shishijimicin A and calicheamicin $\gamma_1^I$, thereby saving steps in the post-coupling sequence to the final target. Thus, and as shown in Scheme 1, oxidation of oxime 5 to the corresponding nitrile-oxide (5a) with the improved conditions involving t-BuOCl followed by spontaneous [3+2] dipolar cycloaddition of the latter intermediate (see 5a, Scheme 1) led to 11 in 81% overall yield and ≥10:1 dr (as compared to 51% yield and ca. 4:1 dr in the previous route) (Smith et al., 1993). Conversion of the latter compound to ketone 12 (deprotection/oxidation) proceeded smoothly as previously reported (two steps, 92% overall yield) (Smith et al., 1993). The subsequent coupling of 12 with enediyne fragment 13, however, was improved by using LiHMDS in the presence of $LaCl_3.2LiCl$ (Krasovskiy et al., 2006a) affording, after in situ acetylation, the desired enediyne 14 in 90% overall yield (as compared to 69% yield under the originally employed conditions) (Smith et al., 1993). Removal of the MEM group from 14, followed by Swern oxidation of the resulting secondary alcohol and concomitant oxidation of the isoxazoline to the isoxazole moiety furnished keto-isoxazole 15 (85% overall yield for the two steps). The latter intermediate served admirably as a substrate for the exclusively E-selective HWE olefination that followed (15a: $(MeO)_2P(O)CH_2CO_2Me$, LiHMDS), leading to E-α,β-unsaturated methyl ester 16 in 96% yield. TIPS-acetylene acetate 16 was then transformed, in 94% overall yield, to terminal acetylene TES-ether 17 through a sequence involving removal of the acetate group ($K_2CO_3$), cleavage of the TIPS moiety (TBAF), and silylation (TESOTf). Rupture of the isoxazole moiety within 17 was then achieved more conveniently and efficiently than before (Smith et al., 1993) through the use of Fe in $EtOH:H_2O$ (83%), and the resulting amino aldehyde was captured by phthaloyl chloride (PhthCl) in the presence of pyridine to afford N-phthalide aldehyde 18 (81%). The direct and stereoselective cyclization of terminal acetylene aldehyde 18 to cyclic enediyne 19 (via intermediate 18a, see Scheme 1) with $LiHMDS-LaCl_3.2LiCl$ (Krasovskiy et al., 2006) in THF in 85% yield represents an improvement over the previously used three-step sequence requiring inversion of the opposite configuration at C8 obtained from the same substrate (18) through the use of KHMDS in toluene (Smith et al., 1993). The N-phthalide moiety of cyclic enediyne 19 was then converted to the desired methyl carbamate group by reaction with $MeNHNH_2$, followed by exposure of the resulting amine to triphosgene in the presence of pyridine and MeOH as previously reported (Smith et al., 1993), affording enediyne lactone 20 in 81% overall yield. Reduction of the lactone moiety within 20 was achieved in one step and 92% yield, through the employment of $NaBH_4$—$CeCl_3.7H_2O$ (as opposed to two steps and 84% overall yield in the original route) (Smith et al., 1993), providing an additional improvement in the overall sequence to enediyne diol 21. Finally, conversion of 21 to the targeted enediyne thioacetate fragment 4 was accomplished efficiently by sequential treatment with excess TMSCN (bis-silylation), AcOH (selective primary TMS cleavage), $Ph_3P$-DEAD-AcSH (Mitsunobu reaction, thioacetate formation) and HF.py (secondary TMS cleavage) in 95% overall yield.

Scheme 1: Synthesis of enediyne thioacetate fragment 4

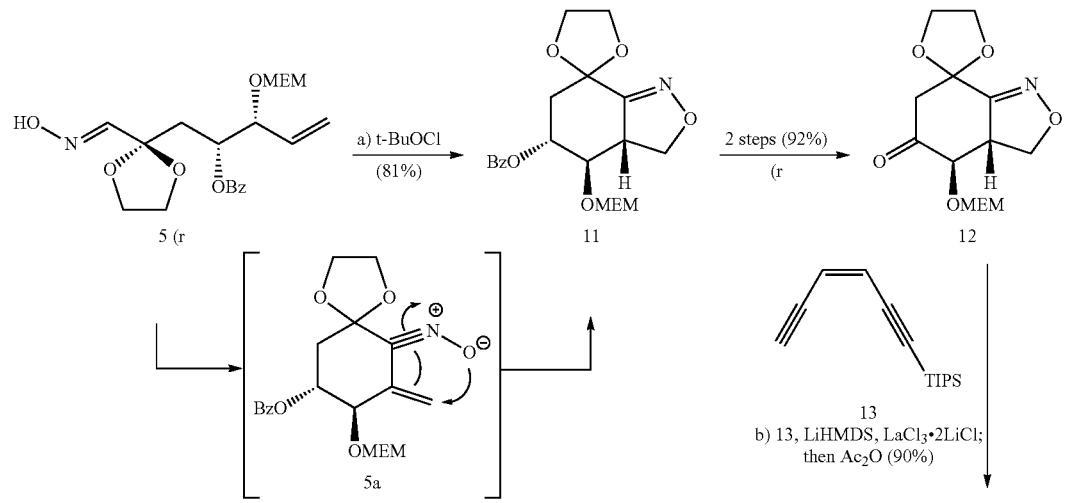

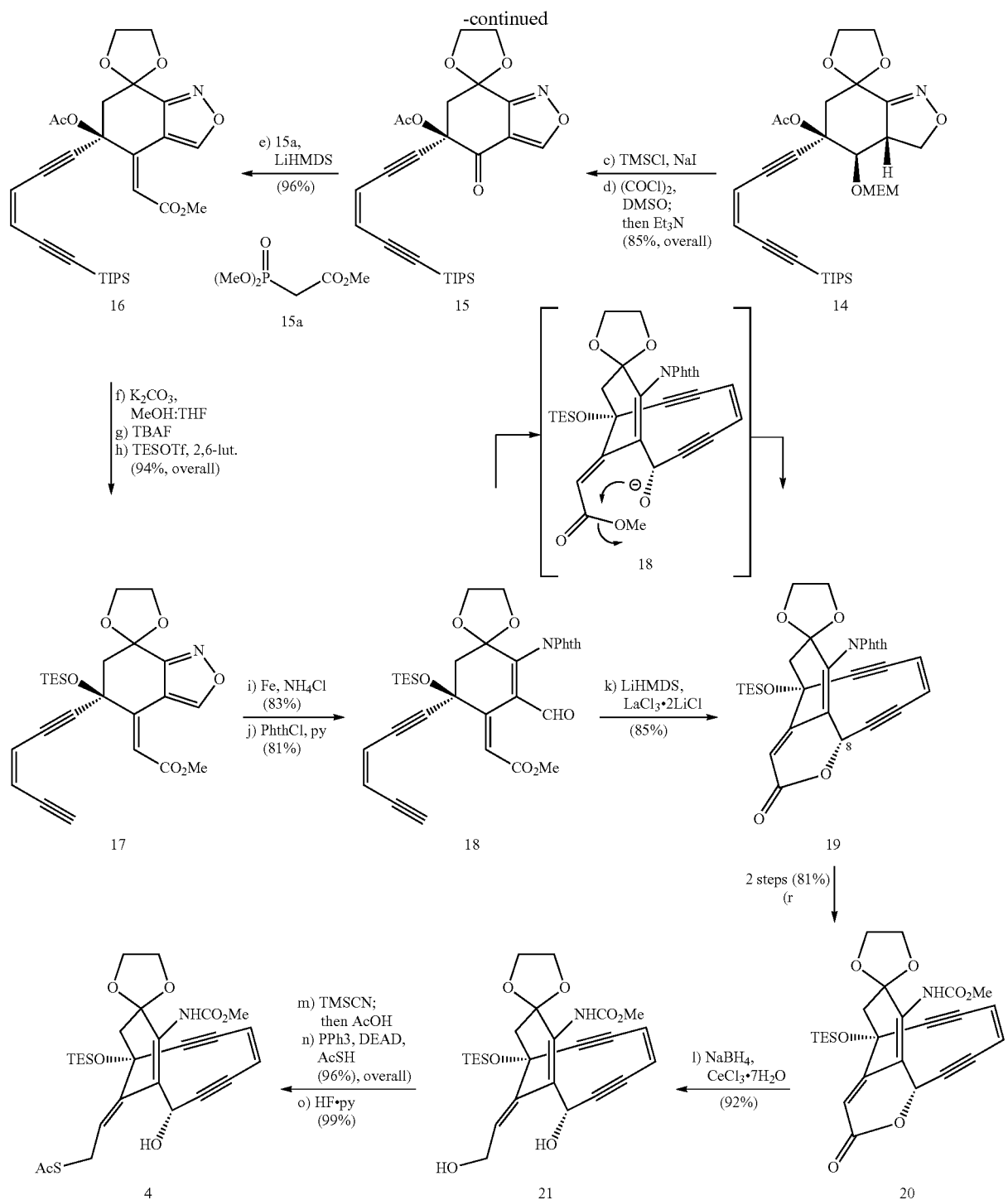
Scheme 2 summarizes the construction of iodocarboline 6 (Scheme 2A) and disaccharide aldehyde 7 (Scheme 2B). Thus, carboline 22 (Scheme 2A, prepared in 52% overall yield from the commercially available 5-methoxytryptamine 8 through a known, three-step sequence) (Schott et al., 2006) was silylated (TBSOTf, Et₃N, 97% yield) to afford 23, which was converted to carbamate 24 (KHMDS, ClCO₂Me, 98% yield). The latter compound was reacted with 2,2,6,6-tetramethyl piperidyl magnesium chloride.lithium chloride complex (TMPMgCl.LiCl) (Krasovskiy et al., 2006b) and I₂, furnishing the desired iodocarboline 6 in 83% yield.

fluoride 10 (Nicolaou et al., 2011 and Badalassi et al., 1997) as depicted in Scheme 2B. Thus, benzoylation of the free hydroxyl group of 25 (BzCl, Et₃N, 97% yield) followed by sequential treatment of the resulting benzoate glucal 26 with in situ generated DMDO and o-nitrobenzyl alcohol

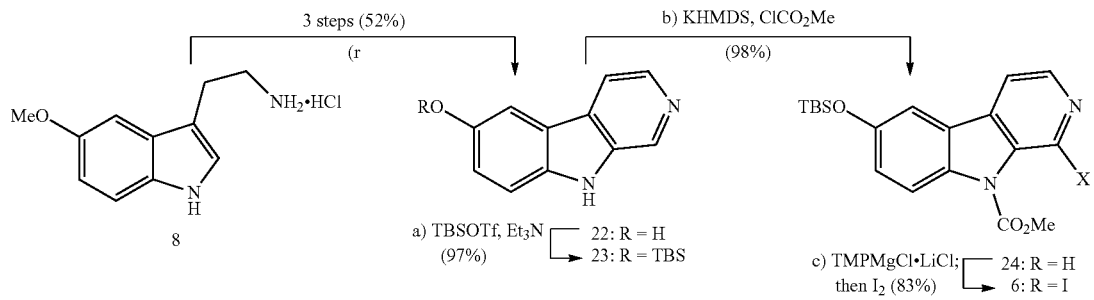

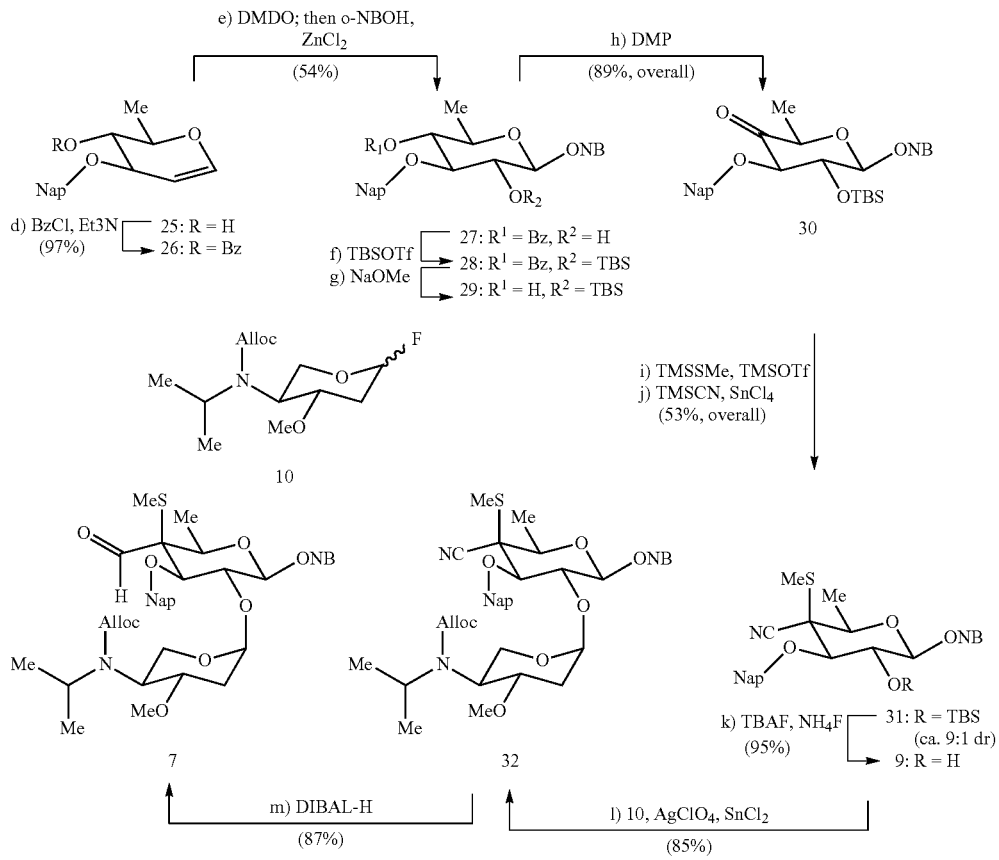

Reagents and conditions: a) TBSOTf (1.05 equiv.), Et₃N (3.0 equiv.), DMF, 0° C., 30 min, 97%; b) ClCO₂Me (1.1 equiv.), KHMDS (1.05 equiv.), THF, 0° C., 30 min, 98%; c) TmPMgCl•LiCl (4.0 equiv.), THF, -78 to 25° C., 4 h; then I₂ (5.0 equiv.), THF, -78 to 0° C., 30 min, 83%; d) BzCl (1.0 equiv.), Et₃N (1.1 equiv.), CH₂Cl₂, 0° C., 30 min, 97%: e) Oxone® (5.0 equiv.), NaHCO₃ (25 equiv.), acetone:H₂O:CH₂Cl₂ (1:3:4), 25° C., 4 h; then o-NBOH (3.0 equiv.), ZnCl₂ (1.5 equiv.), 4Å MS, THF, -78 to 25° C., 4 h, 54%; f) TBSOTf (1.05 equiv.), Et₃N (1.1 equiv.), CH₂Cl₂, 0° C., 30 min; g) NaOMe (10.0 equiv.), MeOH, 40° C., 24 h; h) DMP (1.2 equiv.), CH₂Cl₂, 0 to 25° C., 1 h, 89% for the three steps; i) TMSSMe (2.5 equiv.), TMSOTf (1.5 equiv.), toluene, -20 to 0° C., 30 min, 61%; j) TMSCN (3.5 equiv.), SnCl₄ (1.5 equiv.), CH2Cl2, 0° C., 3 h, 87% (ca. 9:1 dr); k) TBAF (5.0 equiv.), NH₄F (10.0 equiv.), THF, 0° C., 1 h, 95%; l) 10 (2.2 equiv.), AgClO₄ (2.5 equiv.), SnCl₂ (2.5 equiv.), 4Å MS, THF, -78 to 25° C., 12 h, 85%; m) DIBAL-H (3.0 equiv.), CH₂Cl₂, -78° C., 45 min, 87%. KHMDS = potassium bis(trimethylsily)amide; TMP = 2,2,6,6-tetramethyl piperidinyl; DMDO = dimethyldioxirane; o-NBOH = o-nitrobenzyl alcohol; DMP = Dess-Martin Periodinane; DIBAL-H = diisobutylaluminum hydride.

The required disaccharide 7 was synthesized from the readily available glucal 25 (Tanaka et al., 2010) and glycosyl (o-NBOH) furnished hydroxy-o-nitrobenzyl ether 27 in 54% overall yield via the corresponding epoxide intermediate (Halcomb & Danishefsky, 1989). The newly generated hydroxyl group of the latter compound was converted to its TBS ether (TBSOTf, Et$_3$N) affording 28, from which the benzoate moiety was cleaved (NaOMe) to give alcohol 29. DMP oxidation of this intermediate led to ketone 30 in 89% overall yield for the three steps from 27. Reaction of ketone 30 with TMSSMe in the presence of TMSOTf furnished the corresponding methylthioketal (Nicolaou et al., 2011 and Evans et al., 1977), which underwent stereoselective cyanation (Reetz & Starke, 1984) upon exposure to TMSCN and SnCl$_4$ to afford nitriles 31 and 4-epi-31 (ca. 9:1 dr, 53% yield for the two steps). Removal of the TBS group from nitrile 31 (TBAF, NH$_4$F) (Fürstner & Weintritt, 1998) gave carbohydrate acceptor 9 (95% yield), whose coupling with carbohydrate donor 10 (Nicolaou et al., 2011 and Badalassi et al., 1997) proceeded smoothly in the presence of AgClO$_4$ and SnCl$_2$ to afford stereoselectively the desired α-glycoside 32 in 85% yield. Finally, DIBAL-H reduction of the nitrile group within 32 led to the targeted aldehyde 7 in 87% yield.

The coupling of iodocarboline 6 and disaccharide aldehyde 7 proceeded through the lithio-derivative of the former (generated with t-BuLi at −78° C.) and led to alcohol 33 (86% yield, ca. 1:1 dr, inconsequential) as shown in Scheme 3. Treatment of carboline carbamate 33 with NaOH in EtOH led to the corresponding free amine, whose oxidation with DMP gave ketone 34 in 68% yield over the two steps. Photolytic cleavage (Nicolaou et al., 1993) of the o-nitrobenzyl ether moiety from the latter compound, followed by sequential treatment with DDQ (removal of naphthyl group) and Cl$_3$CCN—NaH (trichloroacetimidate formation) resulted, stereoselectively, in the formation of the coveted trichloroacetimidate 3 (53% overall yield, β-anomer exclusively).

Scheme 3: Coupling of iodocarboline 6 and aldehyde 7 and elaboration of the product to trichloroacetimidate 3.

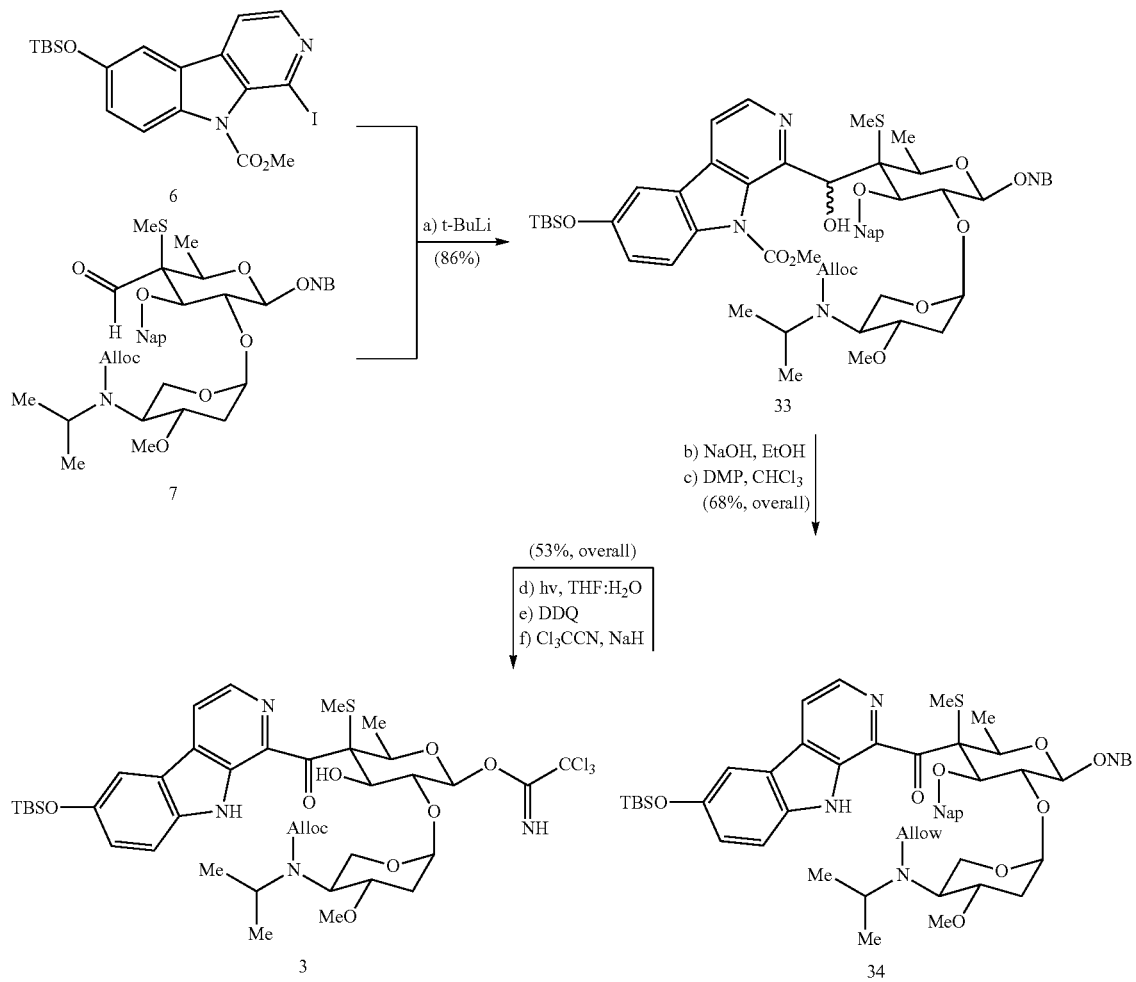

Reagents and conditions: a) 6 (3.0 equiv.), t-BuLi (6.0 equiv.), THF, -78° C., 30 min; then 7, -78 to -35° C., 40 min, 86% (ca. 1:1 dr) based on 7; b) NaOH (3.0 equiv.), EtOH, 0 to 25° C., 2.5 h; c) DMP (1.1 equiv.), CHCl$_3$, 0 to35° C., 10 min, 68% for the two steps; d) hv, THF:H$_2$O (10:1), 4.5 h; e) DDQ (2.5 equiv.), CH$_2$Cl$_2$:H$_2$O (10:1), 30° C., 1.5 h; f) NaH (2.0 equiv.), Cl$_3$CCN:CH$_2$Cl$_2$ (1:2), 25° C., 5 min, 53% for the three steps. DDQ = 2,3-dichloro-5,6-dicyano-1,4-benzoquinone.

Having assembled the two advanced intermediates, trichloroacetimidate 3 and hydroxy enediyne 4, the next objective became their coupling and elaboration of the resulting product to shishijimicin A (1). Scheme 4 depicts how this challenging task was accomplished. Indeed, it was after considerable experimentation that the two fragments (such as 3 and 4) were joined through the action of BF$_3$.Et$_2$O to afford, selectively, β-glycoside 2 (26% yield). Note that the corresponding naphthyl ether trichloroacetimidate proved resistant to glycosidation, presumably due to severe steric hindrance, an effect also assumed to be responsible for the observed, rather low yield of the reaction between 3 and 4. Enediyne thioacetate 2 was transformed to the protected Finally, cleavage of the ketal moiety from precursor 38 gave the targeted natural product, shishijimicin A (1), in 73% yield. The physical data of synthetic 1 matched those reported for the natural substance (Oku et al., J. Am. Chem. Soc., 125:2044-2045, 2003).

Scheme 4: Coupling of fragments 3 and 4 and total synthesis of shishijimicin A (1).

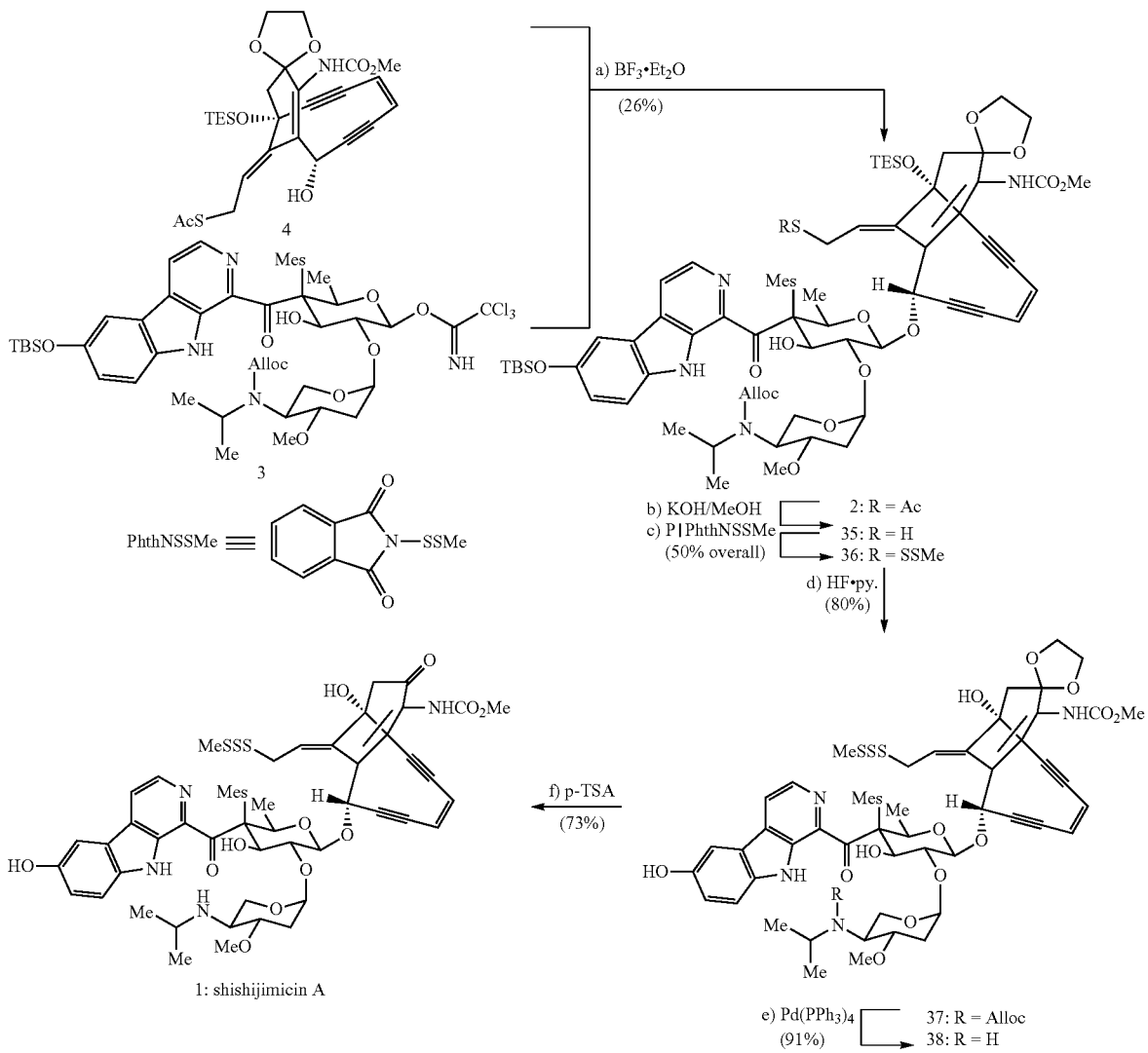

Reagents and conditions: a) BF$_3$•OEt$_2$ (3.5 equiv.), 4Å MS, CH$_2$Cl$_2$, -78 to -40° C., 1 h, 26% based on 3; b) KOH (10.0 equiv.), MeOH, -5° C., 1.5 h; then AcOH (10.0 equiv.); c) PhthNSSMe (6.0 equiv.), CH$_2$Cl$_2$, 0° C., 15 min, 50% for the two steps; d) HF•py:THF (1:20), 0 to 25° C., 4 h, 80%; e) Pd(PPh$_3$)$_4$ (0.5 equiv.), morpholine (15 equiv.), THF, 0° C., 45 min, 91%; f) p-TSA (3.0 equiv.), THF:acetone:H$_2$O (20:20:1), 25° C., 48 h, 73%. p-TSA = p-toluemesulfonic acid.

form of shishijimicin A, precursor 36, through sequential treatment with KOH in MeOH (acetate cleavage) and N-methyldithiophthalimide (PhthNSSMe (Harpp & Ash, 1971), 50% overall yield) via thiol derivative 35. Desilylation of 36 with HF.py furnished advanced intermediate 37 (80% yield) from which the Alloc protecting group was removed by exposure to Pd(PPh$_3$)$_4$ cat., leading to shishijimicin A penultimate precursor ketal 38 (91% yield).

Monosaccharide analog 45 (KCN-LL-4) was prepared as outlined in Scheme 5. Starting from modified saccharide 39, the free hydroxyl group was methylated using methyl iodide in the presence of a strong base such as NaH in 68% yield to generate methylated saccharide 40. The methylated saccharide 40 was reduced with DIBAL-H to generate aldehyde 41. Aldehyde 41 was reacted with iodocarboline 6 was carried out with $^t$BuLi to generate in a 77% yield coupling product alcohol 42a and 42b (as diastereomers). Following a basic work-up, the diastereomeric mixture 42a and 42b was oxidized with Dess-Martin periodinane to generate ketone 43 in 63% yield. Coupling of the aldehyde 43 was affected with the enediyne unit 4 with deprotection of some of the hydroxyl groups on the saccharide in four steps with a 10% yield to generate enediyne thioacetate 44. The enediyne thioacetate 44 was reacted with an activated methyldisulfide and subjected to deprotection with fluoride and acid to generate the monosaccharide shishijimicin analog 45 (KCN-LL-4) with a 42% yield in three steps.

Starting from ketone 34, the secondary amine in the lower saccharide was deprotected and then acetylated using acetic anhydride to generate N-acetyl derivative 46 in 78% yield. Following deprotection, the enediyne component 4 was coupled with N-acetyl derivative 46 in 7.4% yield over four steps to generate enediyne thioacetate 47 which was covered to the corresponding trisulfide analog 48 under basic conditions followed by deprotection using fluoride and acid.

Scheme 5: Synthesis of Monosaccharide Derivative KCN-LL-4 (45)

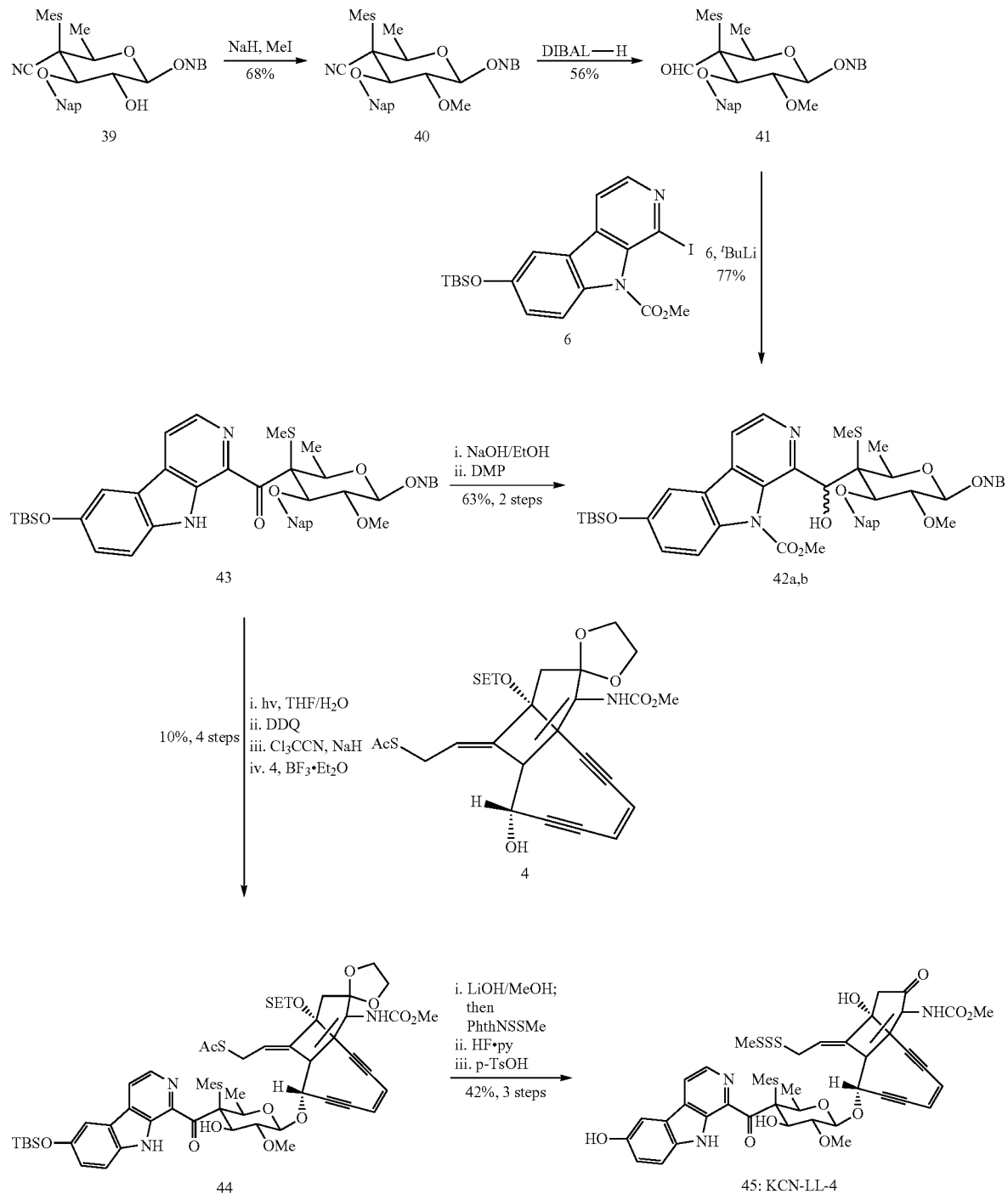

Scheme 6: Synthesis of Shishijimicin A analog, KCN-LL-3 (48)

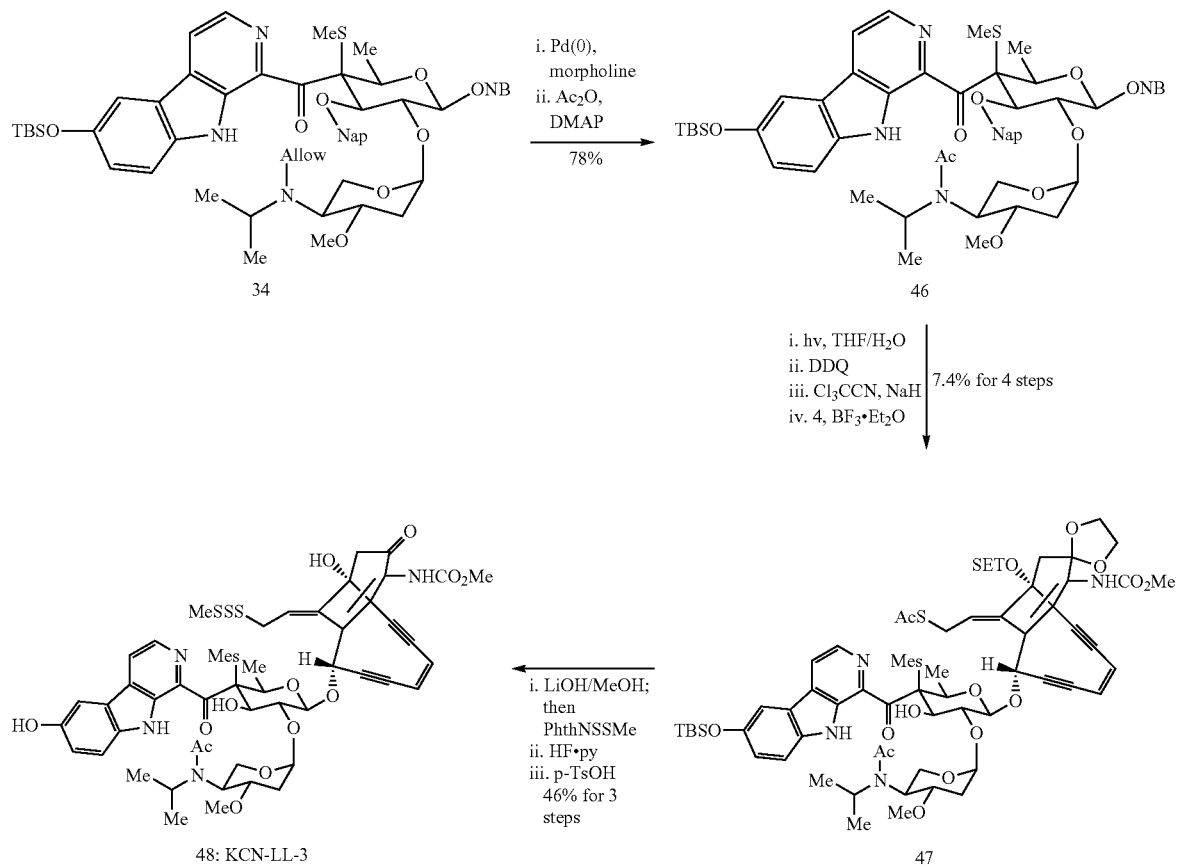

Starting with carbonyl 49, the carbonyl was converted to dimethylthio compound 50 by the reaction of TMSSMe and TMS triflate in 94% yield. The dimethylthio compound 50 was reacted with TMS cyanide in the presence of tin(IV) chloride to obtain cyano compound 51. This compound was reacted using tributyltin hydride in the presence of radical initiator AIBN to obtain reduced cyano compound 52 in 99% yield and 1.4:1 diastereomeric ratio. Anomeric cyano compound 53 was prepared in four steps and 63% yield from cyano compound 17. The pivaloyl protecting group in compound 53 was removed with LiOH in 71% yield to obtain hydroxyl 54. Saccharide 10 was coupled to hydroxyl 54 by coupling with tin(II) chloride and silver perchlorate in 95% yield to generate disaccharide 55. The cyano group of 55 was reduced with DIBAL-H to obtain aldehyde 56 in 85% yield. The iodocarboline 6 was coupled with the disaccharide 56 in the presence of t-butyllithium to obtain diastereomeric alcohols 57a and 57b. Deprotection of the carboline followed by oxidation of the alcohol generated carbonyl 58 in 70% yield over two steps. Following deprotection and activation, the enediyne unit 4 was coupled to carbonyl 58 in three steps and 15% yield to generate enediyne thioacetate 59. After removal of the acetyl group, the methyl trisulfide 60 was generated. After the methyl trisulfide 60 was deprotected using fluoride, then palladium (0), and finally acid to generate shishijimicin analog 61 (KCN-LL-5).

Scheme 7: Synthesis of Shishijimicin A analog, KCN-LL-5 (61)

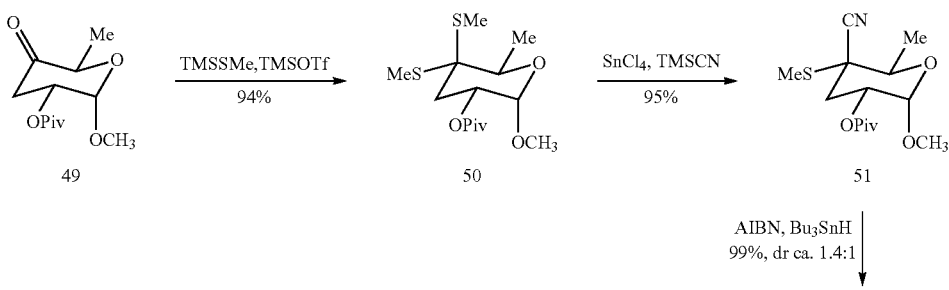

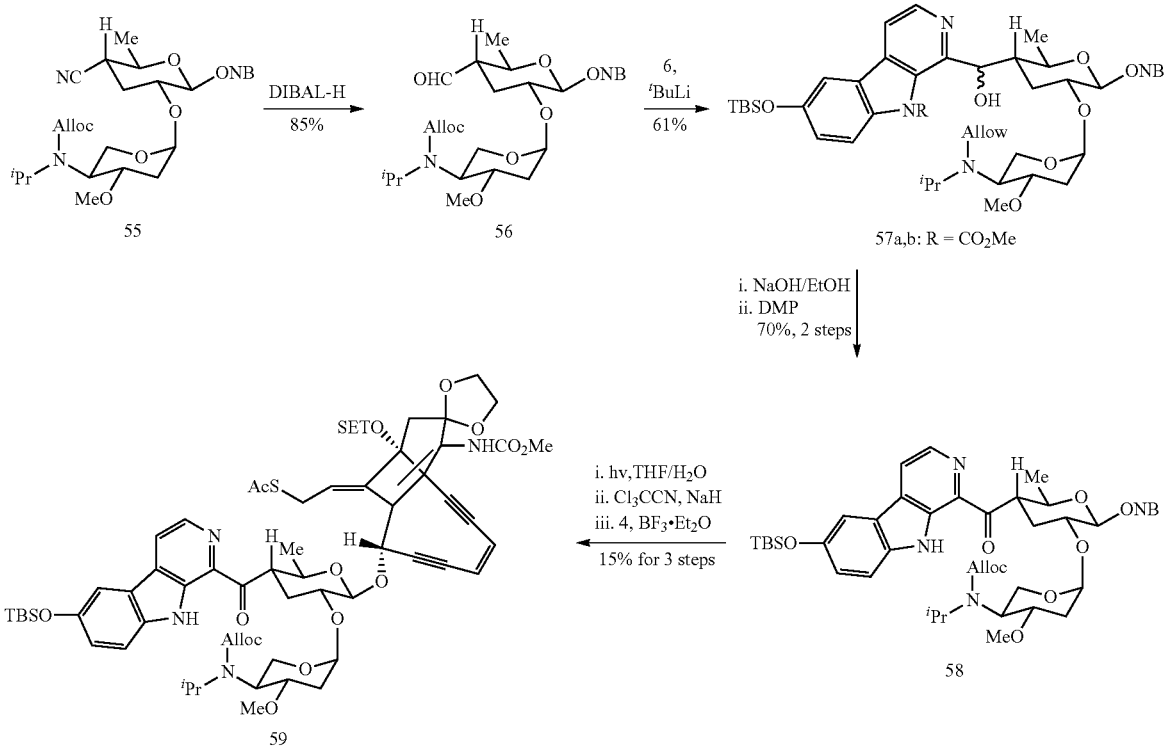

Example 2—General Methods and Materials

All reactions were carried out under an argon atmosphere with dry solvent under anhydrous conditions, unless otherwise noted. Dry acetonitrile (MeCN), dimethylformamide (DMF), dichloromethane ($CH_2Cl_2$), tetrahydrofuran (THF) and toluene were obtained by passing commercially available pre-dried, oxygen-free formulations through activated alumina columns Anhydrous benzene, acetone, chloroform ($CHCl_3$), methanol (MeOH), ethanol (EtOH) and nitromethane ($MeNO_2$) were purchased from commercial suppliers and stored under argon. Yields refer to chromatographically and spectroscopically ($^1$H NMR) homogenous material, unless otherwise stated. Reagents were purchased at the highest commercial quality and used without further purification, unless otherwise noted. Reactions were monitored by thin-layer chromatography (TLC) carried out on S-2 0.25 mm E. Merck silica gel plates (60F-254) using UV light as visualizing agent and an ethanolic solution of phosphomolybdic acid, an aqueous solution of cerium sulfate or a basic aqueous solution of potassium permanganate as developing agents. E. Merck silica gel (60, particle size 0.040-0.063 mm) was used for flash column chromatography. NMR spectra were recorded on a Bruker DRX-600 instrument and calibrated using residual undeuterated solvent ($CDCl_3$, $\delta_H$=7.26 ppm, $\delta_C$=77.16 ppm; $C_6D_6$, $\delta_H$=7.16 ppm, $\delta_C$=128.06 ppm; $CD_3OD$, $\delta_H$=3.31 ppm, $\delta_C$=49.00 ppm) as an internal reference. The following abbreviations were used to designate multiplicities: s=singlet, d=doublet, t=triplet, q=quartet, quint=quintet, m=multiplet, br=broad. Infrared (IR) spectra were recorded on a Perkin-Elmer 100 FT-IR spectrometer. High-resolution mass spectra (HRMS) were recorded on an Agilent ESI-TOF (time of flight) mass spectrometer using MALDI (matrix-assisted laser desorption ionization) or ESI (electrospray ionization). Optical rotations were recorded on a POLARTRONIC M100 polarimeter at 589 nm, and are reported in units of $10^{-1}$ (deg $cm^2$ $g^{-1}$).

Example 3—Compound Characterization

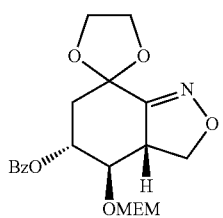

11

Benzoate 11:

To a stirred solution of aldoxime 5 (18.5 g, 45.2 mmol, 1.0 equiv.) in benzene (1800 mL) at 25° C. was added t-BuOCl (14.8 g, 15.4 mL, 136 mmol, 3.0 equiv.). The resulting mixture was stirred at this temperature for 30 min before it was quenched with saturated aqueous $NaHCO_3$ (500 mL) and $Na_2S_2O_3$ (100 mL) and extracted with $CH_2Cl_2$ (3×500 mL). The combined organic layers were washed with brine (300 mL) and dried over anhydrous $Na_2SO_4$. After filtration and evaporation of the solvent, the residue was purified by flash column chromatography (silica gel, EtOAc:hexanes=1:3→1:1) to give benzoate 11 (14.9 g, 36.6 mmol, 81%) as a colorless oil. 11: $R_f$=0.42 (silica gel, EtOAc:hexanes=1:1); [α]20 D=−26.2 (c=1.0, $CHCl_3$); FT-IR (neat) $v_{max}$=2894, 1720, 1451, 1314, 1273, 1196, 1177, 1110, 1071, 1036, 858, 713 $cm^{-1}$; $^1$H NMR ($CDCl_3$, 600 MHz) δ=8.01 (d, J=7.2 Hz, 2H), 7.58 (t, J=7.4 Hz, 1H), 7.45 (t, J=7.8 Hz, 2H), 5.48 (ddd, J=12.1, 9.5, 4.7 Hz, 1H), 4.88 (d, J=7.2 Hz, 1H), 4.69 (dd, J=10.9, 8.7 Hz, 1H), 4.68 (d, J=7.2 Hz, 1H), 4.35 (dd, J=10.8, 8.6 Hz, 1H), 4.23 (td, J=7.2, 5.2 Hz, 1H), 4.14 (ddd, J=7.6, 6.5, 5.1 Hz, 1H), 4.06 (q, J=6.9 Hz, 1H), 3.95 (q, J=7.1 Hz, 1H), 3.85 (t, J=9.7 Hz, 1H), 3.72-3.68 (m, 1H), 3.64 (q, J=10.1 Hz, 1H), 3.54-3.51 (m, 1H), 3.50-3.45 (m, 2H), 3.35 (s, 3H), 2.44 (dd, J=13.2, 4.7 Hz, 1H), 2.11 (dd, J=13.2, 12.1 Hz, 1H) ppm; $^{13}$C NMR ($CDCl_3$, 151 MHz) δ=165.4, 155.2, 133.5, 129.8, 129.8, 128.7, 102.6, 96.1, 81.3, 74.2, 73.1, 71.6, 67.8, 66.1, 64.9, 59.2, 51.7, 39.3 ppm; HRMS (ESI-TOF) calcd for $C_{20}H_{25}NO_8Na^+[M+Na]^+$ 430.1472, found 430.1459.

Ketone 12:

Ketone 12 was prepared from benzoate 11 as previously described (Smith et al., 1993). The physical and spectral data are consistent with those reported (Smith et al., 1993).

TIPS-Enediyne 13:

TIPS-enediyne 13 was prepared as previously described (Lu et al., 1995). The physical and spectral data are consistent with those reported (Lu et al., 1995).

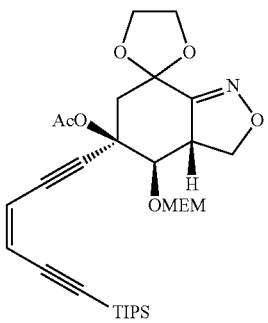

14

Enediyne 14:

To a stirred solution of enediyne 13 (11.5 g, 49.5 mmol, 3.0 equiv.) in THF (150 mL) at −78° C. were added $LaCl_3 \cdot 2LiCl$ (138 mL, 0.6 M in THF, 82.5 mmol, 5.0 equiv.) and LiHMDS (46.2 mL, 1.0 M in THF, 46.2 mmol, 2.8 equiv.) sequentially. The resulting mixture was stirred at this temperature for 30 min. A solution of ketone 12 (4.99 g, 16.5 mmol, 1.0 equiv.) in THF (50 mL) was added dropwise to the above reaction mixture at −78° C. After 30 min at −78° C., $Ac_2O$ (16.8 g, 15.6 mL, 165 mmol, 10.0 equiv.) was added, the cooling bath was removed, and the reaction mixture was allowed to warm to 25° C. and stirred at this temperature for 2 h. It was quenched with saturated aqueous $NaHCO_3$ (100 mL) and extracted with EtOAc (3×200 mL). The combined organic layers were washed with brine (100 mL), dried over anhydrous $Na_2SO_4$, filtered and concentrated under reduced pressure. The crude product was purified by flash column chromatography (silica gel, EtOAc:hexanes=1:4→1:1) to give enediyne 14 (8.58 g, 14.9 mmol, 90%) as a colorless oil. 14: $R_f$=0.38 (silica gel, EtOAc:hexanes=1:1.5); [α]20 D=−4.5 (c=1.0, $CHCl_3$); FT-IR (neat) $v_{max}$=2943, 2892, 2866, 1751, 1463, 1365, 1238, 1213, 1118, 1092, 1038, 1011, 882, 678 $cm^{-1}$; $^1$H NMR ($CDCl_3$, 600 MHz) δ=5.88 (d, J=11.2 Hz, 1H), 5.81 (d, J=11.2 Hz, 1H), 5.13 (d, J=7.4 Hz, 1H), 4.80 (d, J=7.4 Hz, 1H), 4.65 (dd, J=10.7, 8.5 Hz, 1H), 4.29 (dd, J=10.4, 8.6 Hz, 1H), 4.16-4.12 (m, 1H), 4.06-4.02 (m, 1H), 3.97-3.91 (m, 3H), 3.80-3.75 (m, 2H), 3.61-3.57 (m, 1H), 3.53 (t, J=4.6 Hz, 2H), 3.41 (d, J=15.5 Hz, 1H), 3.37 (s, 3H), 2.18 (d, J=15.5 Hz, 1H), 2.09 (s, 3H), 1.09 (s, 21H) ppm; $^{13}$C NMR (CDCl$_3$, 151 MHz) δ=169.6, 155.0, 120.8, 118.3, 103.4, 102.0, 100.5, 97.1, 93.3, 84.2, 84.2, 75.6, 73.5, 71.7, 68.1, 65.3, 65.2, 59.3, 50.2, 41.2, 22.0, 18.8, 18.8, 11.4 ppm; HRMS (ESI-TOF) calcd for C$_{30}$H$_{45}$NO$_8$SiNa$^+$[M+Na]$^+$598.2807, found 598.2789.

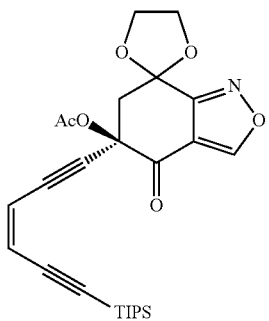

Keto-Isoxazole 15:

To a stirred solution of enediyne MEM-ether 14 (7.94 g, 13.8 mmol, 1.0 equiv.) in MeCN (200 mL) at 0° C. were added NaI (4.14 g, 27.6 mmol, 2.0 equiv.) and TMSCl (6.00 g, 7.01 mL, 55.2 mmol, 4.0 equiv.). The resulting mixture was allowed to warm to 25° C. and stirred at this temperature for 30 min before it was cooled to 0° C. and quenched with MeOH (10 mL). Saturated aqueous NaHCO$_3$ (100 mL) was added and the resulting mixture was extracted with EtOAc (3×100 mL). The combined organic layers were washed with brine (50 mL) and dried over anhydrous Na$_2$SO$_4$. After filtration and evaporation of the solvent, the crude alcohol so obtained was used for the next step without further purification. To a stirred solution of (COCl)$_2$ (7.01 g, 4.74 mL, 55.2 mmol, 4.0 equiv.) in CH$_2$Cl$_2$ (100 mL) was added a solution of DMSO (8.59 g, 7.81 mL, 110 mmol, 8.0 equiv.) in CH$_2$Cl$_2$ (20 mL) at −78° C. The solution was stirred at this temperature for 30 min, and then the above crude alcohol in CH$_2$Cl$_2$ (30 mL) was added dropwise. The reaction mixture was stirred at −78° C. for 30 min and then Et$_3$N (14.0 g, 19.2 mL, 138 mmol, 10.0 equiv.) was added. The resulting mixture was stirred for 30 min at this temperature and then allowed to warm to 25° C. and stirred for another 1 h. The reaction mixture was quenched with saturated aqueous NaHCO$_3$ (100 mL). After extraction with EtOAc (3×100 mL), the combined organic layers were washed with brine (50 mL), dried over anhydrous Na$_2$SO$_4$ and filtered. The solvent was removed under vacuum and the residue was purified by flash column chromatography (silica gel, EtOAc:hexanes=1:10→1:4) to give keto-isoxazole 15 (5.68 g, 11.7 mmol, 85% for the two steps) as a colorless oil. 15: R$_f$=0.44 (silica gel, EtOAc:hexanes=1:4); [α]20 D=+64.3 (c=1.0, CHCl$_3$); FT-IR (neat) v$_{max}$=2943, 2894, 2865, 1744, 1721, 1581, 1465, 1368, 1229, 1168, 1122, 1060, 997, 949, 881, 678 cm$^{-1}$; $^1$H NMR (CDCl$_3$, 600 MHz) δ=9.01 (s, 1H), 5.93 (d, J=11.1 Hz, 1H), 5.84 (d, J=11.1 Hz, 1H), 4.35 (td, J=7.0, 5.5 Hz, 1H), 4.24 (t, J=6.5 Hz, 2H), 4.10 (q, J=7.1 Hz, 1H), 3.51 (d, J=13.8 Hz, 1H), 2.67 (d, J=13.8 Hz, 1H), 2.11 (s, 3H), 1.10 (s, 21H) ppm; $^{13}$C NMR (CDCl$_3$, 151 MHz) δ=181.1, 169.5, 162.1, 161.6, 121.3, 118.4, 115.8, 103.3, 101.2, 100.7, 89.8, 87.6, 77.1, 65.5, 65.4, 43.7, 21.3, 18.8, 11.3 ppm; HRMS (ESI-TOF) calcd for C$_{26}$H$_{33}$NO$_6$SiNa$^+$[M+Na]$^+$506.1969, found 506.1967.

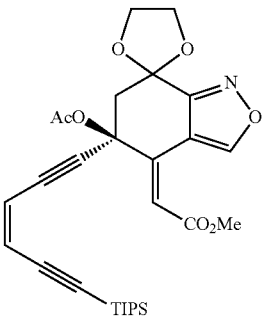

E-α,β-Unsaturated Methyl Ester 16:

To a stirred solution of (MeO)$_2$P(O)CH$_2$CO$_2$Me (4.26 g, 3.79 mL, 23.4 mmol, 2.0 equiv.) in THF (100 mL) was added LiHMDS (17.6 mL, 1.0 M in THF, 17.6 mmol, 1.5 equiv.) at −78° C. A solution of keto-isoxazole 15 (5.68 g, 11.7 mmol, 1.0 equiv.) in THF (30 mL) was added dropwise at this temperature. The reaction mixture was stirred for 30 min at −78° C. and then allowed to warm to 25° C. and stirred at this temperature for 1 h. The resulting mixture was quenched with saturated aqueous NaHCO$_3$ (100 mL). After extraction with EtOAc (3×100 mL), the combined organic layers were washed with brine (50 mL), dried over anhydrous Na$_2$SO$_4$ and filtered. The solvent was removed under vacuum and the residue was purified by flash column chromatography (silica gel, EtOAc:hexanes=1:30→1:5) to give E-α,β-unsaturated methyl ester 16 (6.04 g, 11.2 mmol, 96%) as a colorless oil. 16: R$_f$=0.48 (silica gel, EtOAc:hexanes=1:4); [α]20 D=+40.7 (c=1.0, CHCl$_3$); FT-IR (neat) v$_{max}$=2945, 2894, 2865, 1758, 1721, 1644, 1465, 1365, 1228, 1206, 1183, 1056, 1010, 948, 882, 678, 661 cm$^{-1}$; $^1$H NMR (CDCl$_3$, 600 MHz) δ=9.59 (s, 1H), 6.84 (s, 1H), 5.97 (d, J=11.1 Hz, 1H), 5.94 (d, J=11.1 Hz, 1H), 4.35-4.28 (m, 2H), 4.16-4.07 (m, 2H), 3.76 (s, 3H), 3.45 (d, J=15.0 Hz, 1H), 2.59 (d, J=15.0 Hz, 1H), 1.93 (s, 3H), 1.06 (s, 21H) ppm; $^{13}$C NMR (CDCl$_3$, 151 MHz) δ=169.1, 166.3, 161.9, 160.5, 138.5, 121.5, 119.6, 118.4, 111.6, 103.3, 100.8, 100.5, 91.4, 87.8, 76.7, 65.6, 65.1, 51.9, 44.4, 21.9, 18.8, 11.3 ppm; HRMS (ESI-TOF) calcd for C$_{29}$H$_{37}$NO$_7$SiNa$^+$[M+Na]$^+$ 562.2232, found 562.2211.

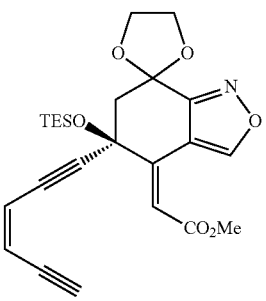

Terminal Acetylene 17:

To a stirred solution of methyl ester 16 (5.45 g, 10.1 mmol, 1.0 equiv.) in THF (50 mL) and MeOH (50 mL) was added K$_2$CO$_3$ (1.40 g, 10.1 mmol, 1.0 equiv.) at 0° C. The mixture was allowed to warm to 25° C. and stirred at this temperature for 3 h. The resulting mixture was quenched with saturated aqueous NaHCO$_3$ (100 mL) and extracted with EtOAc (3×100 mL). The combined organic layers were washed with brine (50 mL), dried over anhydrous Na$_2$SO$_4$ and filtered. The solvent was removed under vacuum and the residue so obtained was dissolved in THF (50 mL). TBAF (10.1 mL, 1.0 M in THF, 10.1 mmol, 1.0 equiv.) was added to the stirred solution dropwise at 0° C. The reaction mixture was stirred for 10 min at this temperature before it was quenched with saturated aqueous NaHCO$_3$ (100 mL) and extracted with EtOAc (3×100 mL). The combined organic layers were washed with brine (50 mL), dried over anhydrous Na$_2$SO$_4$ and filtered. The solvent was removed under vacuum and the residue so obtained was dissolved in CH$_2$Cl$_2$ (50 mL). To this stirred solution were added sequentially 2,6-lutidine (2.16 g, 2.34 mL, 20.2 mmol, 2.0 equiv.) and TESOTf (4.02 g, 3.44 mL, 15.2 mmol, 1.5 equiv.) at 0° C. The resulting mixture was allowed to warm to 25° C. and stirred at this temperature for 2 h. The reaction mixture was quenched with saturated aqueous NaHCO$_3$ (100 mL) and extracted with CH$_2$Cl$_2$ (3×100 mL). The combined organic layers were washed with brine (50 mL), dried over anhydrous Na$_2$SO$_4$ and filtered. The solvent was removed under reduced pressure and the residue was purified by flash column chromatography (silica gel, EtOAc:hexanes=1:20→1:5) to give terminal acetylene 17 (4.31 g, 9.46 mmol, 94% for the three steps) as a colorless solid. 17: R$_f$=0.31 (silica gel, EtOAc:hexanes=1:10); [α]20 D=−5.8 (c=1.0, CHCl$_3$); FT-IR (neat) v$_{max}$=3299, 2955, 2877, 1720, 1645, 1471, 1199, 1119, 1057, 1009, 747 cm$^{-1}$; $^1$H NMR (CDCl$_3$, 600 MHz) δ=9.50 (s, 1H), 6.70 (s, 1H), 5.90 (dd, J=11.0, 0.6 Hz, 1H), 5.84 (dd, J=11.0, 2.3 Hz, 1H), 4.38-4.31 (m, 2H), 4.18-4.11 (m, 2H), 3.76 (s, 3H), 3.28 (dd, J=2.3, 0.7 Hz, 1H), 2.72 (d, J=14.2 Hz, 1H), 2.62 (d, J=14.2 Hz, 1H), 0.92 (t, J=7.9 Hz, 9H), 0.70 (q, J=7.9 Hz, 6H) ppm; $^{13}$C NMR (CDCl$_3$, 151 MHz) δ=166.8, 161.4, 161.1, 144.0, 120.4, 120.2, 114.9, 112.3, 100.9, 96.0, 85.6, 85.5, 80.4, 72.0, 65.1, 64.9, 51.8, 50.0, 7.0, 6.1 ppm; HRMS (ESI-TOF) calcd for C$_{24}$H$_{30}$NO$_6$Si$^+$[M+H]$^+$ 456.1837, found 456.1829.

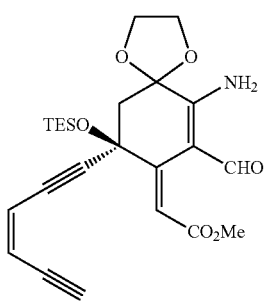

17a-SI

Free Amine 17a-SI:

To a stirred solution of isoxazole 17 (105 mg, 0.230 mmol, 1.0 equiv.) in EtOH (3.5 mL) and H$_2$O (3.5 mL) were added NH$_4$Cl (615 mg, 11.5 mmol, 50 equiv.) and Fe (128 mg, 2.30 mmol, 10.0 equiv.). The resulting suspension was stirred at 60° C. and Fe (63.7 mg, 1.15 mmol, 5.0 equiv.) was added every two hours (3 portions in total). The reaction mixture was stirred for another 2 h and was then filtered through Celite® and the residue was washed with EtOH (3×10 mL). The solvent was removed under vacuum and the residue was purified by flash column chromatography (silica gel, EtOAc:hexanes=1:5→1:1) to give free amine 17a-SI (87.3 mg, 0.191 mmol, 83%) as a colorless oil. 17a-SI: R$_f$=0.41 (silica gel, EtOAc:hexanes=1:1); [α]20 D=−32.2 (c=1.0, CHCl$_3$); FT-IR (neat) v$_{max}$=3397, 3275, 2954, 2910, 2876, 1704, 1644, 1599, 1498, 1434, 1371, 1218, 1164, 1077, 1003, 745 cm$^{-1}$; $^1$H NMR (CDCl$_3$, 600 MHz) δ=9.23 (s, 1H), 6.30 (s, 1H), 5.90 (dd, J=11.0, 0.5 Hz, 1H), 5.83 (dd, J=10.9, 2.3 Hz, 1H), 4.09-4.04 (m, 4H), 3.69 (s, 3H), 3.34 (dd, J=2.2, 0.5 Hz, 1H), 2.51 (d, J=14.0 Hz, 1H), 2.37 (d, J=14.0 Hz, 1H), 0.95 (t, J=7.9 Hz, 9H), 0.71 (q, J=7.8 Hz, 6H) ppm; $^{13}$C NMR (CDCl$_3$, 151 MHz) δ=190.3, 167.9, 158.2, 153.1, 120.6, 119.9, 110.0, 103.5, 102.8, 98.2, 85.5, 83.5, 80.6, 70.7, 65.6, 65.6, 51.4, 49.7, 7.1, 6.1 ppm; HRMS (ESI-TOF) calcd for C$_{24}$H$_{31}$NO$_6$SiNa$^+$[M+Na]$^+$ 480.1813, found 480.1808.

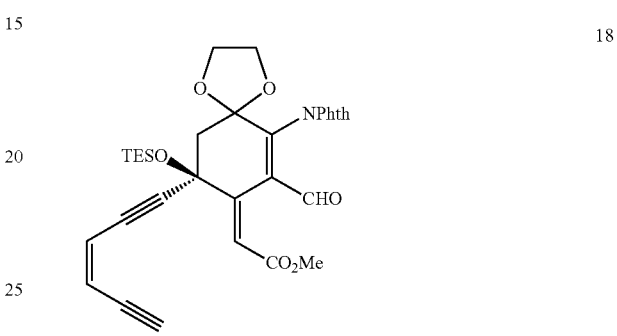

18

N-Phthalide Aldehyde 18:

To a stirred solution of free amine 17a-SI (4.51 g, 9.86 mmol, 1.0 equiv.) in MeNO$_2$ (200 mL) were added pyridine (3.12 g, 3.19 mL, 39.4 mmol, 4.0 equiv.) and phthaloyl chloride (3.00 g, 2.13 mL, 14.8 mmol, 1.5 equiv.) at 0° C. After stirring at this temperature for 30 min, the resulting mixture was quenched with saturated aqueous NaHCO$_3$ (100 mL) and extracted with CH$_2$Cl$_2$×100 mL). The combined organic layers were washed with brine (50 mL), dried over anhydrous Na$_2$SO$_4$ and filtered. The solvent was removed under vacuum and the residue was dissolved in CH$_2$Cl$_2$ (50 mL). Silica gel (20 g) was added to this solution and the resulting suspension was stirred at 25° C. for 2 h, before it was concentrated to dryness and washed with 15% MeOH in EtOAc (100 mL). The filtrate was dissolved in Ac$_2$O (30 mL) and stirred at 25° C. for 1 h. The excess Ac$_2$O was removed under reduced pressure and the residue was purified by flash column chromatography (silica gel, EtOAc:hexanes=1:5→1:1) to give N-phthalide aldehyde 18 (4.70 g, 7.99 mmol, 81%) as a colorless oil. 18: R$_f$=0.36 (silica gel, EtOAc:hexanes=1:1.5); [α]20 D=−3.8 (c=1.0, CHCl$_3$); FT-IR (neat) v$_{max}$=2955, 2877, 1731, 1367, 1273, 1215, 1181, 1144, 1107, 1001, 951, 882, 716 cm$^{-1}$; $^1$H NMR (CDCl$_3$, 600 MHz) δ=9.40 (s, 1H), 7.95-7.89 (m, 2H), 7.78-7.75 (m, 2H), 6.65 (s, 1H), 6.08 (d, J=11.0 Hz, 1H), 5.88 (dd, J=11.0, 2.4 Hz, 1H), 3.96-3.91 (m, 2H), 3.85-3.76 (m, 2H), 3.69 (s, 3H), 3.32 (dd, J=2.4, 1.0 Hz, 1H), 2.61 (d, J=13.7 Hz, 1H), 2.51 (d, J=13.7 Hz, 1H), 1.00 (t, J=7.9 Hz, 9H), 0.85-0.75 (m, 6H) ppm; $^{13}$C NMR (CDCl$_3$, 151 MHz) δ=185.4, 166.5, 166.5, 166.4, 148.2, 137.7, 137.0, 134.5, 134.4, 132.3, 132.2, 124.2, 124.0, 120.8, 119.7, 118.0, 105.5, 95.6, 85.5, 85.3, 80.8, 71.2, 65.9, 65.9, 52.1, 51.1, 7.1, 6.1 ppm; HRMS (ESI-TOF) calcd for C$_{32}$H$_{33}$NO$_8$SiNa$^+$[M+Na]$^+$ 610.1868, found 610.1860.

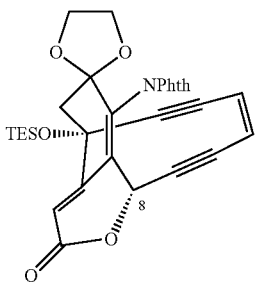

19

Lactone 19:

To a stirred solution of N-phthalide aldehyde 18 (2.17 g, 3.69 mmol, 1.0 equiv.) in THF (150 mL) was added LaCl$_3$·2LiCl (18.5 mL, 0.6 M in THF, 11.1 mmol, 3.0 equiv.) at −78° C. The resulting mixture was stirred at this temperature for 30 min before LiHMDS (7.38 mL, 1.0 M in THF, 7.38 mmol, 2.0 equiv.) was added dropwise. The reaction mixture was stirred at −78° C. for 1 h before it was quenched with saturated aqueous NaHCO$_3$ (100 mL). After extraction with EtOAc (3×100 mL), the combined organic layers were washed with brine (50 mL), dried over anhydrous Na$_2$SO$_4$ and filtered. The solvent was removed under vacuum and the residue was purified by flash column chromatography (silica gel, EtOAc:hexanes=1:5→1:1) to give lactone 19 (1.74 g, 3.13 mmol, 85%) as a colorless oil. 19: R$_f$=0.42 (silica gel, EtOAc:hexanes=1:1); [α]20 D=−364.8 (c=1.0, CHCl$_3$); FT-IR (neat) v$_{max}$=2957, 2877, 1789, 1732, 1467, 1368, 1273, 1240, 1181, 1114, 1018, 1004, 951, 880, 840, 753, 718 cm$^{-1}$; $^1$H NMR (CDCl$_3$, 600 MHz) δ=7.97-7.91 (m, 2H), 7.82-7.79 (m, 2H), 6.27 (s, 1H), 6.07 (d, J=9.7 Hz, 1H), 5.91 (dd, J=9.7, 1.7 Hz, 1H), 5.74 (d, J=1.7 Hz, 1H), 3.97-3.87 (m, 3H), 3.58 (q, J=7.2 Hz, 1H), 2.55 (d, J=13.5 Hz, 1H), 2.50 (d, J=13.5 Hz, 1H), 1.02 (t, J=7.9 Hz, 9H), 0.84-0.72 (m, 6H) ppm; $^{13}$C NMR (CDCl$_3$, 151 MHz) δ=166.5, 165.9, 161.8, 153.2, 134.9, 134.9, 134.8, 131.9, 131.8, 126.0, 125.6, 124.3, 124.3, 123.3, 111.9, 105.9, 99.0, 95.1, 91.8, 91.0, 69.7, 68.1, 65.8, 65.6, 46.6, 7.1, 6.1 ppm; HRMS (ESI-TOF) calcd for C$_{31}$H$_{29}$NO$_7$SiNa$^+$[M+Na]$^+$578.1606, found 578.1590.

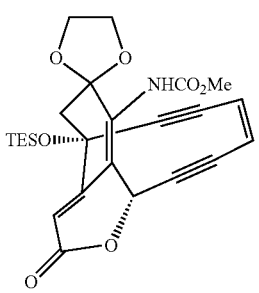

20

Methyl Carbamate 20:

To a stirred solution of lactone 19 (2.25 g, 4.05 mmol, 1.0 equiv.) in benzene (150 mL) at 25° C. was added MeNHNH$_2$ (1.87 g, 2.14 mL, 40.5 mmol, 10.0 equiv.). The resulting mixture was stirred at this temperature for 30 min. The solvent and excess MeNHNH$_2$ were removed under vacuum and the residue was purified by flash column chromatography (silica gel, EtOAc:hexanes=1:2→2:1) to give the corresponding free amine. To a stirred solution of so obtained free amine in CH$_2$Cl$_2$ (200 mL) were sequentially added pyridine (4.81 g, 4.92 mL, 60.8 mmol, 15 equiv.) and triphosgene (3.62 g, 12.2 mmol, 3.0 equiv.) at 0° C. The reaction mixture was stirred at this temperature for 1 h and then treated with MeOH (25 mL). The resulting mixture was stirred for another 1 h at this temperature and then quenched with saturated aqueous NaHCO$_3$ (100 mL). After extraction with CH$_2$Cl$_2$ (3×100 mL), the combined organic layers were washed with brine (50 mL), dried over anhydrous Na$_2$SO$_4$ and filtered. The solvent was removed under vacuum and the residue was purified by flash column chromatography (silica gel, EtOAc:hexanes=1:3→1:1) to give methyl carbamate 20 (1.59 g, 3.28 mmol, 81% for the two steps) as a colorless oil. 20: R$_f$=0.36 (silica gel, EtOAc:hexanes=1:1); [α]20 D=632.3 (c=1.0, CHCl$_3$); FT-IR (neat) v$_{max}$=3290, 2957, 2911, 2877, 1722, 1670, 1505, 1459, 1325, 1298, 1250, 1226, 1181, 1112, 1090, 1017, 1003, 835, 746, 739 cm$^{-1}$; $^1$H NMR (CDCl$_3$, 600 MHz) δ=6.18 (s, 1H), 6.11 (br s, 1H), 5.92 (d, J=9.6 Hz, 1H), 5.89 (br s, 1H), 5.83 (dd, J=9.5, 1.7 Hz, 1H), 4.20 (ddd, J=7.5, 5.9, 4.0 Hz, 1H), 4.10 (ddd, J=7.6, 5.8, 3.9 Hz, 1H), 4.01-3.93 (m, 2H), 3.76 (s, 3H), 2.46 (d, J=13.6 Hz, 1H), 2.27 (d, J=13.6 Hz, 1H), 1.00 (t, J=7.9 Hz, 9H), 0.82-0.69 (m, 6H) ppm; $^{13}$C NMR (CDCl$_3$, 151 MHz) δ=162.7, 154.6, 154.2, 128.2, 124.8, 123.6, 111.0, 105.0, 99.4, 96.5, 90.9, 88.1, 69.4, 68.9, 66.1, 65.5, 53.5, 45.6, 7.1, 6.1 ppm; HRMS (ESI-TOF) calcd for C$_{25}$H$_{29}$NO$_7$SiNa$^+$[M+Na]$^+$506.1606, found 506.1598.

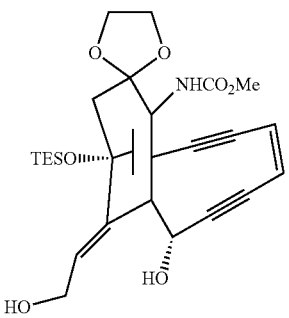

21

Diol 21:

To a stirred solution of methyl carbamate 20 (202 mg, 0.418 mmol, 1.0 equiv.) in MeOH (10 mL) at 25° C. was added CeCl$_3$·7H$_2$O (466 mg, 1.25 mmol, 3.0 equiv.). The resulting mixture was stirred at this temperature for 30 min before it was cooled to 0° C. NaBH$_4$ (31.6 mg, 0.836 mmol, 2.0 equiv.) was added at this temperature and the resulting mixture was allowed to warm to 25° C. and stirred for another 2 h before it was diluted with EtOAc (50 mL) and H$_2$O (50 mL). The organic layer was separated and the aqueous layer was extracted with EtOAc (3×50 mL). The combined organic layers were washed with brine (50 mL), dried over anhydrous Na$_2$SO$_4$ and filtered. The solvent was removed under vacuum and the residue was purified by flash column chromatography (silica gel, EtOAc:hexanes=1:1→3:1) to give diol 21 (188 mg, 0.385 mmol, 92%) as a colorless oil. 21: R$_f$=0.52 (silica gel, EtOAc); [α]20 D=−311.4 (c=0.5, CHCl$_3$); FT-IR (neat) v$_{max}$=3357, 2952, 2911, 2876, 1714, 1626, 1497, 1470, 1372, 1318, 1235, 1192, 1164, 1151, 1086, 1018, 823, 739 cm$^{-1}$; $^1$H NMR (CD$_3$OD, 600 MHz) δ=6.17 (t, J=6.4 Hz, 1H), 5.95 (d, J=9.4 Hz, 1H), 5.85 (dd, J=9.4, 1.6 Hz, 1H), 5.61 (d, J=0.8 Hz, 1H), 4.27 (d, J=6.3 Hz, 2H), 4.10-4.07 (m, 1H), 3.97-3.94 (m, 1H), 3.91-3.87 (m, 1H), 3.84-3.80 (m, 1H), 3.69 (s, 3H), 2.52 (d, J=13.2 Hz, 1H), 2.09 (d, J=13.2 Hz, 1H), 1.03 (t, J=7.9 Hz, 9H), 0.83-0.74 (m, 6H) ppm; $^{13}$C NMR (CD$_3$OD, 151 MHz) δ=137.8, 128.5, 125.1, 123.9, 106.9, 102.8, 86.4, 86.1, 72.8, 66.7, 66.3, 63.9, 62.4, 54.2, 53.1, 49.6, 7.4, 7.2 ppm; HRMS (ESI-TOF) calcd for C$_{25}$H$_{33}$NO$_7$SiNa$^+$[M+Na]$^+$ 510.1919, found 510.1924.

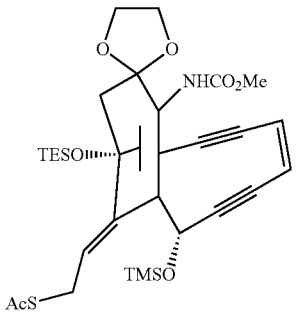

21a-SI

Thioacetate 21a-SI:

A solution of diol 21 (188 mg, 0.385 mmol, 1.0 equiv.) in TMSCN (1.0 mL) was stirred for 30 min at 25° C. The excess TMSCN was removed under reduced pressure and the residue was dissolved in THF (10 mL). A solution of AcOH (1.93 mL, 1.0 M in H$_2$O, 1.93 mmol, 5.0 equiv.) was added to the above reaction mixture at 0° C. After stirring at this temperature for 30 min (primary TMS group was removed), the resulting mixture was quenched with saturated aqueous NaHCO$_3$ (20 mL) and extracted with EtOAc (3×30 mL). The combined organic layers were washed with brine (10 mL), dried over anhydrous Na$_2$SO$_4$, and filtered. The solvent was removed under vacuum and the resulting primary alcohol was used for the next step without further purification. To a stirred solution of PPh$_3$ (506 mg, 1.93 mmol, 5.0 equiv.) in THF (10 mL) at 0° C. was added diethylazodicarboxylate (336 mg, 303 μL, 1.93 mmol, 5.0 equiv.). The resulting mixture was stirred at this temperature for 30 min before AcSH (147 mg, 136 μL, 1.93 mmol, 5.0 equiv.) and so obtained primary alcohol in THF (2.0 mL) were added sequentially at 0° C. After stirring at this temperature for 5 min, the resulting mixture was quenched with saturated aqueous NaHCO$_3$ (10 mL) and extracted with EtOAc (3×20 mL). The combined organic layers were washed with brine (10 mL), dried over anhydrous Na$_2$SO$_4$ and filtered. The solvent was removed under reduced pressure and the so obtained residue was purified by flash column chromatography (silica gel, EtOAc:hexanes=1:5→1:2) to give TMS-protected secondary alcohol 21a-SI (229 mg, 0.370 mmol, 96% for the three steps) as a colorless oil. 21a-SI: R$_f$=0.58 (silica gel, EtOAc:hexanes=1:1.5); [α]20 D=−206.0 (c=1.0, CHCl$_3$); FT-IR (neat) v$_{max}$=3355, 2955, 2877, 1737, 1689, 1493, 1252, 1224, 1191, 1166, 1152, 1114, 1084, 1014, 870, 845, 741 cm$^{-1}$; $^1$H NMR (CDCl$_3$, 600 MHz) δ=6.01 (dd, J=9.2, 6.4 Hz, 1H), 5.86 (d, J=9.3 Hz, 1H), 5.79 (br s, 1H), 5.77 (dd, J=9.4, 1.5 Hz, 1H), 4.09-4.06 (m, 1H), 3.99-3.85 (m, 4H), 3.78 (dd, J=13.9, 9.3 Hz, 1H), 3.73 (s, 3H), 2.47 (d, J=13.3 Hz, 1H), 2.31 (s, 3H), 2.06 (d, J=13.3 Hz, 1H), 0.97 (t, J=7.9 Hz, 9H), 0.72 (q, J=7.8 Hz, 6H), 0.23 (s, 9H) ppm; $^{13}$C NMR (151 MHz, CDCl$_3$) δ=195.9, 137.4, 129.0, 124.3, 124.2, 123.0, 105.9, 102.1, 101.9, 100.1, 85.6, 84.5, 71.7, 65.6, 65.3, 64.0, 53.1, 52.8, 30.7, 30.5, 7.2, 6.4, 0.4 ppm; HRMS (ESI-TOF) calcd for C$_{30}$H$_{43}$NO$_7$SSi$_2$Na$^+$[M+Na]$^+$ 640.2191, found 640.2183.

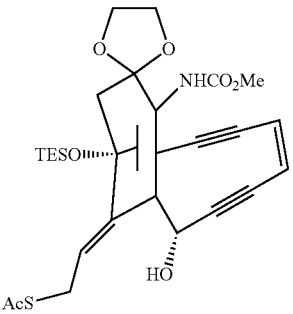

4

Thioacetate 4:

To a stirred solution of the TMS-protected thioacetate 21a-SI (229 mg, 0.370 mmol, 1.0 equiv.) in THF (10 mL) was added HF.py (0.5 mL, 30% HF in pyridine) at 0° C. The resulting mixture was stirred at this temperature for 30 min and then quenched with saturated aqueous NaHCO$_3$ (20 mL). After extraction with EtOAc (3×20 mL), the combined organic layers were washed with brine (10 mL), dried over anhydrous Na$_2$SO$_4$ and filtered. The solvent was removed under vacuum and the residue was purified by flash column chromatography (silica gel, EtOAc:hexanes=1:3→1:1) to give thioacetate 4 (200 mg, 0.366 mmol, 99%) as a colorless oil. 4: R$_f$=0.46 (silica gel, EtOAc:hexanes=1:1); [α]20 D=−394.7 (c=1.0, CHCl$_3$); FT-IR (neat) v$_{max}$=3386, 2955, 2911, 2876, 1723, 1685, 1498, 1458, 1414, 1353, 1319, 1297, 1259, 1233, 1192, 1164, 1151, 1111, 1008, 963, 976, 950, 743 cm$^{-1}$; $^1$H NMR (CDCl$_3$, 600 MHz) δ=6.43 (br s, 1H), 6.13 (t, J=8.4 Hz, 1H), 5.85 (d, J=9.5 Hz, 1H), 5.82 (dd, J=9.4, 1.3 Hz, 1H), 5.69 (d, J=6.4 Hz, 1H), 4.00-3.90 (m, 6H), 3.75 (s, 3H), 3.69 (br s, 1H), 2.49 (d, J=13.9 Hz, 1H), 2.31 (s, 3H), 2.17 (d, J=13.9 Hz, 1H), 0.98 (t, J=7.9 Hz, 9H), 0.78-0.68 (m, 6H) ppm; $^{13}$C NMR (CDCl$_3$, 151 MHz) δ=196.3, 155.2, 138.8, 132.0, 130.3, 124.0, 123.7, 123.4, 105.1, 103.6, 100.5, 86.6, 85.4, 70.3, 65.6, 65.3, 63.9, 53.4, 51.2, 30.5, 30.0, 7.2, 6.3 ppm; HRMS (ESI-TOF) calcd for C$_{27}$H$_{35}$NO$_7$SSiNa$^+$[M+Na]$^+$ 568.1796, found 568.1776.

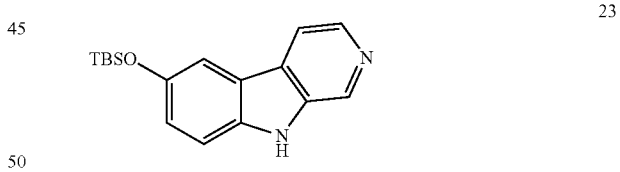

23 tert-Butyldimethylsilyl ether 23:

To a stirred solution of 6-hydroxy-β-carboline 22 (Schott et al., 2006) (5.30 g, 20.0 mmol, 1.0 equiv.) in DMF (45 mL) was slowly added Et$_3$N (6.07 g, 8.36 mL, 60.0 mmol, 3.0 equiv.) at 0° C., followed by slow addition of TBSOTf (4.67 g, 3.80 mL, 21.0 mmol, 1.05 equiv.) at the same temperature. The reaction mixture was stirred at 0° C. for another 30 min before it was quenched with saturated aqueous NaHCO$_3$ (20 mL). The resulting mixture was extracted with EtOAc (3×50 mL) and the organic layers were combined, dried over Na$_2$SO$_4$, filtered, and concentrated under vacuum. The residue was purified by flash column chromatography (silica gel, EtOAc:hexanes=1:2→100% EtOAc) to afford TBS-ether 23 (5.77 g, 19.3 mmol, 97%) which crystallized from CH$_2$Cl$_2$ as a pale yellow solid. 23: R$_f$=0.16 (silica gel, EtOAc); m.p.=166-167° C. (CH$_2$Cl$_2$); FT-IR (neat)

$v_{max}$=3132, 3051, 2955, 2929, 2885, 2857, 2741, 1603, 1578, 1560, 1493, 1463, 1440, 1306, 1272, 1259, 1197, 1162, 1035, 941, 885, 838, 813, 780 cm$^{-1}$; $^1$H NMR (CDCl$_3$, 600 MHz) δ=8.88 (s, 1H), 8.43 (d, J=5.2 Hz, 1H), 8.30 (br s, 1H), 7.90 (d, J=5.2 Hz, 1H), 7.54 (d, J=2.3 Hz, 1H), 7.37 (d, J=8.7 Hz, 1H), 7.11 (dd, J=8.7, 2.4 Hz, 1H), 1.04 (s, 9H), 0.24 (s, 6H) ppm; $^{13}$C NMR (CDCl$_3$, 151 MHz) δ=149.7, 139.1, 136.8, 135.8, 134.0, 128.9, 122.6, 122.4, 114.8, 112.1, 111.6, 25.9, 18.4, 4.2 ppm. HRMS (ESI-TOF) calcd for C$_{17}$H$_{23}$N$_2$OSi$^+$[M+H]$^+$ 299.1574, found 299.1566.

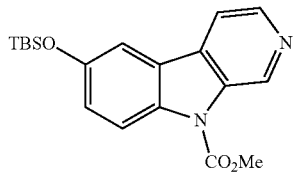

24

N-Methoxycarbonyl-β-Carboline 24:

To a stirred solution of tert-butyldimethylsilyl ether 23 (5.04 g, 16.9 mmol, 1.0 equiv.) in THF (60 mL) was added KHMDS (17.7 mL, 1.0 M in toluene, 17.7 mmol, 1.05 equiv.) at 0° C. The reaction mixture was stirred at this temperature for 30 min, before ClCO$_2$Me (1.76 g, 1.45 mL, 18.6 mmol, 1.1 equiv.) was added at this temperature. The resulting mixture was stirred at 0° C. for 30 min and then quenched with saturated aqueous NaHCO$_3$ (30 mL). The organic layer was separated and the aqueous layer was extracted with EtOAc (3×50 mL). The organic layers were combined, dried over Na$_2$SO$_4$, filtered, and concentrated under vacuum. The resulting residue was purified by flash column chromatography (silica gel, EtOAc:hexanes=1:4→1:1) to afford N-methoxycarbonyl-β-carboline 24 (5.88 g, 16.5 mmol, 98%) as a yellow solid. 24: R$_f$=0.41 (silica gel, EtOAc:hexanes=1:1); m.p.=64-66° C. (EtOAc); FT-IR (neat) $v_{max}$=3040, 2955, 2930, 2886, 2857, 1734, 1595, 1567, 1484, 1468, 1441, 1427, 1355, 1318, 1290, 1247, 1197, 1162, 1062, 1031, 937, 895, 832, 780 cm$^{-1}$; $^1$H NMR (CDCl$_3$, 600 MHz) δ=9.50 (br s, 1H), 8.56 (d, J=5.1 Hz, 1H), 8.18 (br s, 1H), 7.77 (dd, J=5.1, 1.1 Hz, 1H), 7.40 (d, J=2.4 Hz, 1H), 7.11 (dd, J=9.0, 2.5 Hz, 1H), 4.14 (s, 3H), 1.02 (s, 9H), 0.24 (s, 6H) ppm; $^{13}$C NMR (CDCl$_3$, 151 MHz) δ=152.4, 152.3, 143.2, 138.5, 135.1, 133.7, 132.0, 125.1, 122.9, 117.3, 114.1, 111.3, 54.0, 25.8, 18.4, 4.3 ppm. HRMS (ESI-TOF) calcd for C$_{19}$H$_{25}$N$_2$O$_3$Si$^+$[M+H]$^+$ 357.1629, found 357.1630.

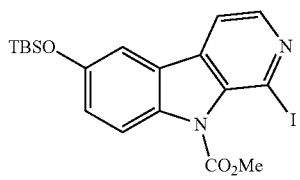

6

Iodocarboline 6:

To a stirred solution of β-carboline 24 (494 mg, 1.39 mmol, 1.0 equiv.) in THF (8 mL) was added freshly prepared TMPMgCl.LiCl (5.60 mL, 1.0 M in THF, 5.60 mmol, 4.0 equiv.) (Krasovskiy, et al., 2006b) at −78° C. The resulting reddish solution was allowed to warm up to 25° C., and stirred for 4 h. The reaction mixture was then cooled back to −78° C., followed by slow addition of I$_2$ solution (6.95 mL, 1.0 M in THF, 6.95 mmol, 5.0 equiv.). The reaction mixture was allowed to warm up to 0° C. over 30 min before it was quenched with saturated aqueous Na$_2$S$_2$O$_3$ (15 mL). EtOAc (20 mL) was added and the two layers were separated. The aqueous layer was extracted with EtOAc (3×30 mL) and the organic layers were combined, dried over Na$_2$SO$_4$, filtered, and concentrated under vacuum. The resulting residue was purified by flash column chromatography (silica gel, EtOAc:hexanes=1:15→1:10) to afford iodocarboline 6 (559 mg, 1.15 mmol, 83%) as a colorless oil. 6: R$_f$=0.51 (silica gel, EtOAc:hexanes=1:4); FT-IR (neat) $v_{max}$=3041, 2953, 2929, 2885, 2857, 1742, 1622, 1584, 1540, 1473, 1437, 1418, 1397, 1335, 1304, 1241, 1218, 1202, 1162, 1046, 947, 894, 833, 802, 780, 734 cm$^{-1}$; $^1$H NMR (CDCl$_3$, 600 MHz) δ=8.32 (d, J=5.0 Hz, 1H), 8.03 (d, J=8.9 Hz, 1H), 7.75 (d, J=5.0 Hz, 1H), 7.37 (d, J=2.4 Hz, 1H), 7.13 (dd, J=9.0, 2.5 Hz, 1H), 4.10 (s, 3H), 1.02 (s, 9H), 0.23 (s, 6H) ppm; $^{13}$C NMR (CDCl$_3$, 151 MHz) δ=152.8, 151.3, 143.7, 139.0, 135.4, 134.7, 124.3, 123.7, 116.4, 113.7, 111.3, 105.1, 54.1, 25.8, 18.4, −4.2 ppm. HRMS (ESI-TOF) calcd for C$_{19}$H$_{24}$IN$_2$O$_3$Si$^+$[M+H]$^+$ 483.0595, found 483.0585.

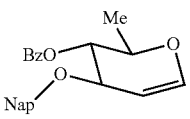

26

Benzoate 26:

To a stirred solution of glucal 25 (Tanaka et al., 2010) (13.5 g, 50.0 mmol, 1.0 equiv.) in CH$_2$Cl$_2$ (250 mL) were sequentially added Et$_3$N (5.56 g, 7.66 mL, 55.0 mmol, 1.1 equiv.) and benzoyl chloride (7.38 g, 6.10 mL, 52.5 mmol, 1.05 equiv.) at 0° C. The mixture was stirred at the same temperature for 30 min before being quenched with saturated aqueous NaHCO$_3$ solution (50 mL). The organic layer was separated and the aqueous layer was extracted with CH$_2$Cl$_2$ (3×100 mL). The organic layers were combined, dried over Na$_2$SO$_4$, and concentrated under vacuum. The resulting residue was purified by flash column chromatography (silica gel, EtOAc:hexanes=1:20→1:12) to afford benzoate 26 (18.2 g, 48.6 mmol, 97%) as a white foam. 26: R$_f$=0.58 (silica gel, EtOAc:hexanes=1:4); [α]20 D=−74.6 (c=0.2, CHCl$_3$); FT-IR (neat) $v_{max}$=3061, 2983, 2935, 2872, 1721, 1646, 1602, 1509, 1451, 1387, 1334, 1315, 1266, 1249, 1176, 1111, 1069, 1027, 1000, 952, 856, 817, 748, 710 cm$^{-1}$; $^1$H NMR (CDCl$_3$, 600 MHz) δ=8.05-7.99 (m, 2H), 7.79-7.75 (m, 1H), 7.72 (s, 1H), 7.71-7.68 (m, 2H), 7.61-7.55 (m, 1H), 7.46-7.41 (m, 4H), 7.39 (dd, J=8.4, 1.7 Hz, 1H), 6.47 (dd, J=6.2, 1.4 Hz, 1H), 5.40 (dd, J=7.5, 5.7 Hz, 1H), 4.96 (dd, J=6.2, 3.0 Hz, 1H), 4.83 (d, J=12.2 Hz, 1H), 4.75 (d, J=12.2 Hz, 1H), 4.28-4.23 (m, 1H), 4.21 (quint, J=6.8 Hz, 1H), 1.39 (d, J=6.6 Hz, 3H) ppm; $^{13}$C NMR (CDCl$_3$, 151 MHz) δ=165.7, 145.1, 135.8, 133.4, 133.3, 133.1, 130.0, 129.9, 128.6, 128.3, 128.0, 127.8, 126.6, 126.1, 125.9, 125.9, 100.0, 72.9, 72.9, 72.3, 70.3, 16.8 ppm. HRMS (ESI-TOF) calcd for C$_{24}$H$_{22}$O$_4$Na$^+$[M+Na]$^+$ 397.1410, found 397.1398.

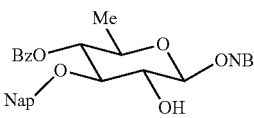

27 o-Nitrobenzyl-β-Pyranoside Alcohol 27:

To a stirred solution of benzoate 26 (9.45 g, 25.2 mmol, 1.0 equiv.) in $CH_2Cl_2$ (60 mL) were sequentially added acetone (11.9 g, 15.0 mL, 204 mmol, 8.0 equiv.), $NaHCO_3$ (53.0 g, 631 mmol, 25 equiv.) and $H_2O$ (45 mL), followed by a slow addition of Oxone® (38.8 g, 126 mmol, 5.0 equiv.). The mixture was vigorously stirred for 4 h until no starting material was present (TLC). The reaction mixture was partitioned with $H_2O$ (100 mL) and $CH_2Cl_2$ (100 mL). The organic layer was separated and the aqueous layer was extracted with $CH_2Cl_2$ (3×50 mL). The organic layers were combined and volatiles were evaporated under vacuum. The crude epoxide so-obtained was dissolved in THF (100 mL), followed by addition, with stirring, of o-nitrobenzyl alcohol (11.6 g, 75.5 mmol, 3.0 equiv.) and 4 Å molecular sieves (50 g). The resulting mixture was cooled to −78° C. and stirred for 30 min before slow addition of a $ZnCl_2$ solution (38.0 mL, 1.0 M in THF, 38.0 mmol, 1.5 equiv.) at this temperature. The reaction mixture was allowed to warm to 25° C. over 4 h and then quenched with saturated aqueous $NaHCO_3$ (100 mL). The resulting mixture was filtered through a layer of Celite® and partitioned with $H_2O$ (100 mL) and $CH_2Cl_2$ (100 mL). The organic layer was separated and the aqueous layer was extracted with $CH_2Cl_2$ (3×60 mL). The organic layers were combined, dried over $Na_2SO_4$, filtered, and concentrated under vacuum. The so obtained residue was purified by flash column chromatography (silica gel, EtOAc:hexanes=1:7→1:3) to afford alcohol 27 (7.41 g, 13.6 mmol, 54%) as a white solid. 27: $R_f$=0.16 (silica gel, EtOAc:hexanes=1:4); m.p.=132-134° C. ($CH_2Cl_2$); [α]20 D=−36.4 (c=0.5, $CHCl_3$); FT-IR (neat) $v_{max}$=3498, 3059, 2982, 2924, 2857, 1722, 1602, 1578, 1523, 1450, 1340, 1314, 1266, 1171, 1113, 1080, 1068, 1037, 1026, 979, 942, 901, 857, 819, 790, 753, 728, 710 $cm^{-1}$; $^1$H NMR ($CDCl_3$, 600 MHz) δ=8.08 (dd, J=8.2, 1.3 Hz, 1H), 7.98-7.92 (m, 2H), 7.89-7.84 (m, 1H), 7.72-7.68 (m, 1H), 7.67 (td, J=7.6, 1.3 Hz, 1H), 7.64-7.60 (m, 2H), 7.58-7.53 (m, 2H), 7.50-7.45 (m, 1H), 7.43-7.37 (m, 4H), 7.29-7.26 (m, 1H), 5.29 (d, J=14.6 Hz, 1H), 5.19-5.08 (m, 2H), 4.94 (d, J=11.9 Hz, 1H), 4.88 (d, J=11.9 Hz, 1H), 4.53 (d, J=7.7 Hz, 1H), 3.82 (dd, J=9.1, 7.7 Hz, 1H), 3.75 (t, J=9.2 Hz, 1H), 3.64 (dq, J=9.7, 6.2 Hz, 1H), 2.49 (s, 1H), 1.26 (d, J=6.2 Hz, 3H) ppm; $^{13}$C NMR ($CDCl_3$, 151 MHz) δ=165.6, 147.5, 135.6, 134.0, 133.9, 133.4, 133.3, 133.0, 129.9, 129.8, 129.3, 128.6, 128.5, 128.3, 128.0, 127.8, 127.0, 126.1, 126.1, 125.9, 124.8, 102.5, 81.3, 75.2, 75.0, 74.7, 70.7, 68.2, 17.6 ppm. HRMS (ESI-TOF) calcd for $C_{31}H_{29}NO_8Na^+[M+Na]^+$ 566.1785, found 566.1763.

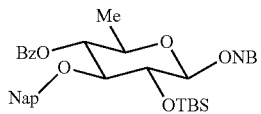

28

Tert-Butyldimethylsilyl Ether 28:

To a stirred solution of alcohol 27 (1.59 g, 2.93 mmol, 1.0 equiv.) in $CH_2Cl_2$ (30 mL) was added $Et_3N$ (326 mg, 0.449 mL, 3.23 mmol, 1.1 equiv.) and TBSOTf (812 mg, 0.661 mL, 3.07 mmol, 1.05 equiv.) at 0° C. The reaction mixture was stirred at 0° C. for 30 min before it was quenched with saturated aqueous $NaHCO_3$ (20 mL). The organic layer was separated and the aqueous layer was extracted with $CH_2Cl_2$ (3×30 mL). The organic layers were combined, dried over $Na_2SO_4$, filtered, and concentrated under vacuum. The crude TBS-ether 28 so obtained was used for the next step without further purification. 28: $R_f$=0.56 (silica gel, EtOAc:hexanes=1:4); [α]20 D=67.0 (c=1.0, $CHCl_3$); FT-IR (neat) $v_{max}$=3060, 2954, 2929, 2894, 2856, 1725, 1602, 1578, 1525, 1472, 1462, 1451, 1387, 1340, 1264, 1168, 1112, 1093, 1068, 1042, 1026, 987, 940, 902, 856, 838, 817, 780, 729, 710 $cm^{-1}$; $^1$H NMR ($CDCl_3$, 600 MHz) δ=8.12 (dd, J=8.2, 1.2 Hz, 1H), 7.97 (d, J=7.8 Hz, 1H), 7.86-7.81 (m, 2H), 7.69-7.66 (m, 1H), 7.66-7.63 (m, 1H), 7.63-7.60 (m, 1H), 7.54 (s, 1H), 7.50 (d, J=8.4 Hz, 1H), 7.48-7.43 (m, 2H), 7.41-7.36 (m, 2H), 7.28 (t, J=7.7 Hz, 2H), 7.22 (d, J=8.4 Hz, 1H), 5.30 (d, J=15.3 Hz, 1H), 5.18-5.11 (m, 2H), 4.94 (d, J=11.4 Hz, 1H), 4.75 (d, J=11.4 Hz, 1H), 4.55 (d, J=7.5 Hz, 1H), 3.82 (t, J=8.1 Hz, 1H), 3.74 (t, J=9.0 Hz, 1H), 3.67-3.58 (m, 1H), 1.21 (d, J=6.2 Hz, 3H), 0.90 (s, 9H), 0.12 (s, 3H), 0.09 (s, 3H) ppm; $^{13}$C NMR ($CDCl_3$, 151 MHz) δ=165.6, 147.0, 135.6, 134.8, 133.8, 133.2, 133.2, 132.9, 129.7, 129.6, 129.3, 128.4, 128.1, 128.0, 128.0, 127.7, 126.6, 126.0, 125.9, 125.7, 124.8, 103.3, 83.4, 75.7, 75.7, 75.5, 70.5, 68.1, 26.1, 18.3, 17.6, 4.0, 4.0 ppm. HRMS (ESI-TOF) calcd for $C_{37}H_{43}NO_8SiNa^+[M+Na]^+$ 680.2650, found 680.2626.

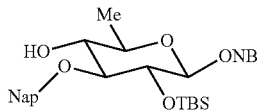

29

Secondary Alcohol 29:

To a stirred solution of crude TBS-ether benzoate 28 (1.95 g, 2.96 mmol, 1.0 equiv.) in MeOH (35 mL) was added NaOMe (1.60 g, 29.6 mmol, 10.0 equiv.) at 25° C. The reaction mixture was stirred at 40° C. for 24 h and then quenched with saturated aqueous $NH_4Cl$ (40 mL). The reaction mixture was concentrated under vacuum and partitioned with $CH_2Cl_2$ (50 mL) and $H_2O$ (50 mL). The organic layer was separated and the aqueous layer was extracted with $CH_2Cl_2$ (3×50 mL). The organic layers were combined, dried over $Na_2SO_4$, filtered, and concentrated under vacuum. The crude secondary alcohol 29 so obtained was used for the next step without further purification. 29: $R_f$=0.36 (silica gel, EtOAc:hexanes=1:4); [α]20 D=26.4 (c=2.0, $CHCl_3$); FT-IR (neat) $v_{max}$=3469, 3057, 2953, 2928, 2895, 2855, 1613, 1578, 1525, 1472, 1462, 1447, 1357, 1340, 1306, 1250, 1158, 1145, 1105, 1067, 1013, 938, 895, 855, 837, 816, 778, 754, 728 $cm^{-1}$; $^1$H NMR ($CDCl_3$, 600 MHz) δ=8.11 (dd, J=8.2, 1.0 Hz, 1H), 7.94 (d, J=7.8 Hz, 1H), 7.89-7.82 (m, 3H), 7.81 (s, 1H), 7.68-7.62 (m, 1H), 7.52-7.46 (m, 3H), 7.44 (t, J=7.6 Hz, 1H), 5.27 (d, J=15.4 Hz, 1H), 5.14 (d, J=12.1 Hz, 1H), 5.10 (d, J=15.3 Hz, 1H), 4.83 (d, J=12.1 Hz, 1H), 4.45 (d, J=7.6 Hz, 1H), 3.69 (dd, J=8.9, 7.6 Hz, 1H), 3.37 (t, J=8.9 Hz, 1H), 3.35-3.29 (m, 1H), 3.29-3.22 (m, 1H), 1.89 (d, J=2.6 Hz, 1H), 1.25 (d, J=6.0 Hz, 3H), 0.92 (s, 9H), 0.17 (s, 3H), 0.10 (s, 3H) ppm; $^{13}$C NMR ($CDCl_3$, 151 MHz) δ=147.1, 136.2, 134.8, 133.7, 133.5, 133.2, 129.3, 128.8, 128.1, 128.0, 127.9, 126.7, 126.5, 126.2, 125.6, 124.8, 103.2, 86.1, 75.8, 75.4, 75.3, 71.8, 67.9, 26.1, 18.3, 17.8, 3.9, 4.1 ppm. HRMS (ESI-TOF) calcd for $C_{30}H_{39}NO_7SiNa^+[M+Na]^+$ 576.2388, found 576.2379.

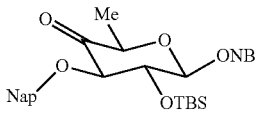

30

Ketone 30:

To a stirred solution of crude secondary alcohol 29 (1.90 g, ca. 2.75 mmol, 1.0 equiv.) in CH$_2$Cl$_2$ (30 mL) was added DMP (1.39 g, 3.27 mmol, 1.2 equiv.) at 0° C. The reaction mixture was allowed to warm to 25° C. and stirred for 1 h, before saturated solutions of aqueous NaHCO$_3$ (10 mL) and Na$_2$S$_2$O$_3$ (10 mL) were added sequentially with stirring. The organic layer was then separated and the aqueous layer was extracted with CH$_2$Cl$_2$ (3×30 mL). The organic layers were combined, dried over Na$_2$SO$_4$, filtered, and concentrated under vacuum. The residue was then purified by flash column chromatography (silica gel, EtOAc:hexanes=1:15→1:10) to afford ketone 30 (1.44 g, 2.61 mmol, 89% for the three steps from 27) as a white foam. 30: $R_f$=0.54 (silica gel, EtOAc:hexanes=1:4); [α]20 D=+30.6 (c=1.5, CHCl$_3$); FT-IR (neat) $v_{max}$=3058, 2952, 2929, 2887, 2856, 1741, 1614, 1578, 1525, 1471, 1462, 1446, 1407, 1359, 1340, 1303, 1251, 1163, 1106, 1066, 1007, 894, 857, 837, 817, 780, 755, 728 cm$^{-1}$; $^1$H NMR (CDCl$_3$, 600 MHz) δ=8.12 (dd, J=8.2, 1.3 Hz, 1H), 7.89 (dd, J=7.9, 1.3 Hz, 1H), 7.86-7.81 (m, 4H), 7.65 (td, J=7.6, 1.3 Hz, 1H), 7.60 (dd, J=8.5, 1.7 Hz, 1H), 7.50-7.43 (m, 3H), 5.31 (d, J=15.3 Hz, 1H), 5.13 (d, J=15.3 Hz, 1H), 5.05 (d, J=10.9 Hz, 1H), 4.83 (d, J=6.8 Hz, 1H), 4.76 (d, J=10.9 Hz, 1H), 4.10-4.02 (m, 2H), 3.97 (dd, J=8.9, 6.8 Hz, 1H), 1.34 (d, J=6.5 Hz, 3H), 0.86 (s, 9H), 0.08 (s, 3H), 0.05 (s, 3H) ppm; $^{13}$C NMR (CDCl$_3$, 151 MHz) δ=203.2, 147.0, 134.9, 134.4, 133.9, 133.4, 133.3, 129.1, 128.2, 128.2, 128.1, 127.8, 127.4, 126.6, 126.2, 126.1, 124.9, 103.1, 84.7, 77.2, 74.1, 73.8, 68.0, 25.9, 18.3, 14.5, −4.2, −4.4 ppm. HRMS (ESI-TOF) calcd for C$_{30}$H$_{37}$NO$_7$SiNa$^+$[M+Na]$^+$ 574.2232, found 574.2214.

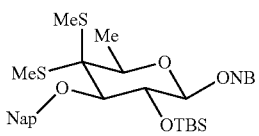

30a-SI

Bis-(Methylthio)-Ketal 30a-SI:

To a stirred solution of ketone 30 (3.64 g, 6.61 mmol, 1.0 equiv.) in toluene (60 mL) were sequentially added TMSSMe (1.98 g, 2.34 mL, 16.5 mmol, 2.5 equiv.) and TMSOTf (2.22 g, 1.80 mL, 9.95 mmol, 1.5 equiv.) at −20° C., and the reaction mixture was allowed to warm to 0° C. Saturated aqueous NaHCO$_3$ (5.0 mL, ca. 5.0 mmol) was added at this temperature, and the resulting mixture was stirred at the same temperature for 30 min before it was quenched with saturated aqueous NaHCO$_3$ (50 mL). The organic layer was separated and the aqueous layer was extracted with EtOAc (3×50 mL). The organic layers were combined, dried over Na$_2$SO$_4$, filtered, and concentrated under vacuum. The residue was purified by flash column chromatography (silica gel, EtOAc:hexanes=1:20→1:15) to afford bis-(methylthio)-ketal 30a-SI (2.54 g, 4.03 mmol, 61%) as a pale yellow oil. 30a-SI: $R_f$=0.61 (silica gel, EtOAc:hexanes=1:4); [α]20 D=+38 (c=1.0, CHCl$_3$); FT-IR (neat) $v_{max}$=3056, 2952, 2926, 2883, 2855, 1613, 1603, 1577, 1524, 1471, 1462, 1444, 1359, 1339, 1305, 1252, 1155, 1114, 1090, 1073, 1056, 1010, 873, 857, 837, 814, 779, 755, 728 cm$^{-1}$; $^1$H NMR (CDCl$_3$, 600 MHz) δ=8.10 (dd, J=8.2, 1.3 Hz, 1H), 7.99 (d, J=7.8 Hz, 1H), 7.86-7.79 (m, 4H), 7.67-7.63 (m, 1H), 7.59 (dd, J=8.4, 1.6 Hz, 1H), 7.50-7.45 (m, 2H), 7.43 (t, J=8.1 Hz, 1H), 5.27 (d, J=15.5 Hz, 1H), 5.09 (d, J=15.5 Hz, 1H), 5.04 (q, J=11.0 Hz, 2H), 4.46 (d, J=7.5 Hz, 1H), 4.32 (dd, J=8.7, 7.5 Hz, 1H), 3.77 (q, J=6.4 Hz, 1H), 3.53 (d, J=8.7 Hz, 1H), 2.35 (s, 3H), 2.17 (s, 3H), 1.44 (d, J=6.3 Hz, 3H), 0.87 (s, 9H), 0.09 (s, 3H), 0.05 (s, 3H) ppm; $^{13}$C NMR (CDCl$_3$, 151 MHz) δ=147.0, 136.2, 135.0, 133.7, 133.3, 132.9, 129.5, 128.1, 127.9, 127.8, 127.8, 126.1, 126.1, 125.8, 125.8, 124.7, 104.2, 87.9, 77.1, 76.6, 74.7, 67.8, 66.0, 26.1, 18.3, 16.4, 13.7, 12.7, −3.8 ppm. HRMS (ESI-TOF) calcd for C$_{32}$H$_{43}$NO$_6$S$_2$SiNa$^+$[M+Na]$^+$ 652.2193, found 652.2189.

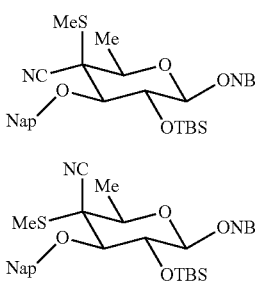

31

4-epi-31

Nitrile 31 and 4-Epi-31:

To a stirred solution of bis-(methylthio)-ketal 30a-SI (1.13 g, 1.79 mmol, 1.0 equiv.) in CH$_2$Cl$_2$ (20 mL) were sequentially added TMSCN (634 mg, 0.800 mL, 6.41 mmol, 3.5 equiv.) and SnCl$_4$ (2.68 mL, 1.0 M in CH$_2$Cl$_2$, 2.68 mmol, 1.5 equiv.) at 0° C. The reaction mixture was stirred at 0° C. for 3 h before it was quenched with saturated aqueous NaHCO$_3$ (20 mL). The reaction mixture was filtered through a layer of Celite® and partitioned with CH$_2$Cl$_2$ (40 mL) and H$_2$O (40 mL). The organic layer was separated and the aqueous layer was extracted with CH$_2$Cl$_2$ (3×20 mL). The organic layers were combined, dried over Na$_2$SO$_4$, filtered, and concentrated under vacuum. The residue was purified by flash column chromatography (silica gel, EtOAc:hexanes=1:15→1:10) to afford a mixture of nitriles 31 and 4-epi-31 (946 mg, 1.55 mmol, 87%, ca. 9:1 dr) as a white foam. 31: $R_f$=0.57 (silica gel, EtOAc:hexanes=1:4); [α]20 D=+2.0 (c=0.6, CHCl$_3$); FT-IR (neat) $v_{max}$=3059, 2953, 2928, 2885, 2856, 2234, 1697, 1612, 1578, 1525, 1471, 1462, 1442, 1386, 1361, 1340, 1304, 1253, 1142, 1107, 1095, 1071, 1044, 1008, 962, 938, 899, 854, 838, 817, 780, 755, 729 cm$^{-1}$; $^1$H NMR (CDCl$_3$, 600 MHz) δ=8.11 (dd, J=8.2, 1.3 Hz, 1H), 7.91 (dd, J=7.9, 1.3 Hz, 1H), 7.87-7.82 (m, 4H), 7.68-7.63 (m, 1H), 7.57-7.53 (m, 1H), 7.51-7.47 (m, 2H), 7.45 (t, J=7.6 Hz, 1H), 5.25 (d, J=15.3 Hz, 1H), 5.09 (d, J=15.3 Hz, 1H), 5.10-5.04 (m, 2H), 4.47 (d, J=7.5 Hz, 1H), 4.14 (dd, J=8.8, 7.5 Hz, 1H), 3.98 (q, J=6.2 Hz, 1H), 3.91 (d, J=8.8 Hz, 1H), 2.43 (s, 3H), 1.53 (d, J=6.2 Hz, 3H), 0.88 (s, 9H), 0.12 (s, 3H), 0.09 (s, 3H) ppm; $^{13}$C NMR (CDCl$_3$, 151 MHz) δ=147.0, 134.9, 134.4, 133.8, 133.3, 133.2, 129.3, 128.2, 128.2, 128.1, 127.8, 127.1, 126.2, 126.2 (2 C), 124.8, 117.1, 104.2, 86.7, 76.5, 72.9, 72.6, 68.1, 53.0, 26.0, 18.3, 16.8, 16.1, 3.9, 4.0 ppm. HRMS (ESI-TOF) calcd for C$_{32}$H$_{40}$N$_2$O$_6$SSiNa$^+$[M+Na]$^+$ 631.2269, found 631.2289. 4-epi-31: $R_f$=0.54 (silica gel, EtOAc:hexanes=1:4); [α]20

D=+60.5 (c=0.4, CHCl$_3$); FT-IR (neat) v$_{max}$=3057, 2953, 2927, 2856, 2236, 1603, 1577, 1525, 1471, 1462, 1447, 1360, 1340, 1304, 1254, 1167, 1154, 1112, 1089, 1051, 1009, 894, 857, 838, 816, 780, 729 cm$^{-1}$; $^1$H NMR (CDCl$_3$, 600 MHz) δ=8.11 (dd, J=8.2, 1.3 Hz, 1H), 7.94 (dd, J=7.9, 1.3 Hz, 1H), 7.89-7.79 (m, 4H), 7.68 (td, J=7.6, 1.3 Hz, 1H), 7.53-7.40 (m, 4H), 5.30-5.08 (m, 4H), 4.47 (d, J=7.6 Hz, 1H), 3.91 (dd, J=9.0, 7.6 Hz, 1H), 3.61-3.48 (m, 2H), 2.36 (s, 3H), 1.53 (d, J=6.2 Hz, 3H), 0.83 (s, 9H), 0.07 (s, 3H), 0.01 (s, 3H) ppm; $^{13}$C NMR (CDCl$_3$, 151 MHz) δ=147.0, 135.6, 134.5, 133.9, 133.4, 132.9, 129.4, 128.2, 128.1, 128.0, 127.8, 126.2, 125.9, 125.1, 124.8, 124.7, 115.0, 103.4, 86.6, 76.8, 74.9, 73.9, 68.1, 54.9, 26.0, 18.2, 16.9, 16.1, −4.0, −4.1 ppm. HRMS (ESI-TOF) calcd for C$_{32}$H$_{40}$N$_2$O$_6$SSiNa$^+$[M+Na]$^+$ 631.2269, found 631.2265.

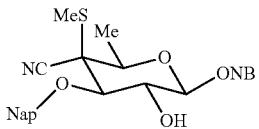

9

Secondary Alcohol 9:

To a stirred solution of nitrile 31 (1.21 g, 1.99 mmol, 1.0 equiv.) in THF (30 mL) were sequentially added NH$_4$F (740 mg, 20.0 mmol, 10.0 equiv.) and freshly prepared TBAF solution (Fürstner & Weintritt, 1998) (10.0 mL, 1.0 M in THF, 10.0 mmol, 5.0 equiv.) at 0° C. The reaction mixture was stirred at 0° C. for 1 h before it was diluted with EtOAc (30 mL) and quenched with saturated aqueous NH$_4$Cl (15 mL). The organic layer was separated and the aqueous layer was extracted with EtOAc (3×30 mL). The organic layers were combined, dried over Na$_2$SO$_4$, filtered, and concentrated under vacuum. The residue so obtained was purified by flash column chromatography (silica gel, EtOAc:hexanes=1:10→1:3) to afford secondary alcohol 9 (934 mg, 1.89 mmol, 95%) as a white foam. 9: R$_f$=0.20 (silica gel, EtOAc:hexanes=1:4); [α]20 D=+18.5 (c=1.0, CHCl$_3$); FT-IR (neat) v$_{max}$=3496, 3057, 2990, 2927, 2869, 2235, 1691, 1613, 1577, 1524, 1441, 1362, 1340, 1272, 1174, 1124, 1091, 1043, 1013, 960, 936, 895, 858, 820, 790, 755, 729 cm$^{-1}$; $^1$H NMR (CDCl$_3$, 600 MHz) δ=8.06 (dd, J=8.1, 0.9 Hz, 1H), 7.88-7.82 (m, 4H), 7.80 (d, J=7.8 Hz, 1H), 7.64 (td, J=7.6, 1.0 Hz, 1H), 7.56 (dd, J=8.3, 1.5 Hz, 1H), 7.51-7.47 (m, 2H), 7.46 (t, J=8.0 Hz, 1H), 5.23 (d, J=14.6 Hz, 1H), 5.10 (dd, J=15.2, 11.1 Hz, 2H), 5.07 (d, J=14.6 Hz, 1H), 4.44 (d, J=7.7 Hz, 1H), 4.16-4.10 (m, 1H), 3.97 (q, J=6.2 Hz, 1H), 3.94 (d, J=9.1 Hz, 1H), 2.47 (s, 3H), 2.39 (d, J=2.7 Hz, 1H), 1.56 (d, J=6.2 Hz, 3H) ppm; $^{13}$C NMR (CDCl$_3$, 151 MHz) δ=147.5, 134.8, 133.8, 133.6, 133.4, 133.3, 129.3, 128.6, 128.6, 128.2, 127.9, 127.5, 126.4, 126.4, 126.3, 124.8, 117.0, 103.4, 85.3, 76.1, 73.1, 72.0, 68.3, 52.8, 16.9, 16.1 ppm. HRMS (ESI-TOF) calcd for C$_{26}$H$_{26}$N$_2$O$_6$SNa$^+$[M+Na]$^+$ 517.1404, found 517.1400.

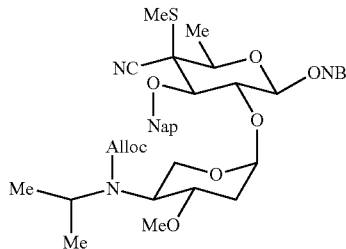

32

Disaccharide Nitrile 32:

A mixture of anhydrous AgClO$_4$ (920 mg, 4.44 mmol, 2.5 equiv.) and SnCl$_2$ (844 mg, 4.45 mmol, 2.5 equiv.) was dried by azeotropic removal of benzene (3×3 mL). The salts were then suspended in THF (10 mL), and powdered, activated 4 Å molecular sieves (2.0 g) were added. The suspension was stirred in the dark at 25° C. for 15 min and then cooled to −78° C. The resulting mixture was stirred at that temperature for 30 min to allow all moisture to be absorbed by the molecular sieves. A solution of fluoride 10$^7$ (1.08 g, 3.91 mmol, 2.2 equiv.) and secondary alcohol 9 (880 mg, 1.78 mmol, 1.0 equiv.) in THF (5 mL) was added slowly to this suspension with stirring, and the mixture was stirred at −78° C. for 1 h. The reaction mixture was allowed to warm slowly to 25° C. over 12 h, diluted with Et$_2$O (15 mL), and filtered through Celite®. The resulting solution was washed with saturated aqueous NaHCO$_3$ (10 mL) and brine (10 mL), dried over Na$_2$SO$_4$, filtered, and concentrated under vacuum. The resulting residue was purified by flash column chromatography (silica gel, EtOAc:hexanes=1:8→1:4) to give disaccharide nitrile 32 (1.13 g, 1.51 mmol, 85% yield based on 9) as a white foam. 32: R$_f$=0.24 (silica gel, EtOAc:hexanes=1:4); [α]20 D=11.1 (c=0.8, CHCl$_3$); FT-IR (neat) v$_{max}$=3058, 2965, 2933, 2299, 2234, 1690, 1648, 1578, 1525, 1440, 1421, 1381, 1363, 1340, 1307, 1284, 1257, 1197, 1165, 1124, 1094, 1075, 1044, 992, 961, 936, 915, 858, 819, 791, 755, 730 cm$^{-1}$; $^1$H NMR (CDCl$_3$, 600 MHz) δ=8.15-8.06 (m, 1H), 8.02-7.89 (m, 1H), 7.88-7.79 (m, 4H), 7.63 (t, J=7.6 Hz, 1H), 7.53-7.46 (m, 3H), 7.45-7.37 (m, 1H), 5.91-5.75 (m, 1H), 5.36-5.25 (m, 2H), 5.23-5.00 (m, 4H), 4.96 (d, J=10.6 Hz, 1H), 4.67-3.72 (m, 10H), 3.18 (s, 3H), 3.14 (m, 1H), 2.46 (br s, 3H), 2.12 (d, J=9.9 Hz, 1H), 1.55 (d, J=6.2 Hz, 3H), 1.40 (t, J=10.6 Hz, 1H), 1.11 (br s, 3H), 0.91 (br s, 3H) ppm; $^{13}$C NMR (CDCl$_3$, 151 MHz) δ=155.1, 146.6, 134.9, 134.4, 133.8, 133.4, 133.3, 133.3, 129.0, 128.6, 128.1, 127.9, 127.8, 127.3, 126.5, 126.5, 126.1, 124.5, 117.1, 116.8, 102.4, 99.4, 87.0, 76.4, 75.5, 72.8, 71.5, 68.3, 67.7, 65.4, 60.8, 56.6, 52.7, 47.7, 36.2, 21.3, 20.9, 16.8, 15.8 ppm. HRMS (ESI-TOF) calcd for C$_{39}$H$_{47}$N$_3$O$_{10}$SNa$^+$[M+Na]$^+$ 772.2874, found 772.2861.

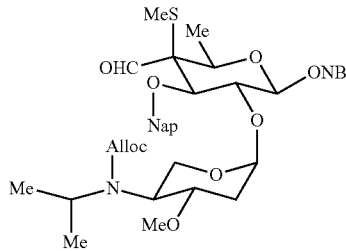

7

Disaccharide Aldehyde 7:

To a stirred solution of disaccharide nitrile 32 (1.04 g, 1.39 mmol, 1.0 equiv.) in $CH_2Cl_2$ (33 mL) was added DIBAL-H (4.15 mL, 1.0 M in $CH_2Cl_2$, 4.15 mmol, 3.0 equiv.) at −78° C. The reaction mixture was stirred at that temperature for 45 min before it was quenched with a mixture of aqueous K/Na tartrates solution (50 mL) and EtOAc (50 mL). The organic layer was separated and the aqueous layer was extracted with EtOAc (3×20 mL). The organic layers were combined, dried over $Na_2SO_4$, filtered, and concentrated under vacuum. The resulting residue was purified by flash column chromatography (silica gel, EtOAc:hexanes=1:6→1:3) to afford disaccharide aldehyde 7 (908 mg, 1.21 mmol, 87% yield) as a white foam. 7: $R_f$=0.33 (silica gel, EtOAc:hexanes=1:3); [α]20 D=32.8 (c=0.7, $CHCl_3$); FT-IR (neat) $v_{max}$=2967, 2936, 2844, 1692, 1648, 1613, 1577, 1525, 1439, 1364, 1340, 1307, 1282, 1257, 1197, 1146, 1124, 1100, 1060, 1033, 1017, 963, 930, 909, 858, 817, 770, 754, 730 $cm^{−1}$; $^1$H NMR ($CDCl_3$, 600 MHz) δ=9.67-9.43 (m, 1H), 8.08 (d, J=6.2 Hz, 1H), 8.01-7.88 (m, 1H), 7.86-7.77 (m, 3H), 7.73 (s, 1H), 7.59-7.44 (m, 3H), 7.38 (d, J=6.9 Hz, 2H), 6.00-5.79 (m, 1H), 5.45-5.02 (m, 5H), 4.98 (d, J=11.0 Hz, 1H), 4.91 (d, J=11.0 Hz, 1H), 4.68 (s, 1H), 4.62-3.64 (m, 9H), 3.32-3.15 (m, 1H), 3.22 (s, 3H), 2.28-2.21 (m, 3H), 2.21 (br s, 3H), 1.50-1.40 (m, 1H), 1.44 (br s, 3H), 1.14 (br s, 3H), 0.95 (br s, 3H) ppm; $^{13}$C NMR ($CDCl_3$, 151 MHz) δ=196.6, 155.3, 146.7, 135.5, 135.1, 133.8, 133.4, 133.3, 133.1, 129.1, 128.4, 128.1, 128.0, 127.9, 126.4, 126.3, 126.2, 125.7, 124.5, 116.9, 102.0, 99.3, 83.6, 75.7, 72.6, 71.8, 71.7, 67.9, 67.4, 66.2, 65.5, 60.8, 56.7, 47.5, 36.3, 21.4, 20.9, 16.7, 12.4 ppm. HRMS (ESI-TOF) calcd for $C_{39}H_{48}N_2O_{11}SNa^+[M+Na]^+$ 775.2871, found 775.2900.

33

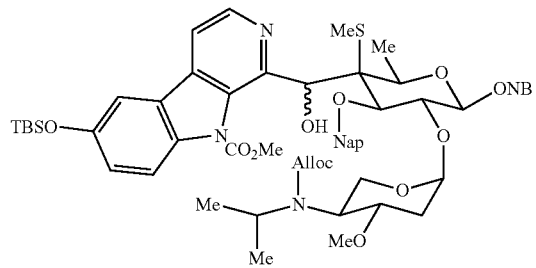

Coupling Product Alcohol 33 (Two Diastereoisomers, a and b):

To a stirred solution of iodocarboline 6 (602 mg, 1.25 mmol, 3.0 equiv.) in THF (10 mL) was slowly added t-BuLi (1.47 mL, 1.7 M in hexanes, 2.50 mmol, 6.0 equiv.) at −78° C. The dark solution so obtained was stirred at that temperature for another 30 min before slow addition of a solution of aldehyde 7 (314 mg, 0.417 mmol, 1.0 equiv.) in THF (3.5 mL). The reaction mixture was stirred at −78° C. for 10 min and then warmed up to −35° C. over 30 min before it was quenched with AcOH (180 mg, 0.176 mL, 3.0 mmol, 7.2 equiv.) at −78° C. The resulting mixture was diluted with EtOAc (15 mL) and treated with saturated aqueous $NaHCO_3$ (7 mL). The organic layer was separated and the aqueous layer was extracted with EtOAc (3×20 mL). The organic layers were combined, dried over $Na_2SO_4$, filtered, and concentrated under vacuum. The resulting residue was purified by flash column chromatography (silica gel, EtOAc:hexanes=1:12→1:3) to give coupling product alcohol 33 as a mixture of diastereoisomers (397 mg, 0.358 mmol, 86% yield based on 7, ca. 1:1 dr, inconsequential) as a brown foam. 33a (less polar): $R_f$=0.33 (silica gel, EtOAc:hexanes=1:3); [α]20 D=28.3 (c=0.6, $CHCl_3$); FT-IR (neat) $v_{max}$=3379, 3057, 2956, 2930, 2858, 1726, 1695, 1578, 1566, 1526, 1487, 1462, 1442, 1382, 1363, 1341, 1278, 1259, 1200, 1166, 1124, 1067, 970, 884, 838, 825, 812, 782, 730 $cm^{−1}$; $^1$H NMR ($CDCl_3$, 600 MHz) δ=8.83 (br s, 1H), 8.50 (d, J=5.1 Hz, 1H), 8.10 (br s, 2H), 7.96 (d, J=5.1 Hz, 1H), 7.74 (d, J=7.9 Hz, 1H), 7.64 (t, J=7.6 Hz, 1H), 7.59 (d, J=8.3 Hz, 1H), 7.54 (d, J=2.3 Hz, 1H), 7.51-7.36 (m, 4H), 7.11 (s, 1H), 7.06 (d, J=8.3 Hz, 1H), 7.02-6.91 (m, 2H), 6.81 (s, 1H), 5.86-5.76 (m, 1H), 5.38 (d, J=15.5 Hz, 1H), 5.34 (s, 1H), 5.29 (q, J=6.3 Hz, 1H), 5.26-5.14 (m, 2H), 5.14-5.04 (m, 2H), 4.80-3.99 (m, 9H), 3.78 (s, 3H), 3.69-3.60 (m, 1H), 3.28-3.15 (m, 1H), 3.08 (s, 3H), 2.44 (s, 3H), 2.13 (dd, J=12.9, 4.6 Hz, 1H), 1.61 (d, J=6.3 Hz, 3H), 1.44-1.37 (m, 1H), 1.07-1.06 (m, 12H), 0.89 (br s, 3H), 0.27 (s, 6H) ppm; $^{13}$C NMR ($CDCl_3$, 151 MHz) δ=157.0, 155.2, 149.9, 146.7, 138.9, 138.1, 136.3, 135.7, 135.5, 133.7, 133.3, 133.1, 132.8, 130.5, 129.4, 128.1, 128.0, 127.7, 127.6, 126.2, 126.0, 125.9, 125.7, 125.1, 124.5, 123.0, 122.2, 116.9, 115.6, 112.8, 111.3, 102.4, 99.6, 85.9, 79.2, 75.5, 74.1, 72.7, 71.6, 67.9, 67.5, 65.5, 62.1, 60.8, 56.7, 55.7, 47.5, 36.4, 25.9, 21.3, 20.9, 18.4, 18.0, 13.1, −4.2 ppm. HRMS (ESI-TOF) calcd for $C_{58}H_{73}N_4O_{14}SSi^+[M+H]^+$ 1109.4608, found 1109.4608. 33b (more polar): $R_f$=0.28 (silica gel, EtOAc:hexanes=1:3); [α]20 D=−4.7 (c=0.3, $CHCl_3$); FT-IR (neat) $v_{max}$=3374, 3055, 2956, 2929, 2857, 1727, 1695, 1579, 1566, 1526, 1487, 1463, 1442, 1364, 1341, 1275, 1200, 1125, 1075, 964, 938, 893, 858, 838, 782, 750, 730 $cm^{−1}$; $^1$H NMR ($CDCl_3$, 600 MHz) δ=8.90 (br s, 1H), 8.49 (d, J=5.1 Hz, 1H), 8.11-8.01 (m, 2H), 7.90 (d, J=5.1 Hz, 1H), 7.88-7.81 (m, 2H), 7.81-7.75 (m, 2H), 7.61 (t, J=7.7 Hz, 1H), 7.51-7.45 (m, 3H), 7.42-7.34 (m, 2H), 6.98 (br d, J=8.4 Hz, 1H), 6.89 (br s, 1H), 6.59 (s, 1H), 5.83 (ddt, J=16.1, 10.5, 5.3 Hz, 1H), 5.36 (br s, 1H), 5.30 (d, J=15.6 Hz, 1H), 5.27-5.16 (m, 1H), 5.15-4.95 (m, 4H), 4.85 (br d, J=11.7 Hz, 1H), 4.73-4.04 (m, 8H), 4.01 (q, J=6.2 Hz, 1H), 3.76 (s, 3H), 3.24-3.10 (m, 1H), 3.18 (s, 3H), 2.61 (s, 3H), 2.23 (br d, J=12.7 Hz, 1H), 1.42-1.34 (m, 1H), 1.33 (d, J=6.3 Hz, 3H), 1.10 (br s, 3H), 1.03 (s, 9H), 0.90 (br s, 3H), 0.23 (s, 3H), 0.22 (s, 3H) ppm; $^{13}$C NMR ($CDCl_3$, 151 MHz) δ=156.4, 155.2, 149.9, 146.6, 139.4, 138.1, 136.7, 135.9, 135.8, 133.7, 133.5, 133.3, 132.9, 130.8, 129.3, 129.0, 128.0, 127.8, 127.6, 126.2, 125.9, 125.6, 125.4, 124.6, 124.4, 122.9, 122.3, 116.8, 115.3, 112.6, 111.2, 102.4, 99.6, 84.7, 82.2, 78.7, 74.7, 72.5, 71.7, 67.9, 67.5, 65.5, 60.8, 60.7, 56.7, 55.6, 47.5, 36.3, 25.9, 21.3, 20.9, 18.4, 16.4, 15.2, 4.2 ppm. HRMS (ESI-TOF) calcd for $C_{58}H_{72}N_4O_{14}SSiNa^+[M+Na]^+$ 1131.4427, found 1131.4410.

34

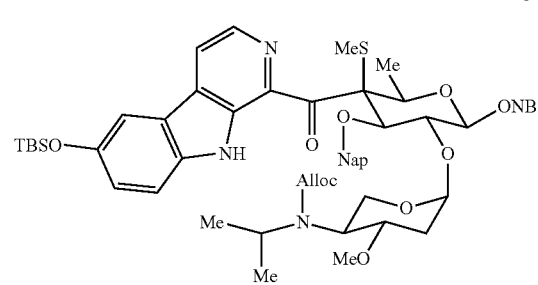

Ketone 34:

To a stirred solution of the coupling product alcohol 33 (a mixture of diastereoisomers, a and b, 636 mg, 0.573 mmol, 1.0 equiv.) in EtOH (12 mL) was slowly added a solution of NaOH in EtOH (3.45 mL, 0.5 M, 1.72 mmol, 3.0 equiv.) at 0° C. The reaction mixture was allowed to warm up to 25° C. and stirred at that temperature for another 2.5 h before it was quenched with saturated aqueous NH$_4$Cl (5 mL). The resulting mixture was concentrated under vacuum to remove all volatiles and the residue so obtained was extracted with EtOAc (3×20 mL). The organic layers were combined, dried over Na$_2$SO$_4$, filtered, and concentrated under vacuum. The resulting residue was dissolved in CHCl$_3$ (40 mL) and DMP (268 mg, 0.630 mmol, 1.1 equiv.) was added to the stirred solution at 0° C. The resulting reaction mixture was allowed to warm up to 35° C. over 5 min and stirring was continued at that temperature for another 5 min. The mixture was quenched with saturated aqueous Na$_2$S$_2$O$_3$ (10 mL) and the organic layer was separated. The aqueous layer was extracted with EtOAc (3×20 mL) and the combined organic layers were dried over Na$_2$SO$_4$, filtered, and concentrated under vacuum. The resulting residue was purified by flash column chromatography (silica gel, EtOAc:hexanes=1:4→1:2) to give ketone 34 (407 mg, 0.388 mmol, 68% for the two steps) as a yellow foam. 34: R$_f$=0.35 (silica gel, EtOAc:hexanes=1:3); [α]20 D=−4.5 (c=0.6, CHCl$_3$); FT-IR (neat) v$_{max}$=3446, 3057, 2957, 2930, 2857, 1695, 1633, 1578, 1525, 1484, 1462, 1420, 1363, 1341, 1306, 1283, 1253, 1184, 1126, 1098, 1047, 1007, 993, 955, 888, 838, 812, 781, 753, 729, 709 cm$^{-1}$; $^1$H NMR (CDCl$_3$, 600 MHz) δ=10.04 (br s, 1H), 8.42 (d, J=4.9 Hz, 1H), 8.19-8.06 (m, 2H), 7.99-7.84 (m, 1H), 7.64 (br s, 1H), 7.52-7.29 (m, 7H), 7.21-7.10 (m, 3H), 6.99 (br s, 1H), 6.17 (br s, 1H), 6.01-5.81 (m, 1H), 5.64 (br s, 1H), 5.52-4.91 (m, 7H), 4.80-3.63 (m, 8H), 3.45-3.03 (m, 1H), 3.23 (s, 3H), 2.64 (br s, 3H), 2.26 (br s, 1H), 1.46 (br s, 1H), 1.23-1.08 (m, 6H), 1.06 (s, 9H), 0.94 (br s, 3H), 0.27 (s, 6H) ppm; $^{13}$C NMR (CDCl$_3$, 151 MHz) δ=197.5, 155.2, 150.3, 146.6, 137.2, 136.2, 136.1, 135.6, 135.5, 134.9, 133.8, 133.3, 132.7, 132.5, 131.9, 129.4, 129.0, 127.7, 127.3, 126.0, 125.8, 125.6, 125.4, 124.6, 124.4, 123.3, 121.5, 119.2, 116.8, 112.5, 111.6, 102.9, 99.5, 88.4, 79.1, 75.0, 74.1, 72.3, 71.7, 68.2, 67.5, 65.5, 60.8, 56.8, 47.6, 36.4, 25.9, 21.3, 20.9, 18.4, 16.5, 14.9, 4.2 ppm. HRMS (ESI-TOF) calcd for C$_{56}$H$_{68}$N$_4$O$_{12}$SSiNa$^+$[M+Na]$^+$ 1071.4216, found 1071.4179.

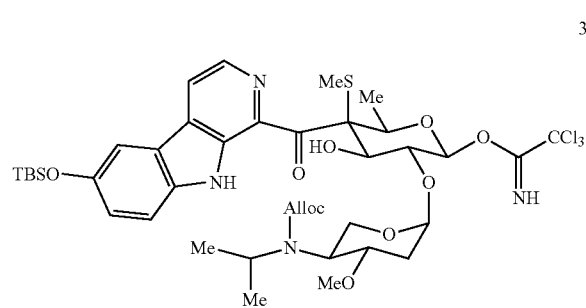

3

Hydroxy Trichloroacetimidate 3:

A solution of o-nitrobenzyl ether ketone 34 (200 mg, 0.191 mmol, 1.0 equiv.) in THF (200 mL) and H$_2$O (20 mL) was irradiated with a Hanovia mercury lamp (450 W) for 4.5 h. The resulting darkened solution was concentrated under vacuum and then extracted with EtOAc (3×10 mL). The organic layers were combined, dried over Na$_2$SO$_4$, filtered, and concentrated under vacuum to afford the corresponding crude lactol (ca. 1:1 mixture of anomers) which was used for the next reaction without further purification. To a vigorously stirred suspension of the crude lactol so obtained as described above in CH$_2$Cl$_2$ (10 mL) and H$_2$O (1.0 mL) was added DDQ (108 mg, 0.477 mmol, 2.5 equiv.) at 25° C. The reaction mixture was stirred at 30° C. for 1.5 h before it was quenched with saturated aqueous NaHCO$_3$ (6 mL). The resulting mixture was extracted with EtOAc (3×15 mL). The organic layers were combined, dried over Na$_2$SO$_4$, filtered, and concentrated under vacuum. The crude hydroxy lactol so obtained was dissolved in CH$_2$Cl$_2$ (5.0 mL) and Cl$_3$CCN (2.5 mL) and to the vigorously stirred solution at 25° C. was added NaH (9.2 mg, 0.38 mmol, 2.0 equiv.) portionwise. The reaction mixture was stirred at that temperature for another 5 min before it was filtered through a thin layer of Celite®. The filtrate was concentrated under vacuum and purified by flash column chromatography (silica gel, EtOAc:hexanes:Et$_3$N=50:10:1→50:25:1) to afford hydroxy trichloroacetimidate 3 (93.0 mg, 0.101 mmol, 53% for the three steps, β-anomer exclusively) as a yellow foam. 3: R$_f$=0.22 (silica gel, EtOAc:hexanes=1:3); [α]20 D=−44.8 (c=0.3, CHCl$_3$); FT-IR (neat) v$_{max}$=3344, 2957, 2930, 2857, 1724, 1670, 1579, 1484, 1463, 1364, 1286, 1252, 1201, 1126, 1075, 1028, 999, 955, 888, 838, 809, 797, 781 cm$^{-1}$; $^1$H NMR (CDCl$_3$, 600 MHz) δ=10.16 (br s, 1H), 8.66 (br s, 1H), 8.50 (d, J=4.9 Hz, 1H), 8.13 (d, J=5.0 Hz, 1H), 7.56 (d, J=2.3 Hz, 1H), 7.44 (d, J=8.7 Hz, 1H), 7.17 (dd, J=8.7, 2.3 Hz, 1H), 6.60 (br s, 1H), 6.17-5.85 (m, 1H), 5.82-5.60 (m, 1H), 5.60-5.39 (m, 1H), 5.36 (br s, 1H), 5.34-5.23 (m, 1H), 5.18 (br s, 1H), 4.71-4.46 (m, 2H), 4.37 (br s, 1H), 4.30-3.31 (m, 6H), 3.23 (s, 3H), 2.45 (br s, 1H), 2.25 (br s, 3H), 1.42-1.16 (m, 10H), 1.04 (s, 9H), 0.24 (s, 6H) ppm; $^{13}$C NMR (CDCl$_3$, 151 MHz) δ=197.8, 161.6, 150.6, 137.6, 136.5, 136.2, 134.6, 133.4, 132.6, 123.8, 121.6, 119.5, 117.3, 112.7, 111.8, 100.6, 98.5, 95.7, 91.8, 76.5, 72.7, 72.5, 72.0, 71.2, 65.9, 65.5, 60.7, 57.1, 46.6, 35.4, 25.9, 21.2, 21.0, 18.4, 17.3, 15.6, −4.2 ppm. HRMS (ESI-TOF) calcd for C$_{40}$H$_{55}$Cl$_3$N$_4$O$_{10}$SSiNa$^+$[M+Na]$^+$ 939.2366, found 939.2354.

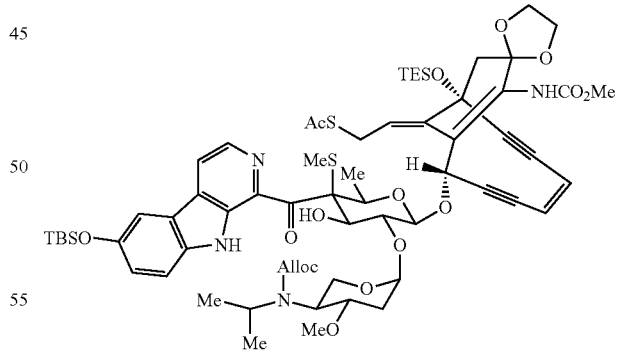

2

Enediyne Thioacetate 2:

A mixture of freshly prepared hydroxy trichloroacetimidate 3 (40.0 mg, 0.0436 mmol, 1.0 equiv.) and thioacetate 4 (38.0 mg, 0.0696 mmol, 1.6 equiv.) was dried by azeotropic removal of benzene (3×3 mL), and dissolved in CH$_2$Cl$_2$ (1.0 mL). Activated 4 Å molecular sieves (120 mg) were added to this solution. The mixture was cooled down to −78° C. and stirred for 30 min, before BF$_3$.OEt$_2$ (0.152 mL, 1.0 M in CH$_2$Cl$_2$, 0.152 mmol, 3.5 equiv.) was added at the same temperature. The reddish solution was stirred at −78° C. for 30 min, −60° C. for 30 min, and finally −40° C. for 10 min, at which temperature a solution of saturated aqueous NaHCO$_3$ (1.5 mL) was added to quench the reaction. The reaction mixture was then filtered through Celite®. The organic layer was separated and the aqueous layer was extracted with EtOAc (3×5 mL). The organic layers were combined, dried over Na$_2$SO$_4$, filtered, and concentrated under vacuum. The resulting residue was purified by PTLC (silica gel, EtOAc:hexanes=1:1) to give enediyne thioacetate 2 (14.7 mg, 0.0113 mmol, 26% yield based on 3) as a yellow foam. 2: R$_f$=0.25 (silica gel, EtOAc:hexanes=2:3); [α]20 D=−106 (c=0.2, MeOH); FT-IR (neat) v$_{max}$=3275, 2956, 2926, 2875, 2856, 1735, 1685, 1676, 1629, 1581, 1484, 1460, 1312, 1284, 1273, 1253, 1231, 1195, 1115, 1082, 1056, 1011, 976, 956, 887, 838, 827, 808, 780, 737 cm$^{-1}$; $^1$H NMR (C$_6$D$_6$, 600 MHz) δ=9.78 (br s, 1H), 7.96 (d, J=4.9 Hz, 1H), 7.78 (br s, 1H), 7.46 (d, J=2.4 Hz, 1H), 7.22 (d, J=4.9 Hz, 1H), 7.08-6.97 (m, 1H), 6.76 (br t, J=8.2 Hz, 1H), 6.67 (d, J=8.7 Hz, 1H), 6.50 (br s, 1H), 5.94 (br s, 1H), 5.78 (td, J=10.8, 5.1 Hz, 1H), 5.65-4.70 (m, 10H), 4.69-4.23 (m, 5H), 4.12 (br s, 1H), 3.85-3.19 (m, 9H), 3.18-2.89 (m, 4H), 2.74 (br s, 1H), 2.60 (br d, J=13.7 Hz, 1H), 2.42 (s, 3H), 1.91 (s, 3H), 1.84 (d, J=6.2 Hz, 3H), 1.61 (br t, J=10.4 Hz, 1H), 1.15 (t, J=7.9 Hz, 9H), 1.10 (s, 3H), 1.07 (s, 9H), 0.98-0.87 (m, 9H), 0.18 (s, 6H) ppm; $^{13}$C NMR (C$_6$D$_6$, 151 MHz) δ=199.0, 195.0, 155.9, 150.5, 137.8, 136.7, 136.0, 135.0, 133.5, 132.4, 125.3, 123.9, 123.5, 121.8, 119.1, 117.1, 112.9, 111.7, 106.4, 104.9, 104.5, 100.8, 100.5, 86.7, 85.2, 80.5, 76.8, 74.1, 72.1, 71.7, 71.3, 66.4, 65.5, 64.4, 61.2, 58.0, 56.4, 52.7, 52.4, 48.8, 37.6, 30.4, 30.2, 30.1, 25.9, 20.8, 18.6, 18.5, 16.0, 14.4, 7.6, 6.9, 4.3 ppm. HRMS (ESI-TOF) calcd for C$_{65}$H$_{88}$N$_4$O$_{16}$S$_2$Si$_2$Na$^+$[M+Na]$^+$1323.5068, found 1323.5038.

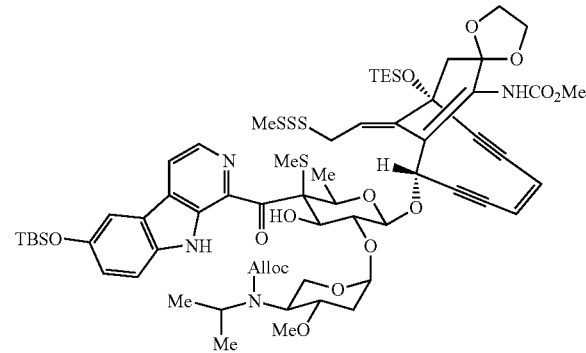

36

Methyl Trisulfide 36:

To a stirred solution of enediyne thioacetate 2 (9.2 mg, 0.0071 mmol, 1.0 equiv.) in MeOH (2.0 mL) was added a solution of KOH (0.14 mL, 0.5 M in MeOH, 0.070 mmol, 10.0 equiv.) at −15° C. The reaction mixture was stirred at −5° C. for 1.5 h until no starting material was present (TLC). AcOH (0.14 mL, 0.5 M in MeOH, 0.070 mmol, 10.0 equiv.) was added at that temperature to neutralize the resulting solution. PhthNSSMe (9.6 mg, 0.043 mmol, 6.0 equiv.) was added at 0° C., and the reaction mixture was stirred at this temperature for 15 min. The solution so obtained was concentrated under vacuum and the residue was purified by PTLC (silica gel, EtOAc:hexanes=2:3) to afford methyl trisulfide 36 (4.7 mg, 0.0035 mmol, 50% for the two steps) as a yellow foam. 36: R$_f$=0.29 (silica gel, EtOAc:hexanes=2:3); [α]20 D=92.5 (c=0.2, CHCl$_3$); FT-IR (neat) v$_{max}$=3413, 2956, 2931, 2877, 1734, 1672, 1579, 1556, 1485, 1462, 1419, 1363, 1311, 1285, 1274, 1252, 1194, 1168, 1144, 1123, 1082, 1056, 1010, 978, 953, 887, 838, 824, 809, 781, 743 cm$^{-1}$; $^1$H NMR (C$_6$D$_6$, 600 MHz) δ=9.80 (br s, 1H), 7.97 (d, J=4.9 Hz, 1H), 7.87-7.49 (m, 1H), 7.47 (d, J=2.4 Hz, 1H), 7.22 (d, J=4.9 Hz, 1H), 7.03 (dd, J=8.7, 2.4 Hz, 1H), 6.97 (br s, 1H), 6.67 (ddd, J=8.3, 5.6, 2.4 Hz, 1H), 6.51 (s, 1H), 5.92 (br s, 1H), 5.78 (br d, J=9.7 Hz, 1H), 5.69-4.66 (m, 10H), 4.66-4.27 (m, 5H), 4.14 (br s, 1H), 3.84-3.22 (m, 9H), 3.22-2.95 (m, 4H), 2.75 (br d, J=12.6 Hz, 1H), 2.63 (br d, J=13.7 Hz, 1H), 2.35 (br s, 3H), 2.29 (br s, 3H), 1.77 (br d, J=6.4 Hz, 3H), 1.65-1.58 (m, 1H), 1.18 (t, J=7.9 Hz, 9H), 1.14-1.09 (br s, 3H), 1.07 (s, 9H), 1.01-0.89 (m, 9H), 0.18 (s, 6H) ppm; $^{13}$C NMR (C$_6$D$_6$, 151 MHz) δ=198.8, 155.8, 150.5, 137.7, 136.7, 136.0, 135.1, 133.5, 132.4, 125.6, 123.8, 123.7, 123.5, 121.8, 119.1, 117.1, 112.9, 111.6, 106.4, 104.7, 104.2, 100.8, 100.4, 86.8, 85.3, 80.3, 76.9, 74.0, 71.9, 71.7, 71.5, 66.3, 65.5, 64.5, 61.2, 57.9, 56.4, 52.9, 52.4, 48.8, 40.1, 37.3, 30.2, 30.2, 25.9, 22.5, 20.9, 18.5, 18.4, 15.9, 7.6, 6.9, −4.3 ppm. HRMS (ESI-TOF) calcd for C$_{64}$H$_{88}$N$_4$O$_{15}$S$_4$Si$_2$Na$^+$ [M+Na]$^+$1359.4560, found 1359.4540.

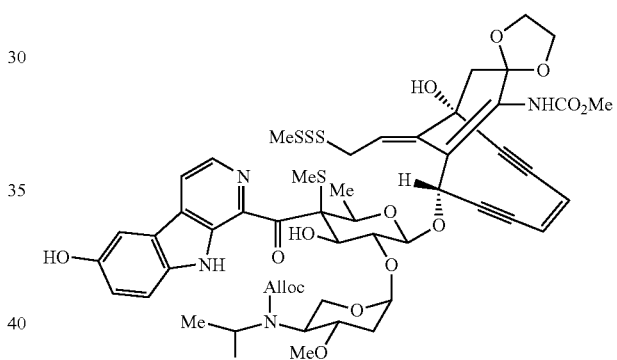

37

Phenol 37:

To a solution of the methyl trisulfide 36 (4.8 mg, 0.0036 mmol, 1.0 equiv.) in THF (1.5 mL) was added HF.py (75 μL, 70% HF in pyridine) at 0° C. The reaction mixture was allowed to warm to 25° C. and stirred for another 4 h, before it was diluted with EtOAc (3 mL) and quenched with saturated aqueous NaHCO$_3$ (2 mL). The organic layer was separated and the aqueous layer was extracted with EtOAc (3×5 mL). The organic layers were combined, dried over Na$_2$SO$_4$, filtered, and concentrated under vacuum. The resulting residue was purified by PTLC (silica gel, EtOAc:hexanes=2:1) to give phenol 37 (3.2 mg, 0.0029 mmol, 80% yield) as a yellow foam. 37: R$_f$=0.27 (silica gel, EtOAc:hexanes=2:1); [α]20 D=−47.0 (c=0.1, CHCl$_3$); FT-IR (neat) v$_{max}$=3358, 2924, 2853, 1664, 1555, 1492, 1462, 1384, 1313, 1287, 1194, 1144, 1123, 1053, 1016, 911, 838, 774, 731 cm$^{-1}$; $^1$H NMR (CD$_3$OD, 600 MHz) δ=8.44 (br s, 1H), 8.21 (d, J=4.9 Hz, 1H), 7.61-7.50 (m, 2H), 7.14 (dd, J=8.8, 2.4 Hz, 1H), 6.41-6.04 (m, 3H), 6.06-5.63 (m, 5H), 5.62-5.13 (m, 5H), 5.08-4.91 (m, 1H), 4.76-4.65 (m, 1H), 4.65-4.47 (m, 2H), 4.43-3.74 (m, 10H), 3.69 (br s, 3H), 3.56-3.35 (m, 1H), 3.25-3.08 (m, 3H), 2.61 (s, 3H), 2.57-2.46 (m, 1H), 2.47-2.24 (m, 4H), 2.26-2.08 (m, 2H), 2.07-1.98 (m, 1H), 1.65-1.50 (m, 1H), 1.31-1.12 (m, 9H) ppm; $^{13}$C NMR (CD$_3$OD, 151 MHz) δ=198.2, 157.5, 153.0, 139.7, 138.0, 137.5, 136.8, 136.5, 134.3, 133.3, 130.9, 130.8, 125.8, 125.5, 125.0, 123.8, 122.6, 120.1, 120.0, 117.8, 114.1, 106.9, 106.8, 102.9, 100.2, 90.6, 87.8, 84.4, 79.3, 74.3, 74.0, 73.8, 73.0, 71.6, 71.3, 67.1, 66.4, 62.4, 62.0, 58.8, 53.1, 51.6, 41.4, 37.0, 36.5, 33.1, 28.1, 26.9, 23.7, 23.1, 17.4, 15.1 ppm. HRMS (ESI-TOF) calcd for C$_{52}$H$_{60}$N$_4$O$_{15}$S$_4$Na$^+$ [M+Na]$^+$ 1131.2830, found 1131.2838.

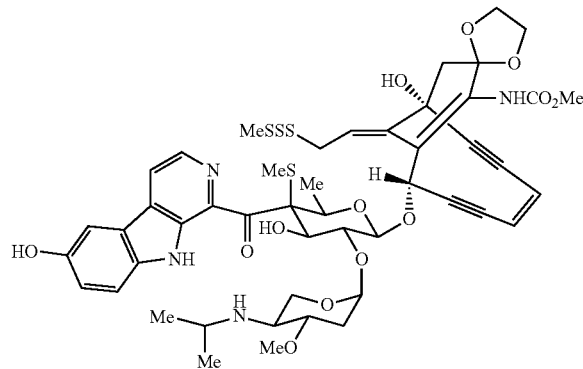

38

Amine 38:

To a stirred solution of phenol 37 (2.5 mg, 0.0023 mmol, 1.0 equiv.) in THF (1.0 mL) were added Pd(PPh$_3$)$_4$ (1.3 mg, 0.0011 mmol, 0.5 equiv.) and morpholine (3.0 mg, 3.0 μL, 0.034 mmol, 15 equiv.) sequentially at 0° C. The reaction mixture was stirred at the same temperature for 45 min before it was concentrated under vacuum. The residue so obtained was purified by PTLC (silica gel, EtOAc:Et$_3$N=12:1) to give free amine 38 (2.1 mg, 0.0021 mmol, 91% yield) as a yellow foam. Note: the free amine 38 so obtained was stabilized with TFA immediately. 38: R$_f$=0.36 (silica gel, EtOAc: Et$_3$N=12:1); [α]20 D=−55.0 (c=0.1, CHCl$_3$); FT-IR (neat) v$_{max}$=3352, 3097, 2925, 2854, 1675, 1496, 1462, 1432, 1380, 1287, 1247, 1201, 1137, 1063, 950, 880, 836, 800, 721 cm$^{-1}$; $^1$H NMR (CD$_3$OD, 600 MHz) δ=8.44 (d, J=4.9 Hz, 1H), 8.24 (d, J=4.9 Hz, 1H), 7.61-7.51 (m, 2H), 7.15 (dd, J=8.8, 2.4 Hz, 1H), 6.43 (dd, J=9.8, 5.3 Hz, 1H), 5.94 (d, J=9.4 Hz, 1H), 5.90 (br s, 1H), 5.86 (dd, J=9.4, 1.5 Hz, 1H), 5.68 (d, J=8.9 Hz, 1H), 5.61 (br t, J=2.9 Hz, 1H), 5.44 (q, J=6.4 Hz, 1H), 4.76 (d, J=7.8 Hz, 1H), 4.37-4.27 (m, 2H), 4.22 (dd, J=14.8, 9.8 Hz, 1H), 4.16-4.09 (m, 1H), 4.07 (dd, J=14.8, 5.4 Hz, 1H), 4.01-3.85 (m, 4H), 3.84-3.73 (m, 4H), 3.59-3.50 (m, 1H), 3.38 (s, 3H), 3.37-3.32 (m, 1H), 2.62 (s, 3H), 2.53-2.45 (m, 2H), 2.43 (s, 3H), 2.09 (d, J=13.1 Hz, 1H), 1.63-1.55 (m, 1H), 1.36-1.32 (m, 6H), 1.21 (d, J=6.4 Hz, 3H) ppm; $^{13}$C NMR (CD$_3$OD, 151 MHz) δ=198.1, 158.4, 153.1, 139.0, 138.0, 137.6, 136.5, 136.3, 133.5, 133.1, 130.0, 129.9, 125.8, 123.6, 122.5, 120.3, 120.2, 114.1, 106.8, 106.7, 104.4, 103.2, 99.8, 99.5, 88.0, 84.7, 80.1, 79.0, 74.8, 74.6, 74.5, 73.2, 72.0, 66.9, 66.4, 58.9, 56.3, 56.1, 53.9, 50.3, 49.6, 41.3, 34.7, 23.1, 20.1, 18.5, 17.2, 15.4 ppm. HRMS (ESI-TOF) calcd for C$_{48}$H$_{56}$N$_4$O$_{13}$S$_4$Na$^+$[M+Na]$^+$1047.2624, found 1047.2618.

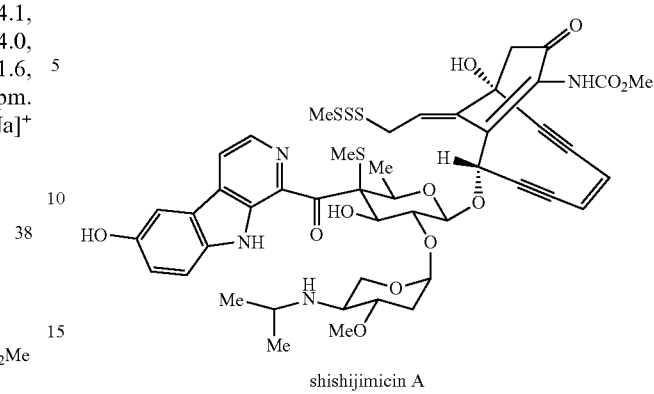

shishijimicin A

Shishijimicin A (1):

To a stirred solution of amine 38 (2.0 mg, 0.0020 mmol, 1.0 equiv.) in THF (0.5 mL) were added acetone (0.5 mL) and H$_2$O (25 μL) sequentially, followed by a slow addition of p-TSA (0.1 M in THF, 58 μL, 0.0058 mmol, 3.0 equiv.) at 25° C. The slightly darkened reaction mixture was stirred at 25° C. for 48 h before it was quenched with saturated aqueous NaHCO$_3$ (2 mL). The organic layer was separated and the aqueous layer was extracted with EtOAc (3×5 mL). The organic layers were combined, dried over Na$_2$SO$_4$, filtered, and concentrated under vacuum. The resulting residue was purified by reversed-phase HPLC (C$_{18}$, φ19×150 mm, Atlantis, 47.5%→52.5% aqueous MeCN containing 0.05% TFA) to afford shishijimicin A (1) (1.4 mg, 73% yield) as a yellow foam. 1: R$_f$=0.13 (silica gel, EtOAc:Et$_3$N 12:1); [α]20 D=−64.6 (c=0.24, MeOH) (Lit. [α]28 D=−66 (c=0.16, MeOH))$^8$; FT-IR (neat) v$_{max}$=3361, 2921, 2851, 1668, 1493, 1461, 1390, 1202, 1140, 1065, 837, 801, 721 cm$^{-1}$; $^1$H NMR (CD$_3$OD, 600 MHz) δ=8.42 (d, J=4.9 Hz, 1H), 8.22 (d, J=4.9 Hz, 1H), 7.56 (d, J=2.4 Hz, 1H), 7.54 (d, J=8.8 Hz, 1H), 7.14 (dd, J=8.7, 2.4 Hz, 1H), 6.52 (dd, J=10.1, 5.2 Hz, 1H), 6.35 (br s, 1H), 6.02 (d, J=9.5 Hz, 1H), 5.95 (dd, J=9.5, 1.7 Hz, 1H), 5.72 (d, J=8.9 Hz, 1H), 5.52 (br t, J=2.6 Hz, 1H), 5.48 (q, J=6.4 Hz, 1H), 4.95 (d, J=7.8 Hz, 1H), 4.34 (dd, J=8.9, 7.7 Hz, 1H), 4.18 (dd, J=14.4, 10.2 Hz, 1H), 4.14 (br t, J=10.8 Hz, 1H), 3.98 (dd, J=14.2, 5.1 Hz, 1H), 3.97 (dd, J=11.7, 4.3 Hz, 1H), 3.82 (td, J=9.7, 4.6 Hz, 1H), 3.75 (br s, 3H), 3.53 (m, 1H), 3.36 (s, 3H), 3.30 (m, 1H), 3.01 (d, J=17.0 Hz, 1H), 2.71 (d, J=17.0 Hz, 1H), 2.57 (s, 3H), 2.48 (ddd, J=13.2, 4.6, 2.3 Hz, 1H), 2.45 (s, 3H), 1.58 (ddd, J=13.4, 10.2, 3.6 Hz, 1H), 1.33 (d, J=6.5 Hz, 3H), 1.31 (d, J=6.5 Hz, 3H), 1.18 (d, J=6.3 Hz, 3H) ppm; $^{13}$C NMR (CDCl$_3$, 151 MHz) δ=197.8, 194.2, 157.8, 153.1, 149.3, 138.6, 138.0, 137.6, 136.5, 136.4, 133.5, 132.6, 128.6, 126.0, 124.1, 122.5, 120.3, 120.2, 114.1, 106.8, 103.0, 102.1, 100.0, 98.8, 89.2, 83.9, 79.9, 79.8, 74.8, 74.6, 74.3, 73.1, 70.7, 59.5, 56.3, 56.1, 54.8, 53.7, 50.6, 41.2, 34.7, 23.0, 19.9, 18.6, 17.2, 15.2 ppm; HRMS (ESI-TOF) calcd for C$_{46}$H$_{52}$N$_4$O$_{12}$S$_4$Na$^+$[M+Na]$^+$1003.2357, found 1003.2351.

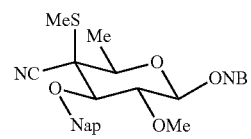

40

Methyl Ether 40:

To a stirred solution of alcohol 39 (Nicolaou, et al., 2015) (170 mg, 0.344 mmol, 1.0 equiv) and CH$_3$I (146 mg, 64 µl, 1.03 mmol, 3.0 equiv) in DMF (8.0 mL) at 0° C. was added washed sodium hydride (16.5 mg, 0.688 mmol, 2.0 equiv) portionwise. The reddish reaction mixture was stirred at this temperature for 40 min before it was quenched with saturated aqueous NH$_4$Cl solution (10 mL). The aqueous layer was extracted with EtOAc (3×15 mL) and the combined organic extracts were washed with brine (15 mL), dried over anhydrous Na$_2$SO$_4$, filtered and concentrated under vacuum. The residue was purified by flash column chromatography (silica gel, EtOAc/hexanes 1:7→1:5) to give methyl ether 40 (119 mg, 0.234 mmol, 68% yield) as a white foam. 40: $^1$H NMR (CDCl$_3$, 600 MHz) δ=8.10 (dd, J=8.2, 1.3 Hz, 1H), 7.91-7.79 (m, 5H), 7.67 (td, J=7.6, 1.3 Hz, 1H), 7.58-7.53 (m, 1H), 7.51-7.43 (m, 3H), 5.28 (d, J=15.1 Hz, 1H), 5.09 (d, J=15.1 Hz, 1H), 5.06 (d, J=10.9 Hz, 1H), 5.03 (d, J=10.9 Hz, 1H), 4.46 (d, J=7.7 Hz, 1H), 3.97-3.89 (m, 2H), 3.72 (dd, J=9.0, 7.6 Hz, 1H), 3.67 (s, 3H), 2.44 (s, 3H), 1.55 (d, J=6.2 Hz, 3H) ppm.

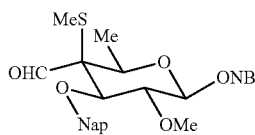

41

Aldehyde 41:

To a stirred solution of methyl ether 40 (120 mg, 0.236 mmol, 1.0 equiv) in CH$_2$Cl$_2$ (6.0 mL) at −78° C. was slowly added DIBAL-H (0.708 mL, 1.0 M in CH$_2$Cl$_2$, 0.708 mmol, 3.0 equiv). The reaction mixture was stirred at this temperature for another 5 min before it was quenched with saturated aqueous Rochelle salt solution (10 mL). The resulting mixture was diluted with EtOAc and the organic layer was separated. The aqueous layer was extracted with EtOAc (3×15 mL) and the organic layers were combined, dried over anhydrous Na$_2$SO$_4$, filtered and concentrated under vacuum. The residue was purified by flash column chromatography (silica gel, EtOAc/hexanes 1:6→1:3) to give aldehyde 41 (66.4 mg, 0.130 mmol, 55% yield) as a white foam. 41: R$_f$=0.61 (silica gel, CH$_2$Cl$_2$); [α]$_D^{20}$=−49 (c=0.75, CHCl$_3$); FT-IR (neat) ν$_{max}$=3057, 2984, 2928, 2860, 1715, 1613, 1577, 1524, 1443, 1361, 1340, 1156, 1121, 1096, 1076, 1035, 858, 819, 753, 729 cm$^{-1}$; $^1$H NMR (CDCl$_3$, 600 MHz) δ=9.58 (s, 1H), 8.10 (dd, J=8.2, 1.3 Hz, 1H), 7.88 (dd, J=7.8, 1.3 Hz, 1H), 7.85-7.79 (m, 4H), 7.63 (td, J=7.6, 1.3 Hz, 1H), 7.50-7.40 (m, 4H), 5.30 (d, J=15.2 Hz, 1H), 5.08 (d, J=15.2 Hz, 1H), 5.02 (d, J=10.7 Hz, 1H), 4.88 (d, J=10.8 Hz, 1H), 4.50 (d, J=7.4 Hz, 1H), 4.18 (d, J=8.9 Hz, 1H), 3.85 (dd, J=8.9, 7.3 Hz, 1H), 3.70 (q, J=6.5 Hz, 1H), 3.67 (s, 3H), 2.22 (s, 3H), 1.44 (d, J=6.4 Hz, 3H) ppm.

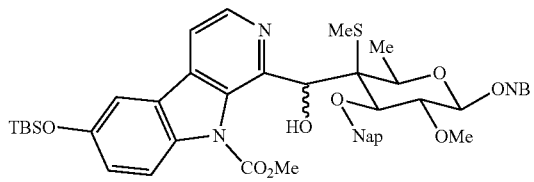

42a, b

Coupling Product Alcohol 42 (Two Diastereoisomers, a and b):

To a stirred solution of iodocarboline 6 (Nicolaou, et al., 2015) 250 mg, 0.518 mmol, 3.0 equiv) in THF (5.0 mL) was slowly added t-BuLi (0.610 mL, 1.7 M in hexanes, 1.04 mmol, 6.0 equiv) at −78° C. The dark solution so obtained was stirred at that temperature for 30 min before of a solution of aldehyde 41 (88.4 mg, 0.173 mmol, 1.0 equiv) in THF (1.2 mL) was slowly added. The reaction mixture was stirred at −78° C. for 10 min and then warmed up to −35° C. over 30 min before it was quenched with AcOH (102 mg, 0.100 mL, 1.70 mmol, 9.8 equiv) at −78° C. The resulting mixture was diluted with EtOAc (6 mL) and treated with saturated aqueous NaHCO$_3$ solution (7 mL). The organic layer was separated and the aqueous layer was extracted with EtOAc (3×10 mL). The organic layers were combined, dried over Na$_2$SO$_4$, filtered, and concentrated under vacuum. The resulting residue was purified by flash column chromatography (silica gel, EtOAc:hexanes=1:12→1:3) to give coupling product alcohol 42 as a mixture of diastereoisomers (115 mg, 0.133 mmol, 77% yield based on 41, ca. 1:1 inconsequential diastereoisomeric mixture) as a brown foam. 42a (less polar): R$_f$=0.41 (silica gel, CH$_2$Cl$_2$); [α]$_D^{20}$=−60 (c=1.0, CHCl$_3$); FT-IR (neat) ν$_{max}$=3396, 3055, 3012, 2955, 2929, 2857, 1742, 1724, 1567, 1525, 1487, 1461, 1442, 1340, 1276, 1259, 1200, 1168, 1125, 1093, 1061, 983, 884, 838, 811, 782, 755, 729 cm$^{-1}$; $^1$H NMR (CDCl$_3$, 600 MHz) δ=8.66 (br s, 1H), 8.43 (d, J=5.1 Hz, 1H), 8.09 (dd, J=8.2, 1.3 Hz, 1H), 7.92 (dd, J=7.9, 1.3 Hz, 1H), 7.90-7.88 (m, 1H), 7.79-7.75 (m, 1H), 7.68-7.63 (m, 2H), 7.59-7.55 (m, 1H), 7.51 (d, J=2.3 Hz, 1H), 7.47-7.41 (m, 3H), 7.25 (br s, 1H), 7.12 (dd, J=8.4, 1.7 Hz, 1H), 7.02 (dd, J=8.7, 2.3 Hz, 1H), 6.86 (d, J=8.6 Hz, 1H), 6.80 (s, 1H), 5.35 (d, J=15.3 Hz, 1H), 5.14-5.02 (m, 2H), 4.89 (d, J=11.2 Hz, 1H), 4.49 (d, J=7.6 Hz, 1H), 4.11 (dd, J=9.1, 7.6 Hz, 1H), 3.77 (d, J=9.1 Hz, 1H), 3.75 (s, 3H), 3.64 (d, J=11.4 Hz, 1H), 3.61 (s, 3H), 2.47 (s, 3H), 1.71 (d, J=6.3 Hz, 3H), 1.06 (s, 9H), 0.26 (s, 3H), 0.26 (s, 3H) ppm; $^{13}$C NMR (CDCl$_3$, 151 MHz) δ=156.73, 149.83, 147.26, 138.66, 138.31, 136.35, 136.34, 135.66, 135.00, 133.77, 133.22, 132.82, 130.40, 129.11, 128.03, 127.75, 126.14, 125.89, 125.31, 125.17, 124.82, 122.87, 122.26, 115.40, 112.77, 111.29, 103.92, 84.77, 84.21, 75.36, 74.05, 72.90, 67.83, 61.45, 60.77, 55.53, 25.94, 18.43, 18.08, 13.26, −4.20 ppm; HRMS (ESI-TOF) calcd for C$_{46}$H$_{54}$N$_3$O$_{10}$SiS$^+$[M+H]$^+$ 868.3294, found 868.3296. 42b (more polar): R$_f$=0.13 (silica gel, CH$_2$Cl$_2$); [α]$_D^{20}$=−71 (c=0.2, CHCl$_3$); FT-IR (neat) ν$_{max}$=3425, 3059, 2955, 2929, 2856, 1761, 1735, 1578, 1566, 1526, 1487, 1460, 1361, 1340, 1274, 1259, 1199, 1123, 1090, 1039, 977, 896, 838, 812, 783, 754, 729 cm$^{-1}$; $^1$H NMR (CDCl$_3$, 600 MHz) δ=8.80 (s, 1H), 8.37 (d, J=5.1 Hz, 1H), 8.11-8.02 (m, 2H), 7.93-7.83 (m, 4H), 7.81 (d, J=5.1 Hz, 1H), 7.63 (td, J=7.6, 1.3 Hz, 1H), 7.55-7.49 (m, 2H), 7.46-7.39 (m, 2H), 7.35 (dd, J=8.4, 1.7 Hz, 1H), 6.79 (dd, J=8.7, 2.3 Hz, 1H), 6.56 (s, 1H), 6.12 (d, J=8.7 Hz, 1H), 5.30 (d, J=15.2 Hz, 1H), 5.20 (d, J=12.7 Hz, 1H), 5.05 (d, J=15.2 Hz, 1H), 4.34 (d, J=7.6 Hz, 1H), 4.28 (d, J=12.7 Hz, 1H), 4.08 (q, J=6.3 Hz, 1H), 3.99 (d, J=9.2 Hz, 1H), 3.87 (dd, J=9.3, 7.6 Hz, 1H), 3.83 (s, 3H), 3.58 (s, 3H), 2.68 (s, 3H), 1.65 (d, J=6.3 Hz, 3H), 1.01 (s, 9H), 0.20 (s, 3H), 0.19 (s, 3H) ppm; $^{13}$C NMR (CDCl$_3$, 151 MHz) δ=155.59, 149.52, 147.28, 139.43, 137.74, 137.41, 135.39, 134.75, 134.72, 133.78, 133.75, 132.84, 130.39, 129.09, 128.19, 128.13, 127.90, 126.26, 125.90, 124.88, 124.86, 124.61, 122.59, 121.72, 114.83, 112.28, 110.95, 103.61, 83.96, 83.75, 83.50, 73.95, 73.03, 67.82, 61.12, 60.60, 55.62, 25.91, 18.38, 16.60, 15.86, −4.27, −4.28 ppm; HRMS (ESI-TOF) calcd for $C_{46}H_{54}N_3O_{10}SiS^+[M+H]^+$ 868.3294, found 868.3314.

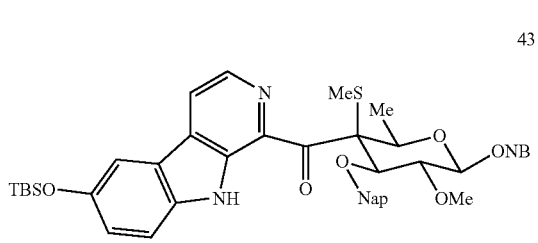

43

Ketone 43:

To a stirred solution of the coupling product alcohol 42 (a mixture of diastereoisomers, a and b, 110 mg, 0.127 mmol, 1.0 equiv) in EtOH (8.0 mL) was slowly added a solution of NaOH in EtOH (0.760 mL, 0.5 M, 0.380 mmol, 3.0 equiv) at 0° C. The reaction mixture was allowed to warm up to 25° C. and stirred at that temperature for another 2.5 h before it was quenched with saturated aqueous $NH_4Cl$ solution (3.0 mL). The resulting mixture was concentrated under vacuum to remove all volatiles and the residue so obtained was extracted with EtOAc (3×10 mL). The organic layers were combined, dried over $Na_2SO_4$, filtered, and concentrated under vacuum. The resulting residue was dissolved in $CHCl_3$ (15 mL) and DMP (59.4 mg, 0.140 mmol, 1.1 equiv) was added to the stirred solution at 0° C. The resulting reaction mixture was allowed to warm up to 35° C. over 5 min and stirring was continued at that temperature for another 5 min. The mixture was quenched with saturated aqueous $Na_2S_2O_3$ solution (5.0 mL) and the organic layer was separated. The aqueous layer was extracted with EtOAc (3×10 mL) and the combined organic layers were dried over $Na_2SO_4$, filtered, and concentrated under vacuum. The resulting residue was purified by flash column chromatography (silica gel, EtOAc/hexanes 1:4→1:2) to give ketone 43 (64.6 mg, 0.0800 mmol, 63% yield over the two steps) as a yellow foam. 43: $R_f$=0.38 (silica gel, EtOAc/hexanes 1:2); $[\alpha]_D^{20}$=−43 (c=0.4, $CHCl_3$); FT-IR (neat) $v_{max}$=3443, 3054, 2953, 2930, 2857, 1661, 1578, 1525, 1483, 1462, 1362, 1341, 1282, 1273, 1251, 1182, 1131, 1104, 1067, 1046, 1008, 978, 950, 887, 839, 811, 782, 752, 728 $cm^{-1}$; $^1$H NMR ($CDCl_3$, 600 MHz) δ=10.02 (s, 1H), 8.17 (d, J=4.8 Hz, 1H), 8.12 (dd, J=8.2, 1.3 Hz, 1H), 8.02 (dd, J=7.8, 1.3 Hz, 1H), 7.75-7.67 (m, 2H), 7.47 (t, J=7.7 Hz, 1H), 7.39 (d, J=2.3 Hz, 1H), 7.36-7.32 (m, 2H), 7.23-7.16 (m, 3H), 7.15-7.10 (m, 3H), 6.96 (dd, J=8.4, 1.3 Hz, 1H), 5.99 (d, J=9.0 Hz, 1H), 5.60 (q, J=6.4 Hz, 1H), 5.40 (d, J=15.3 Hz, 1H), 5.20 (d, J=15.4 Hz, 1H), 4.91 (d, J=7.7 Hz, 1H), 4.81 (d, J=12.2 Hz, 1H), 4.34 (d, J=12.2 Hz, 1H), 4.17 (dd, J=9.0, 7.7 Hz, 1H), 3.77 (s, 3H), 2.65 (s, 3H), 1.11 (d, J=6.5 Hz, 3H), 1.06 (s, 9H), 0.28 (s, 6H) ppm; $^{13}$C NMR ($CDCl_3$, 151 MHz) δ=197.59, 150.22, 147.23, 137.18, 136.08, 136.02, 135.93, 135.11, 134.65, 133.88, 132.66, 132.38, 131.64, 129.15, 128.05, 127.61, 127.34, 127.32, 126.38, 125.81, 125.61, 125.41, 124.83, 123.20, 121.55, 118.93, 112.43, 111.63, 104.45, 86.10, 74.77, 73.97, 72.44, 68.12, 61.23, 25.94, 18.45, 16.51, 15.29, −4.19 ppm; HRMS (ESI-TOF) calcd for $C_{44}H_{50}N_3O_8SiS^+[M+Na]^+$808.3082, found 808.3090.

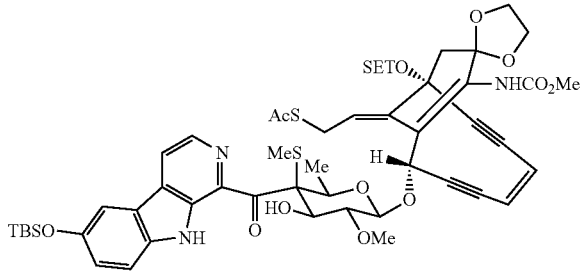

44

Enediyne Thioacetate 44:

A solution of o-nitrobenzyl ether ketone 43 (60.0 mg, 0.0743 mmol, 1.0 equiv) in THF (60 mL) and $H_2O$ (6 mL) was irradiated with a Hanovia mercury lamp (450 W) for 4.5 h. The resulting darkened solution was concentrated under vacuum and then extracted with EtOAc (3×10 mL). The organic layers were combined, dried over $Na_2SO_4$, filtered, and concentrated under vacuum to afford the corresponding crude lactol (ca. 1:1 mixture of anomers) which was used for the next reaction without further purification. To a vigorously stirred suspension of the crude lactol obtained as described above in $CH_2Cl_2$ (5.0 mL) and $H_2O$ (0.5 mL) was added DDQ (42.1 mg, 0.186 mmol, 2.5 equiv) at 25° C. The reaction mixture was stirred at 30° C. for 1.5 h before it was quenched with saturated aqueous $NaHCO_3$ solution (3 mL). The resulting mixture was extracted with EtOAc (3×10 mL). The organic layers were combined, dried over $Na_2SO_4$, filtered, and concentrated under vacuum. The crude hydroxy lactol so obtained was dissolved in $CH_2Cl_2$ (2.4 mL) and $Cl_3CCN$ (0.8 mL) and to the vigorously stirred solution at 25° C. was added NaH (3.6 mg, 0.149 mmol, 2.0 equiv) portionwise. The reaction mixture was stirred at that temperature for another 5 min before it was filtered through a thin layer of Celite®. The filtrate was concentrated under vacuum and purified by flash column chromatography (silica gel, EtOAc/hexanes/$Et_3N$ 50:10:1→50:25:1) to afford hydroxy trichloroacetimidate (21.7 mg, 0.0320 mmol, 43% yield over the three steps) as a yellow foam. This hydroxy trichloroacetimidate was used directly for the next step.

A mixture of freshly prepared hydroxy trichloroacetimidate (12.0 mg, 0.0177 mmol, 1.0 equiv) and thioacetate 4 (Nicolaou, et al., 2015) (15.5 mg, 0.0284 mmol, 1.6 equiv) was dried by azeotropic removal of benzene (3×3 mL), and dissolved in $CH_2Cl_2$ (0.4 mL). Activated 4 Å molecular sieves (80.0 mg) were added to this solution. The mixture was cooled down to −78° C. and stirred for 30 min, before $BF_3 \cdot OEt_2$ (62.0 μL, 1.0 M in $CH_2Cl_2$, 0.0620 mmol, 3.5 equiv) was added at the same temperature. The reddish solution was stirred at −78° C. for 30 min, −60° C. for 30 min, and finally −40° C. for 10 min, at which temperature a solution of saturated aqueous $NaHCO_3$ solution (1.5 mL) was added to quench the reaction. The reaction mixture was then filtered through Celite®. The organic layer was separated and the aqueous layer was extracted with EtOAc (3×5 mL). The organic layers were combined, dried over $Na_2SO_4$, filtered, and concentrated under vacuum. The resulting residue was purified by PTLC (silica gel, EtOAc:hexanes=1:1) to give enediyne thioacetate 8 (4.5 mg, 4.2 μmol, 24% yield based on hydroxy trichloroacetimidate) as a pale yellow foam. 8: $R_f$=0.56 (silica gel, EtOAc/hexanes 1:1); HRMS (ESI-TOF) calcd for $C_{53}H_{69}N_3O_{12}S_2Si_2Na^+[M+Na]^+$ 1082.3753, found 1082.3770.

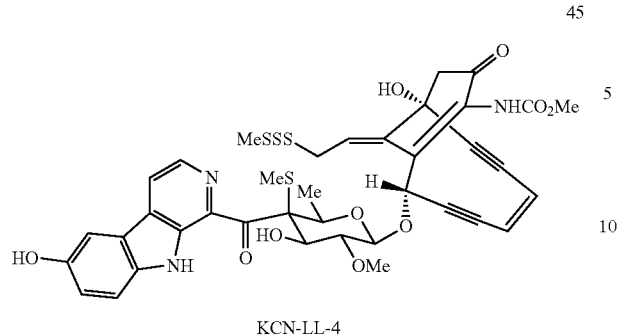

KCN-LL-4

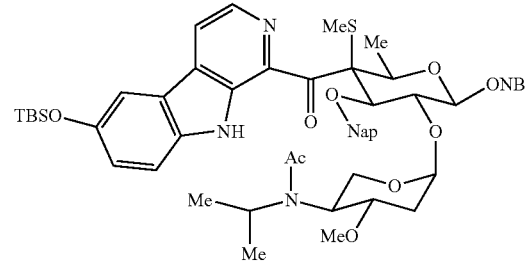

KCN-LL-4 (45):

To a stirred solution of enediyne thioacetate 44 (4.0 mg, 3.8 μmol, 1.0 equiv) in MeOH (0.5 mL) was added a solution of LiOH.H$_2$O (0.38 mL, 0.4 M in MeOH, 0.15 mmol, 40 equiv) at −15° C. The reaction mixture was stirred at this temperature for 20 min until no starting material was present (TLC). AcOH (0.15 mL, 1.0 M in MeOH, 0.15 mmol, 40 equiv) was added at that temperature to neutralize the resulting solution. PhthNSSMe (4.2 mg, 0.019 mmol, 5.0 equiv) was added at 0° C., and the reaction mixture was stirred at this temperature for 15 min. The solution so obtained was concentrated under vacuum and was used directly for the next step without further purification. To a solution of the crude methyl trisulfide in THF (0.5 mL) was added HF.py (30 μL, 70% HF in pyridine) at 0° C. The reaction mixture was allowed to warm to 25° C. and stirred for another 4 h, before it was diluted with EtOAc (2 mL) and quenched with saturated aqueous NaHCO$_3$ solution (2 mL). The organic layer was separated and the aqueous layer was extracted with EtOAc (3×5 mL). The organic layers were combined, dried over Na$_2$SO$_4$, filtered, and concentrated under vacuum to afford crude phenol which was used directly for the next step. To a stirred solution of the so-obtained crude phenol in THF (0.3 mL) were added sequentially acetone (0.2 mL) and H$_2$O (20 μL), followed by a slow addition of p-TSA (0.1 M in THF, 0.19 mL, 19 μmol, 5.0 equiv) at 25° C. The slightly darkened yellowish reaction mixture was stirred at 25° C. for 48 h before it was quenched with saturated aqueous NaHCO$_3$ solution (1.0 mL). The organic layer was separated and the aqueous layer was extracted with EtOAc (3×5 mL). The organic layers were combined, dried over Na$_2$SO$_4$, filtered, and concentrated under vacuum. The resulting residue was purified by PTLC to afford KCN-LL-4 (45, 1.3 mg, 42% yield over the three steps) as yellow foam. 45: $^1$H NMR (CD$_3$OD, 600 MHz) δ=8.41 (d, J=4.9 Hz, 1H), 8.21 (d, J=4.8 Hz, 1H), 7.60-7.51 (m, 2H), 7.14 (dd, J=8.7, 2.4 Hz, 1H), 6.45 (dd, J=10.1, 5.3 Hz, 1H), 6.35 (d, J=1.7 Hz, 1H), 6.01 (d, J=9.5 Hz, 1H), 5.94 (dd, J=9.4, 1.7 Hz, 1H), 5.66 (d, J=8.8 Hz, 1H), 5.51 (q, J=5.8 Hz, 1H), 5.37-5.33 (m, 2H), 5.16 (br s, 1H), 4.93 (d, J=7.7 Hz, 1H), 3.70 (s, 3H), 3.03 (d, J=17.0 Hz, 1H), 2.69 (d, J=17.0 Hz, 1H), 2.55 (s, 3H), 2.49 (s, 3H) ppm.

N-Acetyl Disaccharide 46:

To a stirred solution of N-Alloc disaccharide 34 (Nicolaou, et al., 2015) (165 mg, 0.157 mmol, 1.0 equiv) in THF (10 mL) were added sequentially Pd(PPh$_3$)$_4$ (36.0 mg, 0.0312 mmol, 0.2 equiv) and morpholine (41.1 mg, 41.2 μL, 0.472 mmol, 3.0 equiv) at 0° C. The reaction mixture was stirred at the same temperature for 45 min before it was concentrated under vacuum. The residue so obtained was dissolved in CH$_2$Cl$_2$ (5.0 mL) and Ac$_2$O (80.2 mg, 78.5 μL, 0.787 mmol, 5.0 equiv), pyridine (124 mg, 0.135 mL, 1.57 mmol, 10.0 equiv) and DMAP (19.2 mg, 0.157 mmol, 1.0 equiv) were added sequentially at 0° C. The reaction mixture was allowed to warm to 20° C. and stirred at this temperature for another 48 h before it was quenched with saturated aqueous NaHCO$_3$ solution (5.0 mL). The organic layer was separated and the aqueous layer was extracted with EtOAc (3×15 mL). The combined organic layer was washed with brine (15 mL), dried over anhydrous Na$_2$SO$_4$, filtered and concentrated under vacuum. The residue was purified by flash column chromatography (silica gel, EtOAc/hexanes 1:5→1:3) to give N-acetyl disaccharide 46 (123 mg, 0.122 mmol, 78% yield) as a yellowish foam. 46: R$_f$=0.50 (silica gel, EtOAc/hexanes 1:2); [α]$_D^{20}$=+1.0 (c=0.3, CHCl$_3$); FT-IR (neat) ν$_{max}$=3446, 3057, 2957, 2930, 2857, 1726, 1642, 1578, 1526, 1484, 1462, 1361, 1342, 1284, 1273, 1183, 1145, 1126, 1097, 1047, 1008, 955, 888, 839, 811, 781, 751, 729 cm$^{-1}$; $^1$H NMR (CDCl$_3$, 600 MHz, ca. 1.8:1 ratio rotamers) δ=10.20-9.92 (m, 1H), 8.43 (d, J=4.9 Hz, 1H), 8.19-8.02 (m, 2H), 7.95 (d, J=4.8 Hz, 0.35H), 7.87 (d, J=4.8 Hz, 0.65H), 7.73-7.57 (m, 1H), 7.50-7.35 (m, 4H), 7.34-7.28 (m, 2H), 7.25-7.22 (m, 1H), 7.17-7.10 (m, 3H), 7.05-6.93 (m, 1H), 6.27-6.08 (m, 1H), 5.71-5.56 (m, 1H), 5.49-5.38 (m, 1.3H), 5.35 (br s, 0.7H), 5.26 (d, J=15.3 Hz, 0.65H), 5.19 (d, J=15.6 Hz, 0.35H), 5.08 (d, J=7.6 Hz, 0.65H), 5.03 (d, J=7.4 Hz, 0.35H), 4.78-4.52 (m, 3H), 4.34-4.19 (m, 1H), 3.85-3.46 (m, 1H), 3.28-3.05 (m, 3H), 3.05-2.79 (m, 1H), 2.64 (br s, 3H), 2.01 (s, 1.1H), 1.92 (s, 1.9H), 1.41 (br s, 1.1H), 1.31 (d, J=6.6 Hz, 1.1H), 1.14 (d, J=6.7 Hz, 1.9H), 1.13-1.08 (m, 1.9H), 1.06-1.03 (m, 9H), 1.01 (d, J=6.7 Hz, 1.9H), 0.85 (br s, 1.1H), 0.27-0.23 (m, 6H) ppm; $^{13}$C NMR (CDCl$_3$, 151 MHz, rotamers exist) δ=197.63, 171.55, 170.20, 150.38, 150.23, 146.88, 137.29, 137.18, 136.38, 136.21, 136.14, 136.09, 135.89, 135.60, 135.22, 134.97, 134.87, 134.02, 133.45, 132.74, 132.69, 132.58, 132.43, 132.04, 131.80, 129.64, 128.76, 128.13, 127.86, 127.69, 127.66, 127.57, 127.42, 127.29, 127.26, 126.09, 126.02, 125.99, 125.85, 125.73, 125.56, 125.43, 124.84, 124.19, 123.46, 123.21, 121.50, 121.43, 119.36, 119.17, 112.53, 112.44, 111.61, 103.17, 99.60, 99.04, 75.06, 74.92, 72.32, 71.51, 68.46, 67.46, 60.67, 60.54, 60.38, 57.34, 56.83, 55.54, 49.95, 47.57, 36.95, 35.19, 25.93, 25.92, 24.21, 23.54, 21.36, 20.95, 20.38, 19.91, 18.44, 16.57, 14.95, −4.20 ppm.

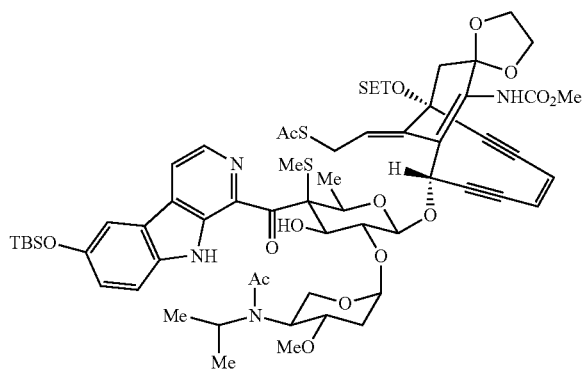

Enediyne Thioacetate 47:

A solution of N-acetyl disaccharide 46 (110 mg, 0.109 mmol, 1.0 equiv) in THF (100 mL) and H₂O (10 mL) was irradiated with a Hanovia mercury lamp (450 W) for 4.5 h. The resulting darkened solution was concentrated under vacuum and then extracted with EtOAc (3×20 mL). The organic layers were combined, dried over Na₂SO₄, filtered, and concentrated under vacuum to afford the corresponding crude lactol which was used for the next reaction without further purification. To a vigorously stirred suspension of the crude lactol obtained as described above in CH₂Cl₂ (6.0 mL) and H₂O (0.6 mL) was added DDQ (61.9 mg, 0.273 mmol, 2.5 equiv) at 25° C. The reaction mixture was stirred at 30° C. for 2 h before it was quenched with saturated aqueous NaHCO₃ solution (6.0 mL). The resulting mixture was extracted with EtOAc (3×20 mL). The organic layers were combined, dried over Na₂SO₄, filtered, and concentrated under vacuum. The crude hydroxy lactol so obtained was dissolved in CH₂Cl₂ (4.0 mL) and Cl₃CCN (1.0 mL) and to the vigorously stirred solution at 25° C. was added NaH (5.2 mg, 0.218 mmol, 2.0 equiv) portionwise. The reaction mixture was stirred at that temperature for another 5 min before it was filtered through a thin layer of Celite®. The filtrate was concentrated under vacuum and purified by flash column chromatography (silica gel, EtOAc:hexanes: Et₃N=60:20:1→40:40:1) to afford hydroxy trichloroacetimidate (54.4 mg, 0.0621 mmol, 57% yield over the three steps) as a yellow foam. This hydroxy trichloroacetimidate was used directly for the next step.

A mixture of freshly prepared hydroxy trichloroacetimidate (28.0 mg, 0.0320 mmol, 1.0 equiv) and thioacetate 4 (Nicolaou, et al., 2015) (22.7 mg, 0.0415 mmol, 1.3 equiv) was dried by azeotropic removal of benzene (3×3 mL), and dissolved in CH₂Cl₂ (0.7 mL). Activated 4 Å molecular sieves (120 mg) were added to this solution. The mixture was cooled down to −78° C. and stirred for 30 min, before BF₃·OEt₂ (0.112 mL, 1.0 M in CH₂Cl₂, 0.112 mmol, 3.5 equiv) was added at the same temperature. The reddish solution was stirred at −78° C. for 30 min, −60° C. for 30 min, and finally −40° C. for 10 min, at which temperature a saturated aqueous NaHCO₃ solution (5.0 mL) was added to quench the reaction. The reaction mixture was then filtered through Celite®. The organic layer was separated and the aqueous layer was extracted with EtOAc (3×5 mL). The organic layers were combined, dried over Na₂SO₄, filtered, and concentrated under vacuum. The resulting residue was purified by PTLC (silica gel, EtOAc/hexanes 1:1) to give enediyne thioacetate 12 (5.2 mg, 4.1 μmol, 13% yield based on hydroxy trichloroacetimidate) as a pale yellow foam. 12: $R_f$=0.42 (silica gel, EtOAc/hexanes 1:1); HRMS (ESI-TOF) calcd for $C_{63}H_{86}N_4O_{15}S_2Si_2Na^+[M+Na]^+$1281.4962, found 1281.4948.

KCN-LL-3 (48):

To a stirred solution of enediyne thioacetate 47 (4.0 mg, 3.2 μmol, 1.0 equiv) in MeOH (0.5 mL) was added a solution of LiOH·H₂O (0.400 mL, 0.4 M in MeOH, 0.160 mmol, 50 equiv) at −15° C. The reaction mixture was stirred at this temperature for 20 min until no starting material was present (TLC). AcOH (0.160 mL, 1.0 M in MeOH, 0.160 mmol, 50 equiv) was added at that temperature to neutralize the resulting solution. PhthNSSMe (4.3 mg, 0.0192 mmol, 6.0 equiv) was added at 0° C., and the reaction mixture was stirred at this temperature for 15 min. The solution so obtained was concentrated under vacuum and was used directly for the next step without further purifications. To a solution of the crude methyl trisulfide in THF (0.8 mL) was added HF·py (40 μL, 70% HF in pyridine) at 0° C. The reaction mixture was allowed to warm to 25° C. and stirred for another 4 h, before it was diluted with EtOAc (2.0 mL) and quenched with saturated aqueous NaHCO₃ solution (2.0 mL). The organic layer was separated and the aqueous layer was extracted with EtOAc (3×3 mL). The organic layers were combined, dried over Na₂SO₄, filtered, and concentrated under vacuum to afford crude phenol which was used directly for the next step. To a stirred solution of the so-obtained crude phenol in THF (0.3 mL) were added acetone (0.2 mL) and H₂O (20 μL) sequentially, followed by a slow addition of p-TSA (0.160 mL, 0.1 M in THF, 0.0160 mmol, 5.0 equiv) at 25° C. The yellowish reaction mixture was stirred at 25° C. for 48 h before it was quenched with saturated aqueous NaHCO₃ solution (2.0 mL). The organic layer was separated and the aqueous layer was extracted with EtOAc (3×3 mL). The organic layers were combined, dried over Na₂SO₄, filtered, and concentrated under vacuum. The resulting residue was purified by PTLC to afford KCN-LL-3 (48, 1.5 mg, 1.5 μmol, 46% yield over the three steps) as yellow foam. 48: ¹H NMR (CD₃OD, 600 MHz) δ=8.47 (d, J=4.9 Hz, 1H), 8.22 (d, J=4.8 Hz, 1H), 7.56 (d, J=2.3 Hz, 1H), 7.54 (d, J=8.8 Hz, 1H), 7.14 (dd, J=8.7, 2.4 Hz, 1H), 6.43 (dd, J=11.1, 4.1 Hz, 1H), 6.36 (s, 1H), 6.04 (d, J=9.5 Hz, 1H), 5.95-5.91 (m, 1H), 5.75 (d, J=8.8 Hz, 1H), 5.62-5.59 (m, 1H), 5.44 (q, J=6.5 Hz, 1H), 4.88 (d, J=7.9 Hz, 1H), 4.72-4.65 (m, 1H), 4.27 (t, J=8.4 Hz, 1H), 4.15 (dd, J=14.8, 11.1 Hz, 1H), 4.12-4.04 (m, 2H), 3.76 (dd, J=14.9, 4.1 Hz, 1H), 3.63 (br s, 3H), 3.45-3.39 (m, 1H), 3.33 (s, 3H), 3.07-2.98 (m, 2H), 2.68 (d, J=17.7 Hz, 1H), 2.51 (s, 3H), 2.44 (s, 3H), 2.37 (dd, J=12.8, 4.5 Hz, 1H), 2.16 (s, 3H), 1.22-1.17 (m, 6H), 1.14 (d, J=6.3 Hz, 3H) ppm; HRMS (ESI-TOF) calcd for $C_{48}H_{53}N_4O_{13}S_4Na^+$ [M+Na]⁺ 1045.2462, found 1045.2455.

Bis-(Methylthio)-Ketal 50:

To a stirred solution of ketone 49 (Zhao & Liu, 2001) (1.37 g, 5.61 mmol, 1.0 equiv) in toluene (45 mL) were sequentially added TMSSMe (1.69 g, 1.99 mL, 14.0 mmol, 2.5 equiv) and TMSOTf (1.87 g, 1.52 mL, 8.41 mmol, 1.5 equiv) at −20° C., and the reaction mixture was allowed to warm to 0° C. Saturated aqueous NaHCO₃ solution (4.20 mL, ca. 4.20 mmol, 0.75 equiv) was added at this temperature, and the resulting mixture was stirred at the same temperature for 15 min before it was quenched with saturated aqueous NaHCO₃ solution (30 mL). The organic layer was separated and the aqueous layer was extracted with EtOAc (3×50 mL). The organic layers were combined, dried over Na₂SO₄, filtered, and concentrated under vacuum. The residue was purified by flash column chromatography (silica gel, EtOAc/hexanes 1:15→1:12) to afford bis-(methylthio)-ketal 50 (1.70 g, 5.27 mmol, 94% yield) as a pale yellow oil. 50: $R_f$=0.55 (silica gel, $CH_2Cl_2$); $[\alpha]_D^{20}$=+86 (c=0.7, CHCl₃); FT-IR (neat) $v_{max}$=2974, 2937, 2922, 2872, 2844, 1790, 1726, 1480, 1455, 1395, 1286, 1194, 1151, 1076, 1052, 1033, 1015, 928, 893 cm⁻¹; ¹H NMR (CDCl₃, 600 MHz) δ=5.18 (ddd, J=11.3, 5.1, 3.6 Hz, 1H), 4.78 (d, J=3.6 Hz, 1H), 4.15 (q, J=6.5 Hz, 1H), 3.40 (s, 3H), 2.17 (dd, J=13.1, 5.1 Hz, 1H), 2.13 (s, 3H), 2.12 (s, 3H), 2.15-2.10 (m, 1H), 1.30 (d, J=6.6 Hz, 3H), 1.20 (s, 9H) ppm; ¹³C NMR (CDCl₃, 151 MHz) δ=178.12, 96.89, 70.86, 67.87, 60.77, 55.41, 38.90, 32.56, 27.22, 15.98, 13.17, 11.15 ppm; HRMS (ESI-TOF) calcd for $C_{14}H_{26}O_4S_2Na^+$[M+Na]⁺345.1165, found 345.1172.

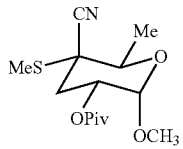

51

α-Methylthionitrile 51:

To a stirred solution of bis-(methylthio)-ketal 50 (1.70 g, 5.27 mmol, 1.0 equiv) in CH₂Cl₂ (50 mL) were sequentially added TMSCN (1.56 g, 2.09 mL, 15.8 mmol, 3.0 equiv) and SnCl₄ (7.90 mL, 1.0 M in CH₂Cl₂, 7.90 mmol, 1.5 equiv) at 0° C. The reaction mixture was stirred at 0° C. for 3 h before it was quenched with saturated aqueous NaHCO₃ solution (30 mL). The reaction mixture was filtered through a layer of Celite® and partitioned with CH₂Cl₂ (30 mL) and H₂O (20 mL). The organic layer was separated and the aqueous layer was extracted with CH₂Cl₂ (3×30 mL). The organic layers were combined, dried over Na₂SO₄, filtered, and concentrated under vacuum. The residue was purified by flash column chromatography (silica gel, EtOAc/hexanes 1:10→1:8) to afford α-methylthionitrile 51 (1.51 g, 5.01 mmol, 95% yield) as a white foam. 51: $R_f$=0.39 (silica gel, EtOAc/hexanes 1:10); $[\alpha]_D^{20}$=+130 (c=0.5, CHCl₃); FT-IR (neat) $v_{max}$=2980, 2937, 2874, 2841, 2232, 1733, 1480, 1456, 1385, 1369, 1282, 1201, 1149, 1075, 1067, 1034, 940, 900, 876 cm⁻¹; ¹H NMR (CDCl₃, 600 MHz) δ=4.94 (ddd, J=12.3, 4.8, 3.5 Hz, 1H), 4.90 (d, J=3.5 Hz, 1H), 3.87 (q, J=6.3 Hz, 1H), 3.39 (s, 3H), 2.38 (ddd, J=12.6, 4.8, 0.9 Hz, 1H), 2.34 (s, 3H), 2.17 (t, J=12.4 Hz, 1H), 1.43 (d, J=6.3 Hz, 3H), 1.20 (s, 9H) ppm; ¹³C NMR (CDCl₃, 151 MHz) δ=177.62, 117.48, 96.36, 68.29, 67.59, 55.76, 46.85, 38.84, 34.23, 27.15, 17.03, 13.37 ppm; HRMS (ESI-TOF) calcd for $C_{14}H_{23}NO_4SNa^+$[M+Na]⁺324.1240, found 324.1246.

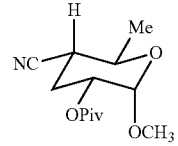

52

Nitrile 52:

To a stirred solution of nitrile 51 (1.01 g, 3.35 mmol, 1.0 equiv) in benzene (50 mL) was added Bu₃SnH (1.95 g, 1.77 mL, 6.70 mmol, 2.0 equiv) and AIBN (55.0 mg, 0.335 mmol, 0.1 equiv). The reaction mixture was heated to 80° C. and stirred for another 1.5 h before it was cooled down and concentrated under vacuum. The residue so obtained was purified by flash column chromatography (silica gel, EtOAc/hexanes 1:8→1:4) to afford nitrile 52 and 4-epi-52 (847 mg, 3.31 mmol, 99% yield, ca. 1.4:1 dr) as white foams. 52: $R_f$=0.49 (silica gel, EtOAc/hexanes 1:4); $[\alpha]_D^{20}$=+158 (c=0.5, CHCl₃); FT-IR (neat) $v_{max}$=2977, 2938, 2911, 2876, 2842, 2245, 1731, 1481, 1460, 1397, 1386, 1364, 1322, 1284, 1195, 1152, 1096, 1079, 1052, 1033, 934, 912, 893, 860 cm⁻¹; ¹H NMR (CDCl₃, 600 MHz) δ=4.74 (d, J=3.4 Hz, 1H), 4.68 (ddd, J=12.0, 5.0, 3.4 Hz, 1H), 3.97 (dq, J=10.2, 6.2 Hz, 1H), 3.41 (s, 3H), 2.55 (ddd, J=12.8, 10.3, 4.1 Hz, 1H), 2.23 (q, J=12.4 Hz, 1H), 2.15 (dt, J=12.4, 4.8 Hz, 1H), 1.38 (d, J=6.2 Hz, 3H), 1.19 (s, 9H) ppm; ¹³C NMR (CDCl₃, 151 MHz) δ=177.94, 118.67, 96.62, 67.68, 64.55, 55.65, 38.88, 34.03, 27.13, 26.77, 19.33 ppm; HRMS (ESI-TOF) calcd for $C_{13}H_{21}NO_4Na^+$[M+Na]⁺278.1363, found 278.1369. 4-epi-52: $R_f$=0.26 (silica gel, EtOAc/hexanes 1:4); $[\alpha]_D^{20}$=+224 (c=0.5, CHCl₃); FT-IR (neat) $v_{max}$=2979, 2938, 2875, 2842, 2241, 1730, 1481, 1458, 1398, 1387, 1366, 1329, 1283, 1219, 1187, 1156, 1140, 1096, 1053, 1033, 1017, 954, 928, 898, 881, 856, 770 cm⁻¹; ¹H NMR (CDCl₃, 600 MHz) δ=5.00 (ddd, J=12.4, 5.0, 3.5 Hz, 1H), 4.88 (d, J=3.4 Hz, 1H), 4.02 (qd, J=6.4, 2.6 Hz, 1H), 3.39 (s, 3H), 2.89 (dt, J=5.2, 2.8 Hz, 1H), 2.22 (td, J=12.6, 4.8 Hz, 1H), 2.10 (dddd, J=12.9, 5.0, 2.8, 0.9 Hz, 1H), 1.36 (d, J=6.4 Hz, 3H), 1.19 (s, 9H) ppm; ¹³C NMR (CDCl₃, 151 MHz) δ=177.71, 118.44, 96.77, 66.68, 62.61, 55.69, 38.81, 34.09, 27.14, 26.16, 18.91 ppm; HRMS (ESI-TOF) calcd for $C_{13}H_{21}NO_4Na^+$ [M+Na]⁺278.1363, found 278.1364.

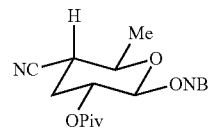

53 o-Nitrobenzyl Ether 53:

To a stirred solution of nitrile 52 (510 mg, 2.00 mmol, 1.0 equiv) in Ac₂O (15.0 mL) was added conc. H₂SO₄ (196 mg, 0.106 mL, 2.00 mmol, 1.0 equiv) at 0° C. The reaction mixture was stirred at this temperature for 2 h before it was quenched with saturated aqueous NaHCO₃ solution (10 mL). The excess Ac₂O was azeotropically removed with toluene and the resulting residue was washed with brine (10 mL). The organic layer was concentrated under vacuum to afford the crude acetate which was dissolved in MeOH (25 mL). To this solution at 0° C. was added methanolic NH₃ (2.86 mL, 7.0 M, 20.0 mmol, 10.0 equiv) and the reaction mixture was then stirred at this temperature for 2 h. All the volatiles were removed under vacuum to give the lactol which was used for the next step without further purification. To a stirred solution of the so-obtained lactol in CH$_2$Cl$_2$ (12 mL) was added Cl$_3$CCN (3.0 mL) and NaH (144 mg, 6.00 mmol, 3.0 equiv) at 0° C. The reaction mixture was allowed to warm to 20° C. and stirred for another 2 h before it was filtered through a layer of Celite®. All the volatiles were removed under vacuum to give the crude trichloroacetimidate which was immediately used for the next step. A mixture of freshly prepared hydroxy trichloroacetimidate and o-nitrobenzyl alcohol (613 mg, 4.00 mmol, 2.0 equiv) was dried by azeotropic removal of benzene (3×6 mL), and dissolved in CH$_2$Cl$_2$ (12 mL). Activated 4 Å molecular sieves (1.0 g) were added to this solution. The mixture was cooled down to −78° C. and stirred for 30 min, before BF$_3$.OEt$_2$ (426 mg, 0.370 mL, 3.0 mmol, 1.5 equiv) was added at the same temperature. The reaction mixture was stirred at −78° C. for 30 min, at which temperature a solution of saturated aqueous NaHCO$_3$ solution (15 mL) was added to quench the reaction. The reaction mixture was then filtered through Celite®. The organic layer was separated and the aqueous layer was extracted with EtOAc (3×30 mL). The organic layers were combined, dried over Na$_2$SO$_4$, filtered, and concentrated under vacuum. The resulting residue was purified by flash column chromatography (silica gel, EtOAc/hexanes 1:5→1:4) to give o-nitrobenzyl ether 53 (474 mg, 1.26 mmol, 63% yield over the four steps) as a white foam. 53: R$_f$=0.59 (silica gel, EtOAc/hexanes 3:7); [α]$_D^{20}$=−101 (c=0.3, CHCl$_3$); FT-IR (neat) ν$_{max}$=2977, 2936, 2873, 2245, 1733, 1614, 1578, 1527, 1480, 1459, 1363, 1342, 1284, 1172, 1151, 1102, 1063, 1038, 1021, 886, 858, 823, 791, 730 cm$^{-1}$; $^1$H NMR (CDCl$_3$, 600 MHz) δ=8.12 (dd, J=8.2, 1.0 Hz, 1H), 7.79 (d, J=7.8 Hz, 1H), 7.63 (t, J=7.6 Hz, 1H), 7.45 (t, J=7.7 Hz, 1H), 5.27 (d, J=15.3 Hz, 1H), 5.03 (d, J=15.3 Hz, 1H), 4.78 (ddd, J=11.3, 7.8, 5.2 Hz, 1H), 4.64 (d, J=7.9 Hz, 1H), 3.79 (dq, J=9.8, 6.1 Hz, 1H), 2.61 (ddd, J=12.8, 9.8, 4.1 Hz, 1H), 2.54 (ddd, J=13.0, 5.2, 4.1 Hz, 1H), 1.87 (td, J=12.9, 11.3 Hz, 1H), 1.48 (d, J=6.1 Hz, 3H), 1.18 (s, 9H) ppm; $^{13}$C NMR (CDCl$_3$, 151 MHz) δ=177.39, 146.85, 134.27, 134.02, 128.61, 128.27, 124.91, 118.25, 102.08, 72.96, 68.22, 67.71, 38.98, 33.79, 31.39, 27.16, 19.53 ppm; HRMS (ESI-TOF) calcd for C$_{19}$H$_{24}$N$_2$O$_6$Na$^+$[M+Na]$^+$399.1527, found 399.1531.

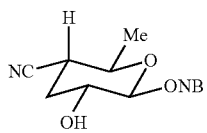

Alcohol 54:

To a stirred solution of o-nitrobenzyl ether 53 (330 mg, 0.877 mmol, 1.0 equiv) in methanol (5.0 mL) was added LiOH.H$_2$O (24.0 mL, 1.0 M in MeOH, 24.0 mmol, 27 equiv) at 0° C. The reaction mixture was allowed to warm to 20° C. and stirred for another 20 min before it was quenched with saturated aqueous NH$_4$Cl solution (50 mL). Methanol was removed in vacuo and the resulting aqueous phase was extracted with EtOAc (3×30 mL). The organic layers were combined, dried over Na$_2$SO$_4$, filtered, and concentrated under vacuum. The resulting residue was purified by flash column chromatography (silica gel, EtOAc/hexanes 1:3→1:2) to give alcohol 54 (183 mg, 0.626 mmol, 71% yield) as a white foam. 54: R$_f$=0.30 (silica gel, EtOAc/hexanes 2:3); [α]$_D^{20}$=+10 (c=0.25, CHCl$_3$); FT-IR (neat) ν$_{max}$=3470, 2980, 2935, 2873, 2244, 1613, 1577, 1525, 1456, 1386, 1343, 1195, 1163, 1101, 1076, 1060, 1020, 924, 859, 822, 792, 730 cm$^{-1}$; $^1$H NMR (CDCl$_3$, 600 MHz) δ=8.06 (d, J=7.9 Hz, 1H), 7.74 (d, J=7.7 Hz, 1H), 7.65 (t, J=7.4 Hz, 1H), 7.48 (t, J=7.7 Hz, 1H), 5.22 (d, J=14.2 Hz, 1H), 5.06 (d, J=14.2 Hz, 1H), 4.40 (d, J=7.6 Hz, 1H), 3.74 (dq, J=9.6, 6.2 Hz, 1H), 3.59-3.48 (m, 1H), 2.56-2.44 (m, 2H), 2.31 (br s, 1H), 1.93-1.78 (m, 1H), 1.45 (d, J=6.1 Hz, 3H) ppm; $^{13}$C NMR (CDCl$_3$, 151 MHz) δ=147.77, 133.73, 133.41, 129.38, 128.76, 124.91, 118.60, 104.49, 72.97, 68.08, 67.99, 34.00, 33.15, 19.52 ppm; HRMS (ESI-TOF) calcd for C$_{14}$H$_{16}$N$_2$O$_5$Na$^+$ [M+Na]$^+$315.0951, found 315.0953.

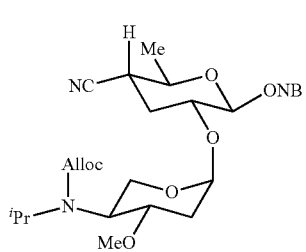

Disaccharide Nitrile 55:

A mixture of anhydrous AgClO$_4$ (314 mg, 1.51 mmol, 2.5 equiv) and SnCl$_2$ (287 mg, 1.51 mmol, 2.5 equiv) was dried by azeotropic removal of benzene (3×5 mL). The salts were then suspended in THF (4.0 mL), and powdered, activated 4 Å molecular sieves (500 mg) were added. The suspension was stirred in the dark at 25° C. for 15 min and then cooled to −78° C. The resulting mixture was stirred at that temperature for 30 min to allow all moisture to be absorbed by the molecular sieves. A solution of fluoride 10 (Nicolaou, et al., 2011) (367 mg, 1.33 mmol, 2.2 equiv) and alcohol 54 (177 mg, 0.606 mmol, 1.0 equiv) in THF (3.0 mL) was added slowly to this suspension with stirring, and the mixture was stirred at −78° C. for 1 h. The reaction mixture was allowed to warm slowly to 25° C. over 12 h, diluted with Et$_2$O (7.0 mL), and filtered through Celite®. The resulting solution was washed with saturated aqueous NaHCO$_3$ solution (15 mL) and brine (10 mL), dried over Na$_2$SO$_4$, filtered, and concentrated under vacuum. The resulting residue was purified by flash column chromatography (silica gel, EtOAc/hexanes 1:4→1:2) to give disaccharide nitrile 55 (317 mg, 0.579 mmol, 95% yield based on 54) as a white foam. 55: R$_f$=0.58 (silica gel, EtOAc/hexanes 2:3); [α]$_D^{20}$=−53 (c=0.3, CHCl$_3$); FT-IR (neat) ν$_{max}$=2966, 2934, 2243, 1693, 1648, 1527, 1444, 1364, 1342, 1307, 1283, 1258, 1198, 1166, 1145, 1123, 1104, 1062, 1046, 993, 913, 858, 791, 771, 731 cm$^{-1}$; $^1$H NMR (CDCl$_3$, 600 MHz) δ=8.09 (br s, 1H), 8.03-7.86 (m, 1H), 7.64 (t, J=7.8 Hz, 1H), 7.54-7.39 (m, 1H), 6.03-5.75 (m, 1H), 5.35-5.09 (m, 4H), 5.09-5.01 (m, 1H), 4.66-3.79 (m, 7H), 3.73 (dq, J=9.7, 6.1 Hz, 1H), 3.63 (ddd, J=11.1, 7.6, 5.0 Hz, 1H), 3.31 (s, 3H), 2.55 (dt, J=13.0, 4.5 Hz, 1H), 2.53-2.45 (m, 1H), 2.32-2.25 (m, 1H), 1.78 (q, J=12.3 Hz, 1H), 1.67-1.50 (m, 1H), 1.43 (d, J=6.1 Hz, 3H), 1.15 (br s, 3H), 1.00 (br s, 3H) ppm; $^{13}$C NMR (CDCl$_3$, 151 MHz) δ=155.45, 147.12, 134.80, 133.82, 133.25, 129.17, 128.65, 128.48, 128.37, 127.97, 125.44, 124.99, 124.70, 118.60, 117.02, 102.66, 102.45, 94.81, 72.66, 71.64, 70.77, 70.02, 67.59, 67.20, 65.58, 60.66, 56.82, 47.40, 36.01, 33.76, 31.19, 26.67, 21.54, 20.96, 20.21, 19.79, 19.58 ppm; HRMS (ESI-TOF) calcd for C$_{27}$H$_{37}$N$_3$O$_9$Na$^+$[M+Na]$^+$570.2422, found 570.2408.

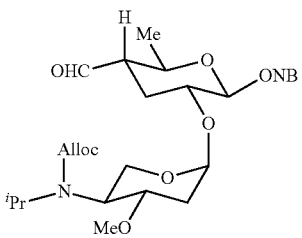

Disaccharide Aldehyde 56:

To a stirred solution of disaccharide nitrile 55 (313 mg, 0.571 mmol, 1.0 equiv) in $CH_2Cl_2$ (10 mL) was added DIBAL-H (1.71 mL, 1.0 M in $CH_2Cl_2$, 1.71 mmol, 3.0 equiv) at −78° C. The reaction mixture was stirred at that temperature for 45 min before it was quenched with a mixture of saturated aqueous Rochelle salt solution (10 mL) and EtOAc (10 mL). The organic layer was separated and the aqueous layer was extracted with EtOAc (3×30 mL). The organic layers were combined, dried over $Na_2SO_4$, filtered, and concentrated under vacuum. The resulting residue was purified by flash column chromatography (silica gel, EtOAc/hexanes 1:2→1:0) to afford disaccharide aldehyde 56 (267 mg, 0.485 mmol, 85% yield) as a white foam. 56: $R_f$=0.38 (silica gel, EtOAc/hexanes 2:3); $[\alpha]_D^{20}$=−57 (c=0.5, $CHCl_3$); FT-IR (neat) $v_{max}$=2934, 2867, 1723, 1694, 1526, 1445, 1365, 1342, 1306, 1282, 1258, 1198, 1165, 1122, 1107, 1072, 1046, 1022, 994, 916, 858, 791, 771, 730 cm$^{-1}$; $^1$H NMR ($CDCl_3$, 600 MHz) δ=9.67 (br s, 1H), 8.09 (d, J=8.0 Hz, 1H), 8.05-7.88 (m, 1H), 7.64 (br s, 1H), 7.43 (br s, 1H), 5.84 (br s, 1H), 5.40-5.00 (m, 6H), 4.68-3.85 (m, 6H), 3.89-3.75 (m, 1H), 3.72 (ddd, J=10.6, 7.2, 4.8 Hz, 1H), 3.45-3.34 (m, 1H), 3.31 (s, 3H), 2.49-2.41 (m, 1H), 2.37 (dt, J=13.1, 4.5 Hz, 1H), 2.28 (d, J=12.8 Hz, 1H), 1.57 (d, J=9.7 Hz, 1H), 1.36 (d, J=6.2 Hz, 3H), 1.15 (br s, 3H), 1.00 (br s, 3H) ppm; $^{13}$C NMR ($CDCl_3$, 151 MHz, rotamers exist) δ=200.64, 155.28, 147.14, 135.14, 133.79, 133.28, 129.15, 128.72, 128.24, 127.87, 124.94, 124.68, 117.05, 102.37, 102.08, 94.67, 71.77, 71.09, 67.36, 67.01, 65.60, 60.57, 56.92, 54.23, 54.02, 47.28, 35.98, 27.59, 27.37, 21.60, 20.97, 20.22, 19.79 ppm; HRMS (ESI-TOF) calcd for $C_{27}H_{38}N_2O_{10}Na^+$[M+Na]$^+$573.2419, found 573.2415.

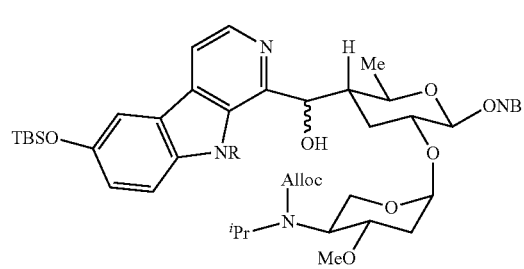

R = $CO_2Me$

Coupling Product Alcohol 57 (Two Diastereoisomers, a and b):

To a stirred solution of iodocarboline 6 (700 mg, 1.45 mmol, 3.0 equiv) in THF (15 mL) was slowly added t-BuLi (1.71 mL, 1.7 M in pentane, 2.90 mmol, 6.0 equiv) at −78° C. The dark solution so obtained was stirred at that temperature for 30 min before slow addition of a solution of disaccharide aldehyde 56 (265 mg, 0.481 mmol, 1.0 equiv) in THF (2.5 mL). The reaction mixture was stirred at −78° C. for 10 min and then warmed up to 35° C. over 30 min before it was quenched with AcOH (208 mg, 0.198 mL, 3.47 mmol, 7.2 equiv) at −78° C. The resulting mixture was diluted with EtOAc (5.0 mL) and treated with saturated aqueous $NaHCO_3$ solution (5.0 mL). The organic layer was separated and the aqueous layer was extracted with EtOAc (3×20 mL). The organic layers were combined, dried over $Na_2SO_4$, filtered, and concentrated under vacuum. The resulting residue was purified by flash column chromatography (silica gel, acetone/$CH_2Cl_2$ 1:30→1:15) to give coupling product alcohol 57 as a mixture of diastereoisomers (266 mg, 0.293 mmol, 61% yield based on 56, ca. 3:1 inconsequential diastereoisomeric mixture) as a brown foam. 57a (less polar): $R_f$=0.72 (silica gel, acetone/$CH_2Cl_2$ 1:10); $[\alpha]_D^{20}$=−21 (c=0.4, $CHCl_3$); FT-IR (neat) $v_{max}$=3327, 2956, 2931, 2858, 1754, 1696, 1578, 1567, 1527, 1488, 1461, 1443, 1363, 1341, 1274, 1261, 1200, 1165, 1123, 1106, 1072, 994, 978, 893, 838, 827, 783, 730 cm$^{-1}$; $^1$H NMR ($CDCl_3$, 600 MHz) δ=8.72 (br s, 1H), 8.35 (d, J=5.2 Hz, 1H), 8.15-8.00 (m, 1H), 8.02-7.91 (m, 1H), 7.85 (br s, 1H), 7.60 (br s, 1H), 7.53 (d, J=2.3 Hz, 1H), 7.47-7.34 (m, 2H), 7.14 (d, J=8.6 Hz, 1H), 6.23 (br s, 1H), 5.83 (br s, 1H), 5.28-4.96 (m, 4H), 4.91 (br s, 1H), 4.68-3.88 (m, 6H), 3.83 (s, 3H), 3.75-3.61 (m, 2H), 3.42-3.28 (m, 1H), 3.23 (s, 3H), 2.40 (br s, 1H), 2.29-2.05 (m, 2H), 1.50 (d, J=6.1 Hz, 3H), 1.50-1.39 (m, 2H), 1.19-1.07 (m, 3H), 1.04 (s, 9H), 0.94 (d, J=6.7 Hz, 3H), 0.24 (s, 6H) ppm; $^{13}$C NMR ($CDCl_3$, 151 MHz) δ=154.91, 149.91, 147.11, 144.98, 138.01, 133.73, 133.26, 129.09, 128.70, 127.80, 124.76, 122.99, 122.09, 117.08, 114.66, 112.38, 111.37, 102.33, 94.27, 80.60, 73.44, 71.82, 66.90, 65.61, 60.28, 56.94, 55.59, 45.89, 35.68, 28.64, 25.92, 21.60, 20.93, 19.99, 18.42, −4.23 ppm; HRMS (ESI-TOF) calcd for $C_{46}H_{62}N_4O_{13}SiNa^+$[M+Na]$^+$929.3975, found 929.3970. 57b (more polar): $R_f$=0.69 (silica gel, acetone/$CH_2Cl_2$ 1:10); $[\alpha]_D^{20}$=−3 (c=0.4, $CHCl_3$); FT-IR (neat) $v_{max}$=3357, 2957, 2931, 2858, 1755, 1696, 1578, 1567, 1527, 1488, 1462, 1443, 1363, 1342, 1275, 1260, 1201, 1165, 1122, 1106, 1074, 1049, 981, 893, 838, 826, 783, 729 cm$^{-1}$; $^1$H NMR ($CDCl_3$, 600 MHz) δ=8.66 (br s, 1H), 8.40 (d, J=5.2 Hz, 1H), 8.08 (d, J=8.1 Hz, 1H), 8.04-7.92 (m, 1H), 7.85 (br s, 1H), 7.62 (br s, 1H), 7.53 (d, J=2.3 Hz, 1H), 7.48-7.36 (m, 2H), 7.14 (d, J=8.8 Hz, 1H), 6.33 (br s, 1H), 5.83 (br s, 1H), 5.30-5.04 (m, 4H), 4.77 (d, J=3.4 Hz, 1H), 4.62-4.33 (m, 3H), 4.34-3.88 (m, 3H), 3.83 (s, 3H), 3.79-3.67 (m, 1H), 3.57 (ddd, J=12.1, 7.3, 5.1 Hz, 1H), 3.37-3.18 (m, 4H), 2.39 (br s, 1H), 2.21-2.08 (m, 1H), 1.96-1.85 (m, 1H), 1.77 (br s, 1H), 1.46 (d, J=6.1 Hz, 3H), 1.43-1.35 (m, 1H), 1.19-1.09 (m, 4H), 1.04 (s, 9H), 0.94 (d, J=6.9 Hz, 3H), 0.25 (s, 6H) ppm; $^{13}$C NMR ($CDCl_3$, 151 MHz) δ=154.98, 149.89, 147.10, 140.66, 138.37, 135.82, 135.42, 134.29, 133.75, 133.26, 130.49, 129.19, 128.82, 127.78, 124.65, 122.97, 122.01, 116.98, 114.41, 112.28, 111.39, 102.64, 94.56, 82.72, 80.47, 72.65, 71.76, 67.20, 66.91, 65.57, 60.34, 56.91, 55.74, 47.16, 46.39, 35.89, 27.42, 21.55, 20.92, 19.32, 18.41 ppm; HRMS (ESI-TOF) calcd for $C_{46}H_{62}N_4O_{13}SiNa^+$[M+Na]$^+$929.3975, found 929.3966.

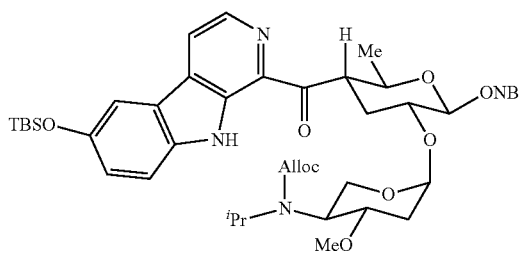

58

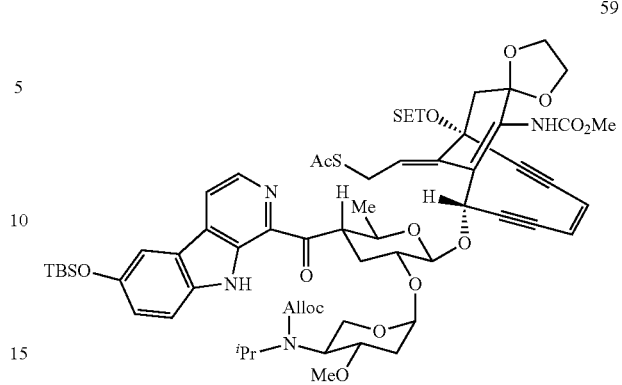

59

Ketone 58:

To a stirred solution of the coupling product alcohol 57 (a mixture of diastereoisomers, a and b, 240 mg, 0.265 mmol, 1.0 equiv) in EtOH (12.0 mL) was slowly added a solution of NaOH in EtOH (1.59 mL, 0.5 M, 0.794 mmol, 3.0 equiv) at 0° C. The reaction mixture was allowed to warm up to 25° C. and stirred at that temperature for another 2 h before it was quenched with saturated aqueous $NH_4Cl$ solution (10.0 mL). The resulting mixture was concentrated under vacuum to remove all volatiles and the residue so obtained was extracted with EtOAc (3×20 mL). The organic layers were combined, dried over $Na_2SO_4$, filtered, and concentrated under vacuum. The resulting residue was dissolved in $CHCl_3$ (10.0 mL) and DMP (124 mg, 0.292 mmol, 1.1 equiv) was added to the stirred solution at 0° C. The resulting reaction mixture was allowed to warm up to 35° C. over 5 min and stirring was continued at that temperature for another 5 min. The mixture was quenched with saturated aqueous $Na_2S_2O_3$ solution (5.0 mL) and the organic layer was separated. The aqueous layer was extracted with EtOAc (3×20 mL) and the combined organic layers were dried over $Na_2SO_4$, filtered, and concentrated under vacuum. The resulting residue was purified by flash column chromatography (silica gel, EtOAc/hexanes 1:6→1:3) to give ketone 58 (157 mg, 0.185 mmol, 70% yield over the two steps) as a yellow foam. 58: $R_f$=0.79 (silica gel, EtOAc/hexanes 1:1); $[α]_D^{20}$=−40 (c=0.35, $CHCl_3$); FT-IR (neat) $v_{max}$=3443, 2958, 2931, 2859, 1697, 1665, 1578, 1526, 1484, 1462, 1379, 1363, 1341, 1285, 1259, 1195, 1166, 1124, 1091, 1057, 996, 957, 889, 879, 839, 810, 781, 729 cm$^{-1}$; $^1$H NMR ($CDCl_3$, 600 MHz) δ=10.16 (br s, 1H), 8.52 (d, J=4.8 Hz, 1H), 8.21-8.02 (m, 3H), 7.67 (br s, 1H), 7.56 (d, J=2.3 Hz, 1H), 7.49-7.37 (m, 2H), 7.15 (dd, J=8.7, 2.3 Hz, 1H), 5.85 (br s, 1H), 5.48-5.00 (m, 5H), 4.69 (d, J=7.4 Hz, 1H), 4.60-4.34 (m, 3H), 4.28 (br s, 1H), 4.13-3.54 (m, 4H), 3.41 (br s, 1H), 3.29 (s, 3H), 2.55 (d, J=12.3 Hz, 1H), 2.24 (d, J=12.5 Hz, 1H), 1.77 (br s, 1H), 1.56-1.47 (m, 1H), 1.20 (d, J=6.1 Hz, 3H), 1.14 (br s, 3H), 1.04 (s, 9H), 0.99 (br s, 3H), 0.24 (s, 6H) ppm; $^{13}$C NMR ($CDCl_3$, 151 MHz) δ=204.66, 150.34, 147.08, 138.06, 136.79, 136.40, 135.59, 134.80, 133.82, 133.31, 131.84, 129.21, 128.81, 128.06, 127.75, 124.67, 123.38, 121.49, 119.68, 117.03, 112.53, 111.81, 102.77, 94.47, 73.64, 71.89, 71.57, 67.20, 66.87, 65.61, 60.44, 57.04, 47.43, 32.04, 25.90, 21.62, 20.97, 19.61, 18.40, 4.23 ppm; HRMS (ESI-TOF) calcd for $C_{44}H_{58}N_4O_{11}SiNa^+$[M+Na]$^+$ 869.3764, found 869.3767.

Enediyne Thioacetate 59:

A solution of o-nitrobenzyl ether ketone 58 (150 mg, 0.177 mmol, 1.0 equiv) in THF (140 mL) and $H_2O$ (14 mL) was irradiated with a Hanovia mercury lamp (450 W) for 4.5 h. The resulting darkened solution was concentrated under vacuum and then extracted with EtOAc (3×30 mL). The organic layers were combined, dried over $Na_2SO_4$, filtered, and concentrated under vacuum to afford the corresponding crude lactol which was used for the next reaction without further purification.

The crude lactol so obtained was dissolved in $CH_2Cl_2$ (4.0 mL) and $Cl_3CCN$ (1.0 mL) and to the vigorously stirred solution at 20° C. was added NaH (8.5 mg, 0.35 mmol, 2.0 equiv) portionwise. The reaction mixture was stirred at that temperature for another 5 min before it was filtered through a thin layer of Celite®. The filtrate was concentrated under vacuum and purified by flash column chromatography (silica gel, EtOAc/hexanes/$Et_3N$ 50:10:1→50:25:1) to afford trichloroacetimidate (80.8 mg, 0.0944 mmol, 53% yield over the two steps) as a yellow foam. This trichloroacetimidate was used directly for the next step.

A mixture of freshly prepared hydroxy trichloroacetimidate (27.0 mg, 0.0315 mmol, 1.0 equiv) and thioacetate 4 (Nicolaou, et al., 2011) (25.0 mg, 0.0458 mmol, 1.5 equiv) was dried by azeotropic removal of benzene (3×3 mL), and dissolved in $CH_2Cl_2$ (1.0 mL). Activated 4 Å molecular sieves (200 mg) were added to this solution. The mixture was cooled down to −78° C. and stirred for 30 min, before $BF_3$·$OEt_2$ (0.110 mL, 1.0 M in $CH_2Cl_2$, 0.110 mmol, 3.5 equiv) was added at the same temperature. The reddish solution was stirred at −78° C. for 30 min, −60° C. for 30 min, and finally −40° C. for 10 min, at which temperature a solution of saturated aqueous $NaHCO_3$ solution (3.0 mL) was added to quench the reaction. The reaction mixture was then filtered through Celite®. The organic layer was separated and the aqueous layer was extracted with EtOAc (3×10 mL). The organic layers were combined, dried over $Na_2SO_4$, filtered, and concentrated under vacuum. The resulting residue was purified by PTLC (silica gel, EtOAc/hexanes 1:1) to give enediyne thioacetate 59 (11.3 mg, 9.12 μmol, 29% yield based on trichloroacetimidate) as a pale yellow foam. 59: $R_f$=0.44 (silica gel, EtOAc/hexanes 1:1); $[α]_D^{20}$=−196 (c=0.15, $CHCl_3$); FT-IR (neat) $v_{max}$=3355, 2955, 2932, 2877, 1740, 1690, 1579, 1484, 1462, 1379, 1285, 1227, 1193, 1121, 1090, 1058, 1005, 957, 880, 839, 810, 780, 739 cm$^{-1}$; $^1$H NMR ($C_6D_6$, 600 MHz) δ=10.04 (br s, 1H), 8.39 (d, J=4.9 Hz, 1H), 7.57 (d, J=2.3 Hz, 1H), 7.47 (d, J=4.8 Hz, 1H), 7.10-7.00 (m, 1H), 6.71 (t, J=9.8 Hz, 2H), 6.45 (br s, 1H), 5.81 (br s, 1H), 5.42 (s, 2H), 5.33-3.97 (m, 14H), 3.73-3.23 (m, 8H), 3.18 (br s, 3H), 3.00 (br s, 1H), 2.80-2.35 (m, 2H), 2.37-2.02 (m, 2H), 1.95 (br s, 3H), 1.53-1.38 (m, 4H), 1.16 (t, J=7.9 Hz, 9H), 1.08 (s, 9H), 1.01-0.87 (m, 6H), 0.18 (s, 6H) ppm; HRMS (ESI-TOF) calcd for $C_{64}H_{86}N_4O_{15}SSi_2Na^+$ [M+Na]$^+$1261.5241, found 1261.5249.

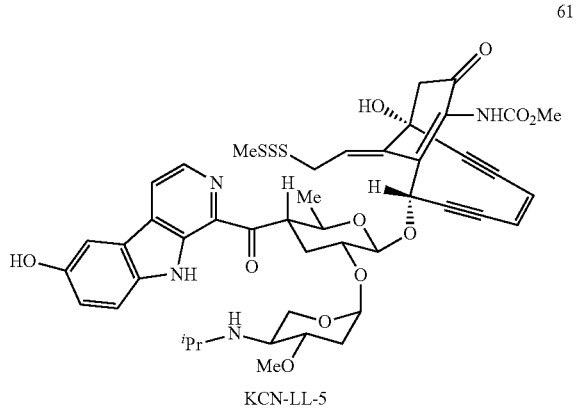

KCN-LL-5

KCN-LL-5 (61):

To a stirred solution of enediyne thioacetate 59 (5.0 mg, 4.0 μmol, 1.0 equiv) in MeOH (0.5 mL) was added a solution of LiOH.H$_2$O (0.200 mL, 0.8 M in MeOH, 0.160 mmol, 40 equiv) at −15° C. The reaction mixture was stirred at this temperature for 20 min until no starting material was present (TLC). AcOH (0.160 mL, 1.0 M in MeOH, 0.160 mmol, 40 equiv) was added at that temperature to neutralize the resulting solution. PhthNSSMe (5.5 mg, 0.024 mmol, 6.0 equiv) was added at 0° C., and the reaction mixture was stirred at this temperature for 15 min. The solution so obtained was concentrated under vacuum to afford crude methyl trisulfide 60 which was used directly for the next step without further purifications. To a solution of the so-obtained crude methyl trisulfide 60 in THF (0.4 mL) was added HF.py (25 μL, 70% HF in pyridine) at 0° C. The reaction mixture was allowed to warm to 25° C. and stirred for another 4 h, before it was diluted with EtOAc (2.0 mL) and quenched with saturated aqueous NaHCO$_3$ solution (2.0 mL). The organic layer was separated and the aqueous layer was extracted with EtOAc (3×10 mL). The organic layers were combined, dried over Na$_2$SO$_4$, filtered, and concentrated under vacuum to afford crude phenol which was dissolved in THF (0.2 mL). To the resulting solution were added sequentially Pd(PPh$_3$)$_4$ (2.8 mg, 2.4 μmol, 0.6 equiv) and morpholine (5.2 mg, 5.3 μL, 0.060 mmol, 15 equiv) at 0° C. The reaction mixture was stirred at the same temperature for 45 min before it was concentrated under vacuum. The residue so obtained was dissolved in THF (0.2 mL) to which acetone (0.1 mL) and H$_2$O (20 μL) were added sequentially, followed by a slow addition of p-TSA (0.200 mL, 0.1 M in THF, 0.0200 mmol, 5.0 equiv) at 20° C. The slightly darkened yellowish reaction mixture was stirred at 20° C. for 48 h before it was quenched with saturated aqueous NaHCO$_3$ (1.0 mL). The organic layer was separated and the aqueous layer was extracted with EtOAc (3×3 mL). The organic layers were combined, dried over Na$_2$SO$_4$, filtered, and concentrated under vacuum. The resulting residue was purified by PTLC (silica gel, EtOAc/Et$_3$N 15:1) to afford KCN-LL-5 (61, 1.5 mg, 1.6 μmol, 41% yield over the four steps) as yellow foam. 61: R$_f$=0.61 (silica gel, EtOAc/Et$_3$N 12:1); [α]$_D^{20}$=−188 (c=0.07, CHCl$_3$); FT-IR (neat) $v_{max}$=3361, 2923, 1663, 1490, 1458, 1332, 1285, 1259, 1056, 1033, 1001, 961, 880, 772, 742 cm$^{-1}$; $^1$H NMR (CD$_3$OD, 600 MHz) δ=8.46 (d, J=4.9 Hz, 1H), 8.23 (d, J=4.9 Hz, 1H), 7.61-7.50 (m, 2H), 7.14 (dd, J=8.8, 2.4 Hz, 1H), 6.44 (dd, J=10.6, 4.5 Hz, 1H), 6.33 (br s, 1H), 6.07 (d, J=9.5 Hz, 1H), 5.98 (d, J=9.5 Hz, 1H), 5.20-5.04 (m, 1H), 4.83 (d, J=7.8 Hz, 1H), 4.31 (ddd, J=13.1, 9.8, 3.7 Hz, 1H), 4.22-4.11 (m, 2H), 3.89 (ddd, J=11.0, 7.5, 4.9 Hz, 1H), 3.85-3.79 (m, 2H), 3.61 (br s, 3H), 3.51 (td, J=9.6, 4.3 Hz, 1H), 3.36 (s, 3H), 3.04 (d, J=17.4 Hz, 1H), 2.83-2.73 (m, 2H), 2.70 (d, J=17.4 Hz, 1H), 2.62-2.55 (m, 1H), 2.55 (s, 3H), 2.27-2.18 (m, 1H), 1.76 (q, J=12.3 Hz, 1H), 1.54-1.47 (m, 1H), 1.18 (d, J=6.1 Hz, 3H), 1.08 (d, J=6.2 Hz, 3H), 1.03 (d, J=6.3 Hz, 3H) ppm; $^{13}$C NMR (CD$_3$OD, 151 MHz) δ=204.36, 153.11, 138.70, 138.22, 137.63, 137.36, 135.93, 133.48, 133.26, 128.57, 126.35, 123.84, 122.38, 120.59, 120.13, 114.10, 106.94, 102.93, 102.37, 95.53, 89.70, 83.89, 77.49, 75.86, 72.65, 71.66, 63.64, 56.95, 56.49, 54.94, 53.04, 49.57, 47.51, 40.94, 34.90, 32.91, 22.87, 22.25, 19.85 ppm; HRMS (ESI-TOF) calcd for $C_{45}H_{50}N_4O_{11}S_3Na^+$ [M+Na]$^+$941.2530, found 941.2536.

Example 4—Biological Activity i. Cytotoxic Assay

Cells were cultured in a T75 flask to ~50-80% confluency and harvested with trypsin into a single cell suspension. Five hundred (500) cells per well were seeded in tissue culture plates in 50 μL/well culture media and incubated at 37° C. for 18-24 hours. Compounds were diluted as 400× final desired concentrations in DMSO. Serial dilutions in DMSO were then diluted in culture media for a final DMSO concentration of 0.25% and 50 μL/well of the final dilution was added to the cells (Vf=100 μL). Upon plating and treatment, cells were returned to the incubator for an additional 72 hours. CellTiter-Glo reagent was prepared per manufacturer's instructions and added at 100 μL/well to the cultures. CellTiter-Glo allows for relative enumeration of metabolically active cells by quantifying intracellular ATP concentrations. After 5 minutes of incubation with CellTiter-Glo at ambient room temperature, 125 μL/well of the Cell Titer Glo/cell lysate solution was transferred into black assay plates, which were then read in a luminometer within 30 minutes. Luminescence readings obtained from cultures that did not receive any treatment (cell culture media only) were set as 100% control and all other luminescence values were normalized to these controls (e.g., Normalized RLU, relative luminescence unit).

ii. Cell Lines

MES SA and MES SA/Dx cells are uterine sarcoma. MES SA Dx cell line was generated from MES SA to achieve upregulation of MDR1. MES-SA/Dx cells exhibit marked cross-resistance to a number of chemotherapeutic agents (including daunorubicin, dactinomycin, vincristine, taxol, colchicine) and moderate cross-resistance to mitomycin C and melphalan. 293T cells are human embryonic kidney cell line.

iii. Activity

The activity of the compounds is described in FIGS. 2A-4C. The IC$_{50}$ was determined for compounds: KCN-LL1, KCN-LL2, KCN-LL3, KCN-LL4, and KCN-LL5 and is shown in Table 1.

TABLE 1
| | IC$_{50}$ of Compounds | | |
|---|---|---|---|
| Compound | MES SA (nM) | MES DX (nM) | 293T (nM) |
| (KCN-LL1) 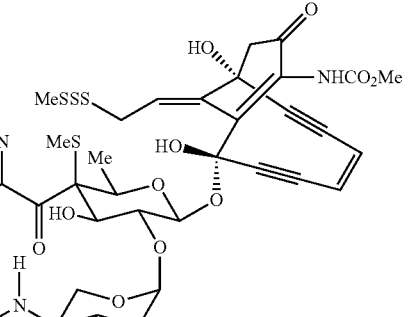 | 0.01261 | N/A | 0.01623 |
| (KCN-LL2) 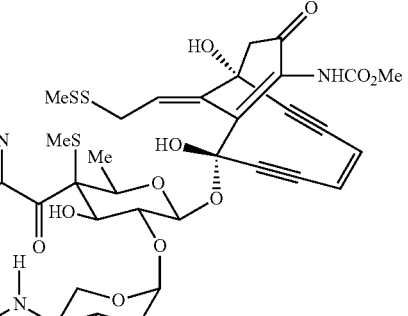 | 0.00067 | 34.64 | 0.001462 |
| (KCN-LL3) 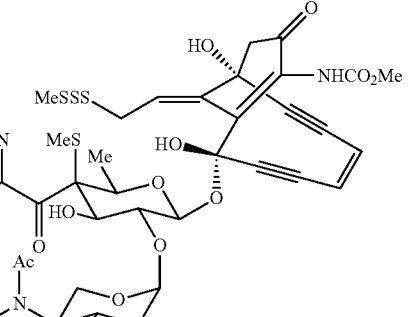 | 1.6 | ~500 | 1.5 |

TABLE 1-continued

IC$_{50}$ of Compounds

| Compound | MES SA (nM) | MES DX (nM) | 293T (nM) |
|---|---|---|---|
| (KCN-LL4) | 2.7 | ~500 | 1.9 |
| (KCN-LL5) | 0.006 | 1.2 | 0.008 |
| N-Ac Calicheamicin γ | 0.02975 | N/A | 0.1515 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference:

Anderson, N. G., *Practical Process Research & Development—A Guide For Organic Chemists*, 2$^{nd}$ ed., Academic Press, New York, 2012.
Badalassi et al., Tetrahedron 53, 14369-14380, 1997.
Chari et al., Angew. Chem. Int. Ed., 53:3796-3827, 2014.
Evans et al., J. Am. Chem. Soc., 99:5009-5017, 1977.
Fürstner & Weintritt, J. Am. Chem. Soc., 120:2817-2825, 1998.
Gomez Paloma et al., J. Am. Chem. Soc., 116:3697-3708, 1994.
Greene's Protective Groups in Organic Chemistry, Wuts and Greene, Ed., 1973
Groneberg et al., J. Am. Chem. Soc., 115:7593-7611, 1993.
Halcomb & Danishefsky, J. Am. Chem. Soc., 111:6661-6666, 1989.
Harpp & Ash, Int. J. Sulfur Chem., Part A., 1:57-59, 1971.
Jones & Bergman, J. Am. Chem. Soc., 94:660-661, 1972.
Krasovskiy et al., Angew. Chem. Int. Ed., 45:2958-2961, 2006b.
Krasovskiy et al., Angew. Chem. Int. Ed., 45:497-500, 2006a.
Lee et al., J. Am. Chem. Soc., 109:3464-3466, 1987a.
Lee et al., J. Am. Chem. Soc., 109:3466-3468, 1987b.
Leonard et al., J. Am. Chem. Soc., 118:10898-10899, 1996.
Lu et al., Can. J. Chem., 73:2253-2262, 1995.
*March's Advanced Organic Chemistry: Reactions, Mechanisms, and Structure*, 2007.
Nicolaou & Montagnon, T. Molecules that changed the world, Wiley-VCH, 2008.
Nicolaou et al., A. Org. Lett., 13:3924-3927, 2011.
Nicolaou et al., J. Am. Chem. Soc., 114:10082-10084, 1992.
Nicolaou et al., J. Am. Chem. Soc., 115:7625-7635, 1993.
Nicolaou, Angew. Chem. Int. Ed., 53:9128-9140, 2014.

Nicolaou, et al., J. Am. Chem. Soc., 137:8716-8719, 2015.
Oku et al., J. Am. Chem. Soc., 125:2044-2045, 2003.
Reetz & Starke, Tetrahedr. Lett., 25:3301-3304, 1984.
Remington's Pharmaceutical Sciences, 15$^{th}$ Ed., 3:624-652, 1035-1038, and 1570-1580, 1990.
Schott et al., Bioorg. Med. Chem. Lett., 16:5840-5843, 2006.
Smith et al., J. Am. Chem. Soc., 115:7612-7624, 1993.
Tanaka et al., Chem. Asian. J. 5, 1407-1424, 2010.
Wu & Senter, Nat. Biotechnol., 23:1137-1146, 2005.
Xiao et al., Bioorg. Med. Chem. Lett., 11:437-441, 2001.
Zhao & Liu, J. Org. Chem., 66:6810-6815, 2001.

What is claimed is:

1. A compound of the formula:

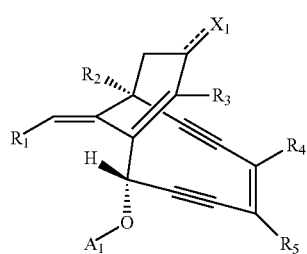

(I)

wherein:
$R_1$ is -alkanediyl$_{(C\le8)}$-(S)$_x$-$A_3$ or -substituted alkanediyl$_{(C\le8)}$-(S)$_x$-$A_3$; wherein:
$A_3$ is hydrogen or alkyl$_{(C\le12)}$, cycloalkyl$_{(C\le12)}$, alkenyl$_{(C\le12)}$, alkynyl$_{(C\le12)}$, aryl$_{(C\le12)}$, heteroaryl$_{(C\le12)}$, aralkyl$_{(C\le12)}$, acyl$_{(C\le12)}$, or a substituted version of any of these groups; and
x is 1, 2, or 3;
$R_2$ is hydroxy, or alkoxy$_{(C\le8)}$, acyloxy$_{(C\le8)}$, or substituted version of either of these groups;
$R_3$ is NHC(O)$R_{16}$, wherein:
$R_{16}$ is alkoxy$_{(C\le8)}$, alkenyloxy$_{(C\le8)}$, alkylamino$_{(C\le8)}$, dialkylamino$_{(C\le8)}$, or substituted version of any of these groups;
$R_4$ and $R_5$ are each independently selected from hydrogen and halo;
$X_1$ is O, S, or NH;
$A_1$ is -alkanediyl$_{(C\le12)}$-C(O)-$A_2$ or -substituted alkanediyl$_{(C\le12)}$-C(O)-$A_2$, or

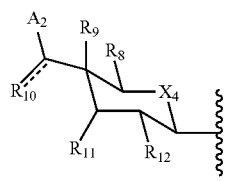

wherein:
$X_4$ is —CH$_2$— or —O—;
$R_8$ is hydrogen, alkyl$_{(C\le8)}$, cycloalkyl$_{(C\le8)}$, substituted alkyl$_{(C\le8)}$, or substituted cycloalkyl$_{(C\le8)}$;
$R_9$ is hydrogen, halo, hydroxy, mercapto, alkyl$_{(C\le8)}$, substituted alkyl$_{(C\le8)}$, alkoxy$_{(C\le8)}$, substituted alkoxy$_{(C\le8)}$, alkylthio$_{(C\le8)}$, substituted alkylthio$_{(C\le8)}$;
$R_{10}$ is hydroxy, oxo, or $R_{10}$ is taken together with $R_{11}$ and is —OCH$A_4$O—;
provided that when $R_{10}$ is oxo then $R_{10}$ and the carbon atom to which it is bound are joined by a double bond, and when $R_{10}$ is taken together with $R_{11}$ then $R_{10}$ and the carbon atom to which it is bound are joined by a single bond;
wherein $A_4$ is aryl$_{(C\le12)}$ or substituted aryl$_{(C\le12)}$, or

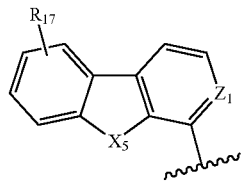

wherein:
$X_5$ is O, S, or NR$_{18}$; wherein:
$R_{18}$ is hydrogen, alkyl$_{(C\le8)}$, substituted alkyl$_{(C\le8)}$, acyl$_{(C\le8)}$, or substituted acyl$_{(C\le8)}$;
$Z_1$ is CH or N; and
$R_{17}$ is hydrogen, hydroxy, amino, hydrazino, carboxy, halo, or nitro; or alkyl$_{(C\le12)}$, alkoxy$_{(C\le12)}$, or a substituted version of either of these groups;
$R_{11}$ is hydrogen, hydroxy, alkoxy$_{(C\le8)}$, or substituted alkoxy$_{(C\le8)}$;
$R_{12}$ is hydrogen, hydroxy, alkoxy$_{(C\le8)}$, substituted alkoxy$_{(C\le8)}$, or
—O-alkanediyl$_{(C\le8)}$-alkylamino$_{(C\le12)}$,
—OC(O)-alkanediyl$_{(C\le8)}$-alkylamino$_{(C\le12)}$, or
OC(O)NH-alkanediyl$_{(C\le8)}$-alkylamino$_{(C\le12)}$, or a substituted version of any of these groups; or

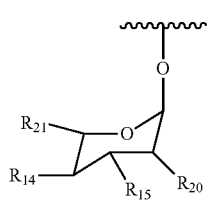

wherein:
$R_{14}$ is amino or hydroxy; or alkoxy$_{(C\le12)}$, alkylamino$_{(C\le12)}$, dialkyl-amino$_{(C\le12)}$, or a substituted version of any of these groups, or —NR$_a$R$_b$, wherein:
$R_a$ and $R_b$ are each hydrogen, alkyl$_{(C\le12)}$, substituted alkyl$_{(C\le12)}$, alkenyl$_{(C\le12)}$, substituted alkenyl$_{(C\le12)}$, —C(O)O-alkanediyl$_{(C\le6)}$-R$_c$, —C(O)-alkanediyl$_{(C\le6)}$-R$_c$, -alkanediyl$_{(C\le6)}$-R$_c$, or a substituted version of either of these group;
wherein:
$R_c$ is hydrogen, amino, carboxy, hydroxyl, acyl$_{(C\le8)}$, alkoxy$_{(C\le8)}$, alkylamino$_{(C\le8)}$, dialkylamino$_{(C\le8)}$, alkylsulfonyl$_{(C\le8)}$, arylsulfonyl$_{(C\le8)}$, or a substituted version of either of these groups;
$R_{15}$ is hydrogen, hydroxy, alkoxy$_{(C\le8)}$, or substituted alkoxy$_{(C\le8)}$;

185

$R_{20}$ and $R_{21}$ are hydrogen, alkyl$_{(C\leq 8)}$, substituted alkyl$_{(C\leq 8)}$, alkoxy$_{(C\leq 8)}$, or substituted alkoxy$_{(C\leq 8)}$;

$A_2$ is hydrogen or

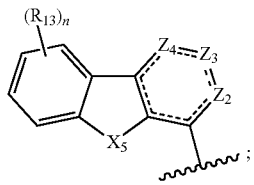

wherein:

$X_5$ is O, S, or $NR_{18}$; wherein:

$R_{18}$ is hydrogen, alkyl$_{(C\leq 8)}$, substituted alkyl$_{(C\leq 8)}$, acyl$_{(C\leq 8)}$, or substituted acyl$_{(C\leq 8)}$;

n is 1, 2, 3, 4, or 5;

$Z_2$, $Z_3$, and $Z_4$ are each independently N or $CR_{13}$; and $R_{13}$ is hydrogen, amino, carboxy, hydroxy, hydrazino, halo, nitro, or mercapto; alkyl$_{(C\leq 12)}$, acyl$_{(C\leq 12)}$, alkoxy$_{(C\leq 12)}$, acyloxy$_{(C\leq 12)}$, or a substituted version of either of these groups; or $A_1$ is

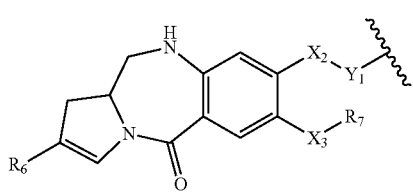

wherein:

$Y_1$ is alkanediyl$_{(C\leq 8)}$ or substituted alkanediyl$_{(C\leq 8)}$;

$X_2$ and $X_3$ are each independently selected from —O—, —S—, or —$NR_{19}$—, wherein:

$R_{19}$ is hydrogen, alkyl$_{(C\leq 6)}$, or substituted alkyl$_{(C\leq 6)}$;

$R_6$ is aryl$_{(C\leq 18)}$, heteroaryl$_{(C\leq 18)}$, or a substituted version of either of these groups;

$R_7$ is alkyl$_{(C\leq 12)}$ or substituted alkyl$_{(C\leq 12)}$;

provided that the compound is not:

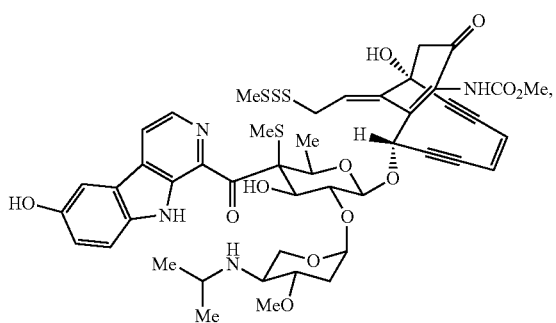

186

-continued

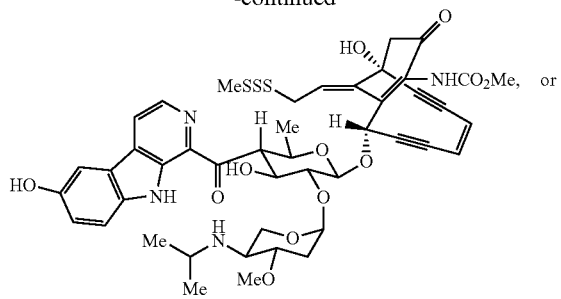

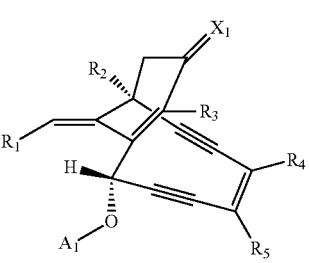

or a pharmaceutically acceptable salt thereof.

2. The compound of claim 1 further defined as:

(I)

[Structure I]

wherein:

$R_1$ is -alkanediyl$_{(C\leq 8)}$-(S)$_x$-$A_3$ or -substituted alkanediyl$_{(C\leq 8)}$-(S)$_x$-$A_3$; wherein:

$A_3$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, heteroaryl$_{(C\leq 12)}$, aralkyl$_{(C\leq 12)}$, acyl$_{(C\leq 12)}$, or a substituted version of any of these groups; and x is 1, 2, or 3;

$R_2$ is hydroxy, or alkoxy$_{(C\leq 8)}$, acyloxy$_{(C\leq 8)}$, or substituted version of either of these groups;

$R_3$ is $NHC(O)R_{16}$, wherein:

$R_{16}$ is alkoxy$_{(C\leq 8)}$, alkylamino$_{(C\leq 8)}$, dialkylamino$_{(C\leq 8)}$, or substituted version of any of these groups;

$R_4$ and $R_5$ are each independently selected from hydrogen and halo;

$X_1$ is O, S, or NH;

$A_1$ is -alkanediyl$_{(C\leq 12)}$-C(O)-$A_2$ or -substituted alkanediyl$_{(C\leq 12)}$-C(O)-$A_2$, or

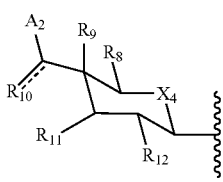

wherein:
X$_4$ is —CH$_2$— or —O—;
R$_8$ is hydrogen, alkyl$_{(C\leq8)}$, cycloalkyl$_{(C\leq8)}$, substituted alkyl$_{(C\leq8)}$, or substituted cycloalkyl$_{(C\leq8)}$;
R$_9$ is hydrogen, hydroxy, mercapto, alkoxy$_{(C\leq8)}$, substituted alkoxy$_{(C\leq8)}$, alkylthio$_{(C\leq8)}$, substituted alkylthio$_{(C\leq8)}$;
R$_{10}$ is oxo or R$_{10}$ is taken together with R$_{11}$ and is —OCHA$_4$O—; provided that when R$_{10}$ is oxo then R$_{10}$ and the carbon atom to which it is bound are joined by a double bond, and when R$_{10}$ is taken together with R$_{11}$ then R$_{10}$ and the carbon atom to which it is bound are joined by a single bond;
wherein A$_4$ is aryl$_{(C\leq12)}$ or substituted aryl$_{(C\leq12)}$, or

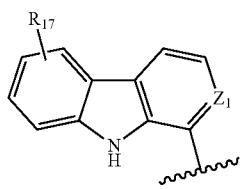

wherein:
Z$_1$ is CH or N; and
R$_{17}$ is hydrogen, hydroxy, amino, hydrazino, carboxy, halo, or nitro; or alkyl$_{(C\leq12)}$, alkoxy$_{(C\leq12)}$, or a substituted version of either of these groups;
R$_{11}$ is hydrogen, hydroxy, alkoxy$_{(C\leq8)}$, or substituted alkoxy$_{(C\leq8)}$;
R$_{12}$ is hydrogen, hydroxy, alkoxy$_{(C\leq8)}$, substituted alkoxy$_{(C\leq8)}$, or —O-alkanediyl$_{(C\leq8)}$-alkylamino$_{(C\leq12)}$,
—OC(O)-alkanediyl$_{(C\leq8)}$-alkylamino$_{(C\leq12)}$, or —OC(O)NH-alkanediyl$_{(C\leq8)}$-alkylamino$_{(C\leq12)}$, or a substituted version of any of these groups; or

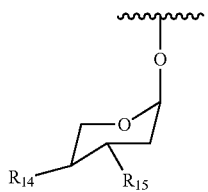

wherein:
R$_{14}$ is amino or hydroxy; or alkoxy$_{(C\leq12)}$, alkylamino$_{(C\leq12)}$, dialkyl-amino$_{(C\leq12)}$, or a substituted version of any of these groups;
R$_{15}$ is hydrogen, hydroxy, alkoxy$_{(C\leq8)}$, or substituted alkoxy$_{(C\leq8)}$;

A$_2$ is hydrogen or

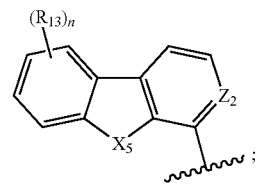

wherein:
X$_5$ is O, S, or NR$_{18}$; wherein:
R$_{18}$ is hydrogen, alkyl$_{(C\leq8)}$, substituted alkyl$_{(C\leq8)}$, acyl$_{(C\leq8)}$, or substituted acyl$_{(C\leq8)}$;
n is 1, 2, 3, or 4;
Z$_2$ is N or CH; and
R$_{13}$ is hydrogen, amino, carboxy, hydroxy, hydrazino, halo, or nitro;
alkyl$_{(C\leq12)}$, acyl$_{(C\leq12)}$, alkoxy$_{(C\leq12)}$, acyloxy$_{(C\leq12)}$, or a substituted version of either of these groups; or
A$_1$ is

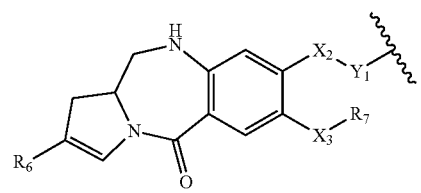

wherein:
Y$_1$ is alkanediyl$_{(C\leq8)}$ or substituted alkanediyl$_{(C\leq8)}$;
X$_2$ and X$_3$ are each independently selected from —O—, —S—, or —NR$_{19}$—, wherein:
R$_{19}$ is hydrogen, alkyl$_{(C\leq6)}$, or substituted alkyl$_{(C\leq6)}$;
R$_6$ is aryl$_{(C\leq18)}$, heteroaryl$_{(C\leq18)}$, or a substituted version of either of these groups;
R$_7$ is alkyl$_{(C\leq12)}$ or substituted alkyl$_{(C\leq12)}$;
provided that the compound is not:

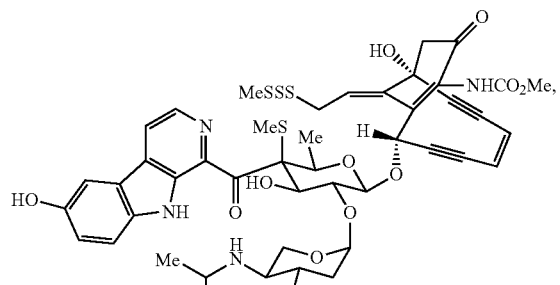

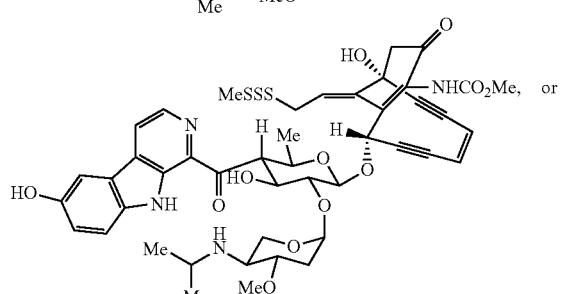

-continued

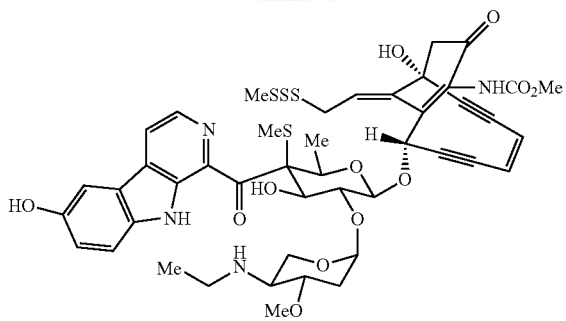

or a pharmaceutically acceptable salt thereof.

3. The compound of claim 1, wherein the compound is further defined as:

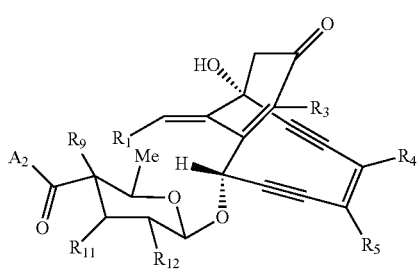

(III)

wherein: $R_1$, $R_3$, $R_4$, $R_5$, $R_9$, $R_{11}$, $R_{12}$, and $A_2$ are as defined above.

4. The compound of claim 1, wherein the compound is further defined as:

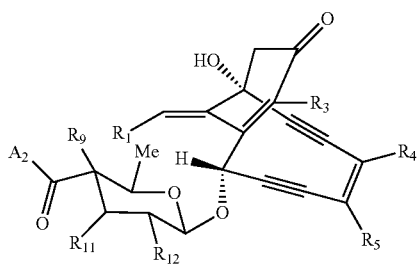

(III)

wherein:

$R_1$ is -alkanediyl$_{(C \leq 8)}$-(S)$_x$-$A_3$ or -substituted alkanediyl$_{(C \leq 8)}$-(S)$_x$-$A_3$; wherein:

$A_3$ is alkyl$_{(C \leq 12)}$, cycloalkyl$_{(C \leq 12)}$, acyl$_{(C \leq 12)}$, or a substituted version of any of these groups; and x is 1, 2, or 3;

$R_3$ is NHC(O)$R_{16}$, wherein:

$R_{16}$ is alkoxy$_{(C \leq 8)}$, alkenyloxy$_{(C \leq 8)}$, alkylamino$_{(C \leq 8)}$, dialkylamino$_{(C \leq 8)}$, or substituted version of any of these groups;

$R_4$ and $R_5$ are each independently selected from hydrogen and halo;

$R_9$ is hydrogen, halo, hydroxy, mercapto, alkyl$_{(C \leq 8)}$, substituted alkyl$_{(C \leq 8)}$, alkoxy$_{(C \leq 8)}$, substituted alkoxy$_{(C \leq 8)}$, alkylthio$_{(C \leq 8)}$, substituted alkylthio$_{(C \leq 8)}$;

$R_{11}$ is hydrogen, hydroxy, alkoxy$_{(C \leq 8)}$, or substituted alkoxy$_{(C \leq 8)}$;

$R_{12}$ is hydrogen, hydroxy, alkoxy$_{(C \leq 8)}$, substituted alkoxy$_{(C \leq 8)}$, or

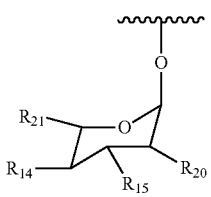

wherein:

$R_{14}$ is amino or hydroxy; or alkoxy$_{(C \leq 12)}$, alkylamino$_{(C \leq 12)}$, dialkyl-amino$_{(C \leq 12)}$, or a substituted version of any of these groups, or —NR$_a$R$_b$, wherein:

$R_a$ and $R_b$ are each hydrogen, alkyl$_{(C \leq 12)}$, substituted alkyl$_{(C \leq 12)}$, alkenyl$_{(C \leq 12)}$, substituted alkenyl$_{(C \leq 12)}$, —C(O)O-alkanediyl$_{(C \leq 6)}$-R$_c$, —C(O)-alkanediyl$_{(C \leq 6)}$-R$_c$, -alkanediyl$_{(C \leq 6)}$-R$_c$, or a substituted version of either of these group; wherein:

$R_c$ is hydrogen, amino, carboxy, hydroxyl, acyl$_{(C \leq 8)}$, alkoxy$_{(C \leq 8)}$, alkylamino$_{(C \leq 8)}$, dialkylamino$_{(C \leq 8)}$, alkylsulfonyl$_{(C \leq 8)}$, arylsulfonyl$_{(C \leq 8)}$, or a substituted version of either of these groups;

$R_{15}$ is hydrogen, hydroxy, alkoxy$_{(C \leq 8)}$, or substituted alkoxy$_{(C \leq 8)}$;

$R_{20}$ and $R_{21}$ are hydrogen, alkyl$_{(C \leq 8)}$, substituted alkyl$_{(C \leq 8)}$, alkoxy$_{(C \leq 8)}$, or substituted alkoxy$_{(C \leq 8)}$;

$A_2$ is

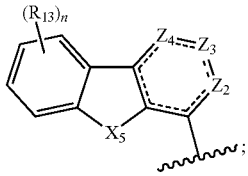

wherein:

$X_5$ is O, S, or NR$_{18}$; wherein:

$R_{18}$ is hydrogen, alkyl$_{(C \leq 8)}$, substituted alkyl$_{(C \leq 8)}$, acyl$_{(C \leq 8)}$, or substituted acyl$_{(C \leq 8)}$;

n is 1, 2, 3, 4, or 5;

$Z_2$, $Z_3$, and $Z_4$ are each independently N or CR$_{13}$; and $R_{13}$ is hydrogen, amino, carboxy, hydroxy, hydrazino, halo, nitro, or mercapto;

alkyl$_{(C \leq 12)}$, acyl$_{(C \leq 12)}$, alkoxy$_{(C \leq 12)}$, acyloxy$_{(C \leq 12)}$, or a substituted version of either of these groups; or or a pharmaceutically acceptable salt thereof.

5. The compound of claim 1, wherein the compound is further defined as:

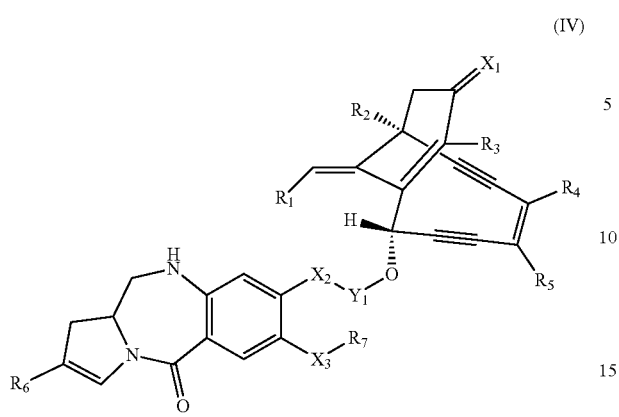

(IV)

wherein: $X_1$, $X_2$, $X_3$, $R_1$, $R_2$, $R_3$, $R_4$, $R_5$, $R_6$, $R_7$, and $Y_1$ are as defined above.

6. The compound of claim 1, wherein the compound is further defined as:

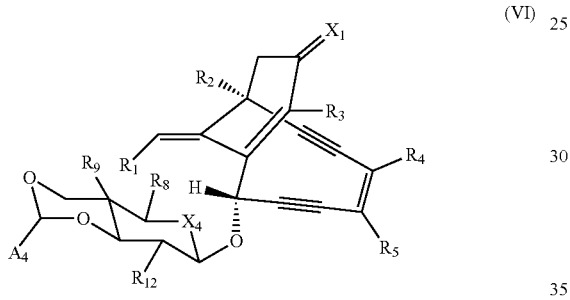

(VI)

wherein: $X_1$, $X_4$, $R_1$, $R_2$, $R_3$, $R_4$, $R_5$, $R_8$, $R_9$, $R_{12}$, and $A_3$ are as defined above.

7. The compound of claim 1, wherein $R_1$ is -alkanediyl$_{(C \leq 8)}$-(S)$_x$-A$_3$, wherein:
A$_3$ is hydrogen,
alkyl$_{(C \leq 12)}$, alkenyl$_{(C \leq 12)}$, alkynyl$_{(C \leq 12)}$, aryl$_{(C \leq 12)}$, heteroaryl$_{(C \leq 12)}$, aralkyl$_{(C \leq 12)}$, acyl$_{(C \leq 12)}$, or a substituted version of any of these groups; and
x is 2 or 3.

8. The compound of claim 7, wherein A$_3$ is alkyl$_{(C \leq 12)}$, substituted alkyl$_{(C \leq 12)}$, acyl$_{(C \leq 12)}$ or substituted acyl$_{(C \leq 12)}$.

9. The compound of claim 1, wherein A$_1$ is:

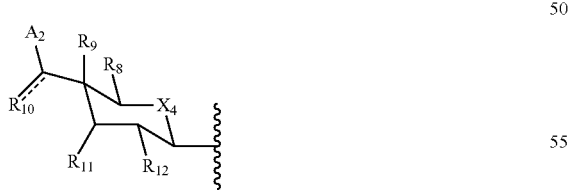

wherein:
$X_4$ is —CH$_2$— or —O—;
$R_8$ is hydrogen, alkyl$_{(C \leq 8)}$, cycloalkyl$_{(C \leq 8)}$, substituted alkyl$_{(C \leq 8)}$, or substituted cycloalkyl$_{(C \leq 8)}$;
$R_9$ is hydrogen, halo, hydroxy, mercapto, alkyl$_{(C \leq 8)}$, substituted alkyl$_{(C \leq 8)}$, alkoxy$_{(C \leq 8)}$, substituted alkoxy$_{(C \leq 8)}$, alkylthio$_{(C \leq 8)}$, substituted alkylthio$_{(C \leq 8)}$;
$R_{10}$ is hydroxy, oxo, or $R_{10}$ is taken together with $R_{11}$ and is —OCHA$_4$O—;

provided that when $R_{10}$ is oxo then $R_{10}$ and the carbon atom to which it is bound are joined by a double bond, and when $R_{10}$ is taken together with $R_{11}$ then $R_{10}$ and the carbon atom to which it is bound are joined by a single bond;

wherein $A_4$ is aryl$_{(C \leq 12)}$ or substituted aryl$_{(C \leq 12)}$, or

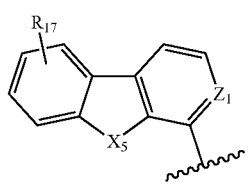

wherein:
$X_5$ is O, S, or NR$_{18}$; wherein:
$R_{18}$ is hydrogen, alkyl$_{(C \leq 8)}$, substituted alkyl$_{(C \leq 8)}$, acyl$_{(C \leq 8)}$, or substituted acyl$_{(C \leq 8)}$;
$Z_1$ is CR$_{17}$ or N; and
$R_{17}$ is hydrogen, hydroxy, amino, hydrazino, carboxy, halo, or nitro; or alkyl$_{(C \leq 12)}$, alkoxy$_{(C \leq 12)}$, or a substituted version of either of these groups;
$R_{11}$ is hydrogen, hydroxy, alkoxy$_{(C \leq 8)}$, or substituted alkoxy$_{(C \leq 8)}$;
$R_{12}$ is hydrogen, hydroxy, alkoxy$_{(C \leq 8)}$, substituted alkoxy$_{(C \leq 8)}$, or —O-alkanediyl(C≤s-alkylamino$_{(C \leq 12)}$, —OC(O)-alkanediyl$_{(C \leq 8)}$-alkylamino$_{(C \leq 12)}$, or —OC(O)NH-alkanediyl$_{(C \leq 8)}$-alkylamino$_{(C \leq 12)}$, or a substituted version of any of these groups; or

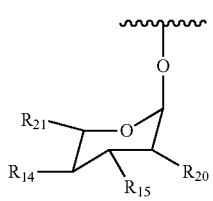

wherein:
$R_{14}$ is amino or hydroxy; or alkoxy$_{(C \leq 12)}$, alkylamino$_{(C \leq 12)}$, dialkyl-amino$_{(C \leq 12)}$, or a substituted version of any of these groups, or —NR$_a$R$_b$, wherein:
R$_a$ and R$_b$ are each hydrogen, alkyl$_{(C \leq 12)}$, substituted alkyl$_{(C \leq 12)}$, alkenyl$_{(C \leq 12)}$, substituted alkenyl$_{(C \leq 12)}$, —C(O)O-alkanediyl$_{(C \leq 6)}$-R$_c$, —C(O)-alkanediyl$_{(C \leq 6)}$-R$_c$, -alkanediyl$_{(C \leq 6)}$-R$_c$, or a substituted version of either of these group; wherein:
R$_c$ is hydrogen, amino, carboxy, hydroxyl, acyl$_{(C \leq 8)}$, alkoxy$_{(C \leq 8)}$, alkylamino$_{(C \leq 8)}$, dialkylamino$_{(C \leq 8)}$, alkylsulfonyl$_{(C \leq 8)}$, arylsulfonyl$_{(C \leq 8)}$, or a substituted version of either of these groups;
$R_{15}$ is hydrogen, hydroxy, alkoxy$_{(C \leq 8)}$, or substituted alkoxy$_{(C \leq 8)}$;
$R_{20}$ and $R_{21}$ are hydrogen, alkyl$_{(C \leq 8)}$, substituted alkyl$_{(C \leq 8)}$, alkoxy$_{(C \leq 8)}$, or substituted alkoxy$_{(C \leq 8)}$.

10. The compound of claim 9, wherein $R_9$ is hydrogen, alkoxy$_{(C \leq 8)}$, substituted alkoxy$_{(C \leq 8)}$, alkylthio$_{(C \leq 8)}$ or substituted alkylthio$_{(C \leq 8)}$.

11. The compound of claim 9, wherein $R_{12}$ is:

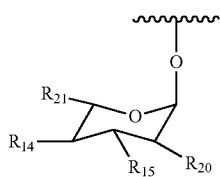

wherein:
$R_{14}$ is amino or hydroxy; or alkoxy$_{(C\le 12)}$, alkylamino$_{(C\le 12)}$, dialkyl-amino$_{(C\le 12)}$, or a substituted version of any of these groups, or —$NR_aR_b$, wherein:
$R_a$ and $R_b$ are each hydrogen, alkyl$_{(C\le 12)}$, substituted alkyl$_{(C\le 12)}$, alkenyl$(C\le 12)$, substituted alkenyl$_{(C\le 12)}$, —C(O)O-alkanediyl$_{(C\le 6)}$-$R_c$, —C(O)-alkanediyl$_{(C\le 6)}$-$R_c$, -alkanediyl$_{(C\le 6)}$-$R_c$, or a substituted version of either of these group; wherein:
$R_c$ is hydrogen, amino, carboxy, hydroxyl, acyl$_{(C\le 8)}$, alkoxy$_{(C\le 8)}$, alkylamino$_{(C\le 8)}$, dialkylamino$_{(C\le 8)}$, alkylsulfonyl$_{(C\le 8)}$, arylsulfonyl$_{(C\le 8)}$, or a substituted version of either of these groups;
$R_{15}$ is hydrogen, hydroxy, alkoxy$_{(C\le 8)}$, or substituted alkoxy$_{(C\le 8)}$; and
$R_{20}$ and $R_{21}$ are hydrogen, alkyl$_{(C\le 8)}$, substituted alkyl$_{(C\le 8)}$, alkoxy$_{(C\le 8)}$, or substituted alkoxy$_{(C\le 8)}$.

12. The compound of claim 9, wherein $A_2$ is further defined as:

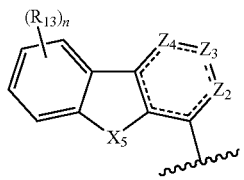

wherein:
$X_5$ is O, S, or $NR_{18}$; wherein:
$R_{18}$ is hydrogen, alkyl$_{(C\le 8)}$, substituted alkyl$_{(C\le 8)}$, acyl$_{(C\le 8)}$, or substituted acyl$_{(C\le 8)}$;
n is 1, 2, 3, 4, or 5;
$Z_2$, $Z_3$, and $Z_4$ are each independently N or $CR_{13}$; and
$R_{13}$ is hydrogen, amino, carboxy, hydroxy, hydrazino, halo, nitro, or mercapto;
alkyl$_{(C\le 12)}$, acyl$_{(C\le 12)}$, alkoxy$_{(C\le 12)}$, acyloxy$_{(C\le 12)}$, or a substituted version of either of these groups.

13. The compound of claim 12, wherein $A_2$ is:

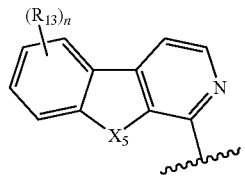

wherein:
$X_5$ is O, S, or $NR_{18}$; wherein:
$R_{18}$ is hydrogen, alkyl$_{(C\le 8)}$, substituted alkyl$_{(C\le 8)}$, acyl$_{(C\le 8)}$, or substituted acyl$_{(C\le 8)}$;
n is 1, 2, 3, or 4;
$R_{13}$ is hydrogen, amino, carboxy, hydroxy, hydrazino, halo, or nitro; or alkyl$_{(C\le 12)}$, acyl$_{(C\le 12)}$, alkoxy$_{(C\le 12)}$, acyloxy$_{(C\le 12)}$, or a substituted version of either of these groups.

14. The compound of claim 1, wherein $A_1$ is:

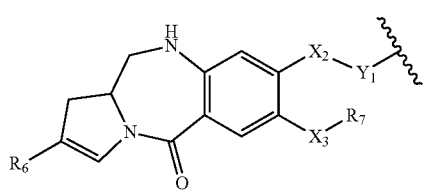

wherein:
$Y_1$ is alkanediyl$_{(C\le 8)}$ or substituted alkanediyl$_{(C\le 8)}$;
$X_2$ and $X_3$ are each independently selected from —O—, —S—, or —$NR_{19}$—, wherein:
$R_{19}$ is hydrogen, alkyl$_{(C\le 6)}$, or substituted alkyl$_{(C\le 6)}$;
$R_6$ is aryl$_{(C\le 18)}$, heteroaryl$_{(C\le 18)}$, or a substituted version of either of these groups;
$R_7$ is alkyl$_{(C\le 12)}$ or substituted alkyl$_{(C\le 12)}$.

15. The compound of claim 1, wherein the compound is further defined as:

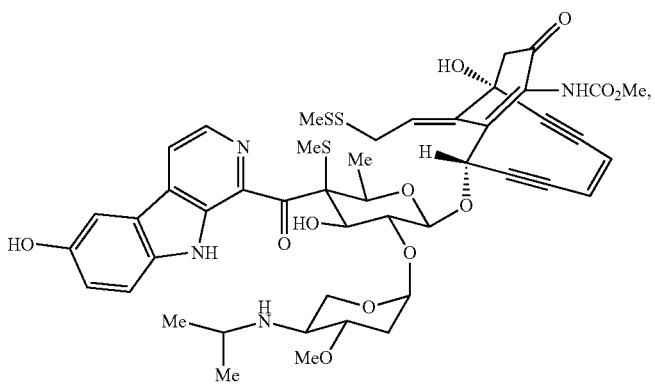

-continued
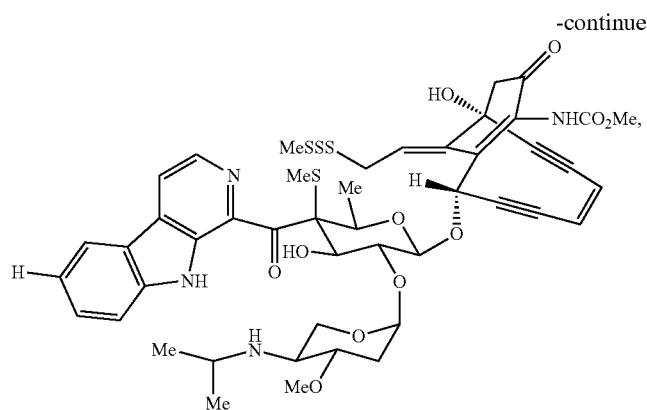
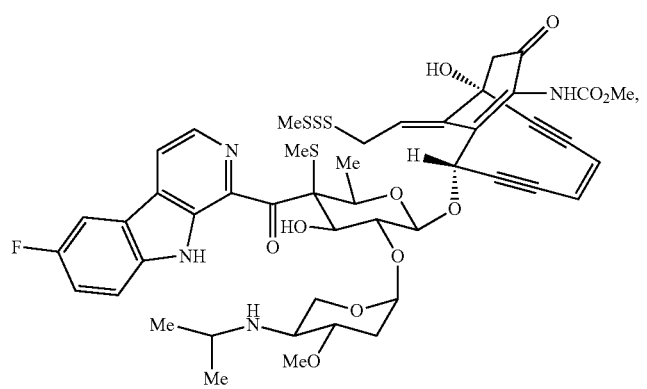
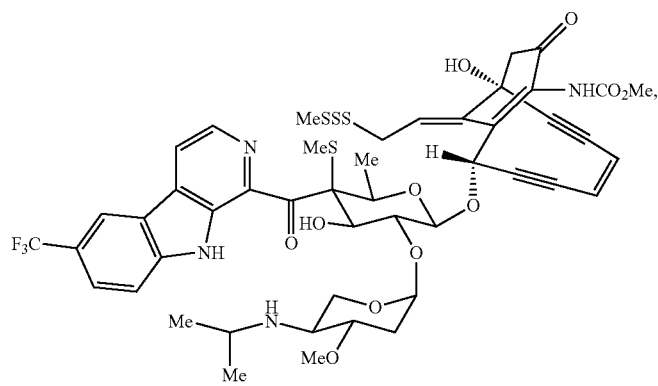
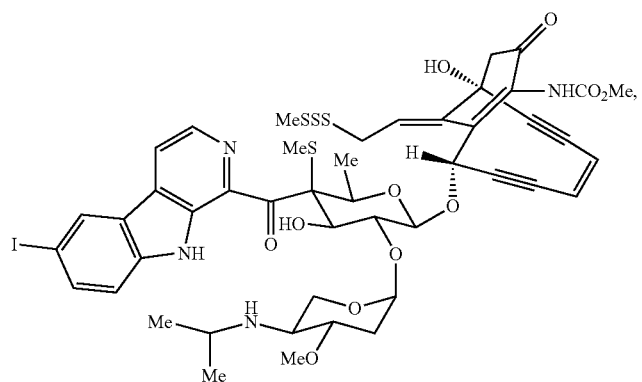

-continued
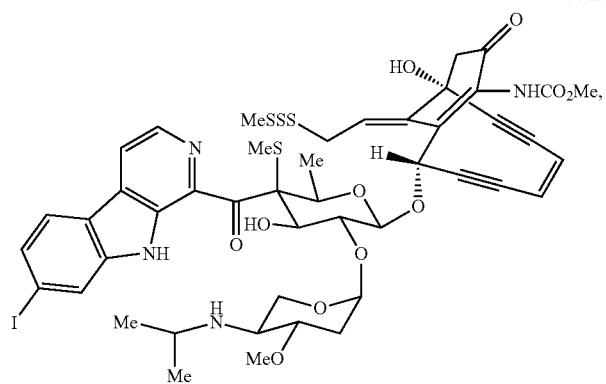
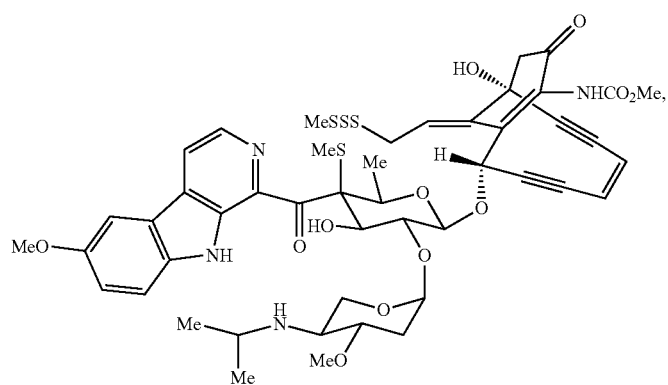
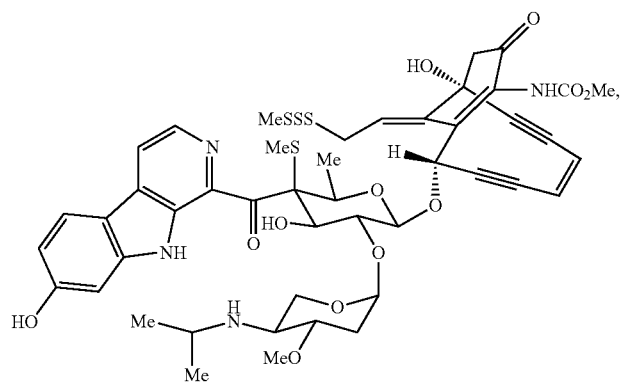
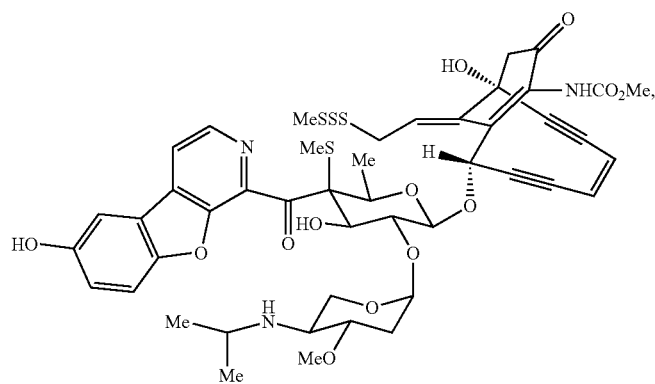

-continued
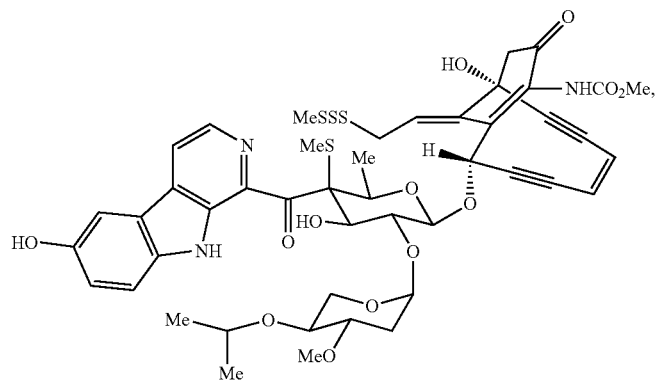
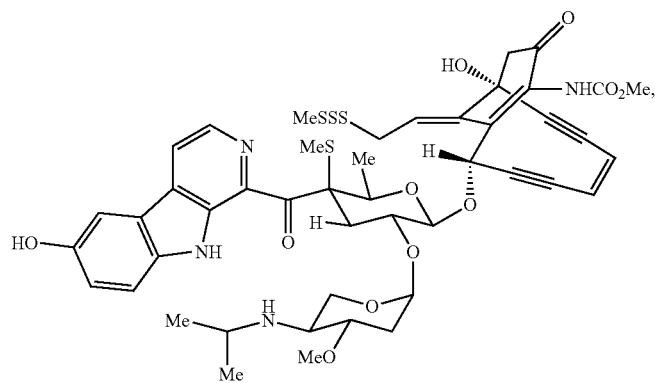
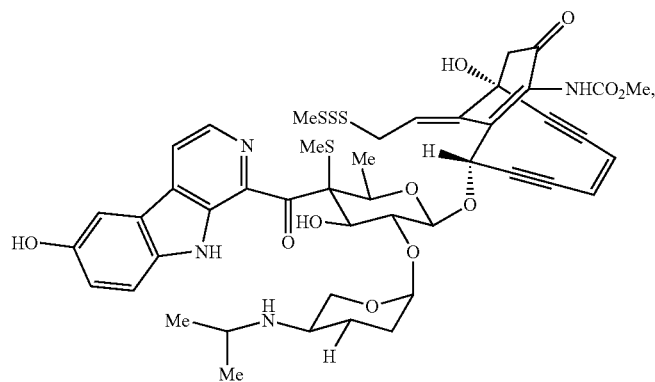
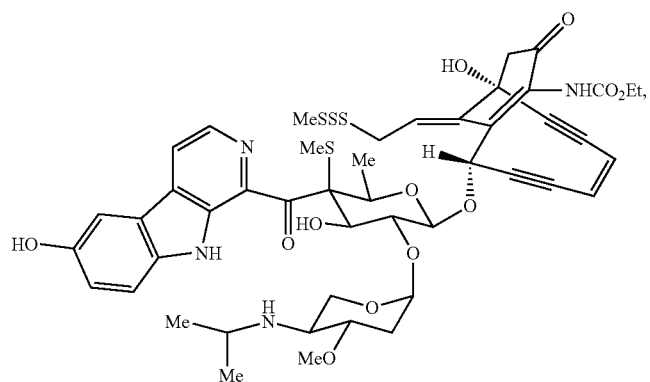

-continued
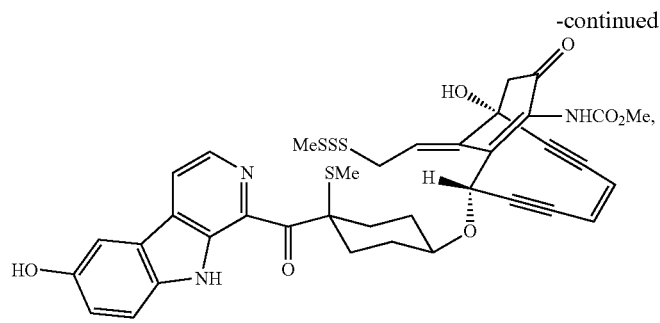
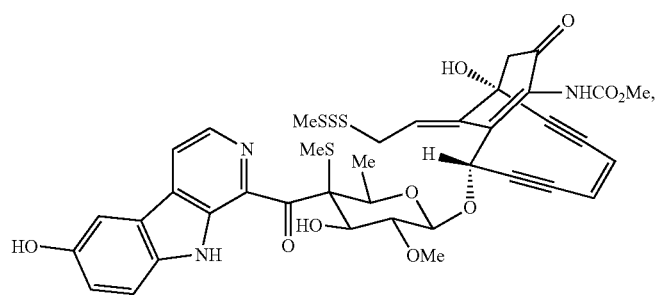
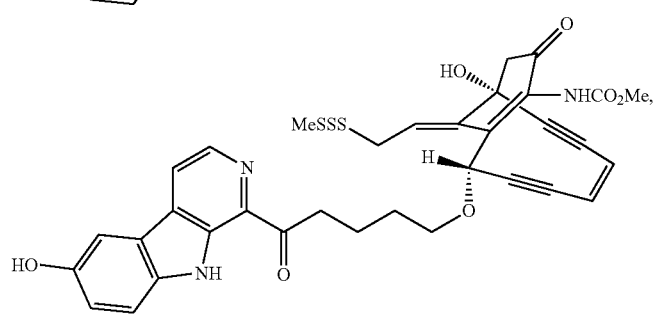
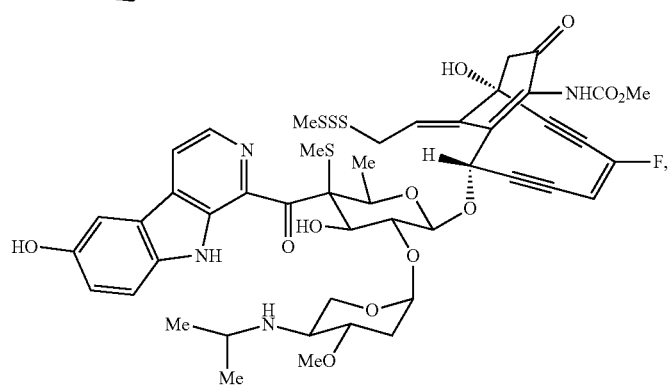
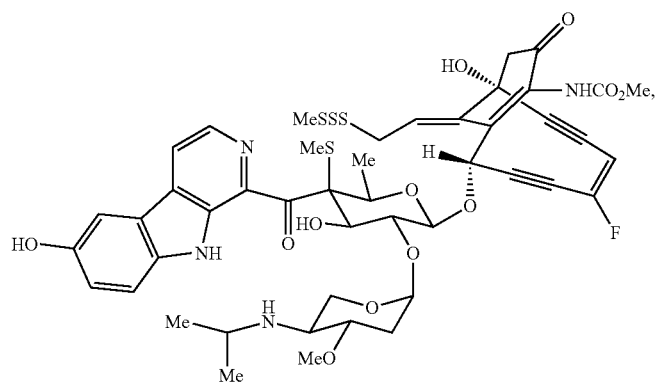

-continued
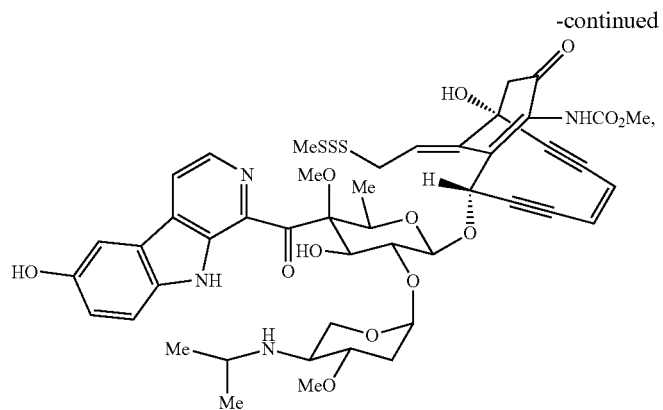
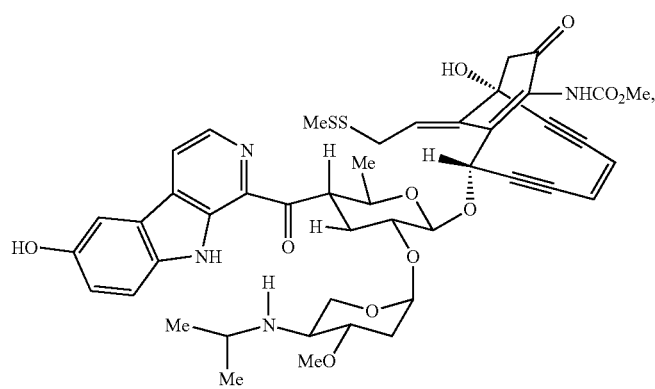
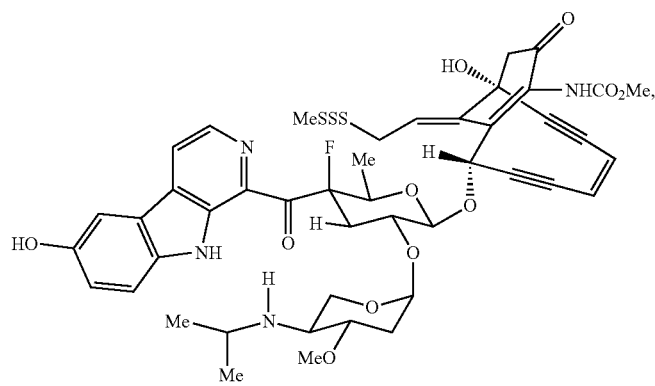
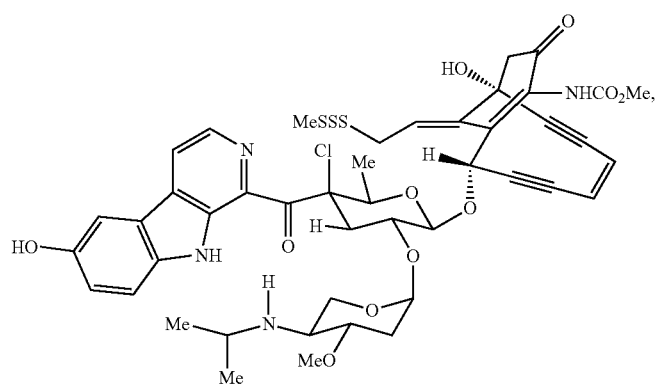

-continued
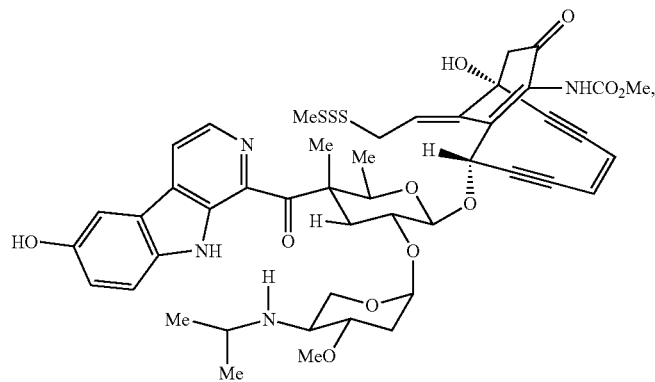
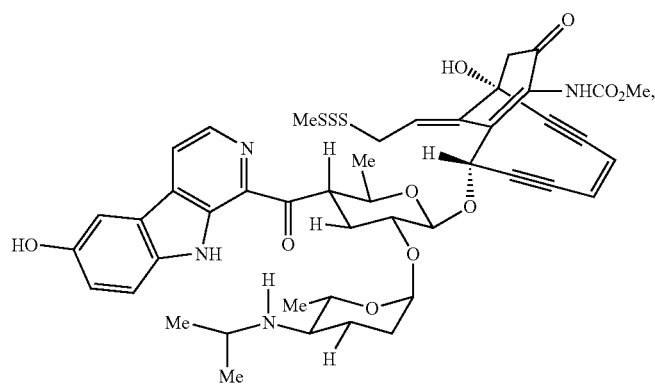
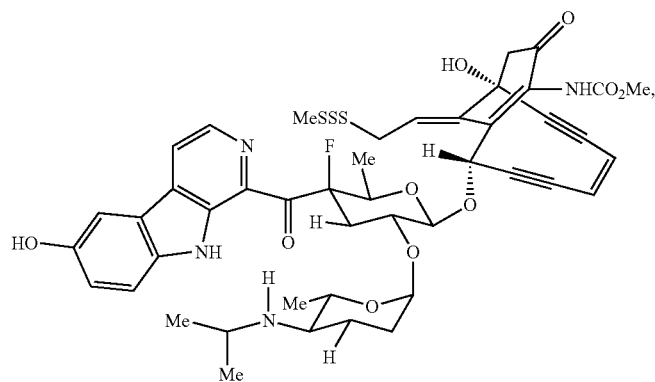
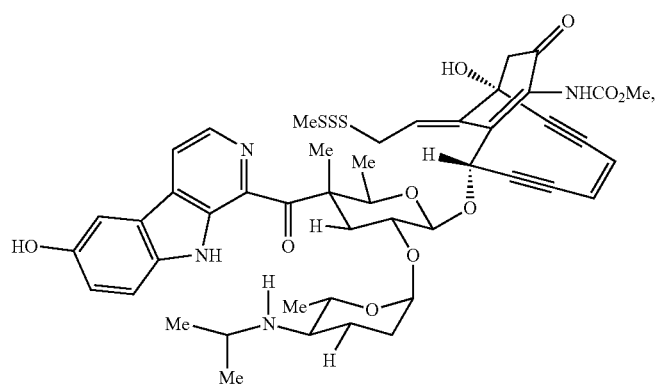

-continued
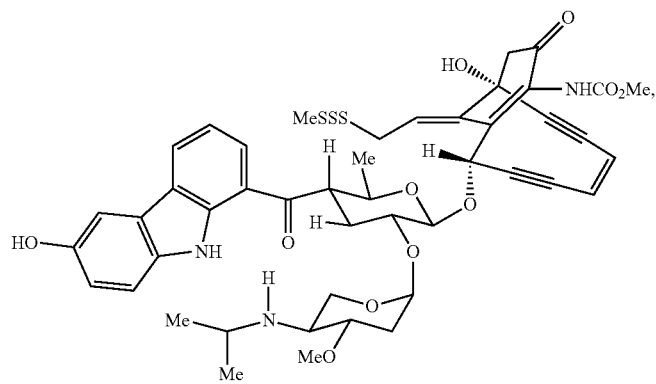
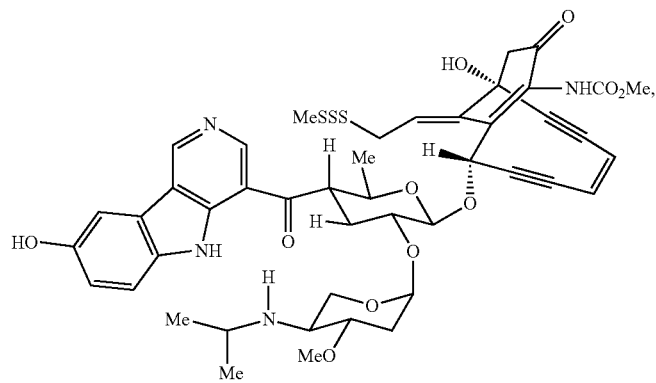
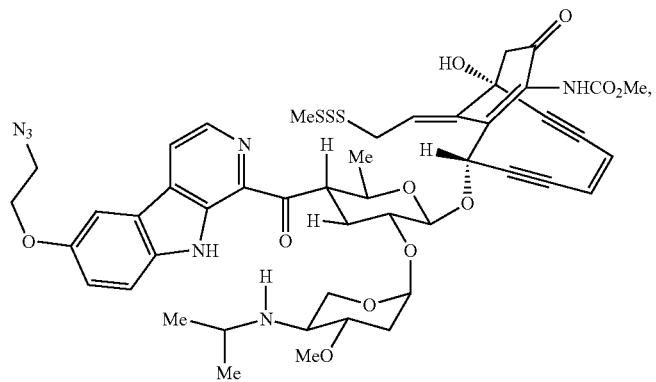
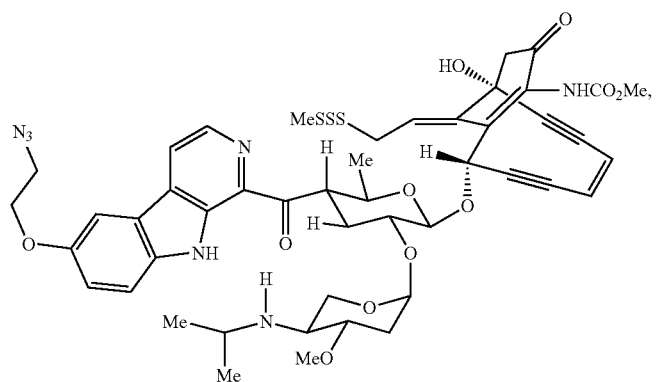

-continued
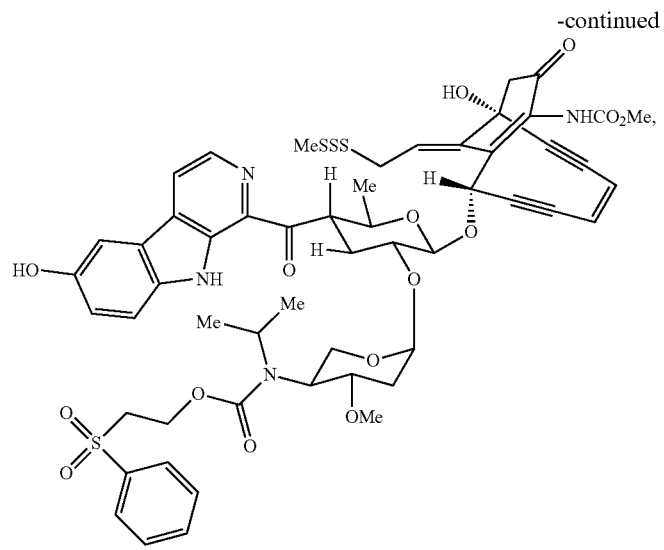
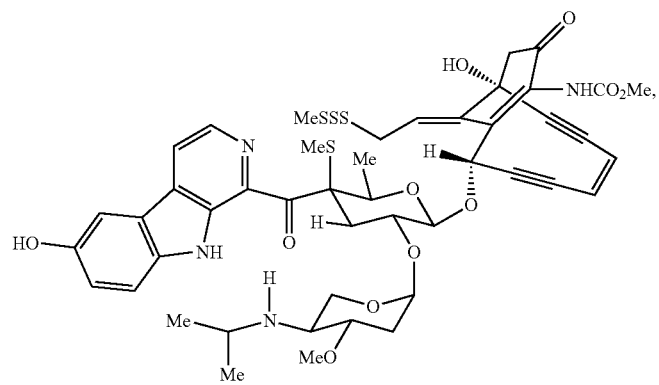
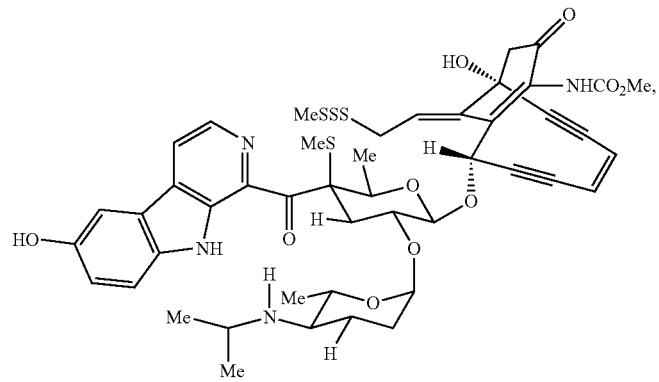
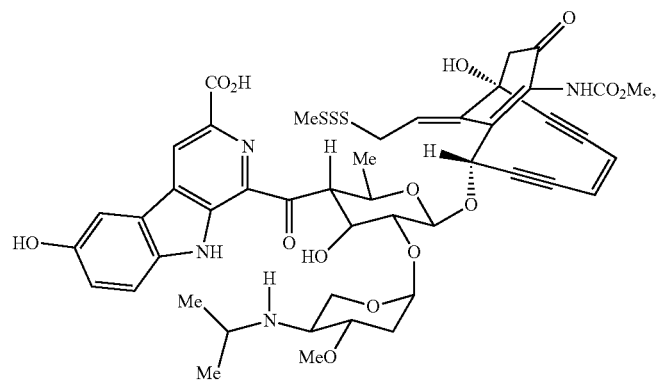

-continued
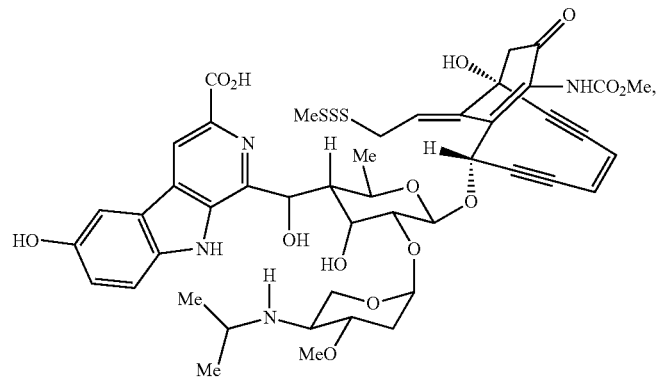
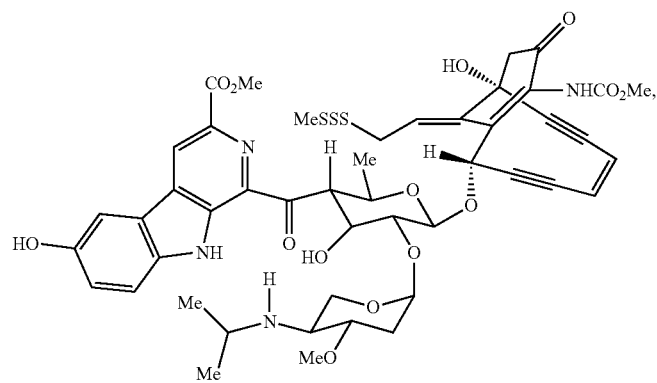
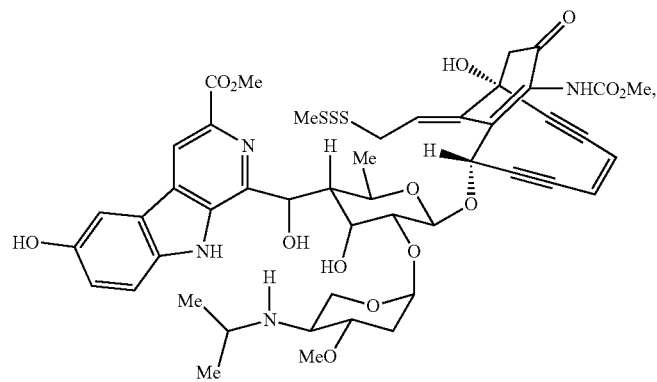
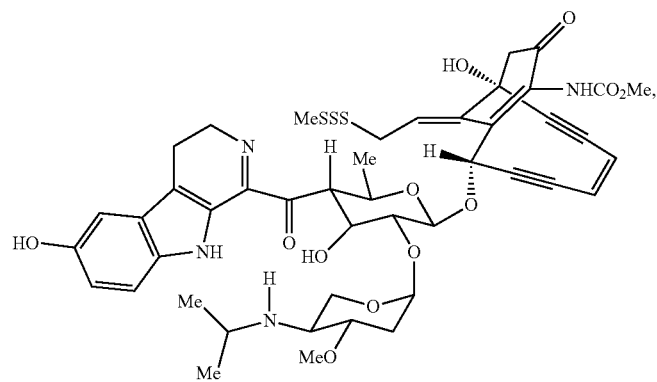

-continued
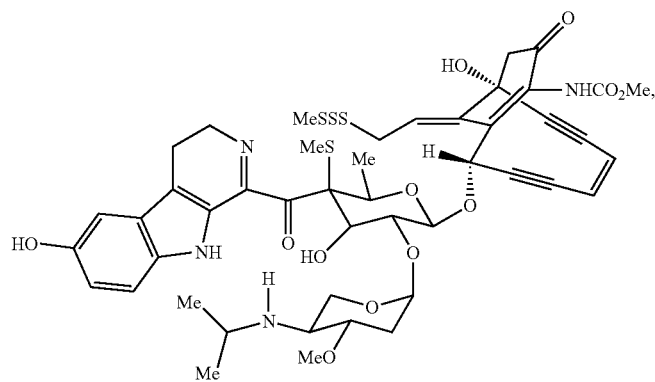
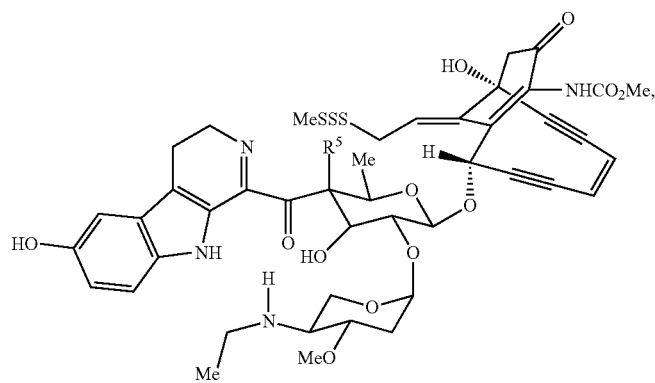
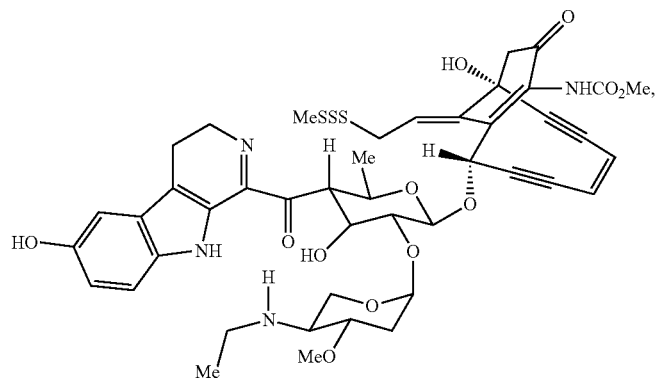
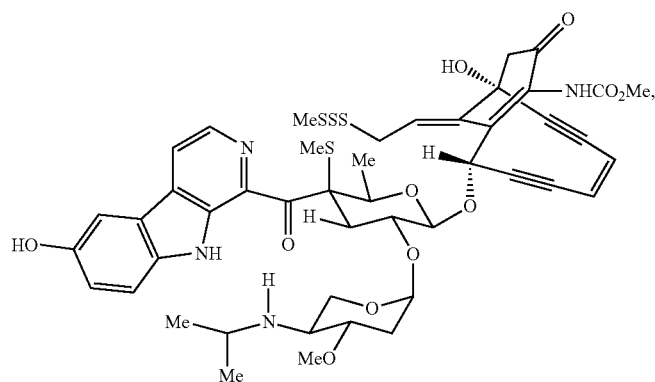

-continued
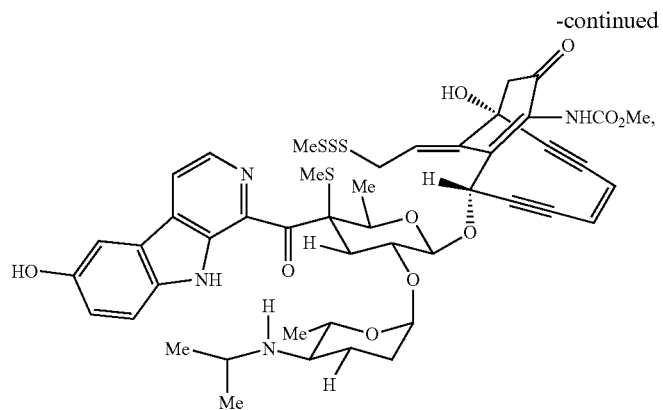
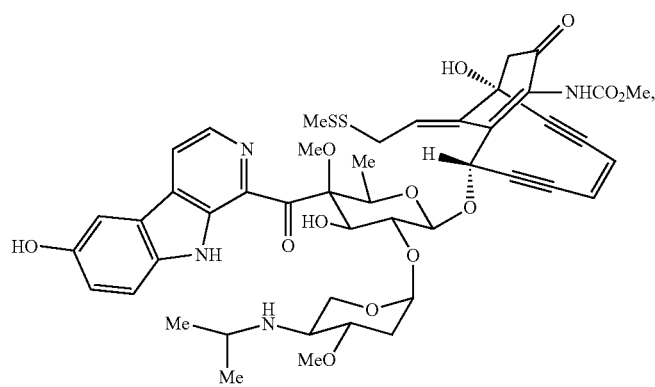
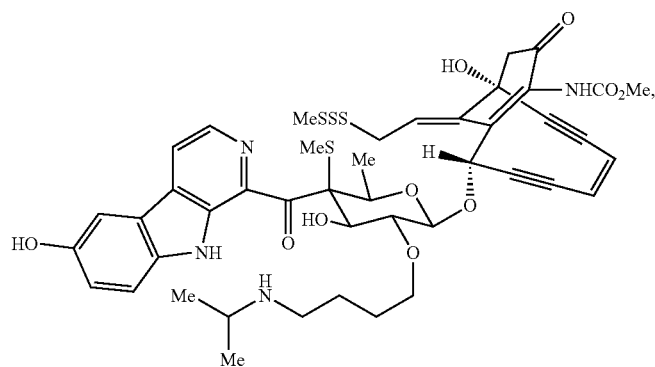
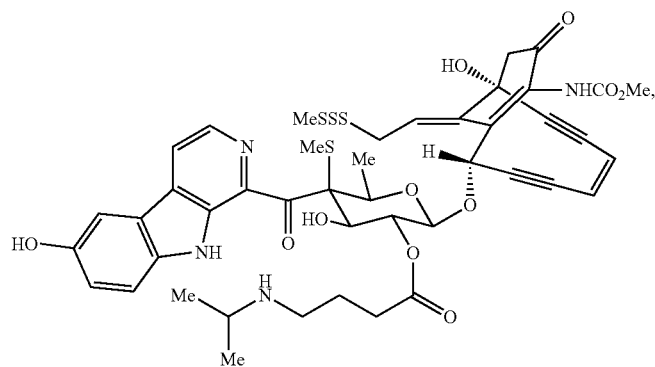

-continued
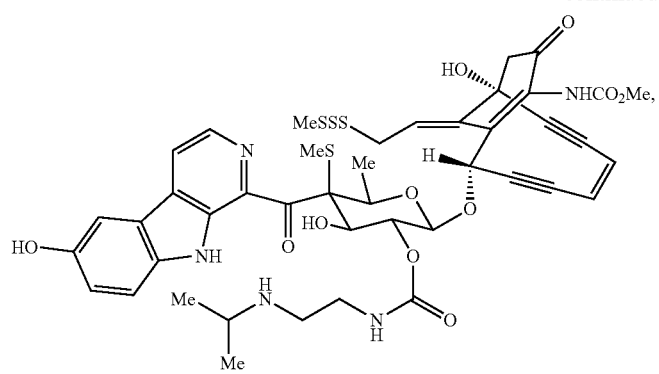
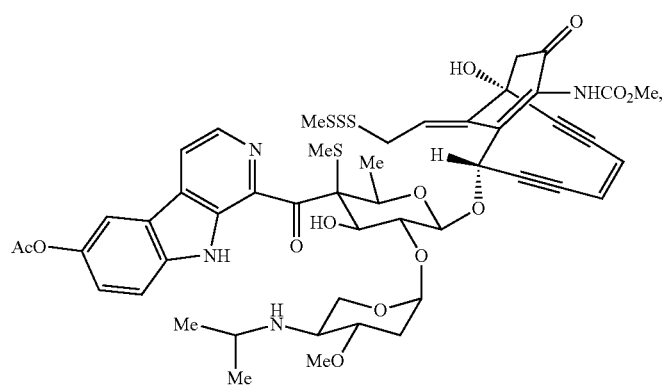
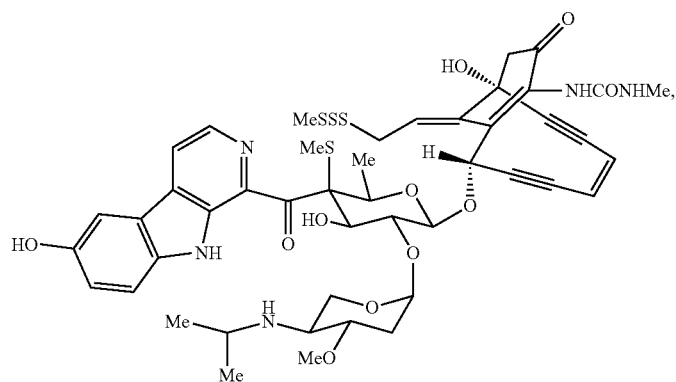
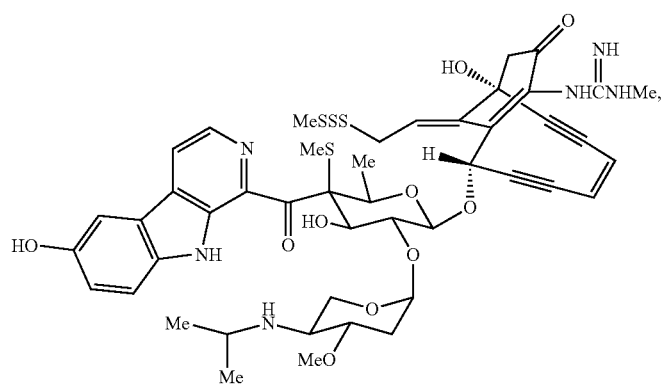

-continued
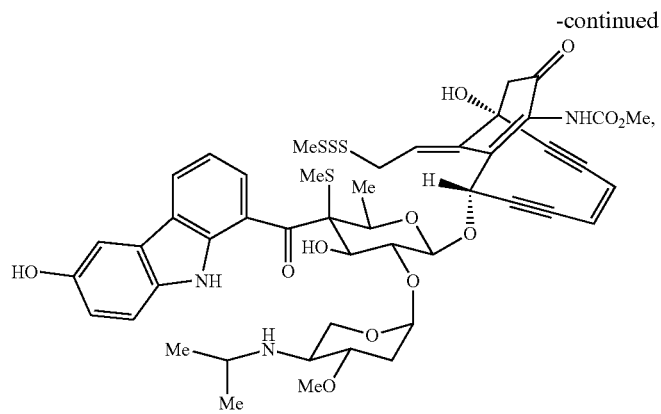
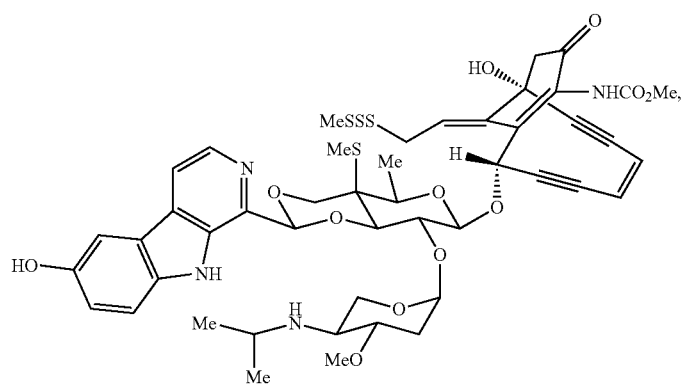
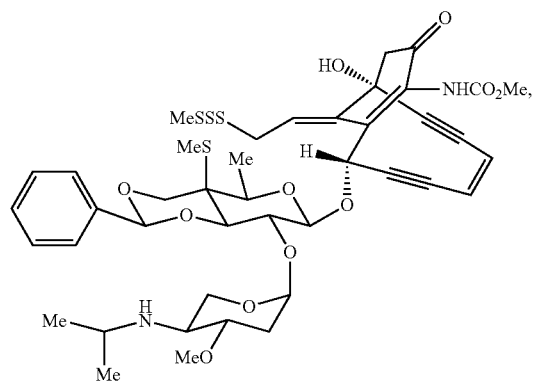
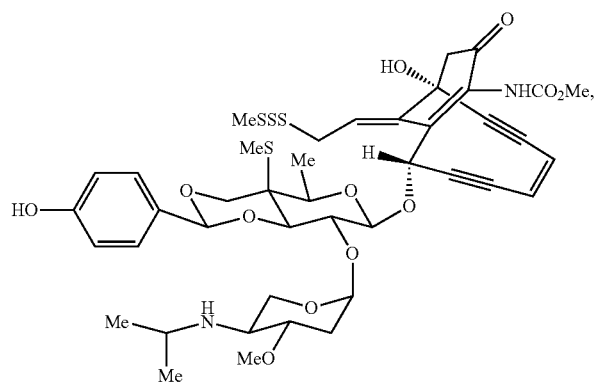

-continued
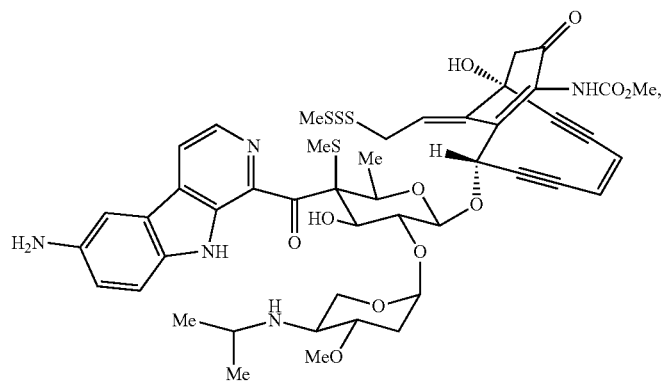
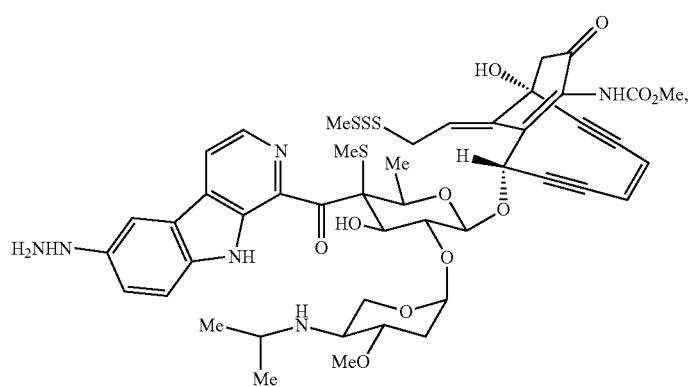
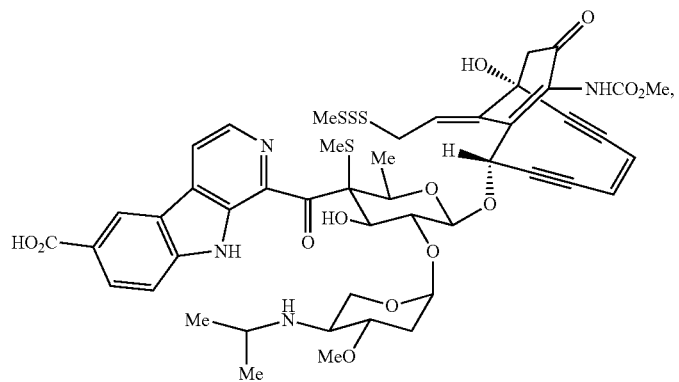
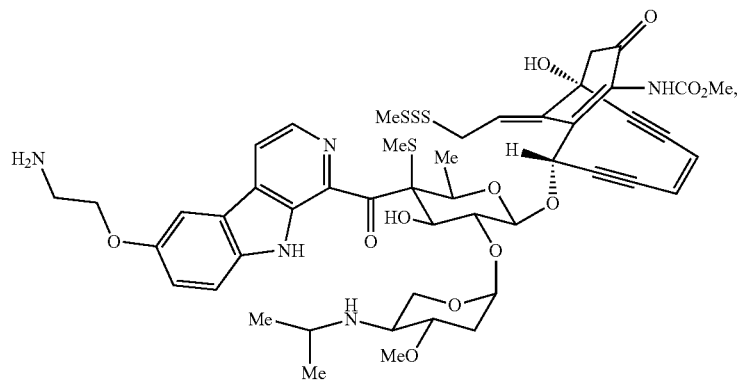

-continued
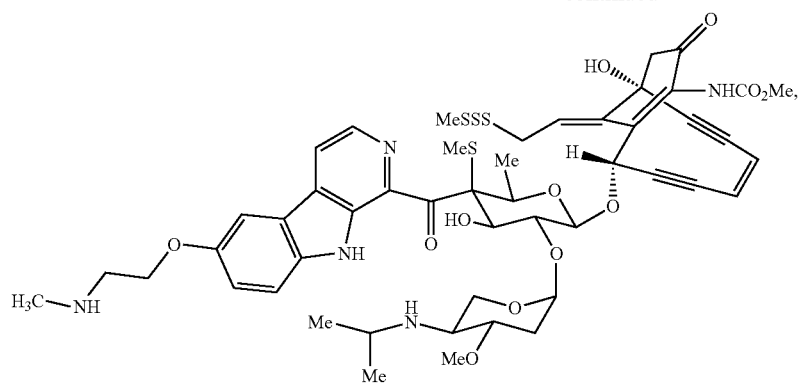
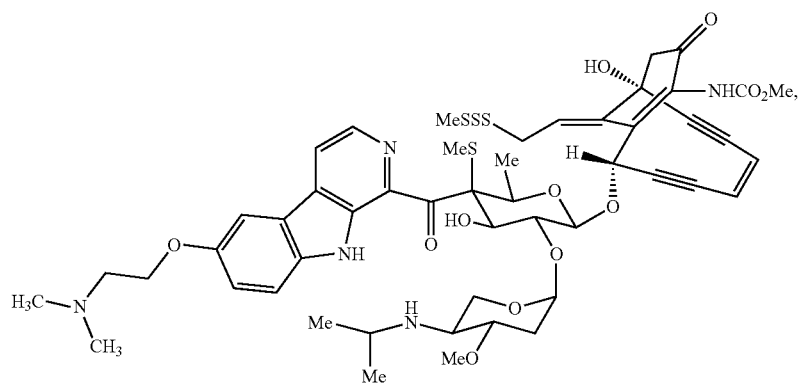
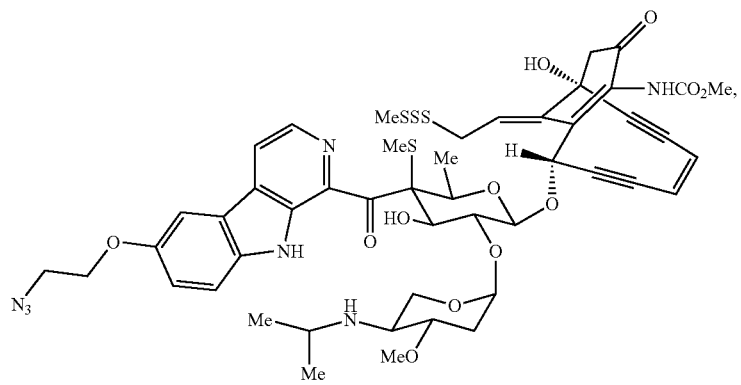
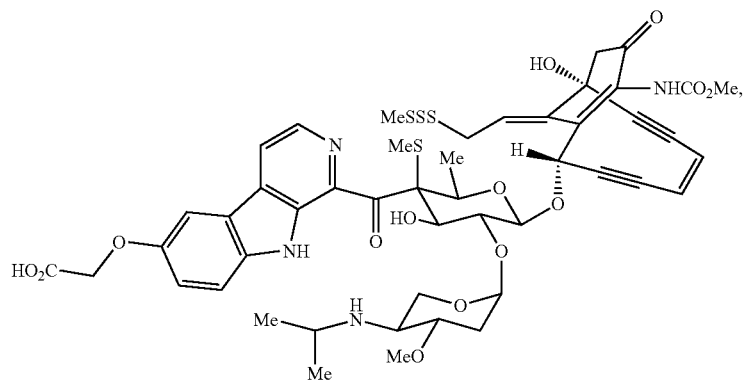

-continued
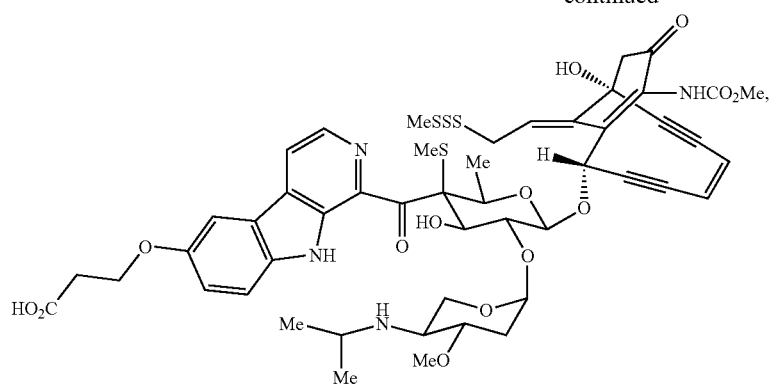
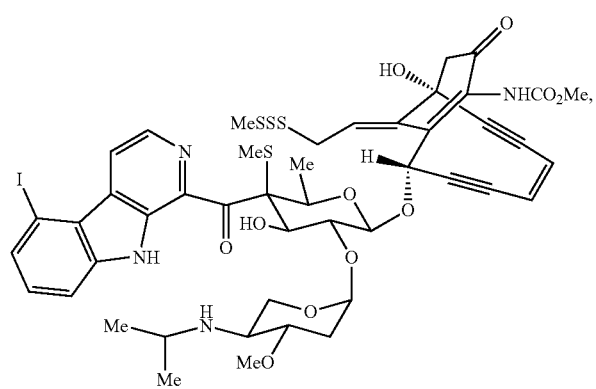
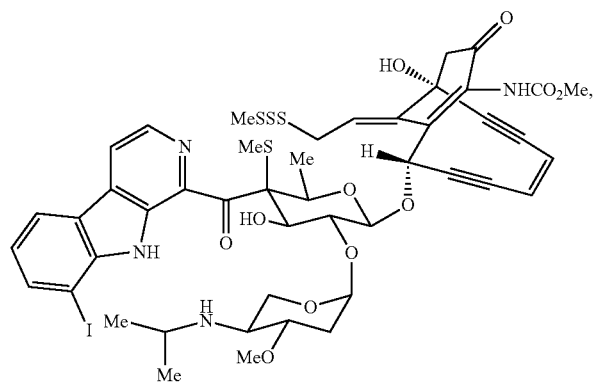
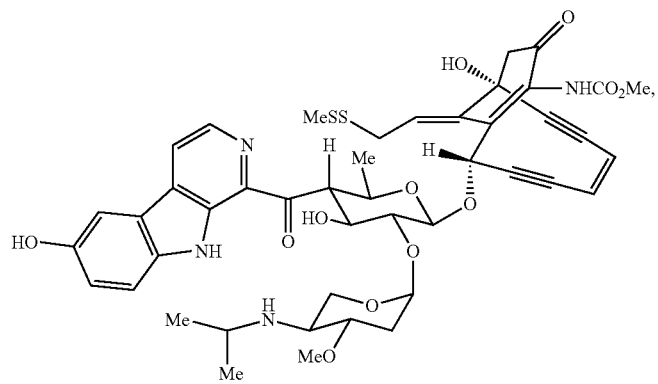

-continued
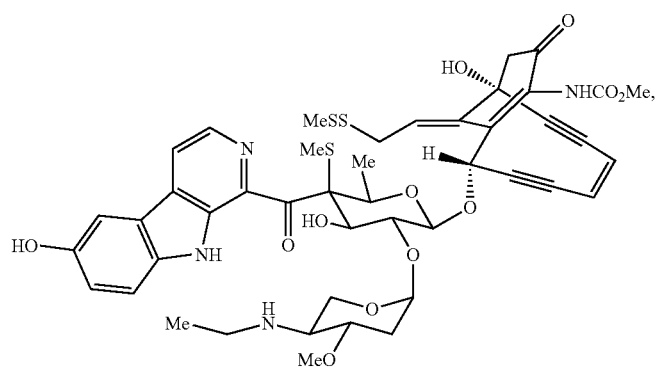
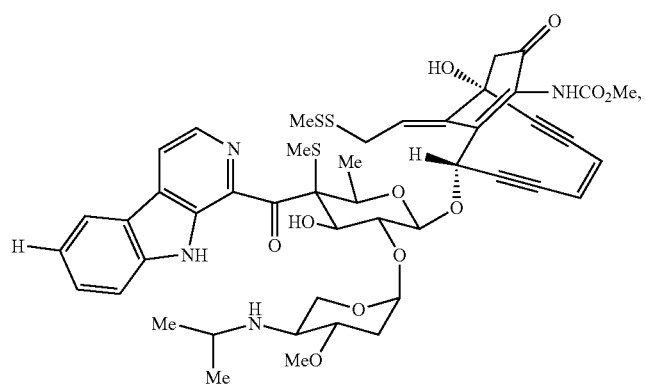
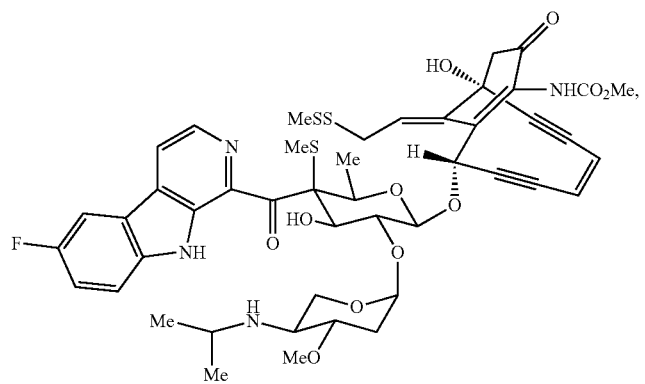
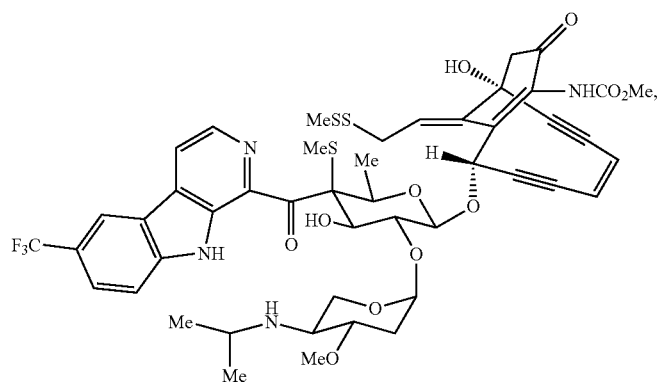

-continued
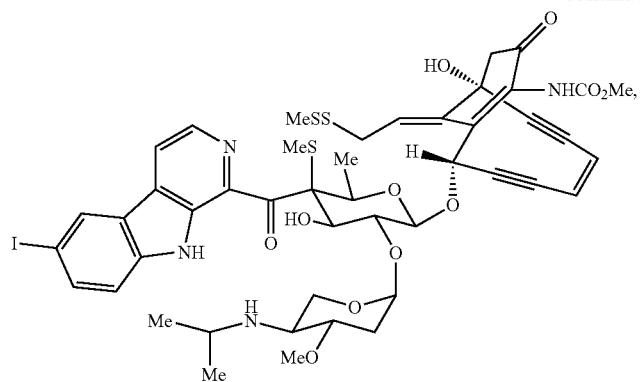
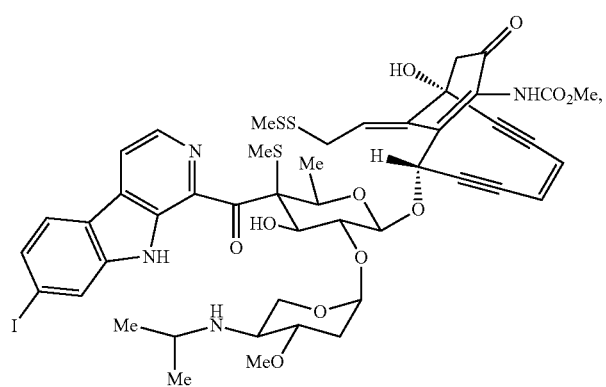
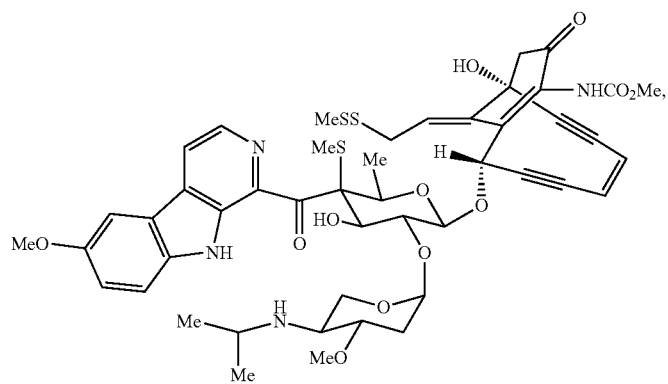
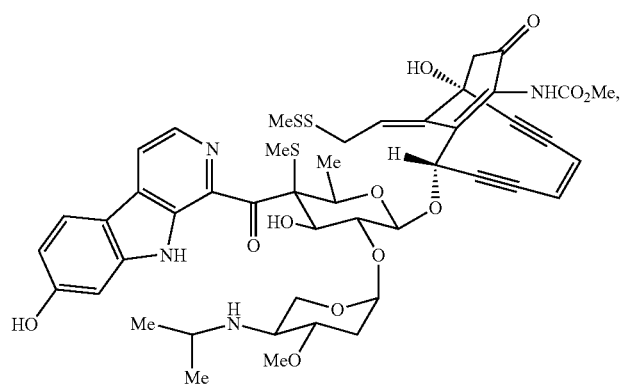

-continued
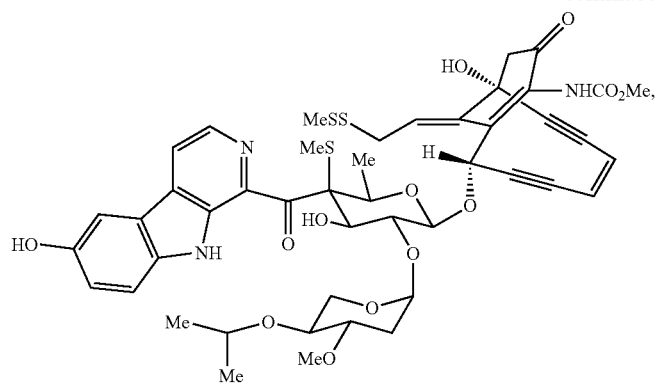
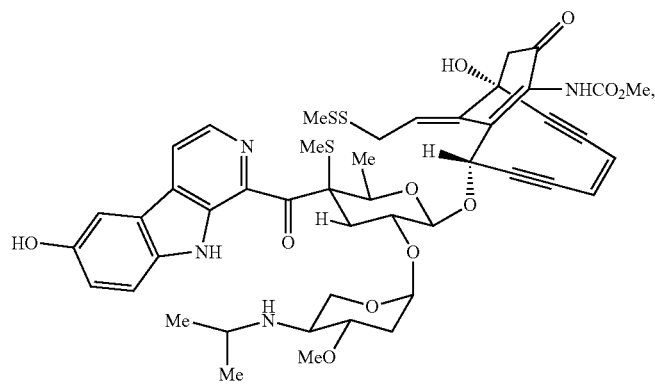
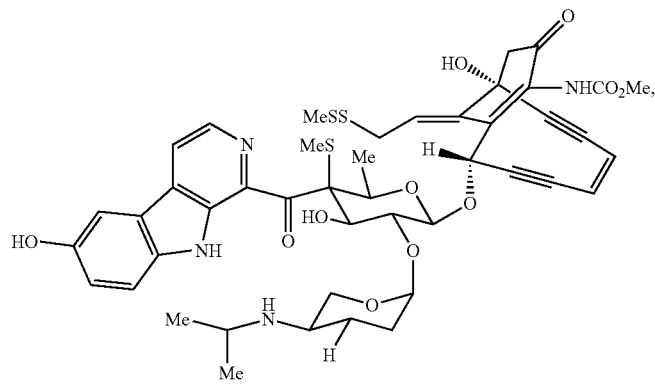
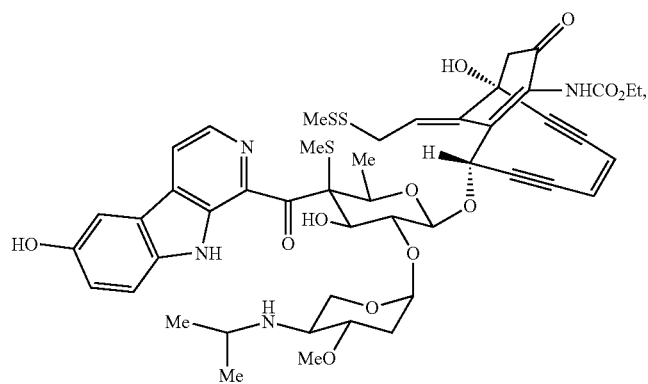

-continued
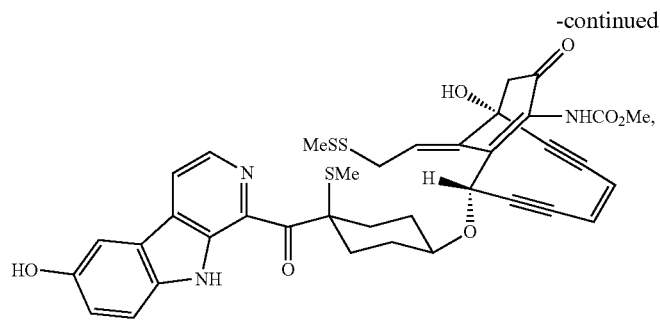
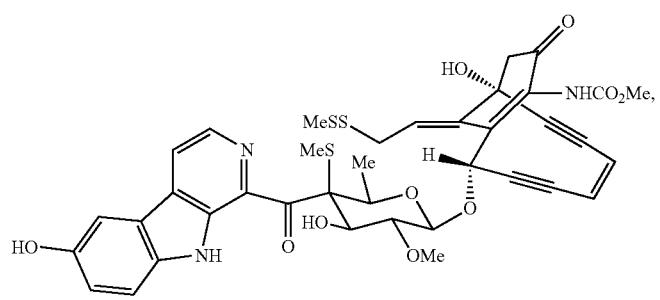
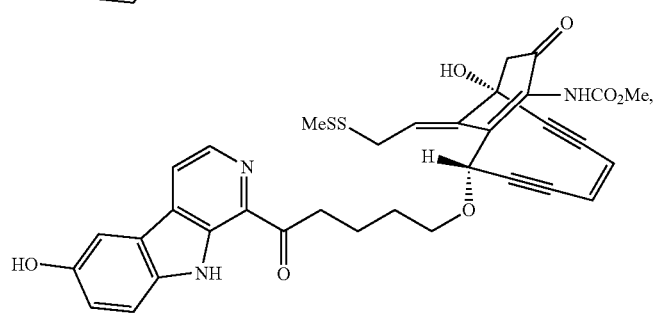
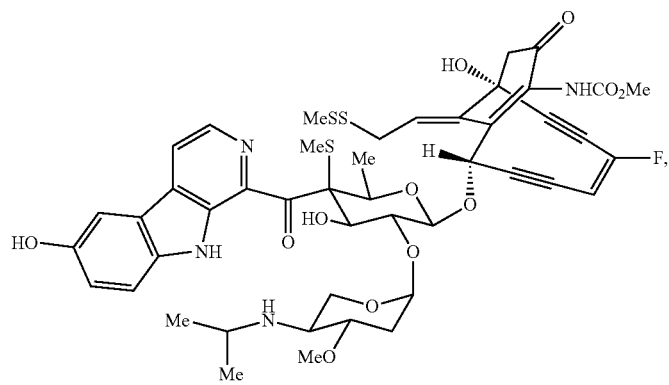
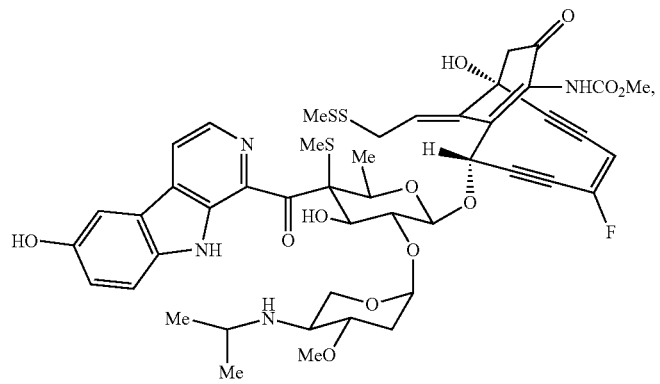

-continued
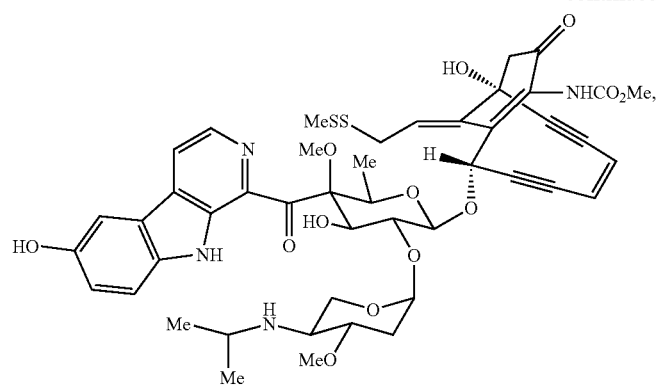
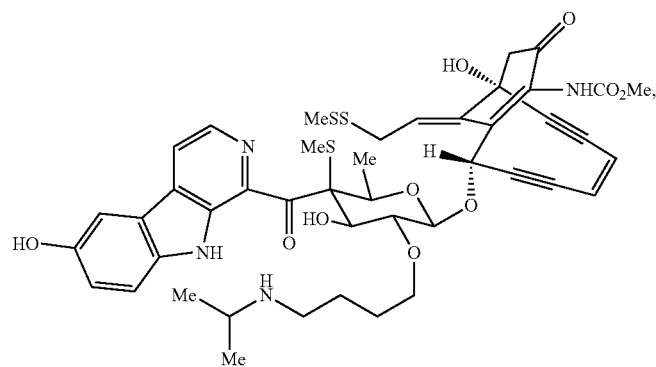
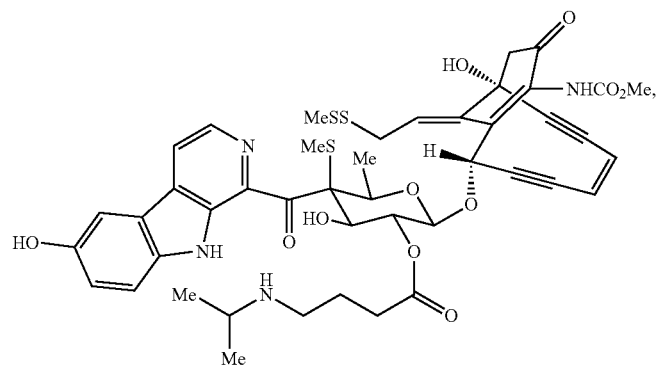
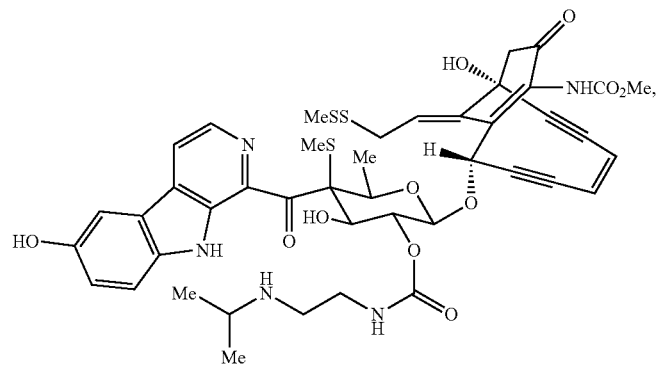

-continued
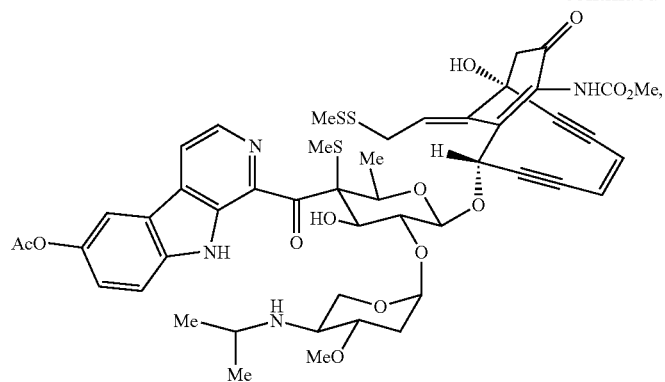
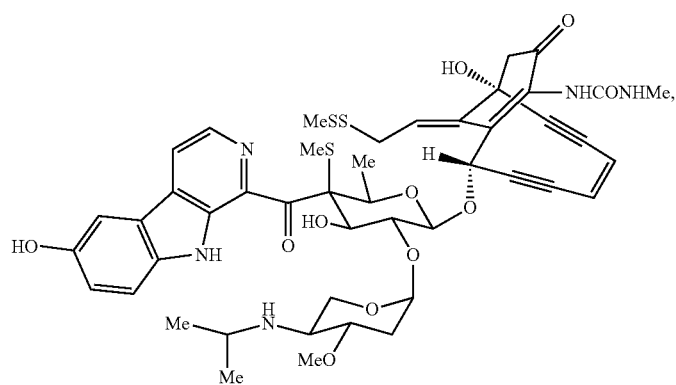
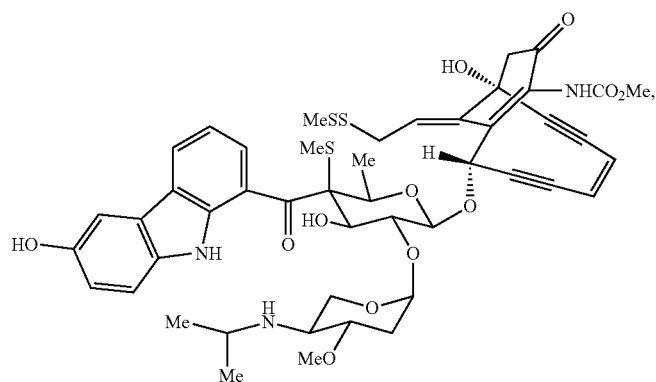
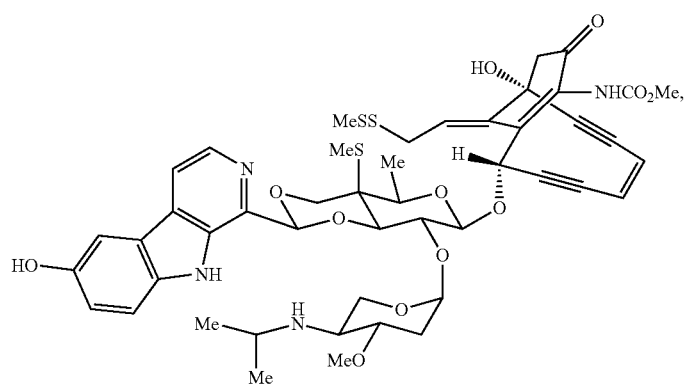

-continued
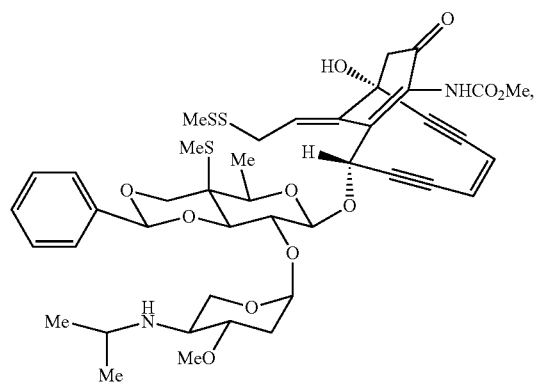
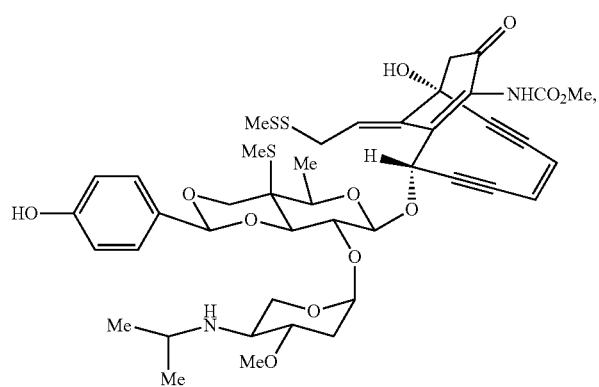
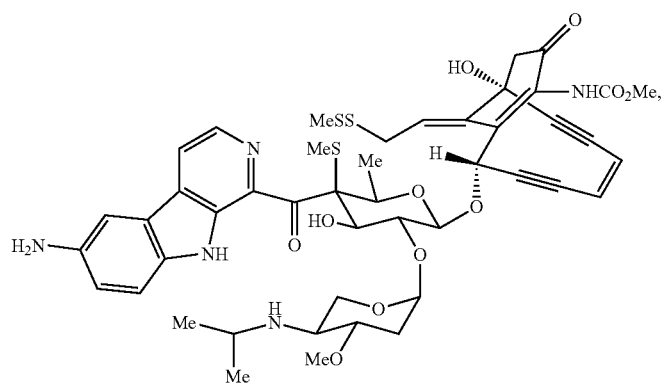
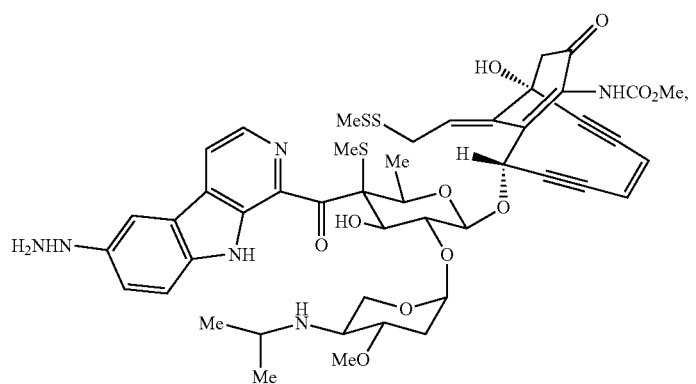

-continued
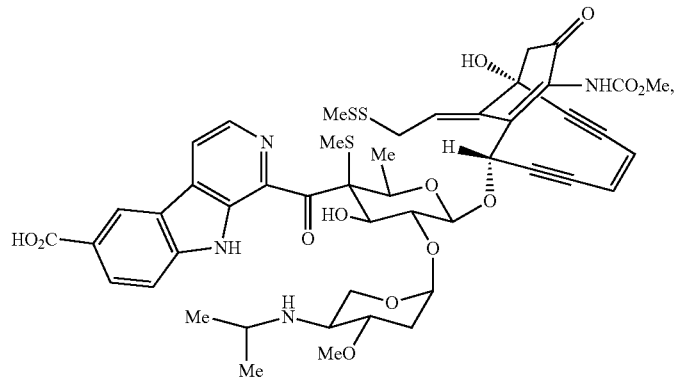
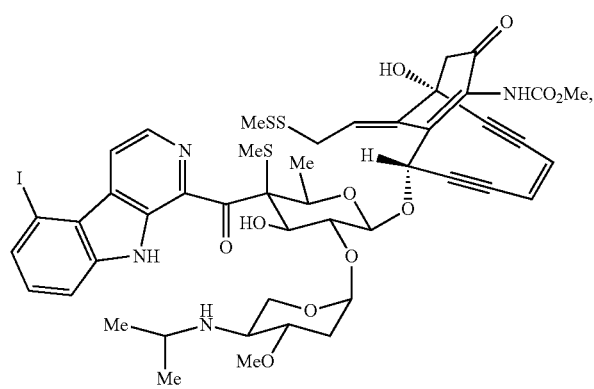
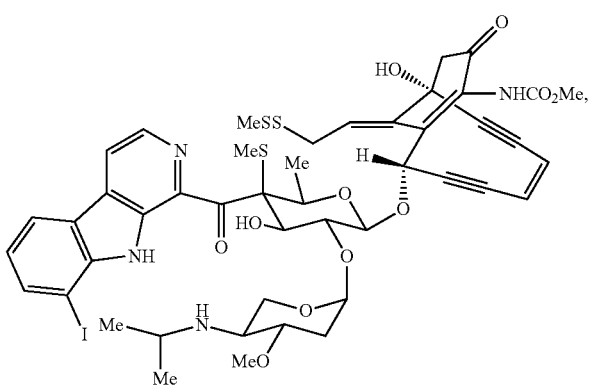
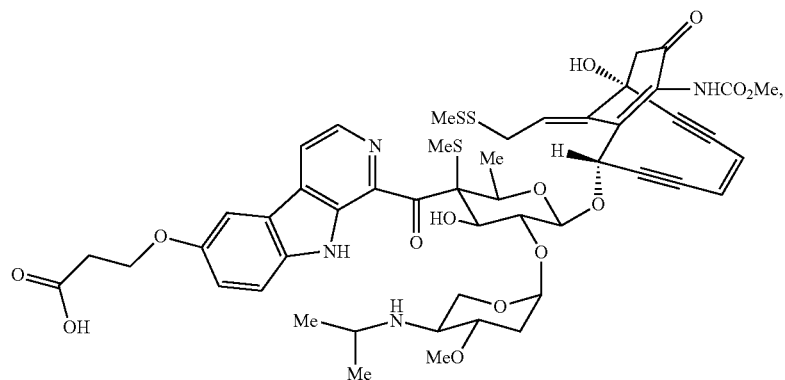
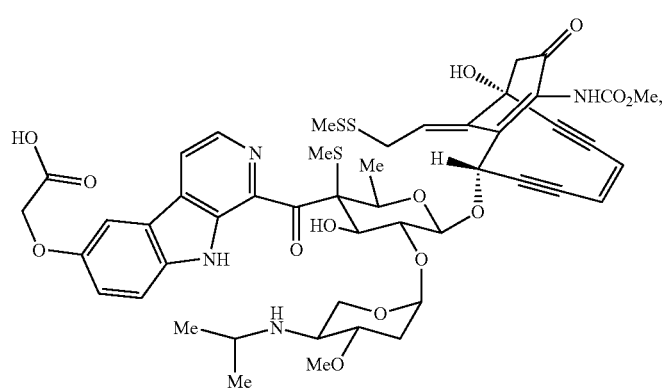

-continued
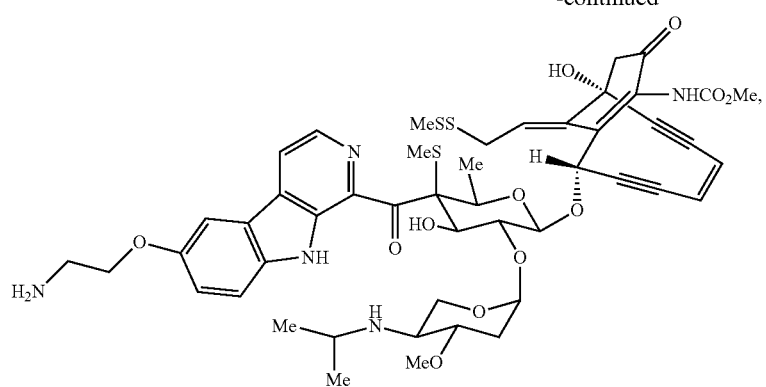
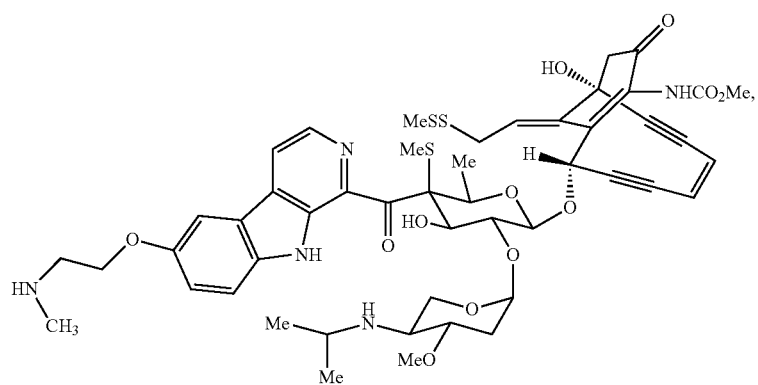
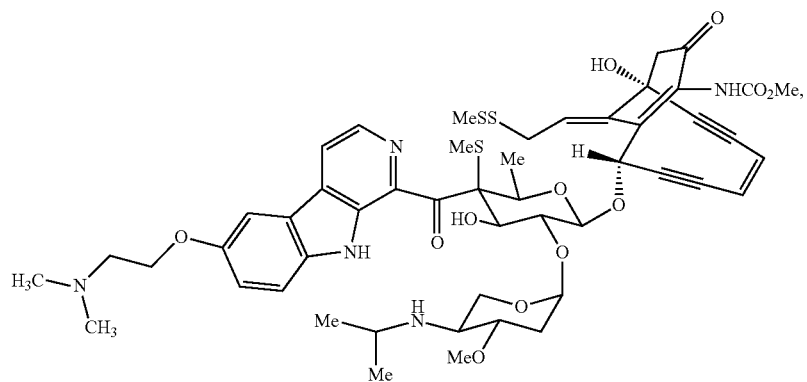
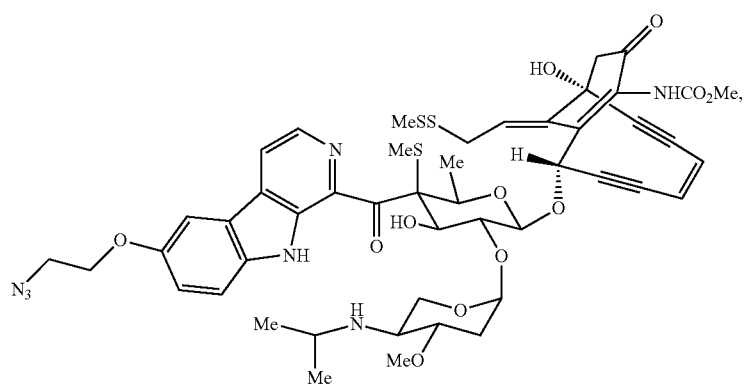

-continued
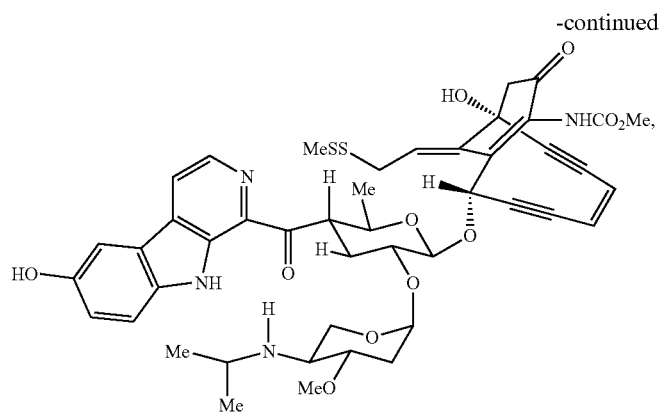
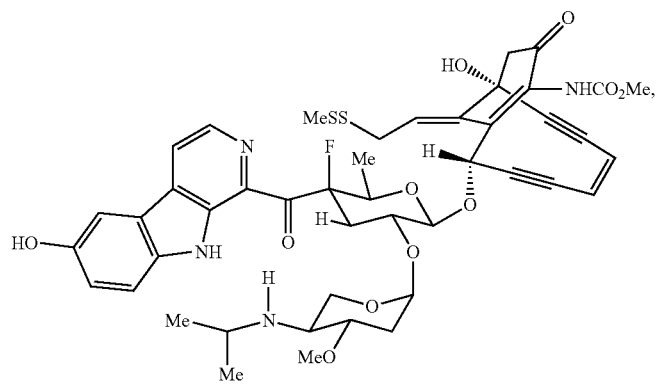
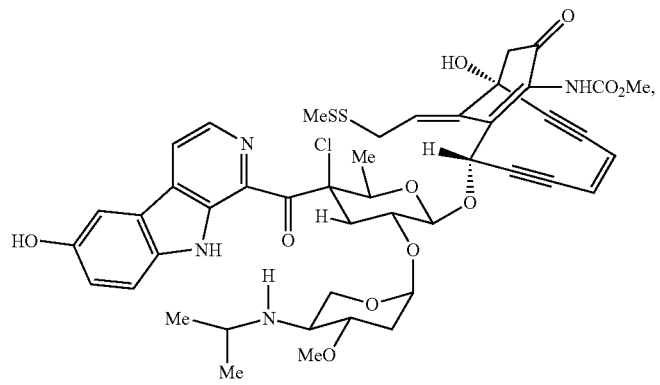
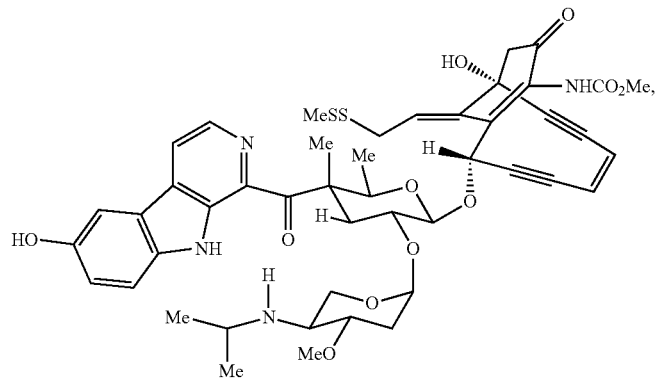

-continued
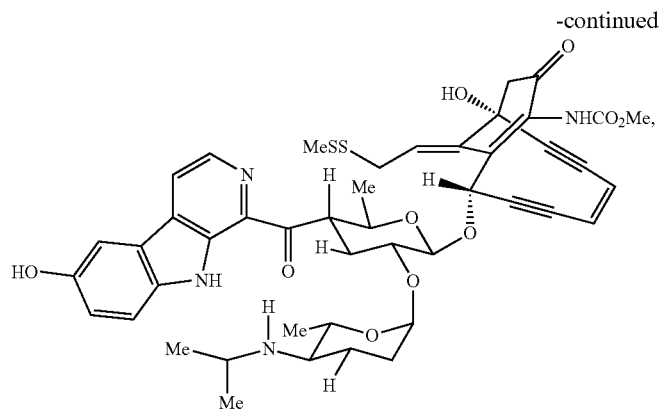
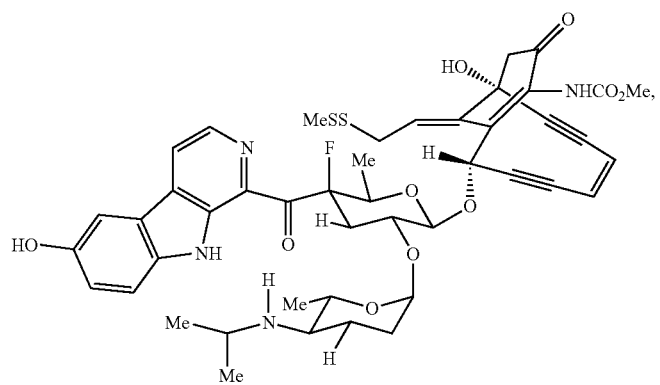
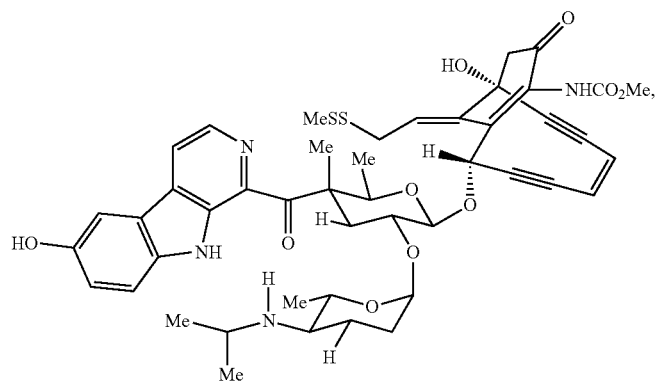
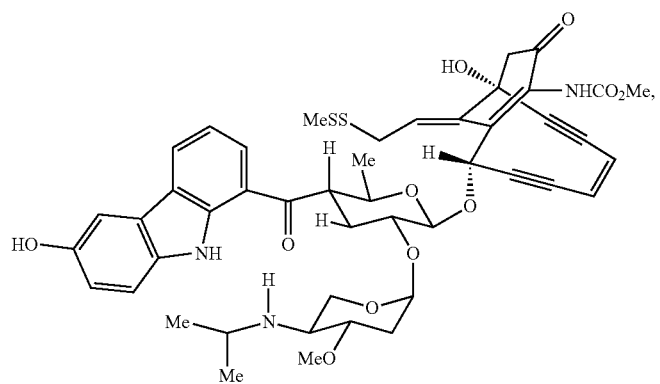

-continued
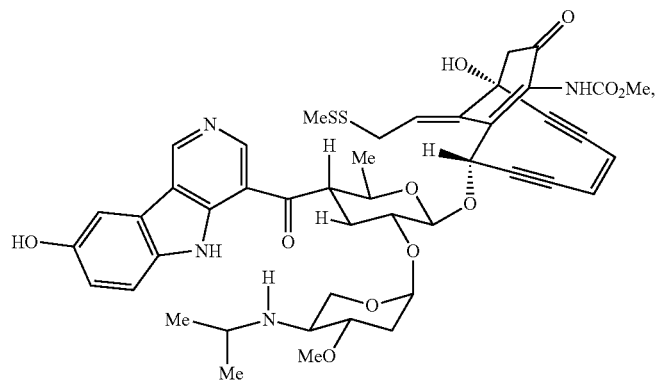
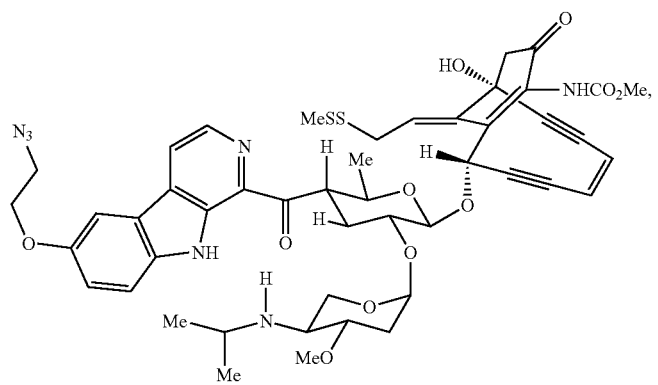
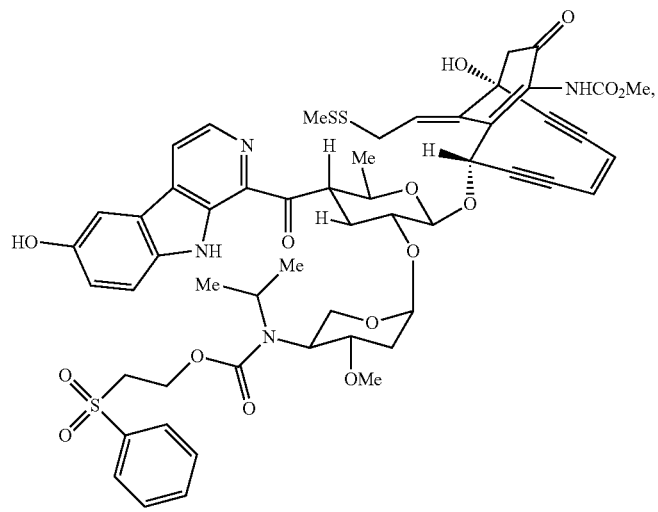
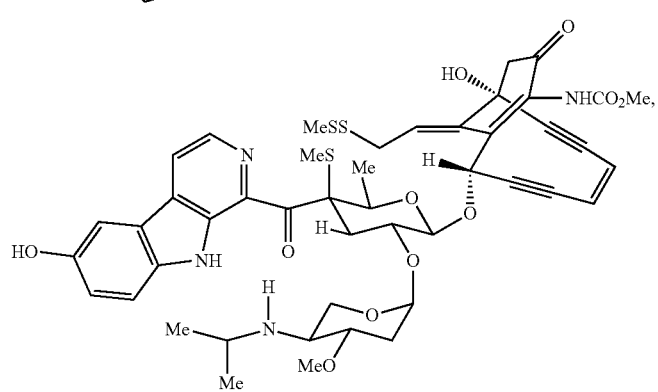

-continued
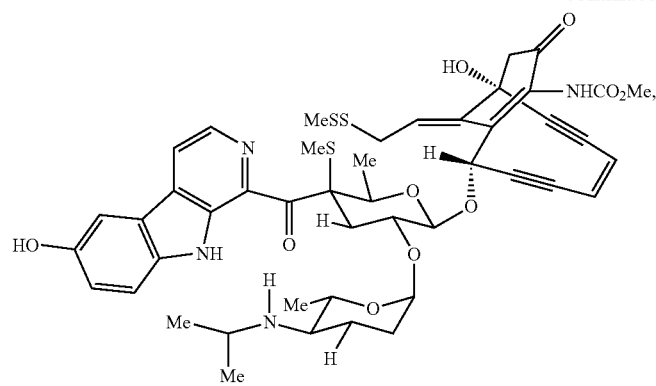
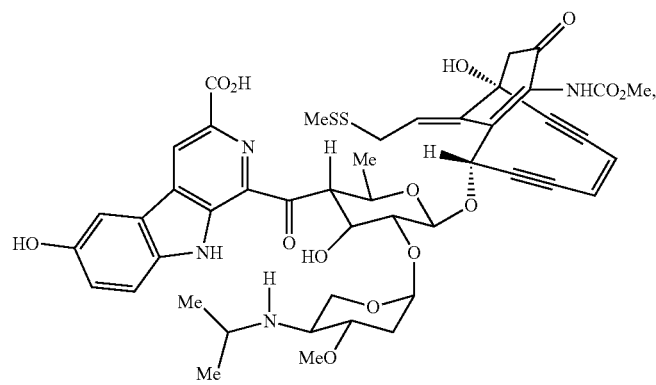
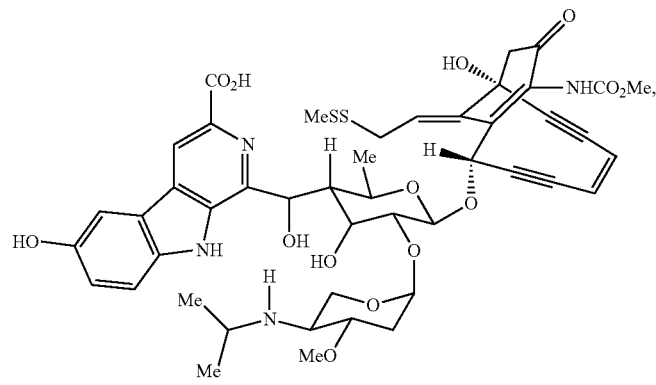
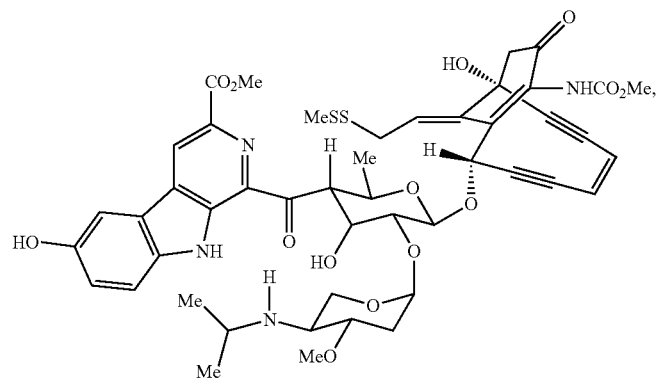

-continued
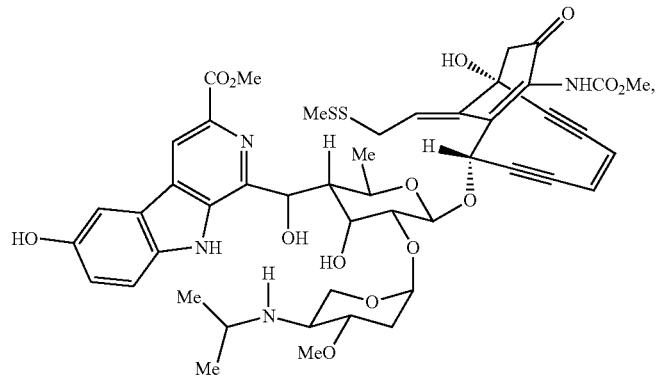
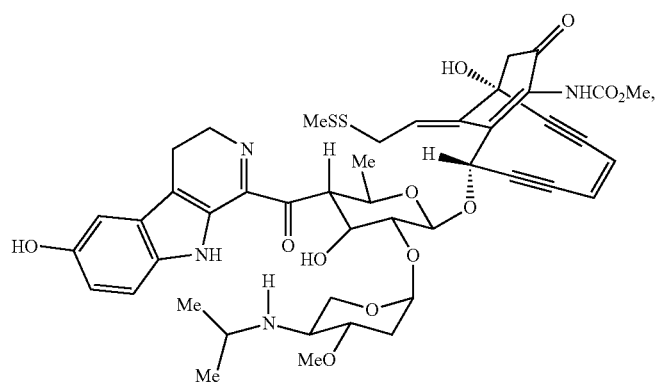
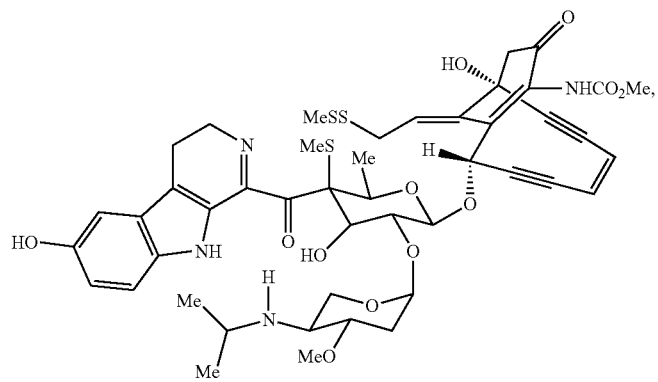
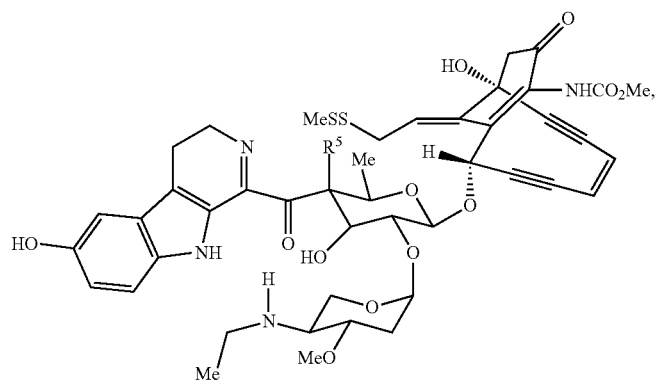

-continued
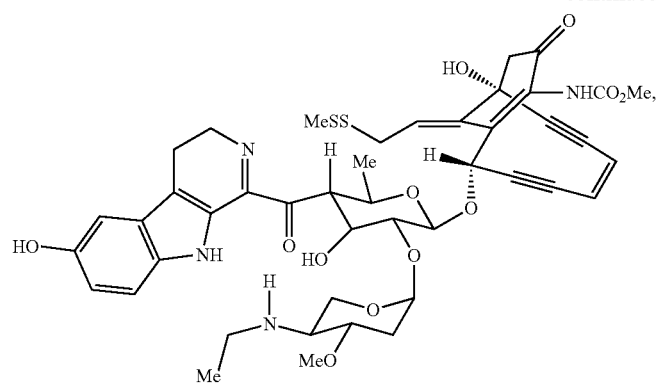
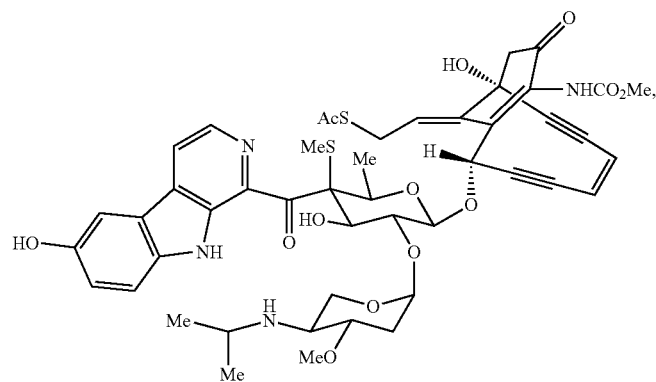
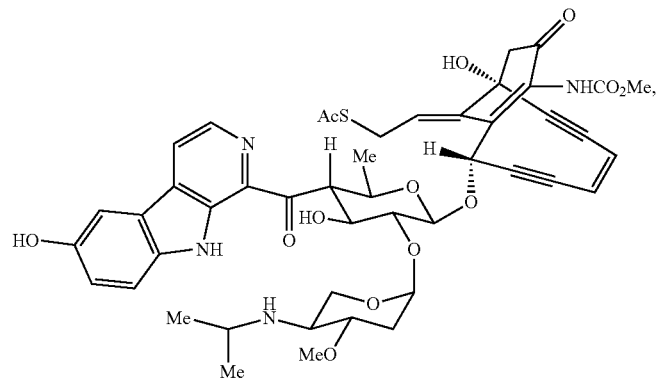
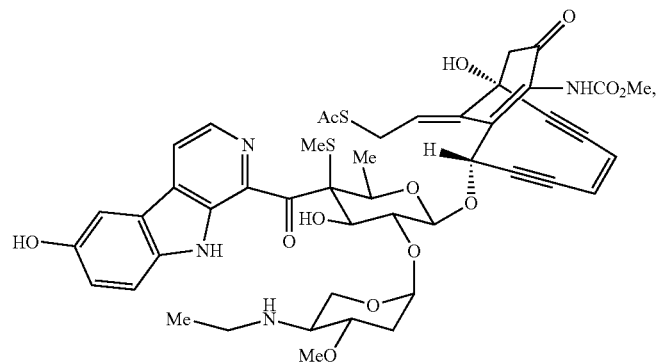

-continued
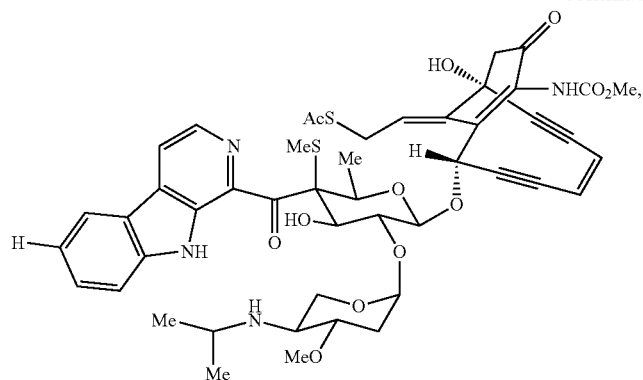
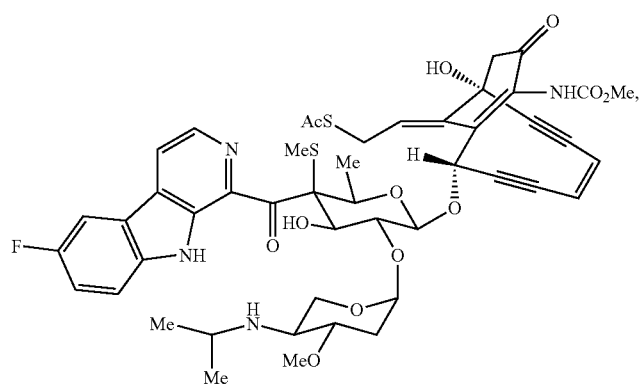
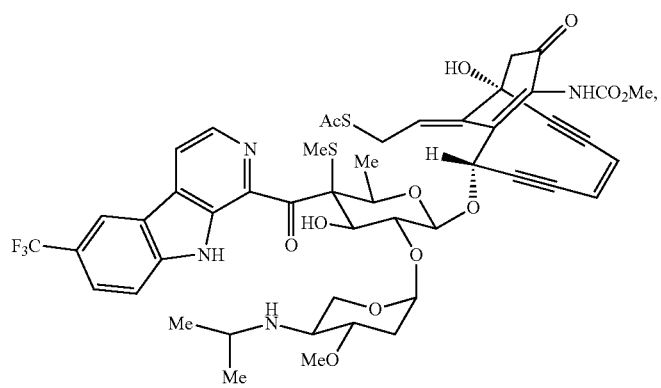
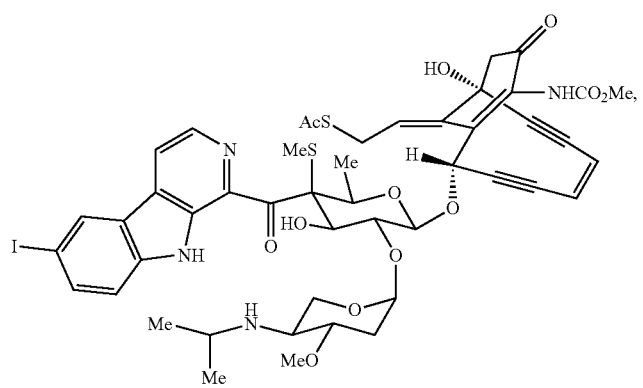

-continued
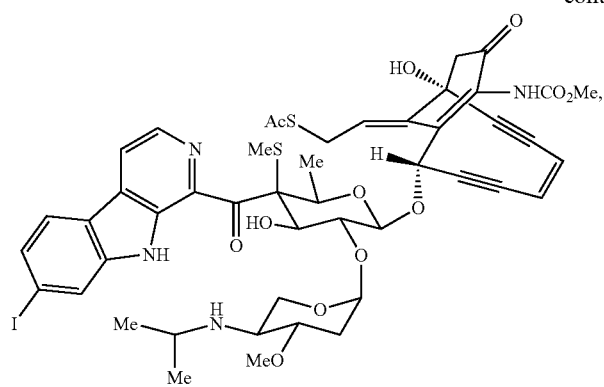
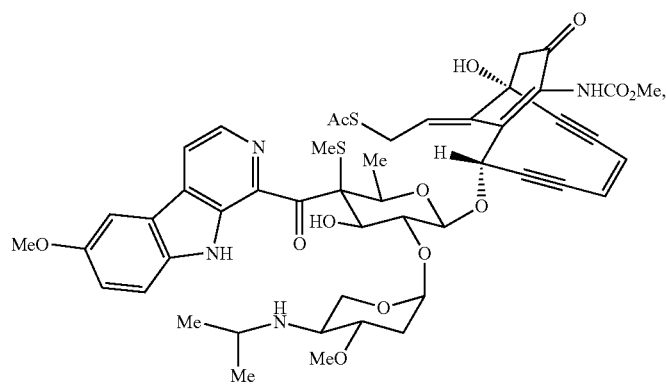
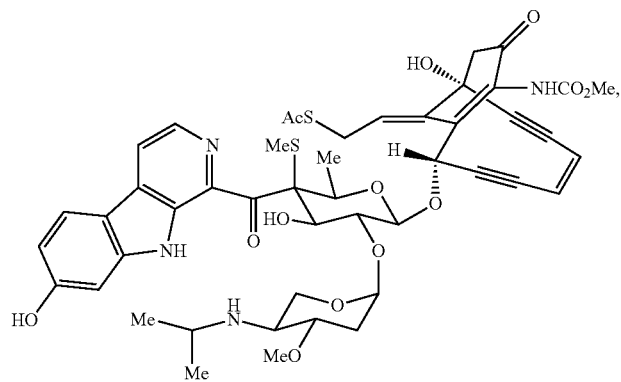
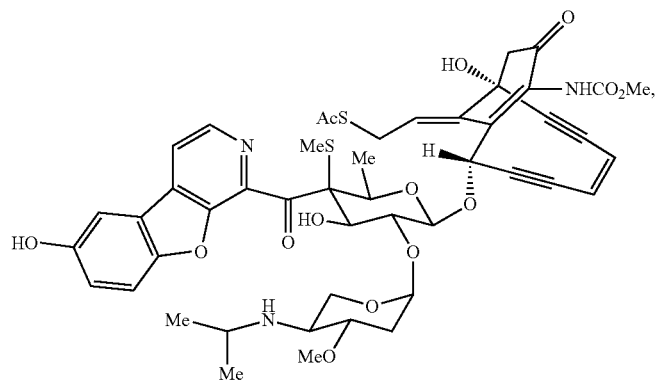

-continued
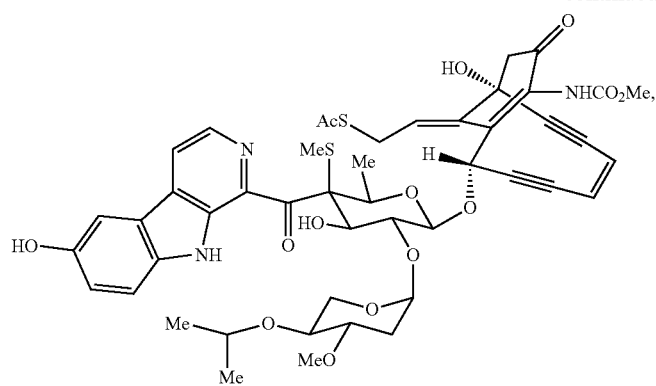
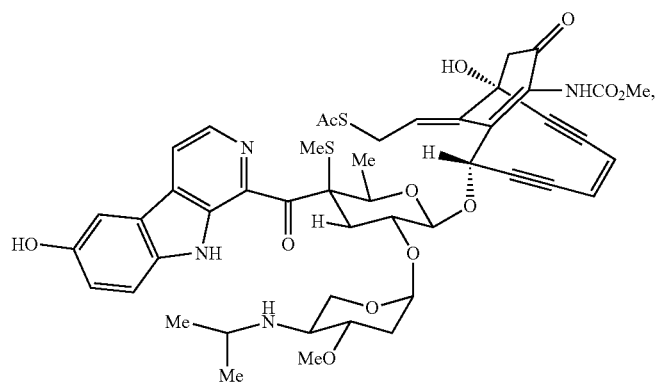
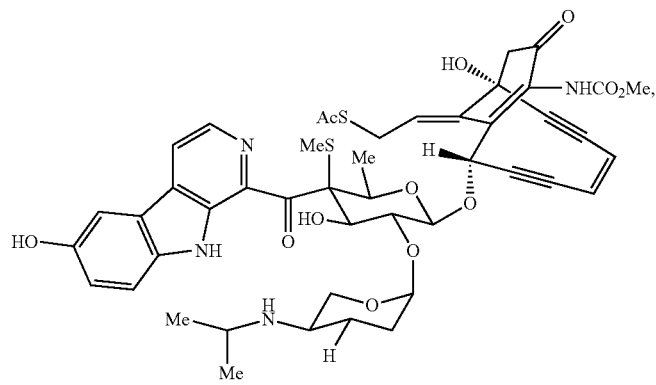
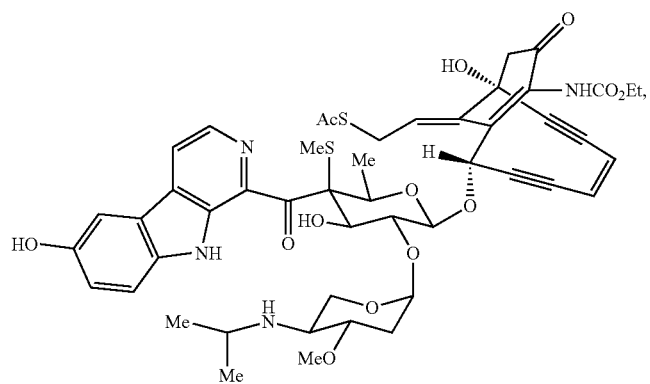

-continued
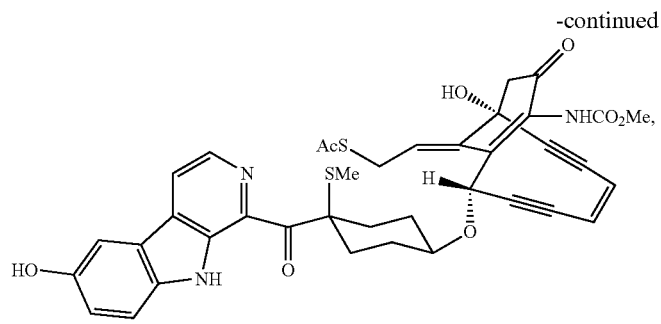
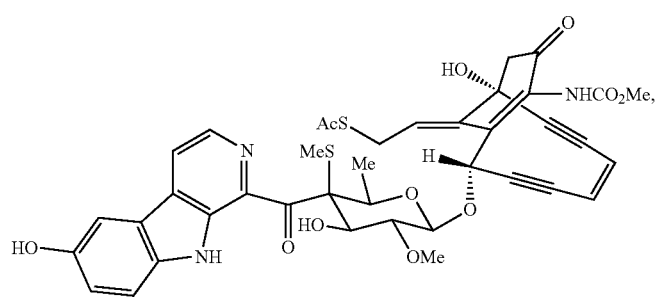
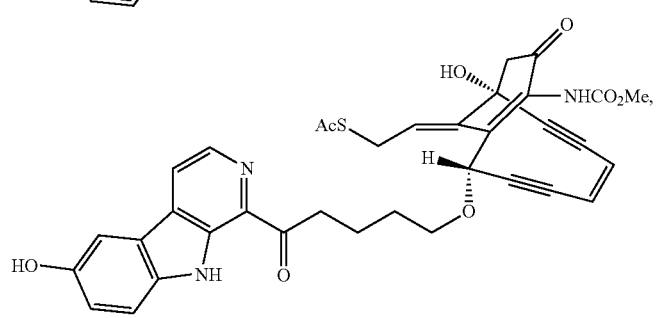
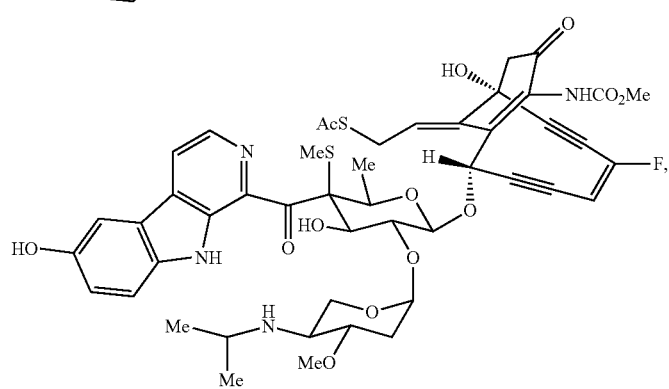
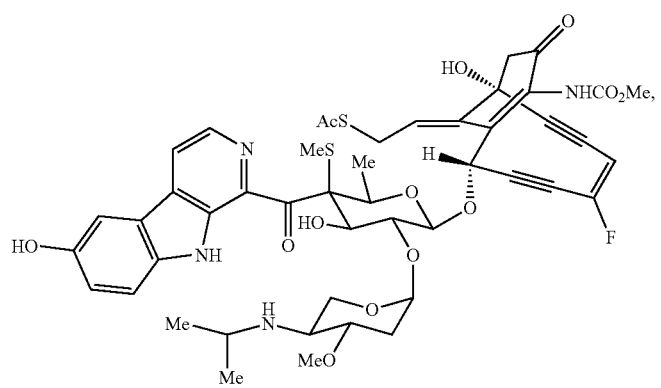

-continued
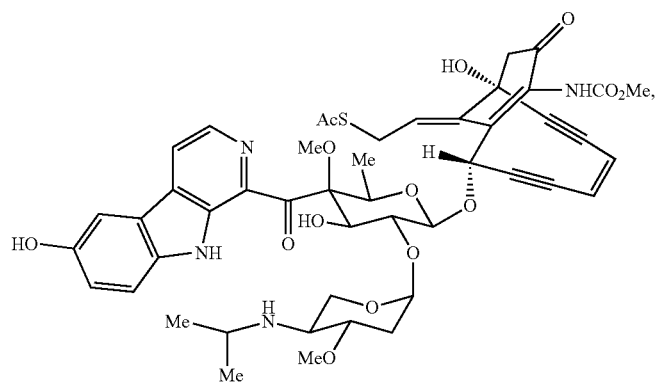
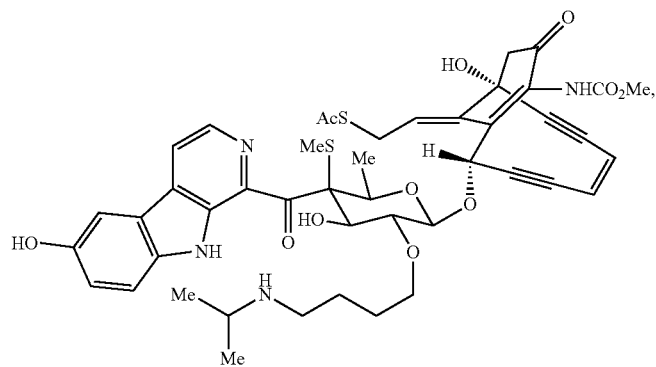
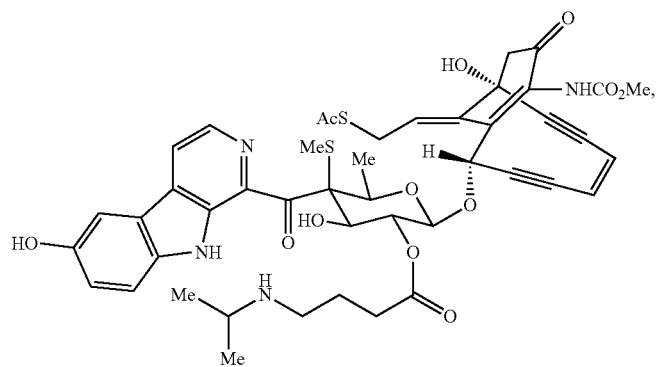
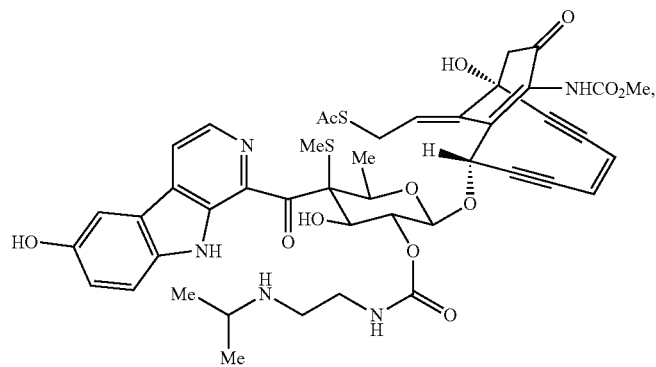

-continued
267
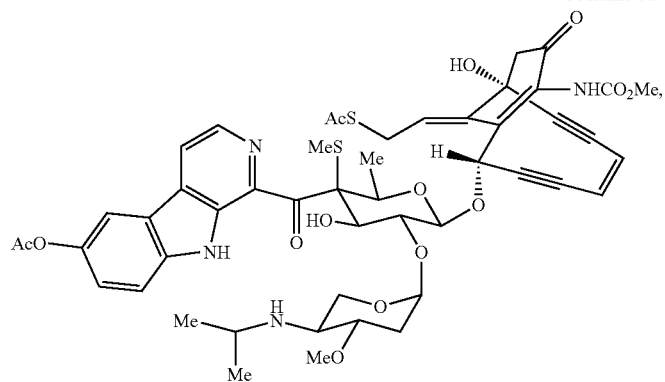
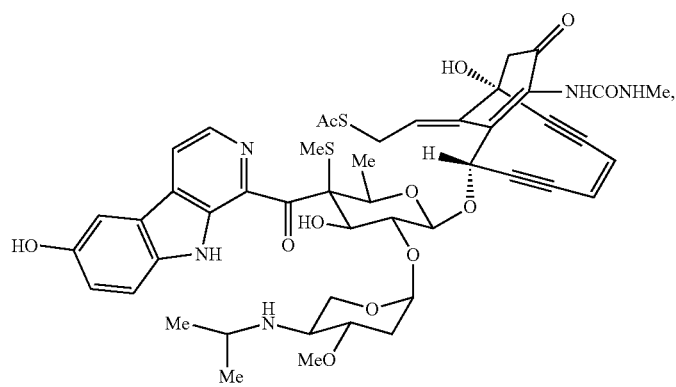
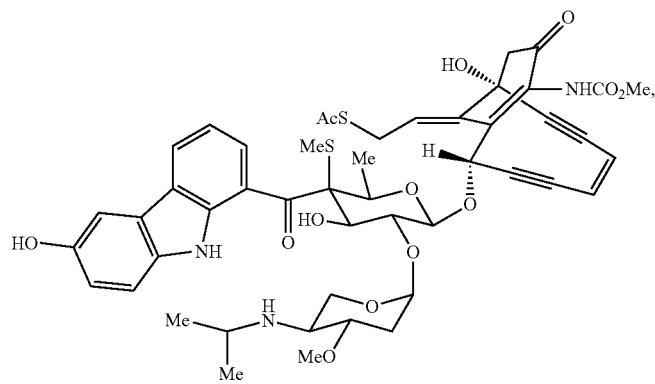
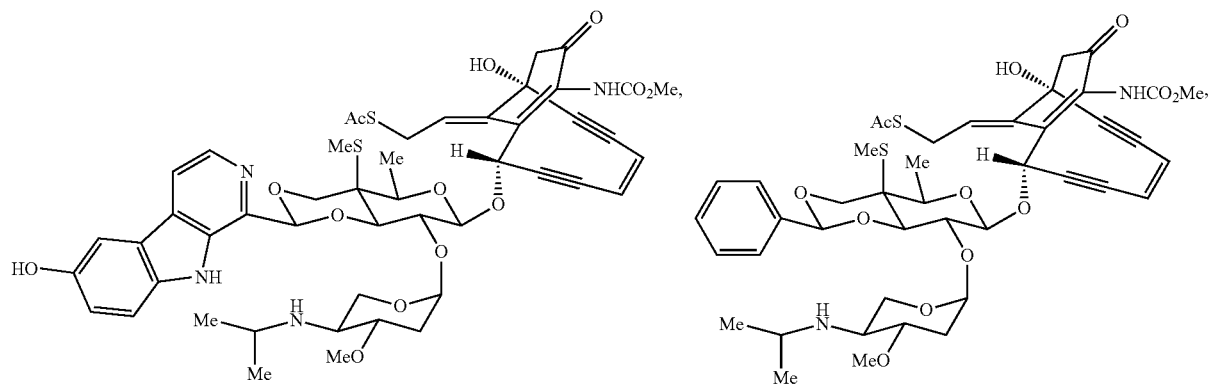
268

-continued
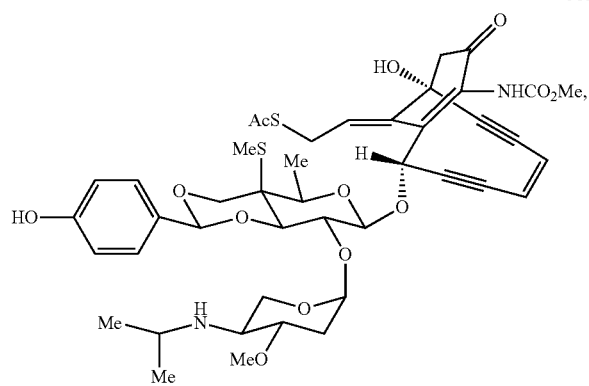
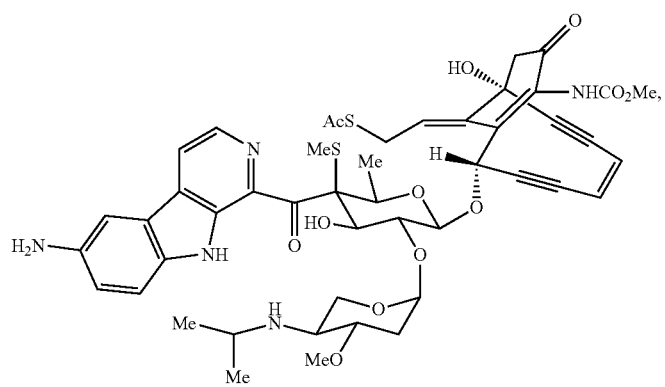
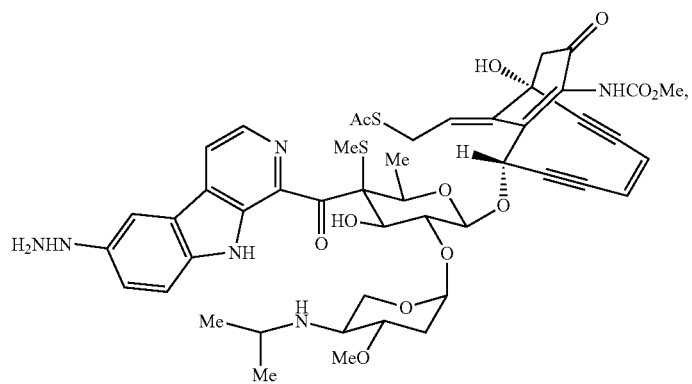
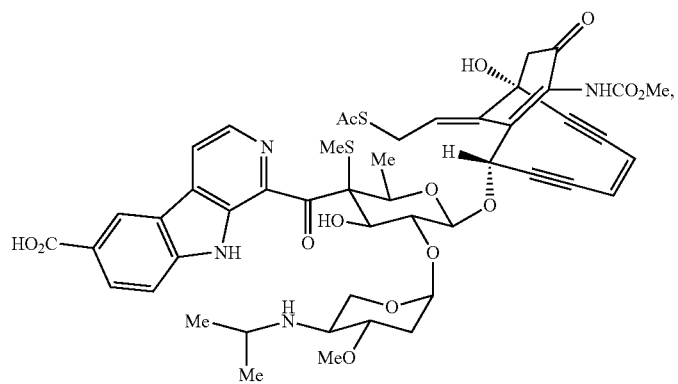

-continued
| 271 | 272 |
|---|---|
| 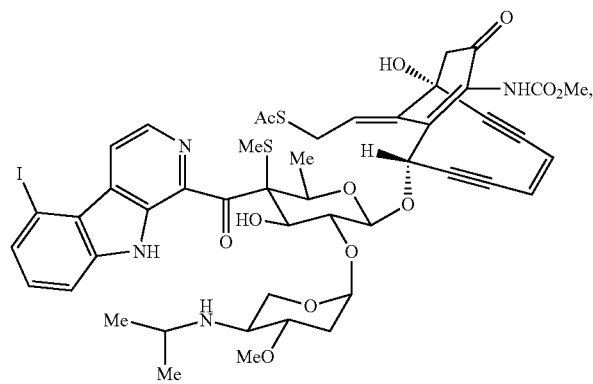 | 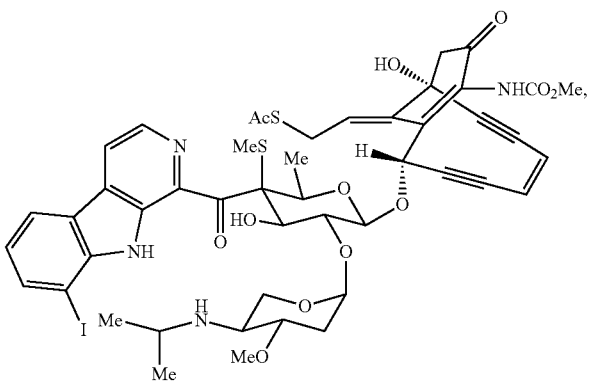 |
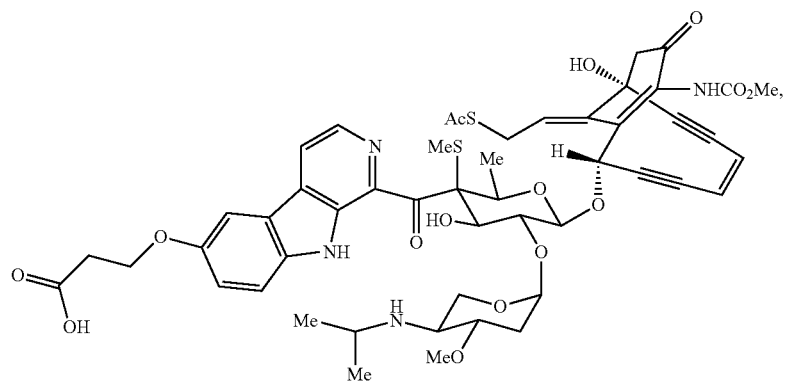
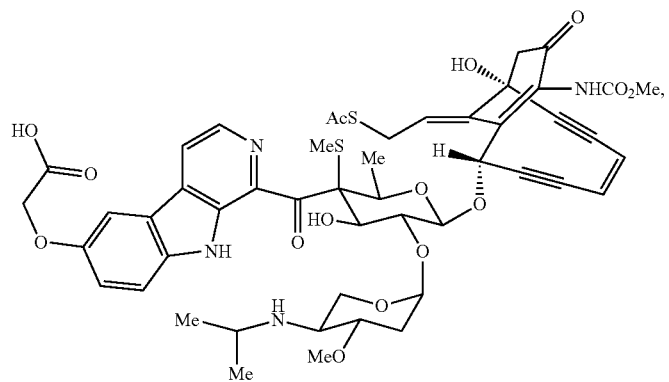
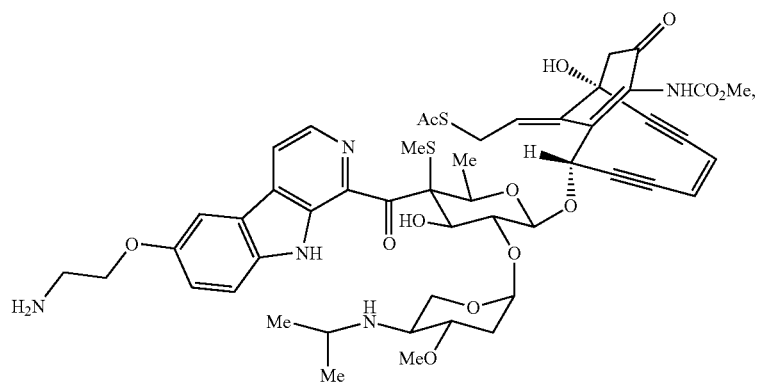

-continued
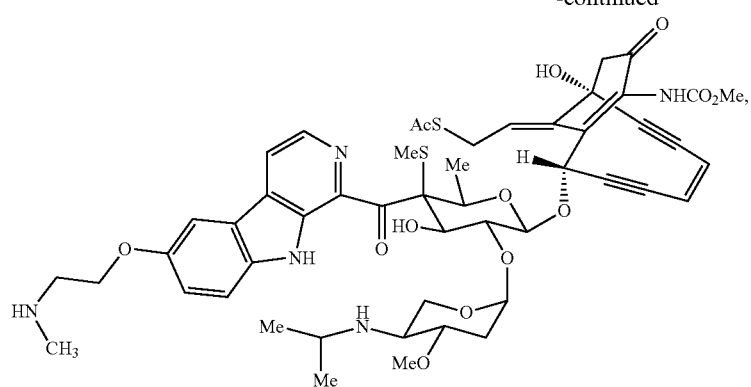
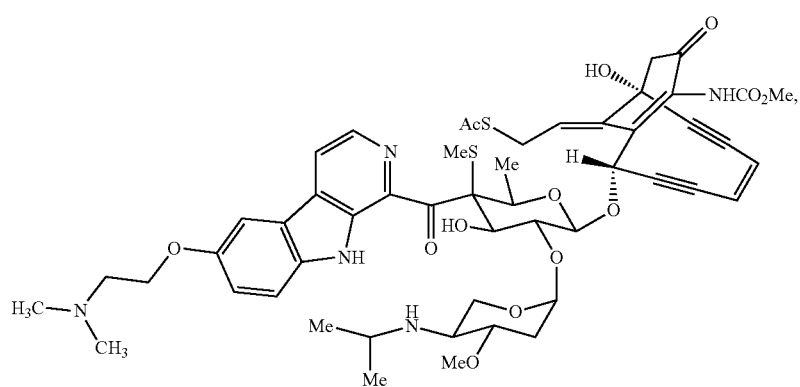
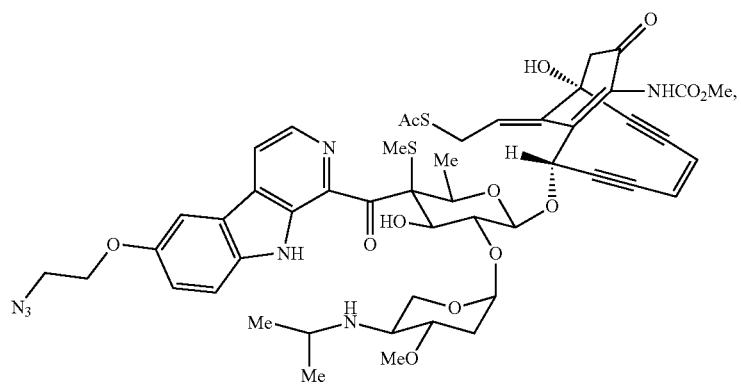
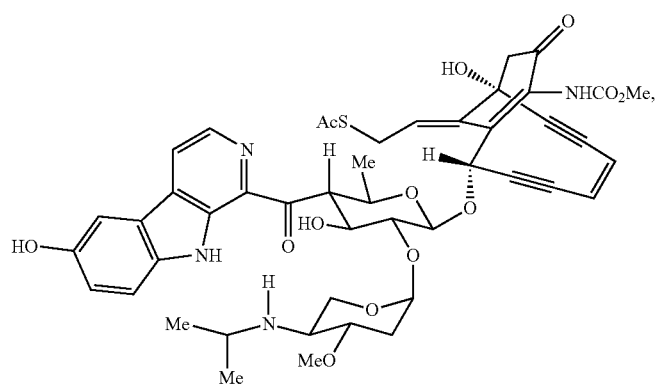

-continued
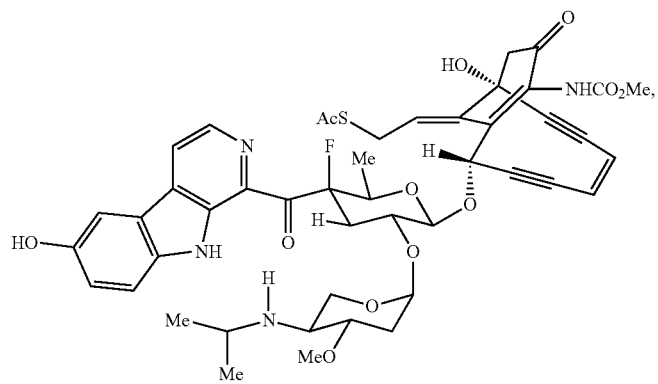
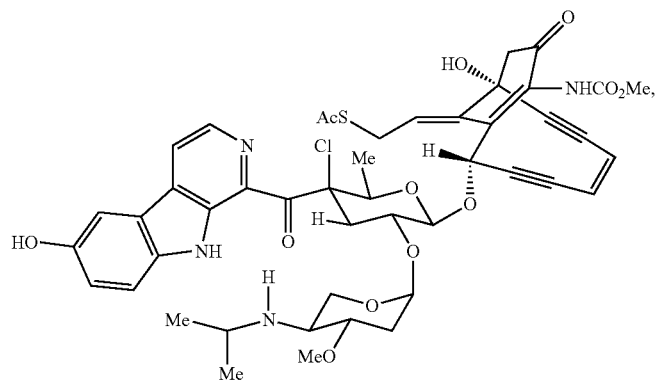
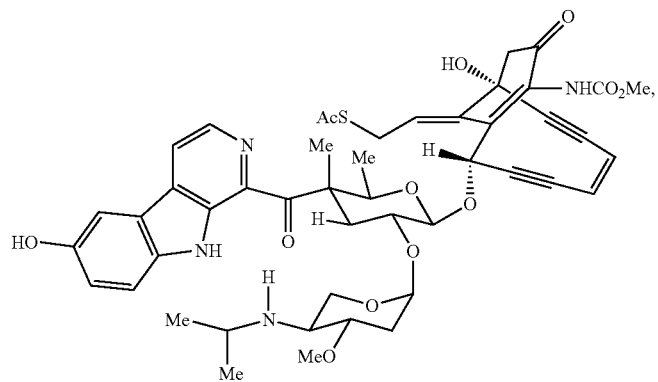
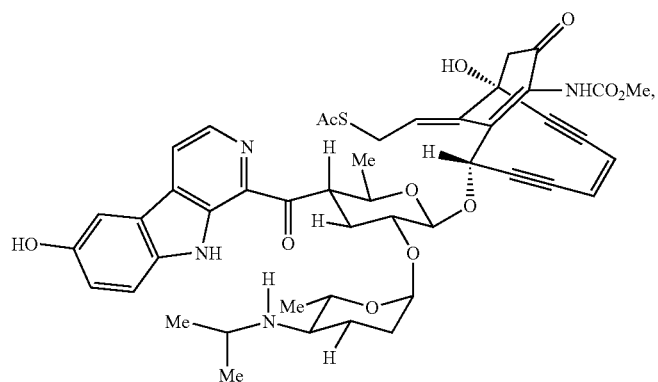

-continued
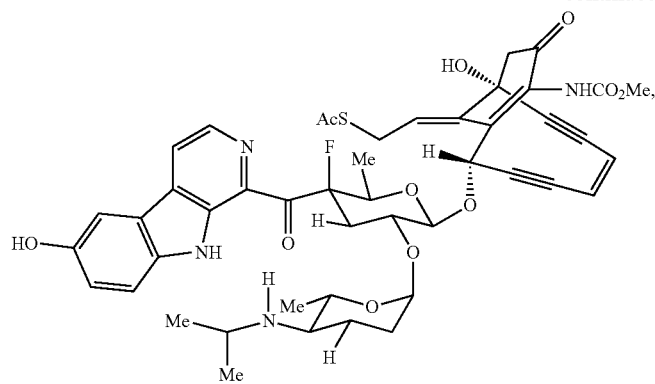
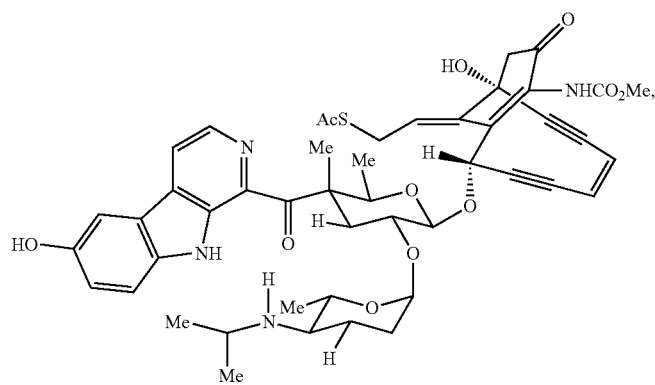
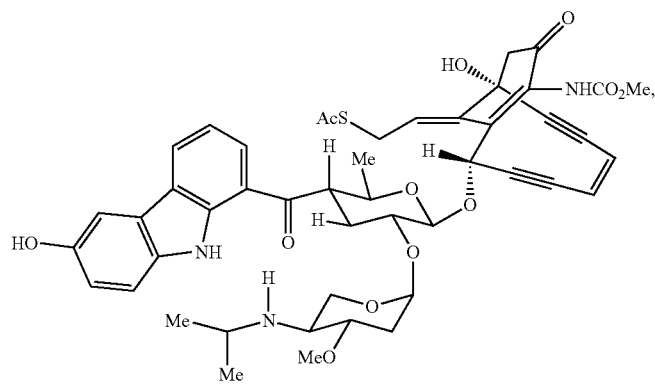
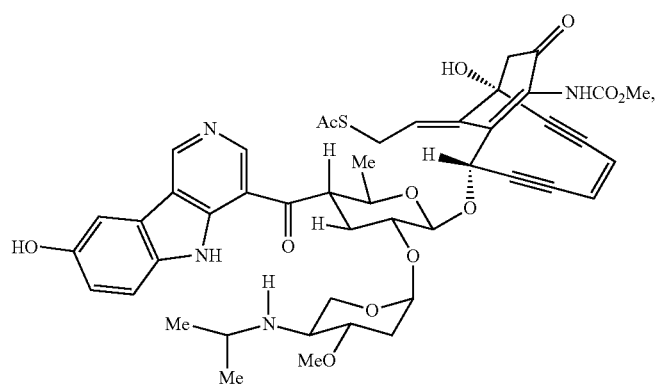

-continued
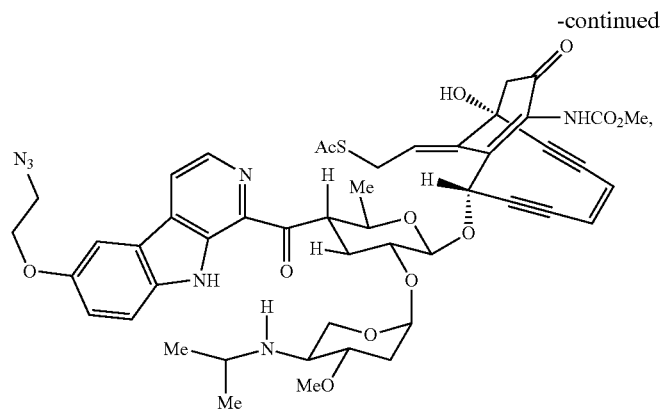
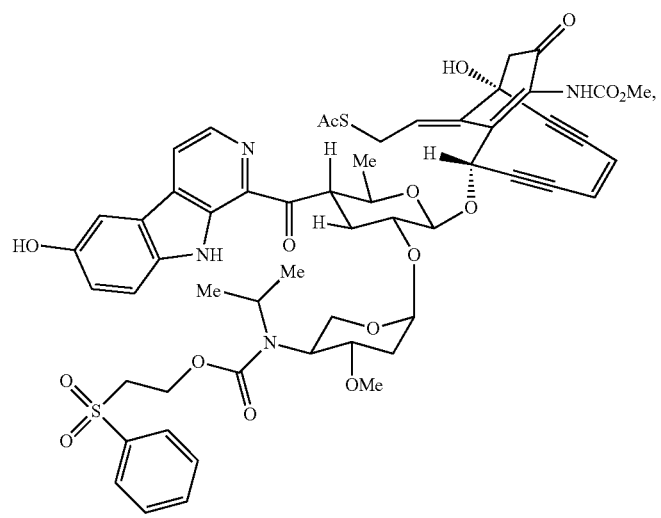
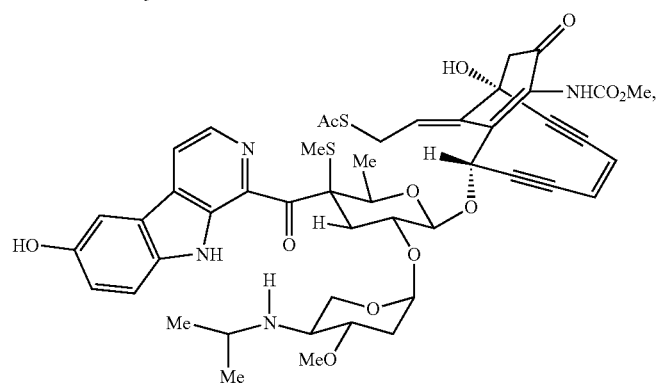
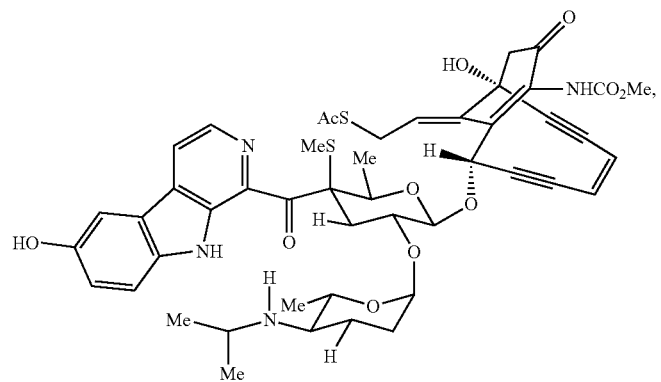

-continued
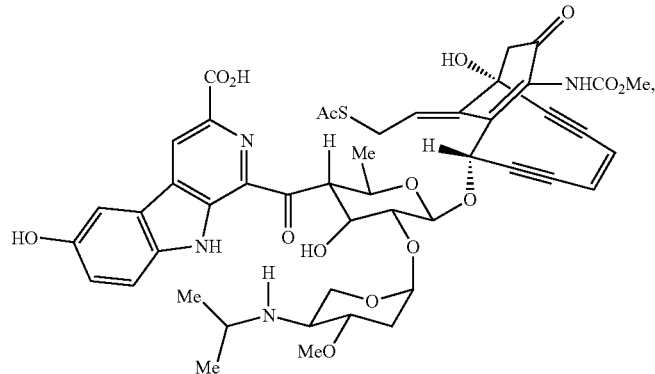
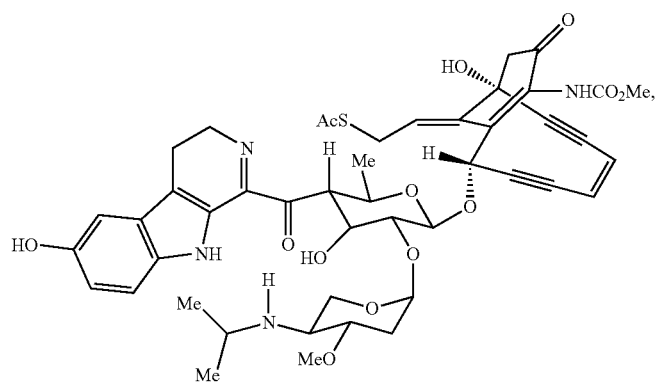
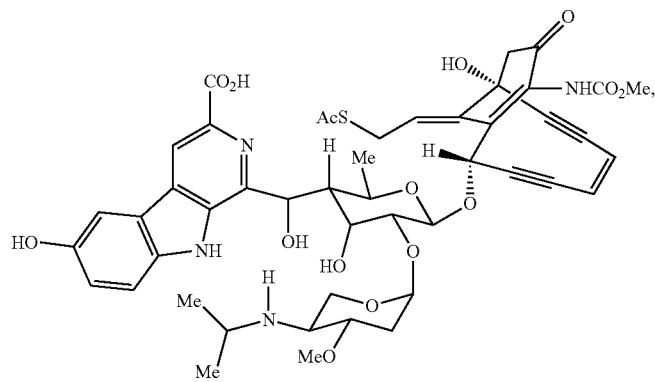
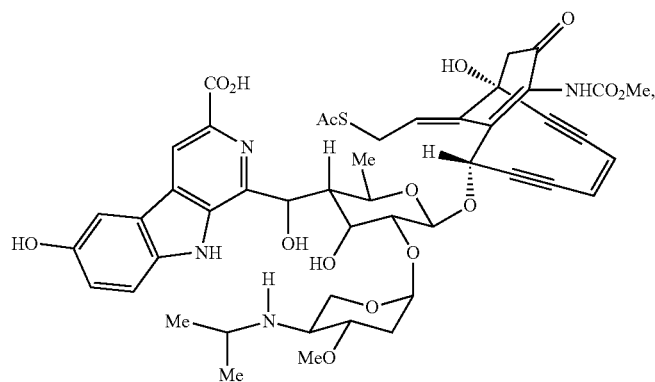

-continued
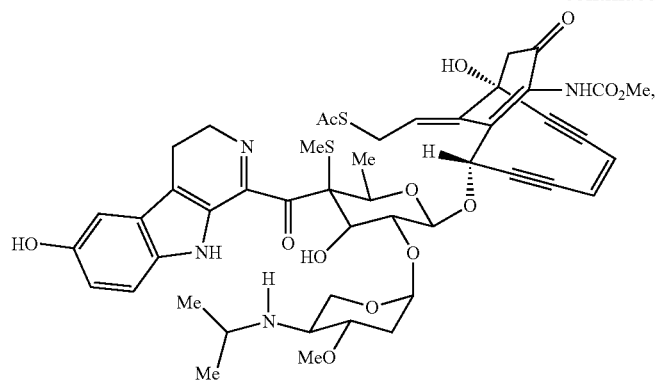
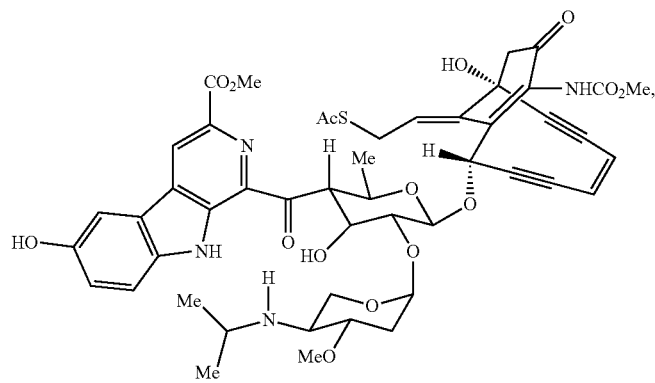
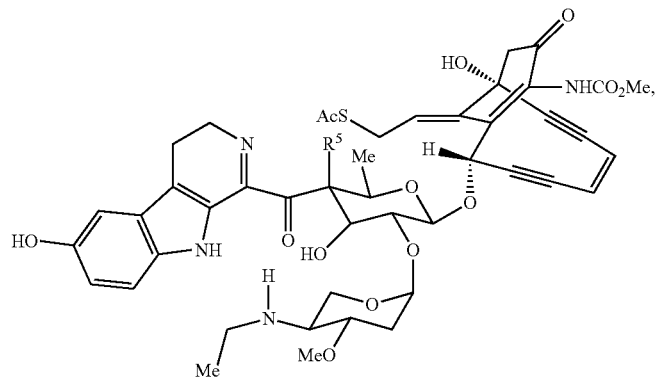
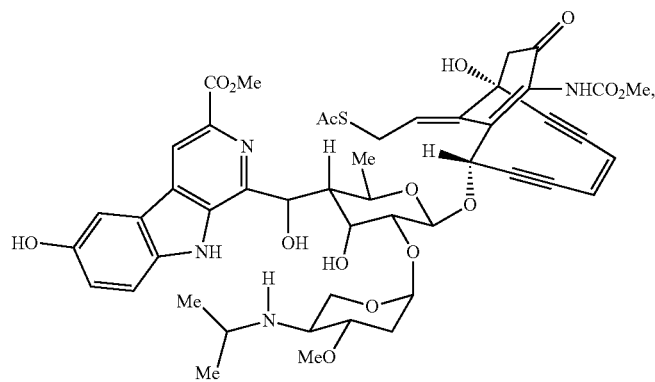

-continued
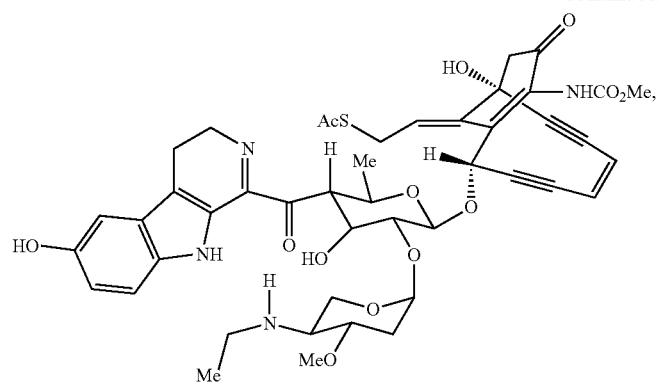
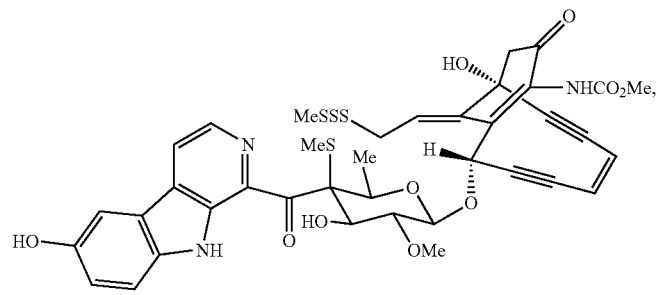
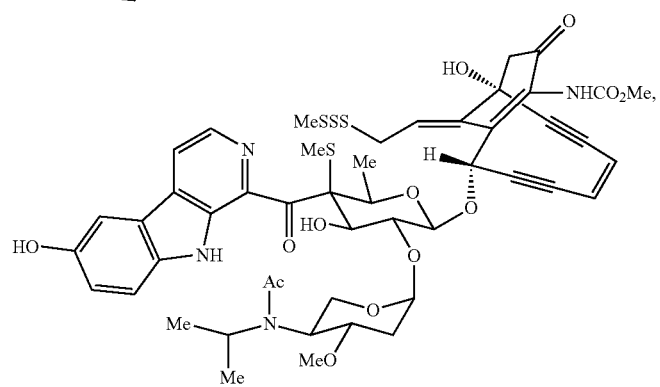
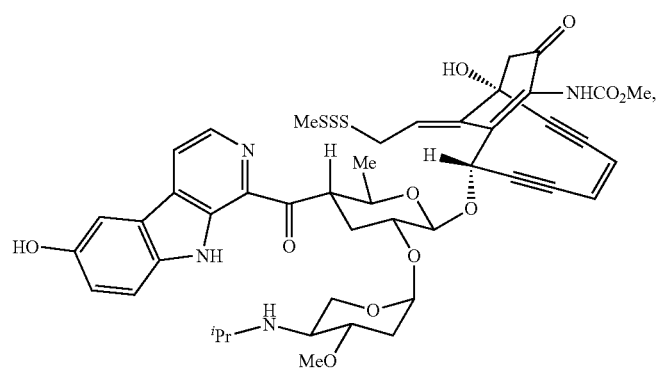
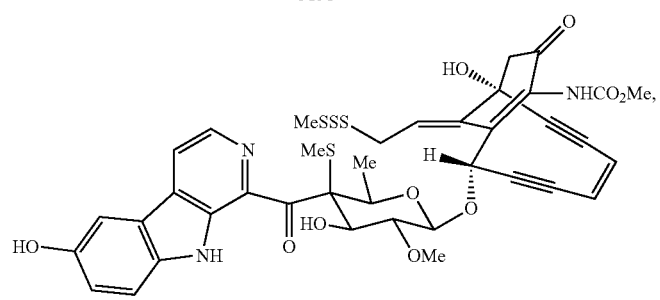

-continued
287
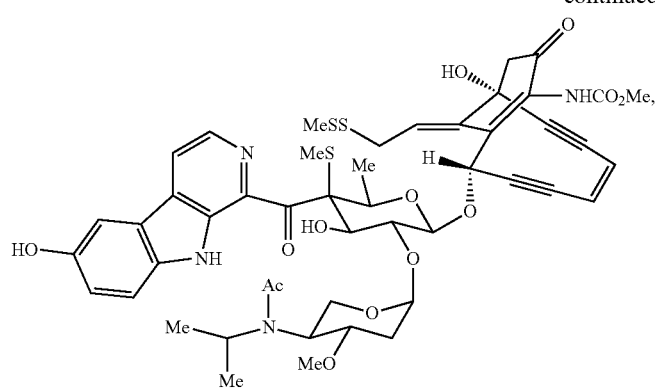
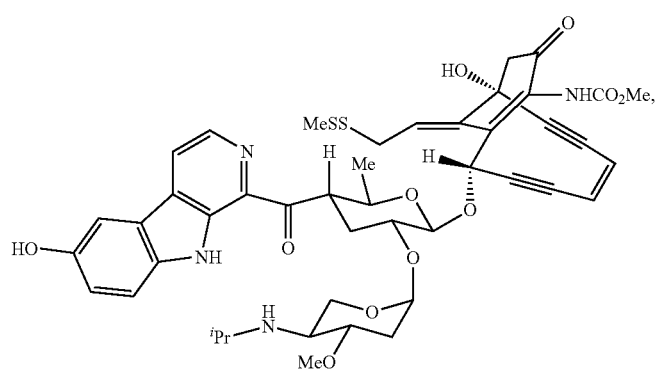
288
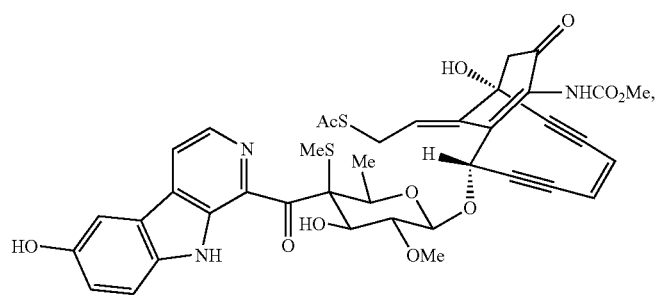
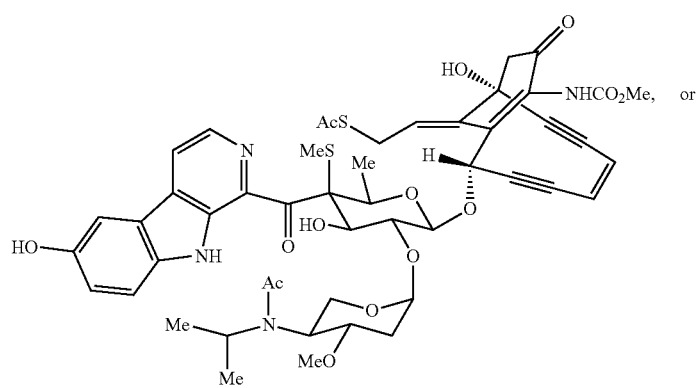

-continued
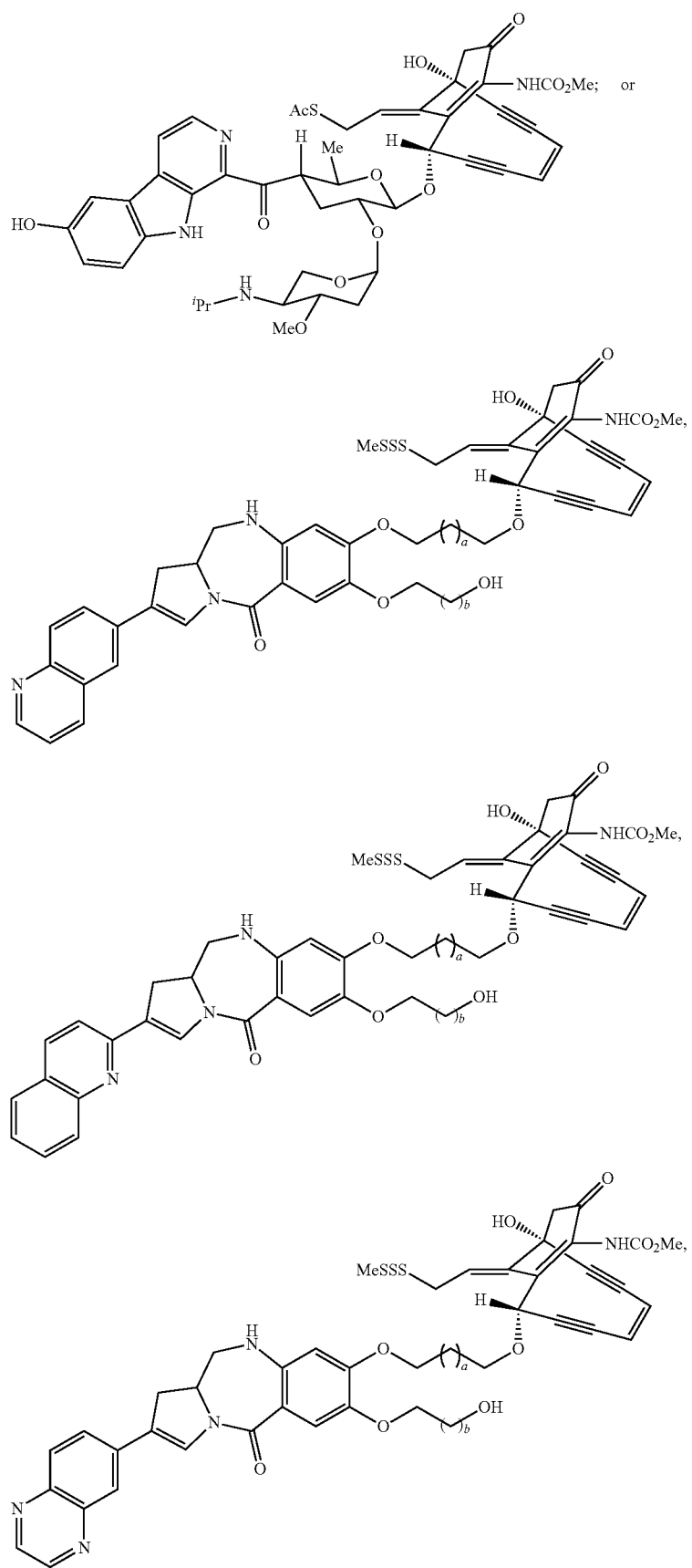

-continued
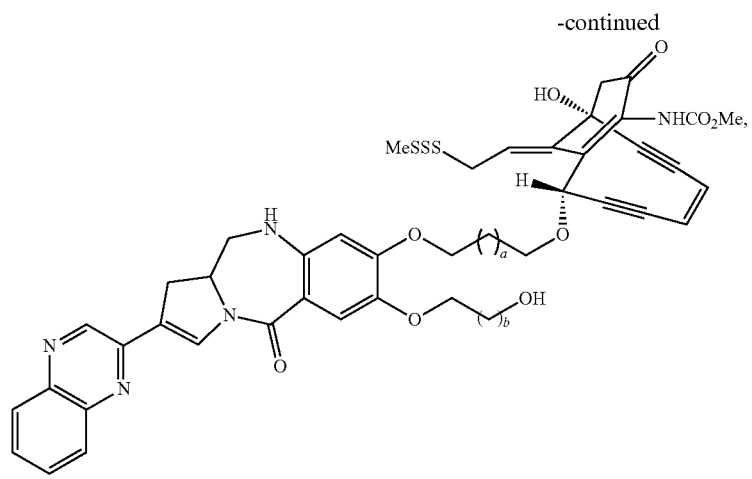
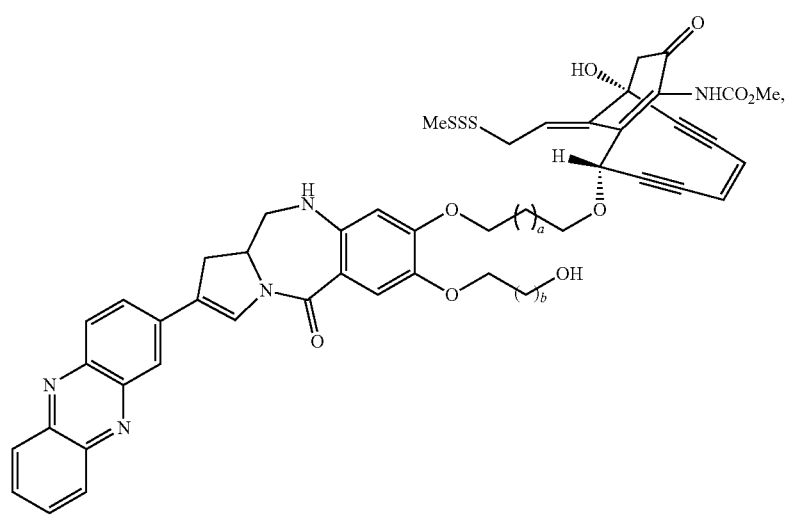
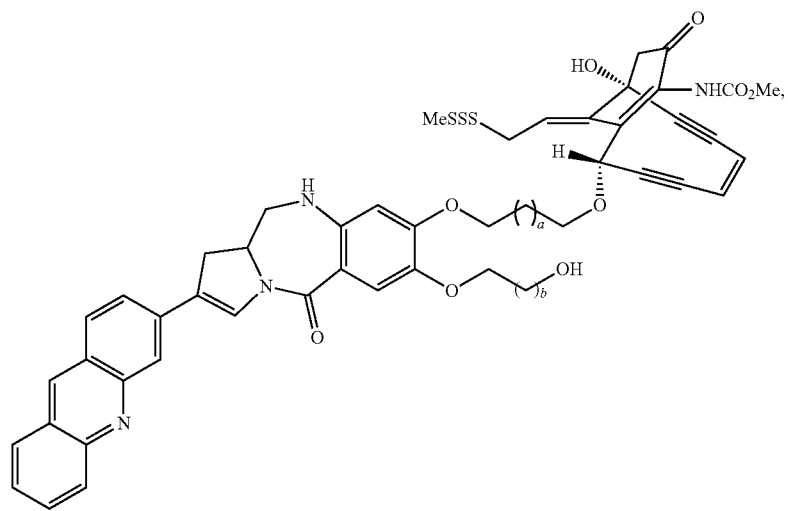

-continued
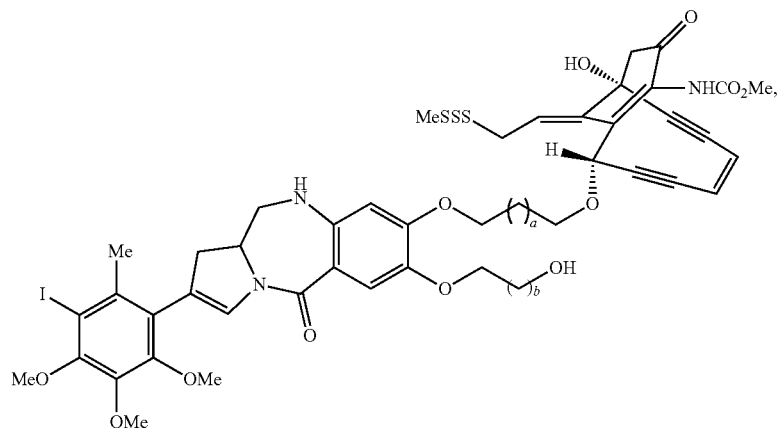
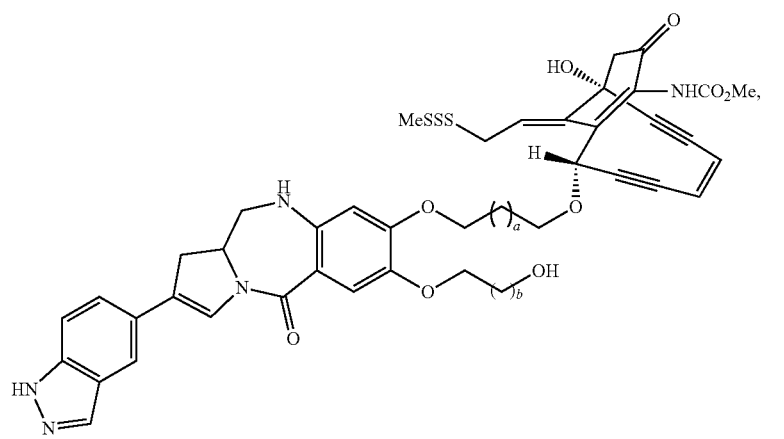
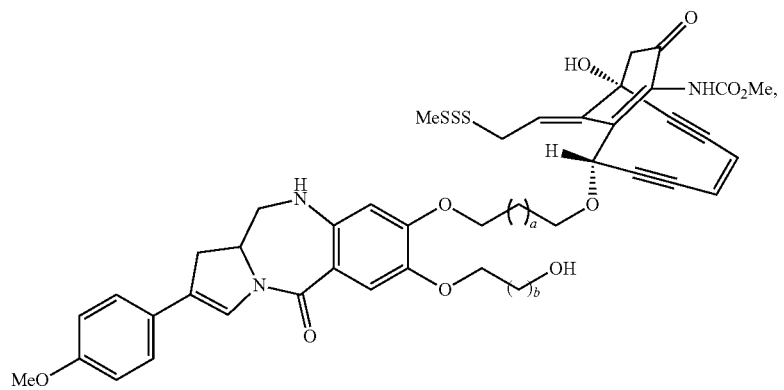
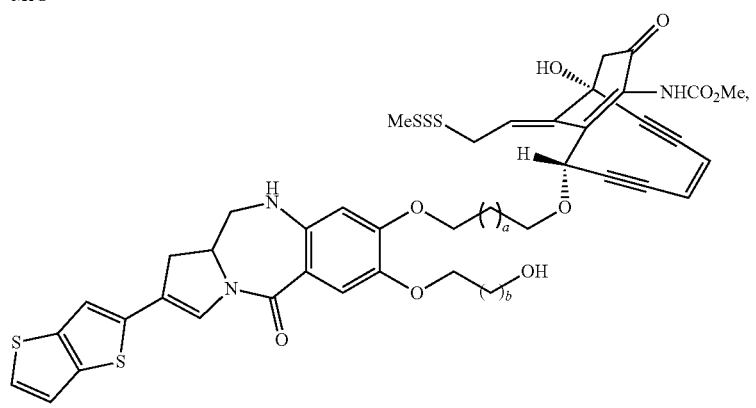

-continued
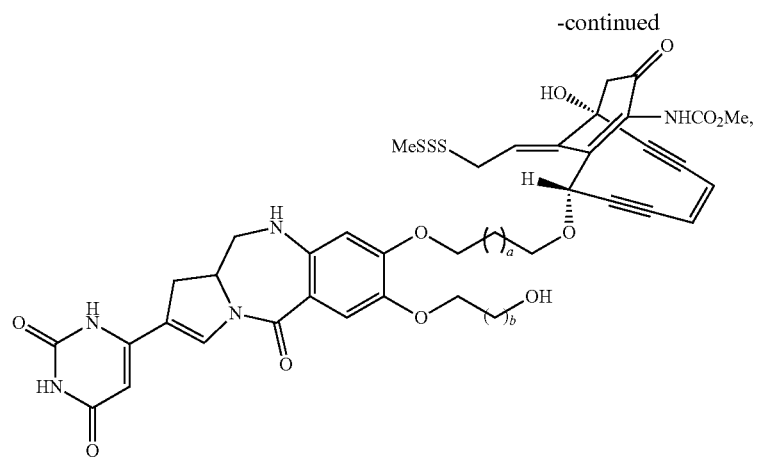
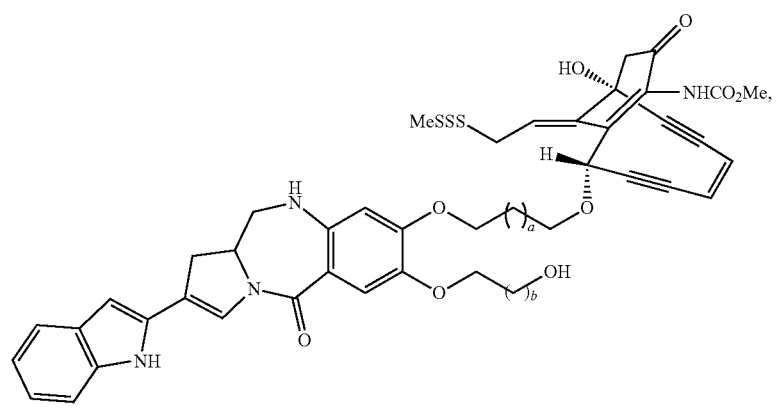
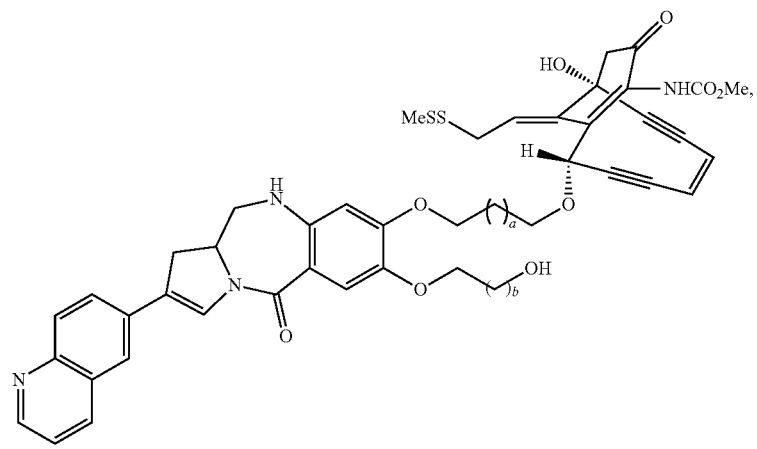
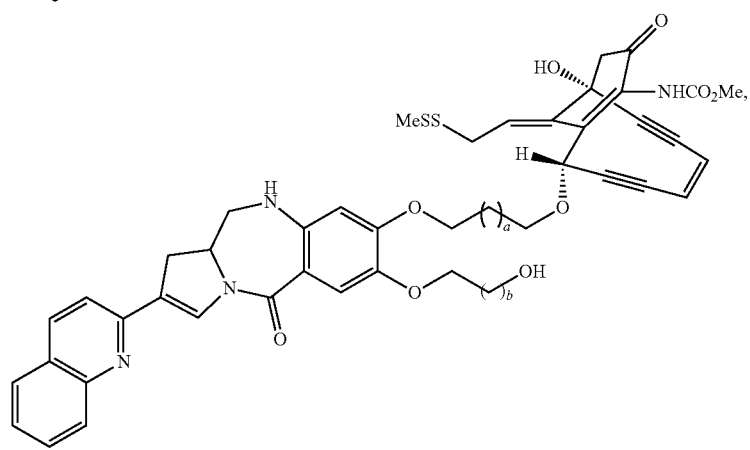

-continued
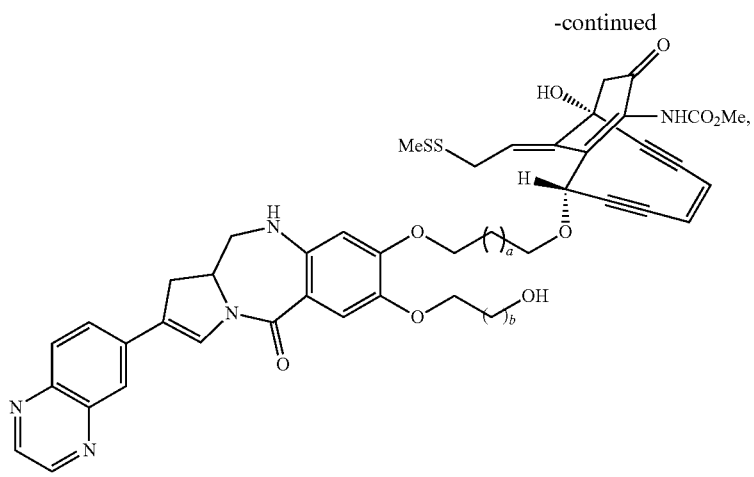
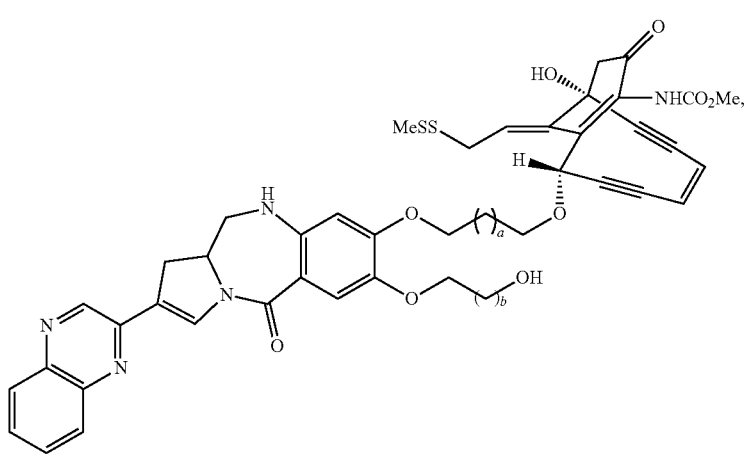
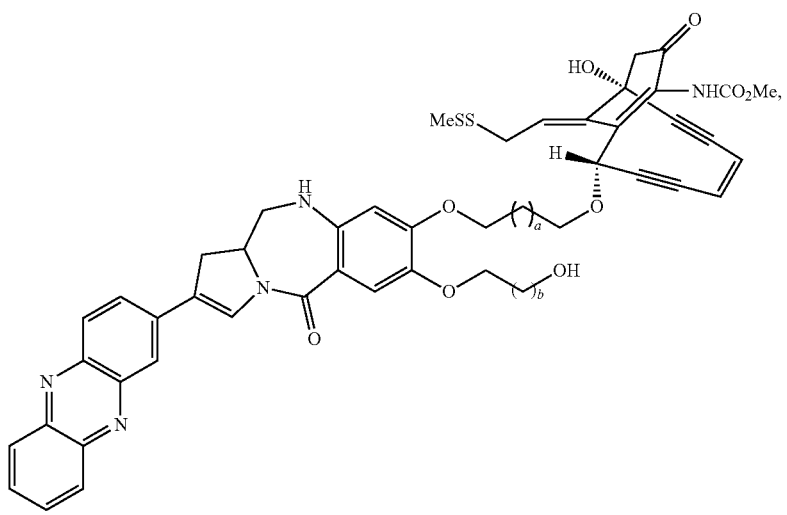

-continued
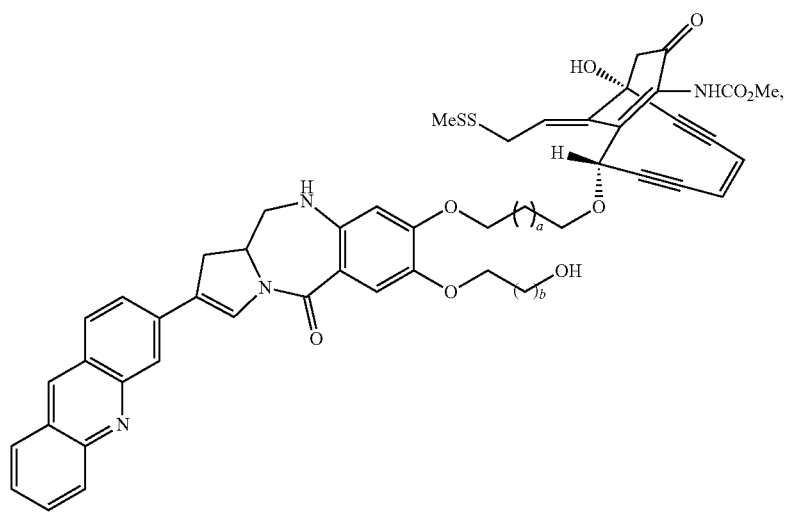
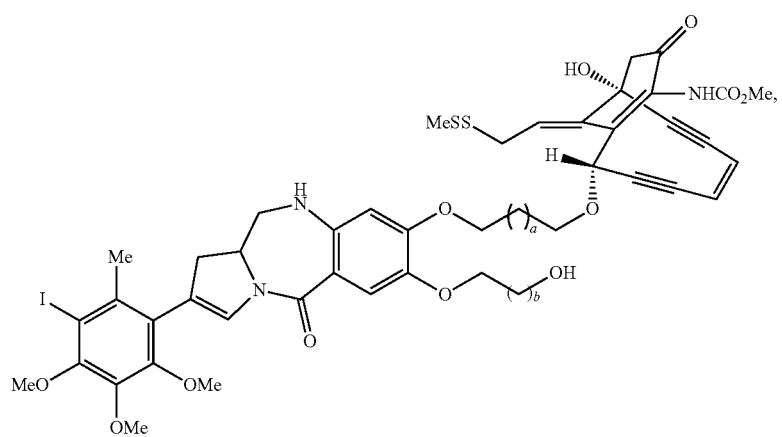
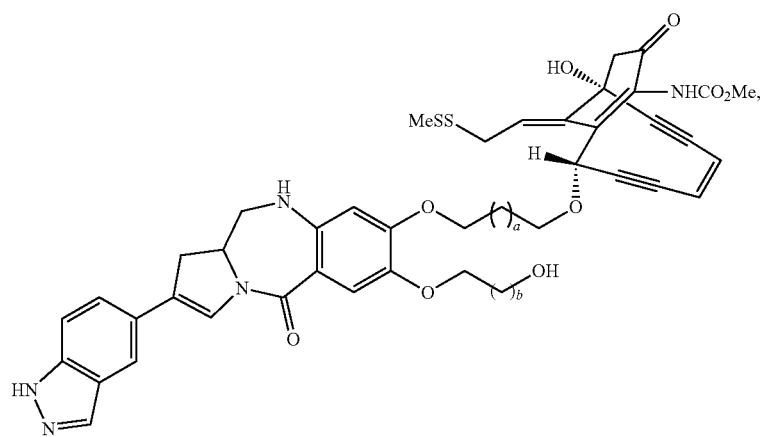

-continued
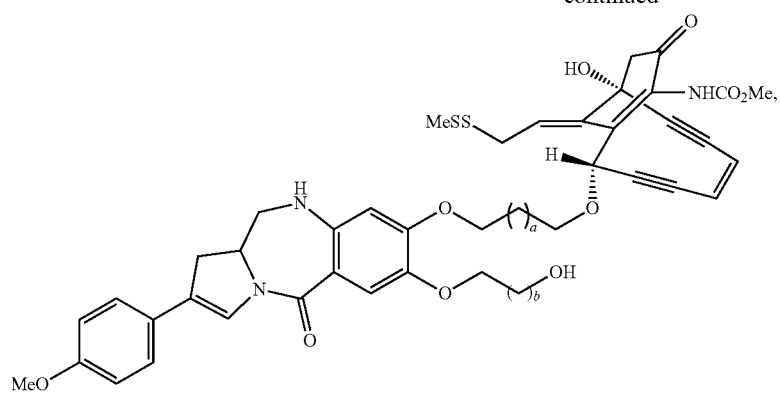
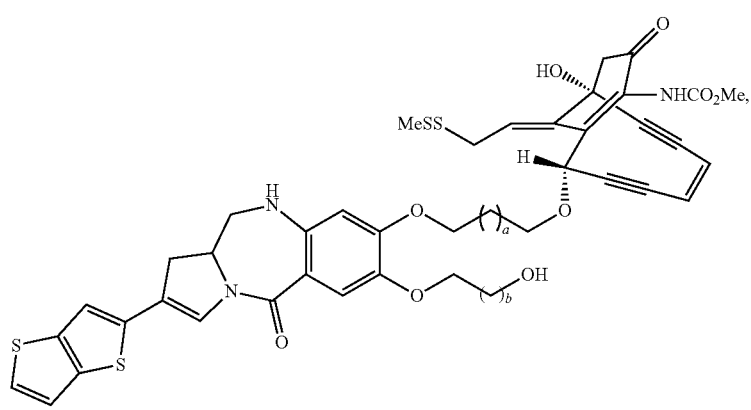
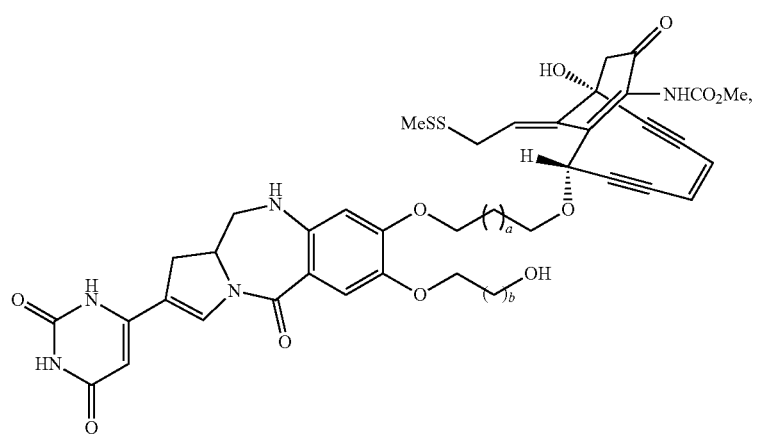
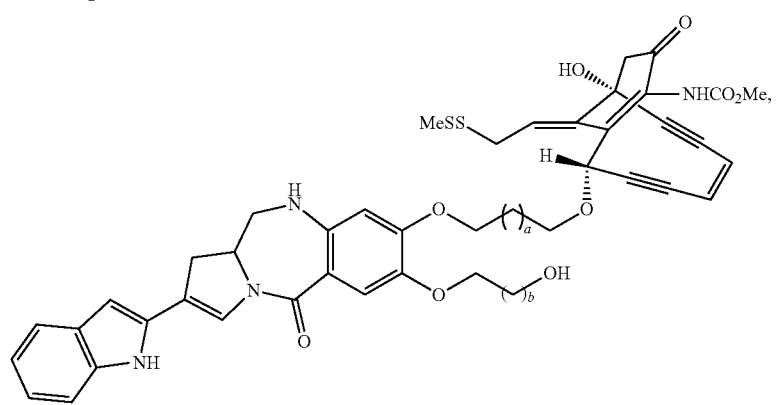

-continued
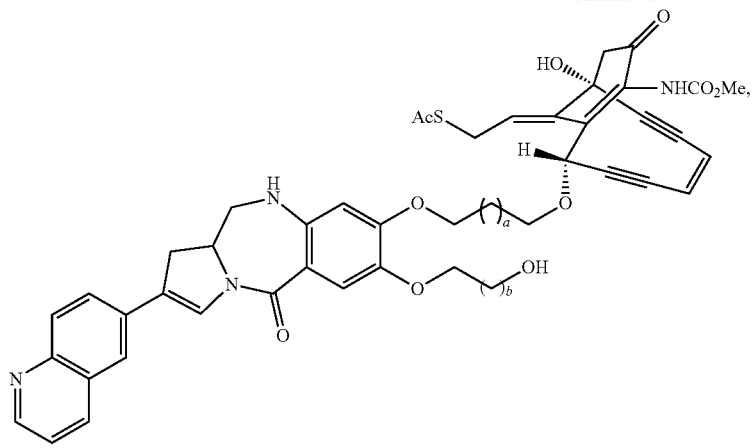
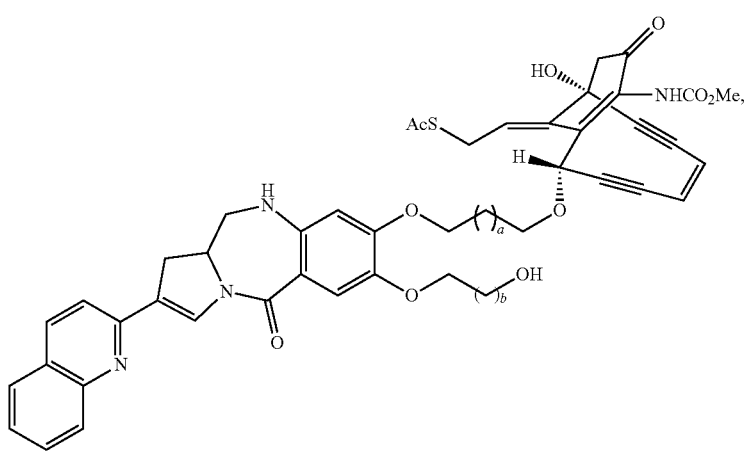
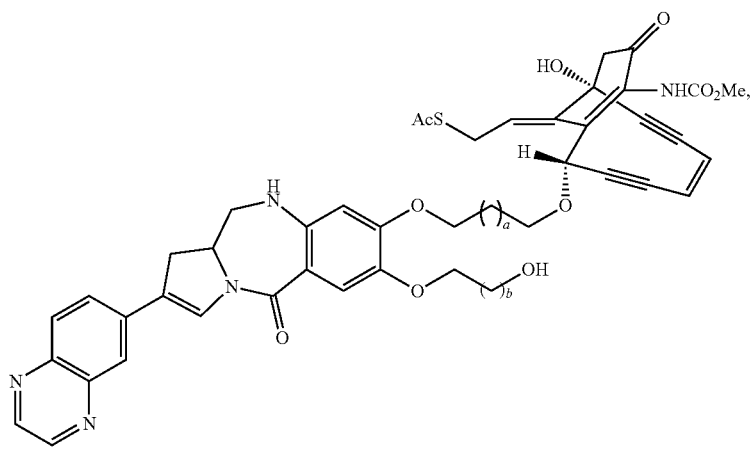

-continued
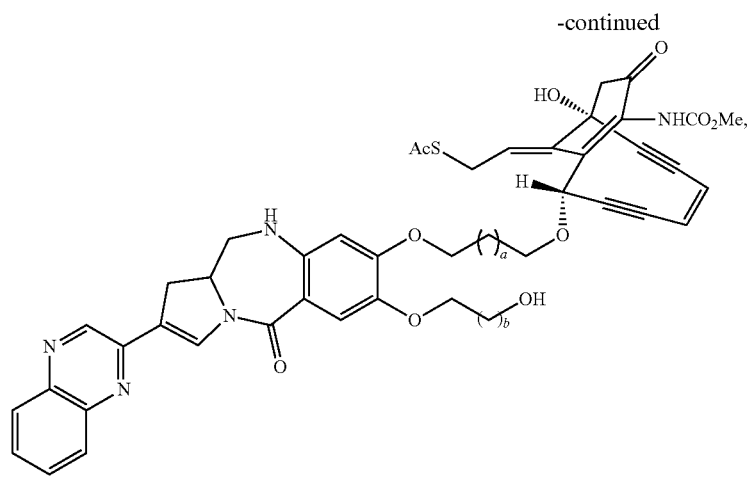
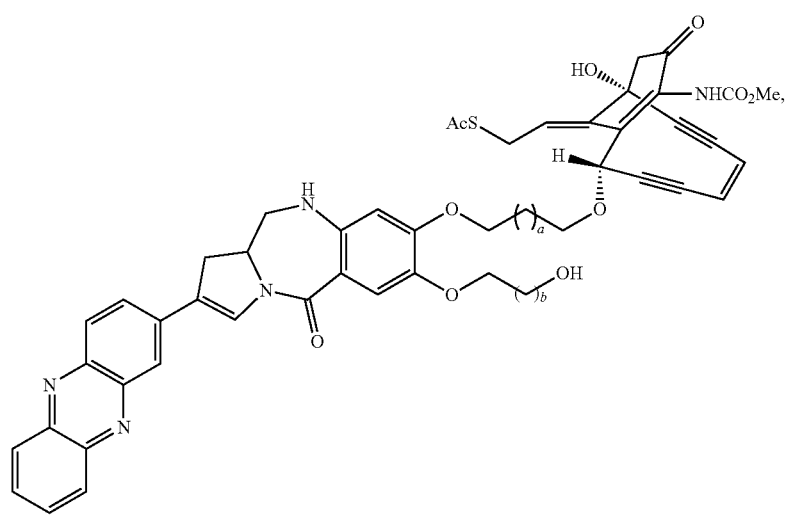
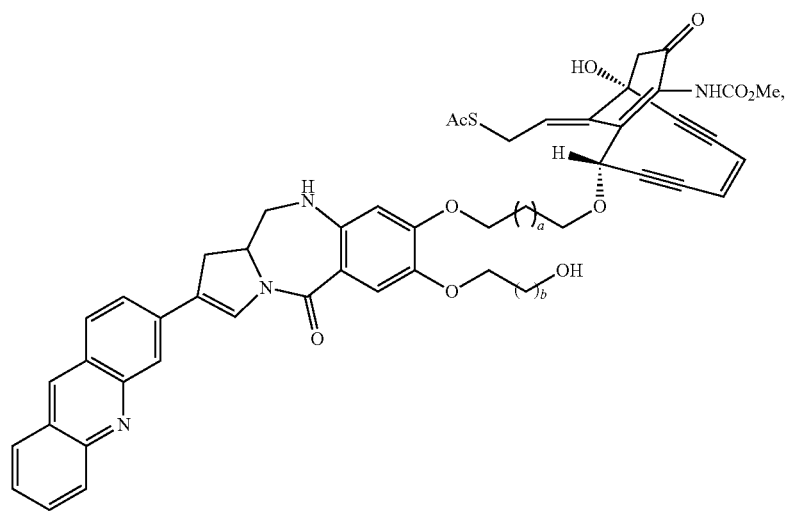

-continued
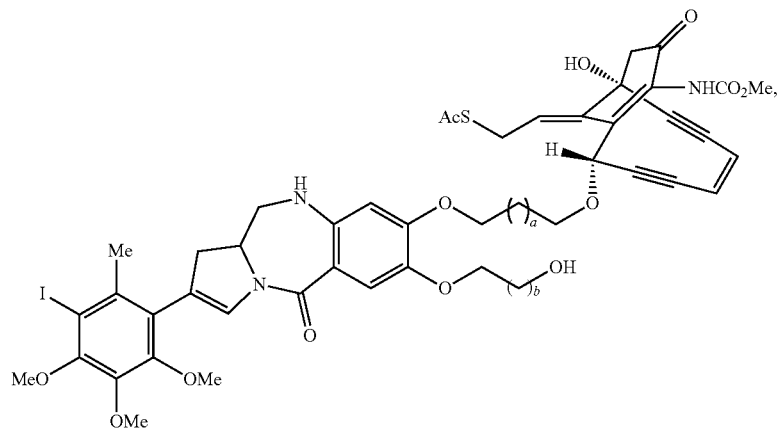
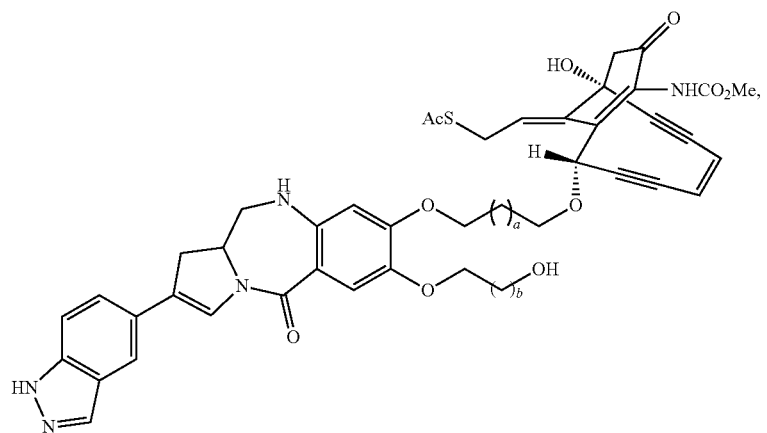
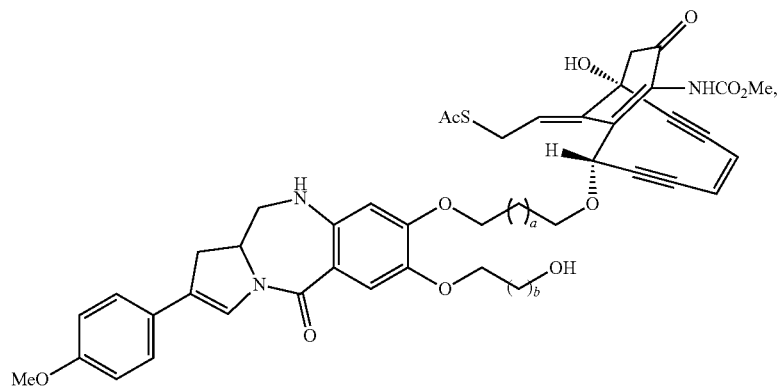
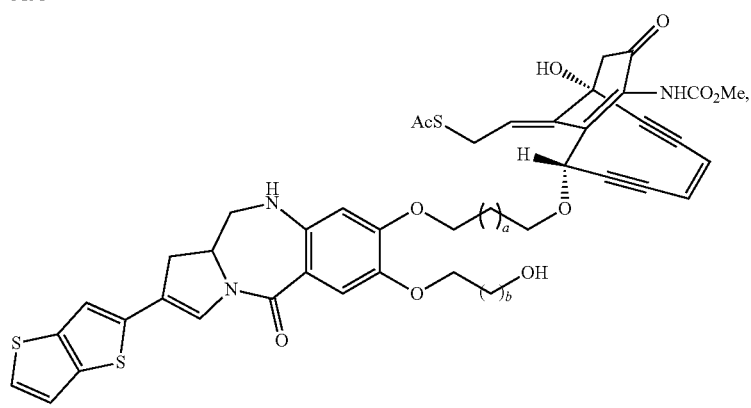

-continued

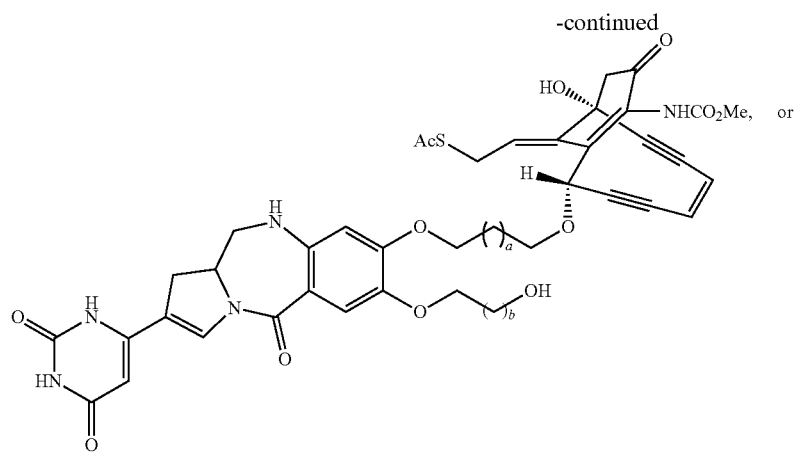

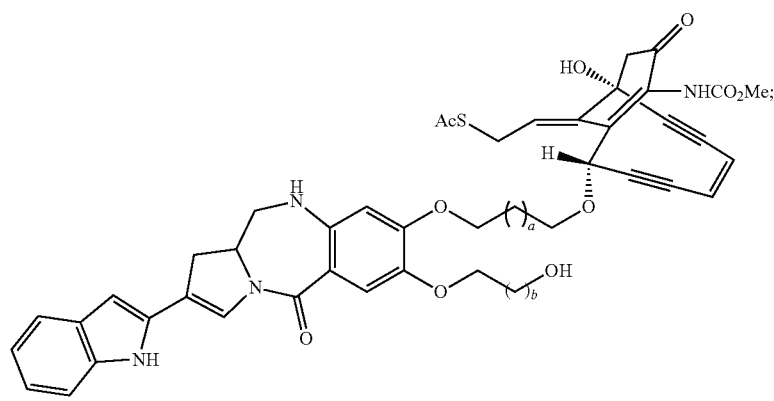

a is 0, 1, 2, 3, 4, or 5; and
b is 1, 2, 3, 4, or 5;
or a pharmaceutically acceptable salt thereof.

16. A pharmaceutical composition comprising:
(A) a compound of claim 1; and
(B) a pharmaceutically acceptable carrier.

17. A method of treating a disease or disorder in a patient comprising administering to the patient in need thereof a therapeutically effective amount of a compound or composition of claim 1.

18. An antibody-drug conjugate comprising:

A-L-(X)$_y$                                    (VIII)

wherein:
A is an antibody or a nanoparticle;
L is a covalent bond or a difunctional linker;
X is a compound of claim 1; and
y is an integer selected from 1, 2, 3, 4, 5, 6, 7, 8, 9, 10, 11, 12, 13, 14, 15, 16, 17, 18, 19, or 20.

19. A method of preparing a compound of the formula:

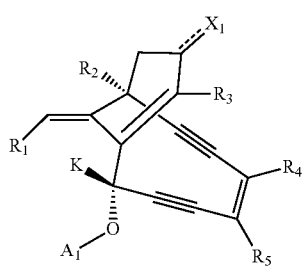

(I)

wherein:
R$_1$ is -alkanediyl$_{(C \leq 8)}$-(S)$_x$-A$_3$ or -substituted alkanediyl$_{(C \leq 8)}$-(S)$_x$-A$_3$; wherein:
A$_3$ is hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, heteroaryl$_{(C \leq 12)}$, aralkyl$_{(C \leq 12)}$, acyl$_{(C \leq 12)}$, or a substituted version of any of these groups; and
x is 1, 2, or 3;

$R_2$ is hydroxy, or alkoxy$_{(C≤8)}$, acyloxy$_{(C≤8)}$, or substituted version of either of these groups, or a protected hydroxy group;

$R_3$ is NHC(O)R$_{16}$, wherein:
  $R_{16}$ is alkoxy$_{(C≤8)}$, alkenyloxy$_{(C≤8)}$, alkylamino$_{(C≤8)}$, dialkylamino$_{(C≤8)}$, or substituted version of any of these groups;

$R_4$ and $R_5$ are each independently selected from hydrogen and halo;

$X_1$ is O, S, or NH, or $X_1$ is a protected carbonyl wherein the protected carbonyl is a group of the formula —O(CH$_2$)$_c$O—, wherein c is 1, 2, 3, or 4;

$A_1$ is -alkanediyl$_{(C≤12)}$-C(O)-A$_2$ or -substituted alkanediyl$_{(C≤12)}$-C(O)-A$_2$; or $A_1$ is:

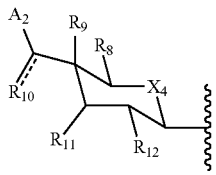

wherein:
  $X_4$ is —CH$_2$— or —O—;
  $R_8$ is hydrogen, alkyl$_{(C≤8)}$, cycloalkyl$_{(C≤8)}$, substituted alkyl$_{(C≤8)}$, or substituted cycloalkyl$_{(C≤8)}$;
  $R_9$ is hydrogen, halo, hydroxy, mercapto, alkyl$_{(C≤8)}$, substituted alkyl$_{(C≤8)}$, alkoxy$_{(C≤8)}$, substituted alkoxy$_{(C≤8)}$, alkylthio$_{(C≤8)}$, substituted alkylthio$_{(C≤8)}$, or a protected hydroxy group or a protected thiol group;
  $R_{10}$ is hydroxy, oxo, or $R_{10}$ is taken together with $R_{11}$ and is —OCHA$_4$O—;
    provided that when $R_{10}$ is oxo then $R_{10}$ and the carbon atom to which it is bound are joined by a double bond, and when $R_{10}$ is taken together with $R_{11}$ then $R_{10}$ and the carbon atom to which it is bound are joined by a single bond;
    wherein A$_4$ is aryl$_{(C≤12)}$ or substituted aryl$_{(C≤12)}$, or

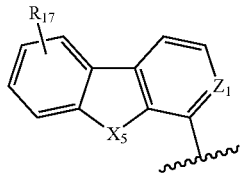

wherein:
  $Z_1$ is CH or N; and
  $R_{17}$ is hydrogen, hydroxy, amino, hydrazino, carboxy, halo, or nitro; or alkyl$_{(C≤12)}$, alkoxy$_{(C≤12)}$, or a substituted version of either of these groups;
  $R_{11}$ is hydrogen, hydroxy, alkoxy$_{(C≤8)}$, or substituted alkoxy$_{(C≤8)}$, or a protected hydroxy group;
  $R_{12}$ is hydrogen, hydroxy, alkoxy$_{(C≤8)}$, substituted alkoxy$_{(C≤8)}$, or a protected hydroxy group, or —O-alkanediyl$_{(C≤8)}$-alkylamino$_{(C≤12)}$, —OC(O)-alkanediyl$_{(C≤8)}$-alkylamino$_{(C≤12)}$, or —OC(O)NH-alkanediyl$_{(C≤8)}$-alkylamino$_{(C≤12)}$, or a substituted version of any of these groups; or

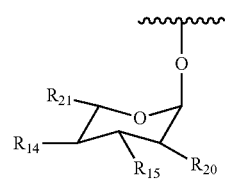

wherein:
  $R_{14}$ is amino or hydroxy; or alkoxy$_{(C≤12)}$, alkylamino$_{(C≤12)}$, dialkyl-amino$_{(C≤12)}$, or a substituted version of any of these groups, or —NR$_a$R$_b$, wherein:
    $R_a$ and $R_b$ are each hydrogen, alkyl$_{(C≤12)}$, substituted alkyl$_{(C≤12)}$, alkenyl$_{(C≤12)}$, substituted alkenyl$_{(C≤12)}$, —C(O)O-alkanediyl$_{(C≤6)}$-R$_c$, —C(O)-alkanediyl$_{(C≤6)}$-R$_c$, -alkanediyl$_{(C≤6)}$-R$_c$, or a substituted version of either of these group;
      wherein:
        $R_c$ is hydrogen, amino, carboxy, hydroxyl, acyl$_{(C≤8)}$, alkoxy$_{(C≤8)}$, alkylamino$_{(C≤8)}$, dialkylamino$_{(C≤8)}$, alkylsulfonyl$_{(C≤8)}$, arylsulfonyl$_{(C≤8)}$, or a substituted version of either of these groups, or
      a protected amino or hydroxy group;
  $R_{15}$ is hydrogen, hydroxy, alkoxy$_{(C≤8)}$, or substituted alkoxy$_{(C≤8)}$, or a protected hydroxy group;
  $R_{20}$ and $R_{21}$ are hydrogen, alkyl$_{(C≤8)}$, substituted alkyl$_{(C≤8)}$, alkoxy$_{(C≤8)}$, or substituted alkoxy$_{(C≤8)}$;

$A_2$ is hydrogen or

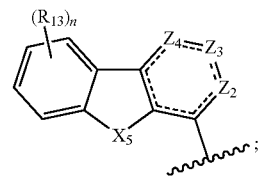

wherein:
  $X_5$ is O, S, or NR$_{18}$; wherein:
    $R_{18}$ is hydrogen, alkyl$_{(C≤8)}$, substituted alkyl$_{(C≤8)}$, acyl$_{(C≤8)}$, or substituted acyl$_{(C≤8)}$, or;
  n is 1, 2, 3, 4, or 5;
  $Z_2$, $Z_3$, and $Z_4$ are each independently N or CR$_{13}$; and
  $R_{13}$ is hydrogen, amino, carboxy, hydroxy, hydrazino, halo, or nitro;
    alkyl$_{(C≤12)}$, acyl$_{(C≤12)}$, alkoxy$_{(C≤12)}$, acyloxy$_{(C≤12)}$, or a substituted version of either of these groups, or a protected thiol, amino, or hydroxy group; or $A_1$ is

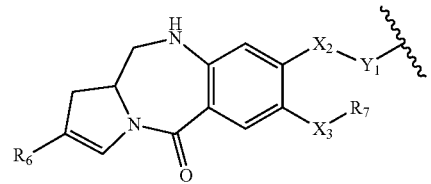

wherein:
Y₁ is alkanediyl$_{(C≤8)}$ or substituted alkanediyl$_{(C≤8)}$;
X₂ and X₃ are each independently selected from —O—, —S—, or —NR₁₉—, wherein:
R₁₉ is hydrogen, alkyl$_{(C≤6)}$, or substituted alkyl$_{(C≤6)}$;
R₆ is aryl$_{(C≤18)}$, heteroaryl$_{(C≤18)}$, or a substituted version of either of these groups;
R₇ is alkyl$_{(C≤12)}$ or substituted alkyl$_{(C≤12)}$;
comprising reacting a compound of the formula:

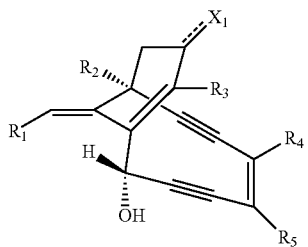 (IX)

wherein:
X₁, R₁, R₂, R₃, R₄, and R₅ are as defined above;
with a compound of the formula:

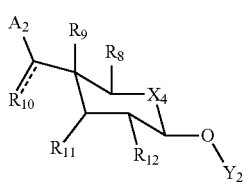 (X)

wherein:
X₄, A₂, R₈, R₉, R₁₀, R₁₁, and R₁₂ are as defined above; and
Y₂ is hydrogen or an activating group; or
with a compound of the formula:

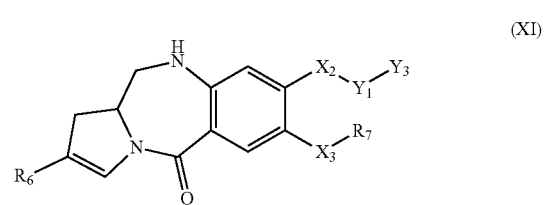 (XI)

wherein:
Y₁, X₂, X₃, R₆, and R₇ are as defined above; and
Y₃ is a leaving group;
wherein the method optionally further comprises reacting the product with a compound of the formula: Y₄-alkanediyl$_{(C≤12)}$-C(O)-A₂ or Y₄-substituted alkanediyl$_{(C≤12)}$-C(O)-A₂;
wherein:
Y₄ is a leaving group;
in the presence of a Lewis acid.

* * * * *

UNITED STATES PATENT AND TRADEMARK OFFICE
CERTIFICATE OF CORRECTION

PATENT NO. : 10,590,158 B2
APPLICATION NO. : 15/740656
DATED : March 17, 2020
INVENTOR(S) : Kyriacos C. Nicolaou et al.

Page 1 of 1

It is certified that error appears in the above-identified patent and that said Letters Patent is hereby corrected as shown below:

In the Claims

In Claim 1, Column 183, Lines 18-27, delete chemical drawing and insert

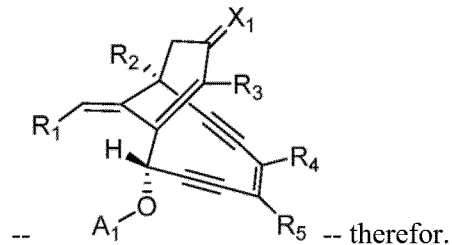

-- therefor.

In Claim 9, Column 192, Line 29, delete "(C≤s" and insert --$(C_{\leq 8})$-- therefor.

In Claim 19, Column 310, Lines 47-58, delete chemical drawing and insert

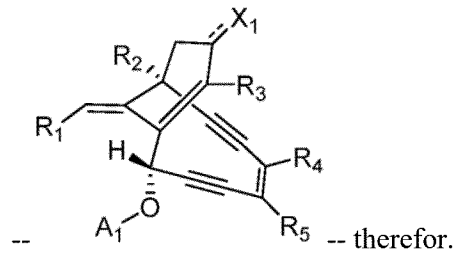

-- therefor.

Signed and Sealed this
First Day of September, 2020

Andrei Iancu
*Director of the United States Patent and Trademark Office*